(12) United States Patent
Kim et al.

(10) Patent No.: US 12,398,316 B2
(45) Date of Patent: Aug. 26, 2025

(54) ORGANIC COMPOUND AND ORGANIC ELECTROLUMINESCENT DEVICE COMPRISING SAME

(71) Applicant: DOOSAN SOLUS CO., LTD., Iksan-si (KR)

(72) Inventors: Hong Suk Kim, Yongin-si (KR); Young Bae Kim, Yongin-si (KR)

(73) Assignee: DOOSAN SOLUS CO., LTD., Iksan-si (KR)

( * ) Notice: Subject to any disclaimer, the term of this patent is extended or adjusted under 35 U.S.C. 154(b) by 686 days.

(21) Appl. No.: 16/626,634

(22) PCT Filed: May 2, 2018

(86) PCT No.: PCT/KR2018/005079
§ 371 (c)(1),
(2) Date: Dec. 26, 2019

(87) PCT Pub. No.: WO2019/004584
PCT Pub. Date: Jan. 3, 2019

(65) Prior Publication Data
US 2020/0227650 A1  Jul. 16, 2020

(30) Foreign Application Priority Data
Jun. 30, 2017 (KR) .................. 10-2017-0083287

(51) Int. Cl.
| | | |
|---|---|---|
| *C09K 11/06* | (2006.01) | |
| *C07D 251/24* | (2006.01) | |
| *C07D 401/14* | (2006.01) | |
| *C07D 403/10* | (2006.01) | |
| *C07D 405/10* | (2006.01) | |
| *C07D 405/14* | (2006.01) | |
| *C07D 409/10* | (2006.01) | |
| *H10K 50/11* | (2023.01) | |
| *H10K 50/15* | (2023.01) | |
| *H10K 50/16* | (2023.01) | |
| *H10K 50/17* | (2023.01) | |
| *H10K 85/60* | (2023.01) | |
| *H10K 101/10* | (2023.01) | |

(52) U.S. Cl.
CPC ............ *C09K 11/06* (2013.01); *C07D 251/24* (2013.01); *C07D 401/14* (2013.01); *C07D 403/10* (2013.01); *C07D 405/10* (2013.01); *C07D 405/14* (2013.01); *C07D 409/10* (2013.01); *H10K 85/654* (2023.02); *H10K 85/6572* (2023.02); *H10K 85/6574* (2023.02); *H10K 85/6576* (2023.02); *C09K 2211/1018* (2013.01); *H10K 50/11* (2023.02); *H10K 50/156* (2023.02); *H10K 50/166* (2023.02); *H10K 50/17* (2023.02); *H10K 2101/10* (2023.02)

(58) Field of Classification Search
CPC .. C07D 231/56; C07D 251/24; C07D 401/14; C07D 403/10; C07D 405/10; C07D 405/14; C07D 409/10; C07D 409/14
See application file for complete search history.

(56) References Cited

U.S. PATENT DOCUMENTS

| | | | | |
|---|---|---|---|---|
| 2008/0036373 | A1* | 2/2008 | Itoh ...................... | H10K 85/346 546/88 |
| 2010/0237769 | A1 | 9/2010 | Park et al. | |
| 2013/0299128 | A1 | 11/2013 | Bergamini | |

FOREIGN PATENT DOCUMENTS

| | | | |
|---|---|---|---|
| CN | 106544006 A | | 3/2017 |
| EP | 0 934 847 A2 | | 8/1999 |
| JP | 2002123012 A | * | 4/2002 |
| JP | 2003-291629 A | | 10/2003 |
| JP | 2005-082701 A | | 3/2005 |
| JP | 2003277743 A | * | 1/2008 |
| JP | 2008-037848 A | | 2/2008 |
| JP | 2014-055131 A | | 3/2014 |
| KR | 10-2010-0118690 A | | 11/2010 |
| KR | 20150121626 | * | 10/2012 |
| KR | 10-2014-0049861 A | | 4/2014 |
| KR | 10-2015-0106067 A | | 9/2015 |
| KR | 10-2015-0109111 A | | 10/2015 |
| KR | 10-2015-0121626 A | | 10/2015 |
| KR | 2015-0110101 A | * | 10/2015 |

(Continued)

OTHER PUBLICATIONS

Yu et al. (Tetrahedron Letters (2015), 56 (11), 1432-1436).*

(Continued)

*Primary Examiner* — Valerie Rodriguez-Garcia
(74) *Attorney, Agent, or Firm* — Sughrue Mion, PLLC

(57) ABSTRACT

A novel compound represented by Chemical Formula 6 below and an organic electroluminescent device including the same are disclosed. The inclusion of the compound in an organic material layer of an organic electroluminescent device, preferably as a light emitting layer, can improve luminous efficiency, driving voltage, lifetime and the like of the organic electroluminescent device:

Chemical Formula 6

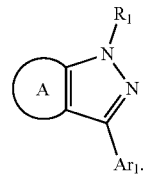

3 Claims, 1 Drawing Sheet

(56) References Cited

FOREIGN PATENT DOCUMENTS

| | | | |
|---|---|---|---|
| KR | 2015-0111441 A | * | 10/2015 |
| KR | 10-2016-0005944 A | | 1/2016 |
| KR | 10-2016-0045019 A | | 4/2016 |
| KR | 10-2016-0057018 | * | 5/2016 |
| KR | 10-2016-0057018 A | | 5/2016 |
| KR | 10-2017-0005853 A | | 1/2017 |
| KR | 10-2017-0023025 A | | 3/2017 |
| KR | 10-2017-0063394 A | | 6/2017 |
| WO | 2007/065010 A2 | | 6/2007 |
| WO | 2010/126270 A1 | | 11/2010 |
| WO | WO 2010/126270 | * | 11/2010 |
| WO | 2014/054912 A1 | | 4/2014 |
| WO | 2015175678 A1 | | 11/2015 |
| WO | 2018/093107 A1 | | 5/2018 |
| WO | 2020/021894 A1 | | 1/2020 |

OTHER PUBLICATIONS

STN CAS Registry 1350026-65-1—Dec. 7, 2011.*
Communication dated Feb. 25, 2022 from the Korean Intellectual Property Office in Application No. 10-2017-0083287.
Y.T. Tao et al., "Organic Light-Emitting Diodes Based on Variously Substituted Pyrazoloquinolines as Emitting Material", Chem. Mater., 2001, pp. 1207-1212, vol. 13, No. 4.
International Search Report for PCT/KR2018/005079 dated Aug. 24, 2018 PCT/ISA/210.
Korean Office Action dated Jan. 16, 2023 in Korean Application No. 10-2017-0083287.

* cited by examiner

【FIG. 1】
【FIG. 2】
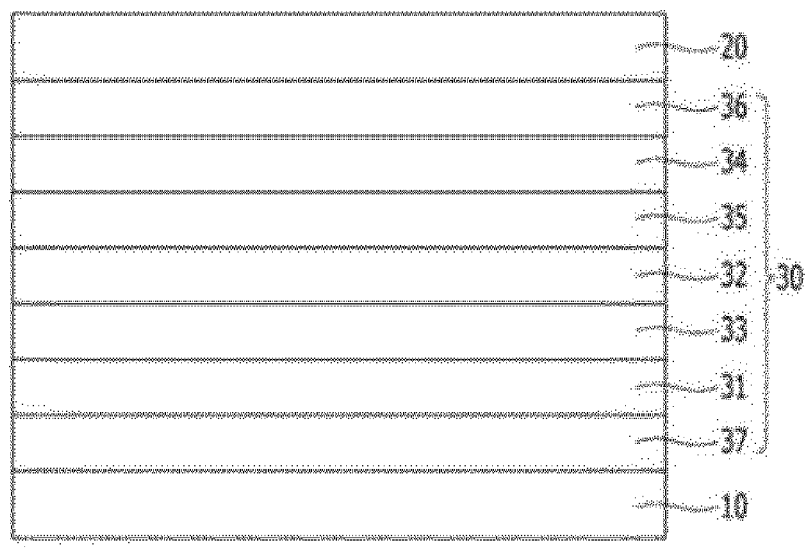

ORGANIC COMPOUND AND ORGANIC ELECTROLUMINESCENT DEVICE COMPRISING SAME

CROSS REFERENCE TO RELATED APPLICATIONS

This application is a National Stage of International Application No. PCT/KR2018/005079 filed May 2, 2018, claiming priority based on Korean Patent Application No. 10-2017-0083287 filed Jun. 30, 2017.

TECHNICAL FIELD

The present invention relates to a novel organic compound capable of being used as a material for an organic electroluminescent device, and an organic electroluminescent device including the same.

BACKGROUND ART

With the observation of organic thin film light emission made by Bemanose in 1950s as a start, studies on organic electroluminescent (EL) devices have been continued leading to blue electroluminescence using a single anthracene crystal in 1965, and in 1987, an organic electroluminescent device having a laminated structure divided into functional layers of a hole layer and a light emitting layer has been proposed by Tang. After that, in order to manufacture organic electroluminescent devices with high efficiency and long lifetime, development has been made in the form of introducing each characteristic organic material layer into the device, which leads to the development of specialized materials used therein.

When a voltage is applied between the two electrodes in an organic electroluminescent device, holes and electrons are injected to an organic material layer from the anode and the cathode, respectively. When the injected holes and electrons meet, excitons are formed, and light emits when these excitons fall back to the ground state. Herein, materials used as the organic material layer may be divided into a light emitting material, a hole injection material, a hole transport material, an electron transport material, an electron injection material and the like depending on the function.

The light emitting material may be divided into, depending on the light emitting color, blue, green and red light emitting materials, and yellow and orange light emitting materials for obtaining better natural colors. In addition, in order to increase color purity and increase luminous efficiency through energy transfer, host/dopant series may be used as the light emitting material.

The dopant material may be divided into fluorescent dopants using organic materials and phosphorescent dopants using metal complex compounds including heavy atoms such as Ir or Pt. Herein, development of phosphorescent materials may enhance luminous efficiency up to 4 times compared to fluorescence theoretically, and therefore, studies on phosphorescent host materials have been widely progressed as well as on phosphorescent dopants.

So far, NPB, BCP, Alq$_3$ and the like have been widely known as materials of a hole injection layer, a hole transport layer, a hole blocking layer and an electron transport layer, and anthracene derivatives have been reported as a material of a light emitting layer. Particularly, among light emitting layer materials, metal complex compounds including Ir such as Firpic, Ir(ppy)$_3$ or (acac)Ir(btp)$_2$ having advantages in terms of efficiency enhancement have been used as blue, green and red phosphorescent dopant materials, and 4,4-dicarbazolylbiphenyl (CBP) has been used as a phosphorescent host material.

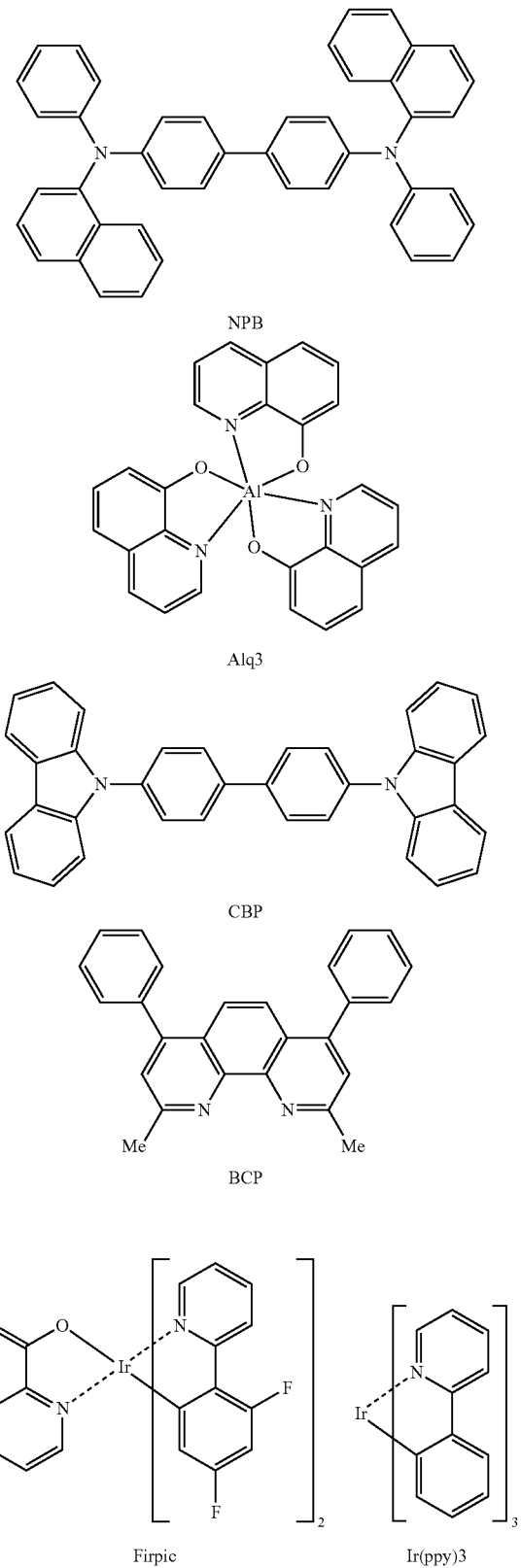

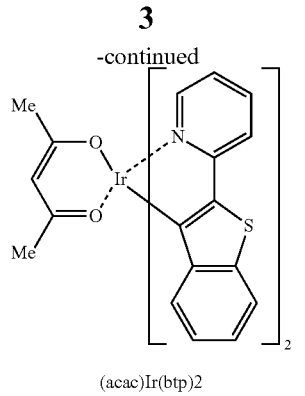

(acac)Ir(btp)2

However, although being advantageous in terms of a light emission property, existing organic material layer materials have a low glass transition temperature and thereby have very unfavorable thermal stability, which is not satisfactory in terms of an organic electroluminescent device lifetime. Accordingly, development of organic material layer materials having superior performance has been required.

DISCLOSURE

Technical Problem

The present invention is directed to providing a novel organic compound capable of being used in an organic electroluminescent device, and having excellent hole and electron injection and transport abilities, a light emitting ability and the like.

The present invention is also directed to providing an organic electroluminescent device including the novel organic compound, and thereby exhibiting a low driving voltage, high luminous efficiency, and an enhanced lifetime.

Technical Solution

In view of the above, one embodiment of the present invention provides a compound represented by the following Chemical Formula 1:

[Chemical Formula 1]

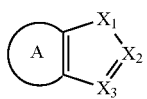

in Chemical Formula 1, $X_1$ is selected from the group consisting of S, O, N($R_1$) and C($R_2$)($R_3$);

$X_2$ and $X_3$ are each independently N or C($Ar_1$), and at least one thereof is C($Ar_1$); and ring A is represented by any one of the following Chemical Formulae 2 to 4;

[Chemical Formula 2]

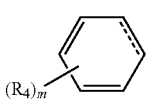

[Chemical Formula 3]

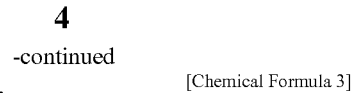

[Chemical Formula 4]

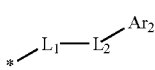

in Chemical Formulae 1 to 4, a dotted line means a part that is fused;

m is an integer of 0 to 4;

n is an integer of 0 to 6;

$R_1$ to $R_4$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylamine group;

the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of $R_1$ to $R_4$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylsilyl group, and when substituted with a plurality of the substituents, these are the same as or different from each other; and $Ar_1$ is a substituent represented by the following Chemical Formula 5, and when $Ar_1$ is present in plural numbers, these are the same as or different from each other;

[Chemical Formula 5]

$$*\!\!-\!\!L_1\!\!-\!\!L_2\!\!-\!\!Ar_2$$

in Chemical Formula 5,

* means a part where a bond is formed;

$L_1$ and $L_2$ are each independently selected from the group consisting of a direct bond, a $C_6$~$C_{18}$ arylene group and a heteroarylene group having 5 to 18 nuclear atoms;

Ar$_2$ is selected from the group consisting of hydrogen, deuterium, halogen, a cyano group, a nitro group, a C$_1$~C$_{40}$ alkyl group, a C$_2$~C$_{40}$ alkenyl group, a C$_2$~C$_{40}$ alkynyl group, a C$_3$~C$_{40}$ cycloalkyl group, a heterocycloalkyl group having 3 to 40 nuclear atoms, a C$_6$~C$_{60}$ aryl group, a heteroaryl group having 5 to 60 nuclear atoms, a C$_1$~C$_{40}$ alkyloxy group, a C$_6$~C$_{60}$ aryloxy group, a C$_3$~C$_{40}$ alkylsilyl group, a C$_6$~C$_{60}$ arylsilyl group, a C$_1$~C$_{40}$ alkylboron group, a C$_6$~C$_{60}$ arylboron group, a C$_6$~C$_{60}$ arylphosphanyl group, a C$_6$~C$_{60}$ mono or diarylphosphinyl group and a C$_6$~C$_{60}$ arylamine group; and the arylene group and the heteroarylene group of L$_1$ and L$_2$, and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of Ar$_2$ are each independently unsubstituted or substituted with one or more types of substituents selected from the group consisting of deuterium, halogen, a cyano group, a nitro group, a C$_1$~C$_{40}$ alkyl group, a C$_2$~C$_{40}$ alkenyl group, a C$_2$~C$_{40}$ alkynyl group, a C$_6$~C$_{60}$ aryl group, a heteroaryl group having 5 to 60 nuclear atoms, a C$_6$~C$_{60}$ aryloxy group, a C$_1$~C$_{40}$ alkyloxy group, a C$_6$~C$_{60}$ arylamine group, a C$_3$~C$_{40}$ cycloalkyl group, a heterocycloalkyl group having 3 to 40 nuclear atoms, a C$_1$~C$_{40}$ alkylsilyl group, a C$_1$~C$_{40}$ alkylboron group, a C$_6$~C$_{60}$ arylboron group, a C$_6$~C$_{60}$ arylphosphanyl group, a C$_6$~C$_{60}$ mono or diarylphosphinyl group and a C$_6$~C$_{60}$ arylsilyl group, and when substituted with a plurality of the substituents, these are the same as or different from each other.

Another embodiment of the present invention provides an organic electroluminescent device including an anode, a cathode, and one or more organic material layers provided between the anode and the cathode, wherein at least one of the one or more organic material layers includes the compound of Chemical Formula 1.

The "alkyl" in the present invention is a monovalent substituent derived from linear or branched saturated hydrocarbon having 1 to 40 carbon atoms. Examples thereof may include methyl, ethyl, propyl, isobutyl, sec-butyl, pentyl, iso-amyl, hexyl and the like, but are not limited thereto.

The "alkenyl" in the present invention is a monovalent substituent derived from linear or branched unsaturated hydrocarbon having one or more carbon-carbon double bonds and having 2 to 40 carbon atoms. Examples thereof may include vinyl, allyl, isopropenyl, 2-butenyl and the like, but are not limited thereto.

The "alkynyl" in the present invention is a monovalent substituent derived from linear or branched unsaturated hydrocarbon having one or more carbon-carbon triple bonds and having 2 to 40 carbon atoms. Examples thereof may include ethynyl, 2-propynyl and the like, but are not limited thereto.

The "aryl" in the present invention means a monovalent substituent derived from aromatic hydrocarbon having a single ring or two or more rings combined and having 6 to 60 carbon atoms. In addition, a monovalent substituent having two or more rings fused with each other, including only carbon (for example, the number of carbon atoms may be from 8 to 60) as a ring-forming atom, and with the whole molecule having non-aromaticity may also be included. Examples of such aryl may include phenyl, naphthyl, phenanthryl, anthryl, fluorenyl and the like, but are not limited thereto. The "heteroaryl" in the present invention means a monovalent substituent derived from monoheterocyclic or polyheterocyclic aromatic hydrocarbon having 5 to 60 nuclear atoms. Herein, one or more carbons, preferably 1 to 3 carbons, in the ring are substituted with a heteroatom selected from among N, O, P, S and Se. In addition, a monovalent group having two or more rings simply attached (pendant) or fused with each other, including a heteroatom selected from among N, O, P, S and Se as a ring-forming atom in addition to carbon, and with the whole molecule having non-aromaticity is interpreted to be included as well. Examples of such heteroaryl may include 6-membered monocyclic rings such as pyridyl, pyrazinyl, pyrimidinyl, pyridazinyl or triazinyl; polycyclic rings such as phenoxathienyl, indolizinyl, indolyl, purinyl, quinolyl, benzothiazole or carbazolyl; 2-furanyl, N-imidazolyl, 2-isoxazolyl, 2-pyridinyl, 2-pyrimidinyl and the like, but are not limited thereto.

The "aryloxy" in the present invention is a monovalent substituent represented by RO—, and R means aryl having 5 to 60 carbon atoms. Examples of such aryloxy may include phenyloxy, naphthyloxy, diphenyloxy and the like, but are not limited thereto.

The "alkyloxy" in the present invention is a monovalent substituent represented by R'O—, and R' means alkyl having 1 to 40 carbon atoms and is interpreted to include a linear, branched or cyclic structure. Examples of such alkyloxy may include methoxy, ethoxy, n-propoxy, 1-propoxy, t-butoxy, n-butoxy, pentoxy and the like, but are not limited thereto.

The "arylamine" in the present invention means amine substituted with aryl having 6 to 60 carbon atoms.

The "cycloalkyl" in the present invention means a monovalent substituent derived from monocyclic or polycyclic non-aromatic hydrocarbon having 3 to 40 carbon atoms. Examples of such cycloalkyl may include cyclopropyl, cyclopentyl, cyclohexyl, norbornyl, adamantine and the like, but are not limited thereto.

The "heterocycloalkyl" in the present invention means a monovalent substituent derived from non-aromatic hydrocarbon having 3 to 40 nuclear atoms, and one or more carbons, preferably 1 to 3 carbons, in the ring are substituted with a heteroatom such as N, O, S or Se. Examples of such heterocycloalkyl may include morpholine, piperazine and the like, but are not limited thereto.

The "alkylsilyl" in the present invention means silyl substituted with alkyl having 1 to 40 carbon atoms, and the "arylsilyl" means silyl substituted with aryl having 5 to 60 carbon atoms.

The "fused ring" in the present invention means a fused aliphatic ring, a fused aromatic ring, a fused heteroaliphatic ring, a fused heteroaromatic ring, or a combined form thereof.

Advantageous Effects

A compound of the present invention has excellent thermal stability, carrier transport ability, light emitting ability and the like, and therefore, is useful as a material of an organic material layer of an organic electroluminescent device.

In addition, an organic electroluminescent device including a compound of the present invention in an organic material layer exhibits greatly enhanced properties in terms of light emitting performance, driving voltage, lifetime, efficiency and the like, and can be effectively used in a full color display panel and the like.

DESCRIPTION OF DRAWINGS

FIG. 1 is a sectional diagram illustrating an organic electroluminescent device according to one embodiment of the present invention.

FIG. 2 is a sectional diagram illustrating an organic electroluminescent device according to one embodiment of the present invention.

MODE FOR DISCLOSURE

Hereinafter, the present invention will be described in detail.

1. Novel Organic Compound

A novel compound of the present invention may be represented by the following Chemical Formula 1:

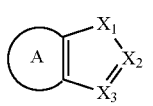

[Chemical Formula 1]

in Chemical Formula 1, $X_1$ is selected from the group consisting of S, O, $N(R_1)$ and $C(R_2)(R_3)$;

$X_2$ and $X_3$ are each independently N or $C(Ar_1)$, and at least one thereof is $C(Ar_1)$; and ring A is represented by any one of the following Chemical Formulae 2 to 4;

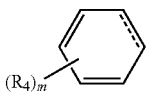

[Chemical Formula 2]

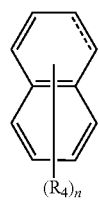

[Chemical Formula 3]

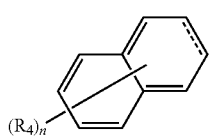

[Chemical Formula 4]

in Chemical Formulae 1 to 4, a dotted line means a part that is fused;

m is an integer of 0 to 4;

n is an integer of 0 to 6;

$R_1$ to $R_4$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylamine group;

the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of $R_1$ to $R_4$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylsilyl group, and when substituted with a plurality of the substituents, these are the same as or different from each other; and $Ar_1$ is a substituent represented by the following Chemical Formula 5, and when $Ar_1$ is present in plural numbers, these are the same as or different from each other;

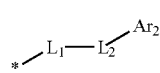

[Chemical Formula 5]

in Chemical Formula 5,

* means a part where a bond is formed;

$L_1$ and $L_2$ are each independently selected from the group consisting of a direct bond, a $C_6$~$C_{18}$ arylene group and a heteroarylene group having 5 to 18 nuclear atoms;

$Ar_2$ is selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylamine group; and the arylene group and the heteroarylene group of $L_1$ and $L_2$, and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of $Ar_2$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2\sim C_{40}$ alkynyl group, a $C_6\sim C_{60}$ aryl group, a heteroaryl group having 5 to 60 nuclear atoms, a $C_6\sim C_{60}$ aryloxy group, a $C_1\sim C_{40}$ alkyloxy group, a $C_6\sim C_{60}$ arylamine group, a $C_3\sim C_{40}$ cycloalkyl group, a heterocycloalkyl group having 3 to 40 nuclear atoms, a $C_1\sim C_{40}$ alkylsilyl group, a $C_1\sim C_{40}$ alkylboron group, a $C_6\sim C_{60}$ arylboron group, a $C_6\sim C_{60}$ arylphosphanyl group, a $C_6\sim C_{60}$ mono or diarylphosphinyl group and a $C_6\sim C_{60}$ arylsilyl group, and when substituted with a plurality of the substituents, these are the same as or different from each other.

More specifically, the compound represented by Chemical Formula 1 of the present invention has an EWG bonding to a 5-membered aromatic ring or a 5-membered aromatic heterring such as indole, indazole, indene, benzofuran, benzothiophene or triazolo, and may be used as a host material since, by having a similar energy level with carbazole, the energy level may be adjusted to be higher than a dopant energy level. Particularly, benzofuran and benzothiophene moieties are electron abundant, and when used as an electron transport layer material of an organic electroluminescent device, mobility increases, and as a result, an increase in the luminous efficiency and a decrease in the driving voltage may be expected. In addition, the 5-membered aromatic ring or the 5-membered aromatic heterring of the present invention has a smaller molecular weight compared to existing compounds, and therefore, may be deposited at a relatively lower deposition temperature when deposited compared to other materials, and favorable processability and enhanced thermal stability may be obtained.

Accordingly, the compound represented by Chemical Formula 1 of the present invention may be used as a material of an organic material layer of an organic electroluminescent device, and may be preferably used as a light emitting layer material (green phosphorescent host material), an electron transport layer/injection layer material, a light emitting auxiliary layer material or an electron transport auxiliary layer material, and more preferably as a light emitting layer material, an electron transport layer material or an electron transport auxiliary layer material. In addition, the organic electroluminescent device including the compound of Chemical Formula 1 may have performance and lifetime properties greatly enhanced, and a full color organic light emitting panel using such an organic electroluminescent device may have its performance maximized.

According to preferred one embodiment of the present invention, the compound may be represented by any one of the following Chemical Formulae 6 to 14:

[Chemical Formula 6]
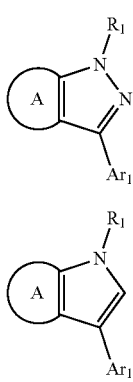

[Chemical Formula 7]
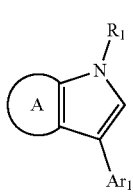

[Chemical Formula 8]
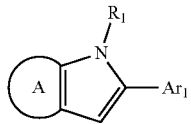

[Chemical Formula 9]
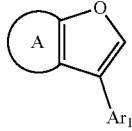

[Chemical Formula 10]
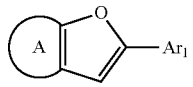

[Chemical Formula 11]
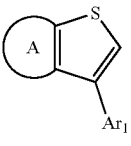

[Chemical Formula 12]
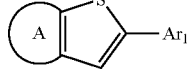

[Chemical Formula 13]
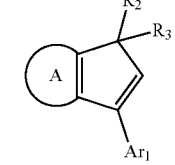

[Chemical Formula 14]
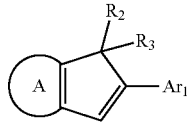

in Chemical Formulae 6 to 14,
ring A, $Ar_1$ and $R_1$ to $R_3$ each have the same definitions as in Chemical Formula 1.

According to preferred one embodiment of the present invention, the compound is preferably represented by any one of Chemical Formulae 6 to 8 in terms of securing low driving voltage and high luminous efficiency, and may be more preferably represented by Chemical Formula 6 or 7, and even more preferably represented by Chemical Formula 8 or 10.

According to preferred one embodiment of the present invention, $R_1$ to $R_4$ are each independently selected from the group consisting of a $C_1\sim C_{40}$ alkyl group, a $C_6\sim C_{60}$ aryl group and a heteroaryl group having 5 to 60 nuclear atoms, and the alkyl group, the aryl group and the heteroaryl group of $R_1$ to $R_4$ are each independently unsubstituted or substituted with one or more types of substituents selected from the group consisting of a $C_1\sim C_{40}$ alkyl group, a $C_6\sim C_{60}$ aryl group and a heteroaryl group having 5 to 60 nuclear atoms, and when substituted with a plurality of the substituents, these may be the same as or different from each other.

According to preferred one embodiment of the present invention, $R_1$ to $R_4$ are each independently selected from the group consisting of a methyl group, an ethyl group, a propyl group, a butyl group, a pentyl group, a phenyl group, a biphenyl group, a terphenyl group, a naphthalenyl group, a pyridinyl group, a pyrimidinyl group, a triazinyl group, a dibenzofuranyl group, a dibenzothiophenyl group, a carbazolyl group, a fluorenyl group, a spirofluorenyl group and a dibenzodioxynyl group, and the methyl group, the ethyl group, the propyl group, the butyl group, the pentyl group, the phenyl group, the biphenyl group, the terphenyl group, the naphthalenyl group, the pyridinyl group, the pyrimidinyl group, the triazinyl group, the dibenzofuranyl group, the dibenzothiophenyl group, the carbazolyl group, the fluorenyl group, the spirofluorenyl group and the dibenzodioxynyl group of $R_1$ to $R_4$ are each independently unsubstituted or substituted with one or more types of substituents selected from the group consisting of a $C_1 \sim C_{40}$ alkyl group, a $C_6 \sim C_{60}$ alylamine group, a $C_6$-$C_{60}$ aryl group and a heteroaryl group having 5 to 60 nuclear atoms, and when substituted with a plurality of the substituents, these may be the same as or different from each other.

According to preferred one embodiment of the present invention, $L_1$ and $L_2$ are each independently a direct bond, or a linker represented by any one of the following Chemical Formulae A-1 to A-7, but are not limited thereto:

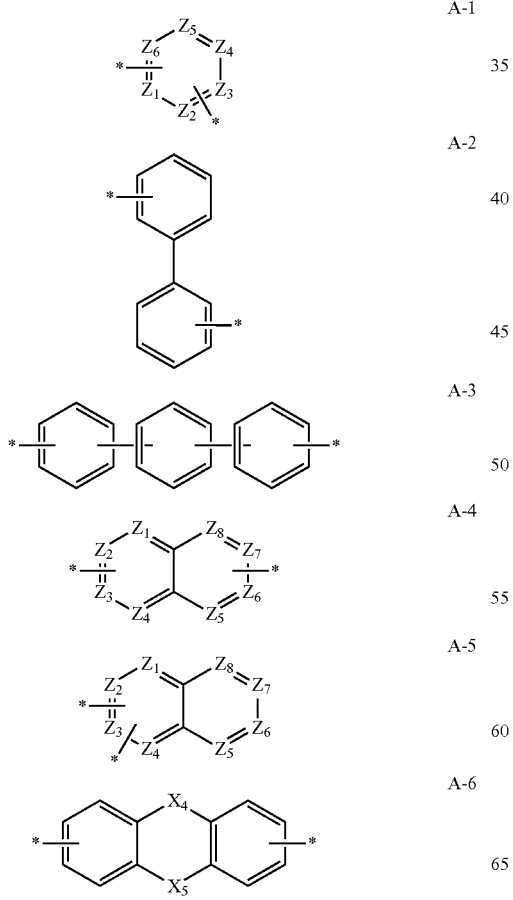

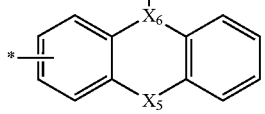

in Chemical Formulae A-1 to A-7,

* means a part where a bond is formed;

$Z_1$ to $Z_8$ are each independently N or $C(R_5)$;

any two of $Z_1$ to $Z_6$ forming a bond as a linker in Chemical Formula A-1 are $C(R_5)$, and herein, $R_5$ is not present;

any one of $Z_1$ to $Z_4$ and any one of $Z_5$ to $Z_8$ forming a bond as a linker in Chemical Formula A-4 are $C(R_5)$, and herein, $R_5$ is not present;

any two of $Z_1$ to $Z_4$ forming a bond as a linker in Chemical Formula A-5 are $C(R_5)$, and herein, $R_5$ is not present;

$X_4$ and $X_5$ are each independently O, S, $N(R_6)$ or $C(R_7)(R_8)$;

$X_6$ is N or $C(R_9)$;

$R_5$ to $R_9$ are each independently selected from the group consisting of hydrogen, deuterium, halogen, a cyano group, a nitro group, a $C_1 \sim C_{40}$ alkyl group, a $C_2 \sim C_{40}$ alkenyl group, a $C_2 \sim C_{40}$ alkynyl group, a $C_3 \sim C_{40}$ cycloalkyl group, a heterocycloalkyl group having 3 to 40 nuclear atoms, a $C_6 \sim C_{60}$ aryl group, a heteroaryl group having 5 to 60 nuclear atoms, a $C_1 \sim C_{40}$ alkyloxy group, a $C_6 \sim C_{60}$ aryloxy group, a $C_3 \sim C_{40}$ alkylsilyl group, a $C_6 \sim C_{60}$ arylsilyl group, a $C_1 \sim C_{40}$ alkylboron group, a $C_6 \sim C_{60}$ arylboron group, a $C_6 \sim C_{60}$ arylphosphanyl group, a $C_6 \sim C_{60}$ mono or diarylphosphinyl group and a $C_6 \sim C_{60}$ arylamine group, or adjacent groups bond to form a fused ring, and when $R_5$ to $R_8$ are each present in plural numbers, these are the same as or different from each other; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of $R_5$ to $R_9$ are each independently unsubstituted or substituted with one or more types of substituents selected from the group consisting of deuterium, halogen, a cyano group, a nitro group, a $C_1 \sim C_{40}$ alkyl group, a $C_2 \sim C_{40}$ alkenyl group, a $C_2 \sim C_{40}$ alkynyl group, a $C_6 \sim C_{60}$ aryl group, a heteroaryl group having 5 to 60 nuclear atoms, a $C_6 \sim C_{60}$ aryloxy group, a $C_1 \sim C_{40}$ alkyloxy group, a $C_6 \sim C_{60}$ arylamine group, a $C_3 \sim C_{40}$ cycloalkyl group, a heterocycloalkyl group having 3 to 40 nuclear atoms, a $C_1 \sim C_{40}$ alkylsilyl group, a $C_1 \sim C_{40}$ alkylboron group, a $C_6 \sim C_{60}$ arylboron group, a $C_6 \sim C_{60}$ arylphosphanyl group, a $C_6 \sim C_{60}$ mono or diarylphosphinyl group and a $C_6 \sim C_{60}$ arylsilyl group, and when substituted with a plurality of the substituents, these are the same as or different from each other.

According to preferred one embodiment of the present invention, $L_1$ and $L_2$ are each independently a direct bond, or a linker represented by any one of the following Chemical Formulae B-1 to B-12, but are not limited thereto:

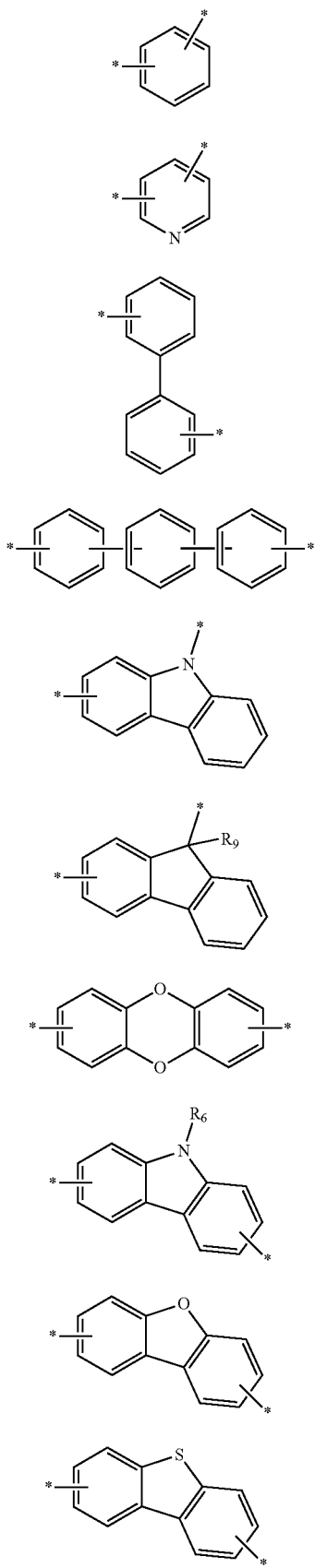

in Chemical Formulae B-1 to B-12,

\* means a part where a bond is formed;

$R_6$ to $R_9$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylamine group; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of $R_6$ to $R_9$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylsilyl group, and when substituted with a plurality of the substituents, these are the same as or different from each other.

According to preferred one embodiment of the present invention, in Chemical Formulae B-1 to B-12, $R_6$ to $R_9$ are each independently selected from the group consisting of hydrogen, a $C_1$~$C_{40}$ alkyl group, a $C_6$~$C_{60}$ aryl group and a heteroaryl group having 5 to 60 nuclear atoms; and the alkyl group, the aryl group and the heteroaryl group of $R_6$ to $R_9$ are each independently unsubstituted or substituted with one or more types of substituents selected from the group consisting of a $C_1$~$C_{40}$ alkyl group, a $C_2$~$C_{40}$ alkenyl group, a $C_2$~$C_{40}$ alkynyl group, a $C_6$~$C_{60}$ aryl group and a heteroaryl group having 5 to 60 nuclear atoms, and when substituted with a plurality of the substituents, these are the same as or different from each other.

According to preferred one embodiment of the present invention, $L_1$ and $L_2$ are each independently a direct bond, or may be a linker selected from the group consisting of Chemical Formulae B-1 to B-3 and B-7 to B-12.

According to preferred one embodiment of the present invention, $Ar_2$ is a $C_6$~$C_{60}$ aryl group, a heteroaryl group having 5 to 60 nuclear atoms, or an mylamine group, and the aryl group, the heteroaryl group and the mylamine group of $Ar_2$ are each independently unsubstituted or substituted with one or more types of substituents selected from the group consisting of a $C_1$~$C_{40}$ alkyl group, a $C_6$~$C_{60}$ mylamine group, a $C_6$~$C_{60}$ aryl group and a heteroaryl group having 5 to 60 nuclear atoms, and when substituted with a plurality of the substituents, these may be the same as or different from each other.

According to preferred one embodiment of the present invention, $Ar_2$ may be a substituent represented by the following Chemical Formula 15:

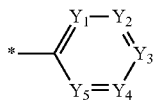

[Chemical Formula 15]

in Chemical Formula 15,
* means a part where a bond is formed;
$Y_1$ to $Y_5$ are each independently N or $C(R_{10})$;
$R_{10}$ is selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylamine group, and when $R_{10}$ is present in plural numbers, these are the same as or different from each other; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of $R_{10}$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylsilyl group, and when substituted with a plurality of the substituents, these are the same as or different from each other.

According to preferred one embodiment of the present invention, the substituent represented by Chemical Formula 15 may be a substituent represented by the following Chemical Formula 16:

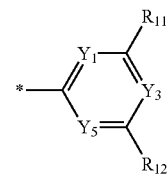

[Chemical Formula 16]

in Chemical Formula 16,
* means a part where a bond is formed;
$R_{11}$ and $R_{12}$ are each independently selected form the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylamine group, or bond to adjacent groups to form a fused ring;

the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of $R_{11}$ and $R_{12}$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylsilyl group, and when substituted with a plurality of the substituents, these are the same as or different from each other; and $Y_1$, $Y_3$ and $Y_5$ each have the same definitions as in Chemical Formula 15.

According to preferred one embodiment of the present invention, the substituent represented by Chemical Formula 15 may be a substituent represented by any one of the following Chemical Formulae C-1 to C-5:

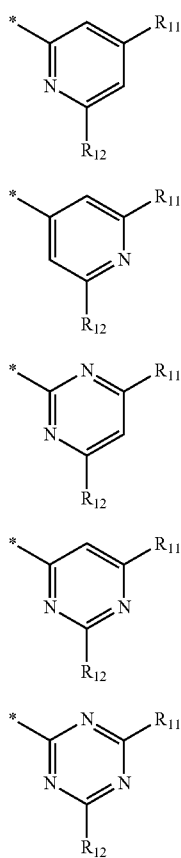

in Chemical Formulae C-1 to C-5,
* means a part where a bond is formed,
$R_{11}$ and $R_{12}$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylamine group, or bond to adjacent groups to form a fused ring; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of $R_{11}$ and $R_{12}$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylsilyl group, and when substituted with a plurality of the substituents, these are the same as or different from each other.

According to preferred one embodiment of the present invention, $R_{11}$ and $R_{12}$ are each independently selected from the group consisting of a $C_1$~$C_{40}$ alkyl group, a $C_6$~$C_{60}$ aryl group and a heteroaryl group having 5 to 60 nuclear atoms, and the alkyl group, the aryl group and the heteroaryl group of $R_{11}$ and $R_{12}$ are each independently unsubstituted or substituted with one or more types of substituents selected from the group consisting of a $C_1$~$C_{40}$ alkyl group, a $C_6$~$C_{60}$ aryl group and a heteroaryl group having 5 to 60 nuclear atoms, and when substituted with a plurality of the substituents, these are the same as or different from each other.

According to preferred one embodiment of the present invention, $R_{11}$ and $R_{12}$ are each independently selected from the group consisting of a phenyl group, a biphenyl group, a pyridinyl group, a pyrimidinyl group, a dibenzofuranyl group, a carbazolyl group, a fluorenyl group and a dibenzothiophenyl group, and the phenyl group, the biphenyl group, the pyridinyl group, the pyrimidinyl group, the dibenzofuranyl group, the carbazolyl group, the fluorenyl group and the dibenzothiophenyl group of $R_{11}$ and $R_{12}$ are each independently unsubstituted or substituted with one or more types of substituents selected from the group consisting of a $C_1$~$C_{40}$ alkyl group, a $C_6$~$C_{60}$ aryl group and a heteroaryl group having 5 to 60 nuclear atoms, and when substituted with a plurality of the substituents, these are the same as or different from each other.

According to preferred one embodiment of the present invention, $R_{11}$ and $R_{12}$ are each independently selected from the group consisting of a phenyl group, a biphenyl group, a pyridinyl group, a pyrimidinyl group, a dibenzofuranyl group, a carbazolyl group, a fluorenyl group and a dibenzothiophenyl group, and the phenyl group, the biphenyl group, the pyridinyl group, the pyrimidinyl group, the dibenzofuranyl group, the carbazolyl group, the fluorenyl group and the dibenzothiophenyl group of $R_{11}$ and $R_{12}$ are each independently unsubstituted or substituted with one or more types of substituents selected from the group consisting of a methyl group, an ethyl group, a propanyl group, a butyl group, a phenyl group, a biphenyl group, a pyridinyl group, a pyrimidinyl group, a dibenzofuranyl group, a carbazolyl group, a fluorenyl group and a dibenzothiophenyl group, and when substituted with a plurality of the substituents, these are the same as or different from each other.

According to preferred one embodiment of the present invention, $Ar_2$ may be a substituent represented by the following Chemical Formula 17:

[Chemical Formula 17]

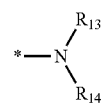

in Chemical Formula 17,
* means a part where a bond is formed;
$R_{13}$ and $R_{14}$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylamine group, or bond to adjacent groups to form a fused ring; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of $R_{13}$ and $R_{14}$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylsilyl group, and when substituted with a plurality of the substituents, these are the same as or different from each other.

According to preferred one embodiment of the present invention, $R_{13}$ and $R_{14}$ are each independently selected from the group consisting of a $C_1$~$C_{40}$ alkyl group, a $C_6$~$C_{60}$ aryl group and a heteroaryl group having 5 to 60 nuclear atoms, and the alkyl group, the aryl group and the heteroaryl group of $R_{13}$ and $R_{14}$ are each independently unsubstituted or substituted with one or more types of substituents selected from the group consisting of a $C_1$~$C_{40}$ alkyl group, a $C_6$~$C_{60}$ aryl group and a heteroaryl group having 5 to 60 nuclear atoms, and when substituted with a plurality of the substituents, these are the same as or different from each other.

According to preferred one embodiment of the present invention, $R_{13}$ and $R_{14}$ are each independently selected from the group consisting of a phenyl group, a biphenyl group, a pyridinyl group, a pyrimidinyl group, a dibenzofuranyl group, a carbazolyl group, a fluorenyl group and a dibenzothiophenyl group, and the phenyl group, the biphenyl group, the pyridinyl group, the pyrimidinyl group, the dibenzofuranyl group, the carbazolyl group, the fluorenyl group and the dibenzothiophenyl group of $R_{13}$ and $R_{14}$ are each independently unsubstituted or substituted with one or more types of substituents selected from the group consisting of a $C_1$~$C_{40}$ alkyl group, a $C_6$~$C_{60}$ aryl group and a heteroaryl group having 5 to 60 nuclear atoms, and when substituted with a plurality of the substituents, these are the same as or different from each other.

According to preferred one embodiment of the present invention, $R_{13}$ and $R_{14}$ are each independently selected from the group consisting of a phenyl group, a biphenyl group, a pyridinyl group, a pyrimidinyl group, a dibenzofuranyl group, a carbazolyl group, a fluorenyl group and a dibenzothiophenyl group, and the phenyl group, the biphenyl group, the pyridinyl group, the pyrimidinyl group, the dibenzofuranyl group, the carbazolyl group, the fluorenyl group and the dibenzothiophenyl group of $R_{13}$ and $R_{14}$ are each independently unsubstituted or substituted with one or more types of substituents selected from the group consisting of a methyl group, an ethyl group, a propanyl group, a butyl group, a phenyl group, a biphenyl group, a pyridinyl group, a pyrimidinyl group, a dibenzofuranyl group, a carbazolyl group, a fluorenyl group and a dibenzothiophenyl group, and when substituted with a plurality of the substituents, these are the same as or different from each other.

The compound represented by Chemical Formula 1 of the present invention may be represented by the following compounds, but is not limited thereto:

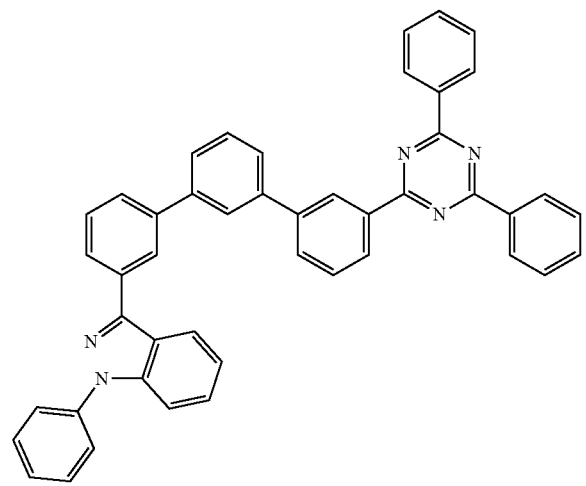

R1

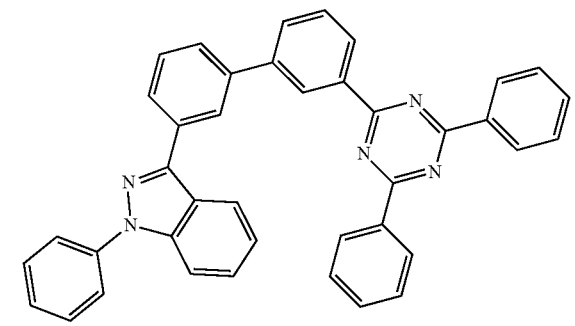

R2

R3
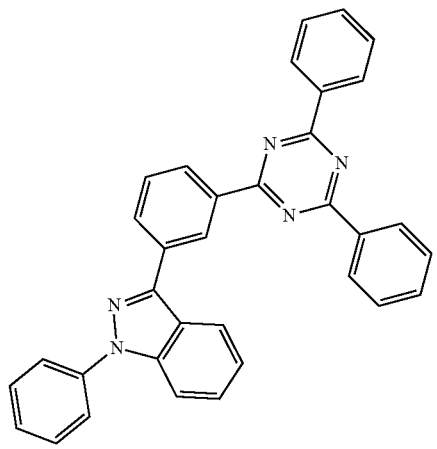
R4
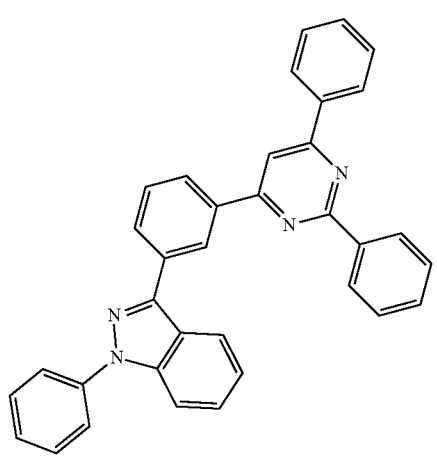
R5
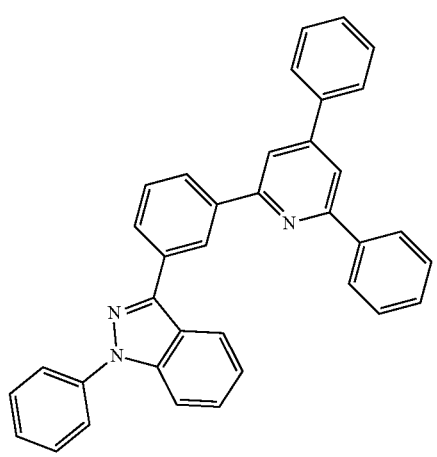
R6
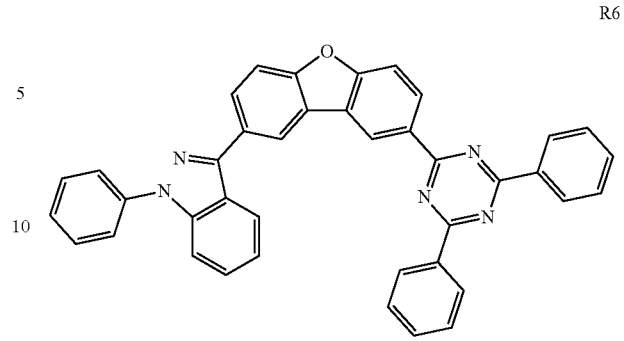
R7
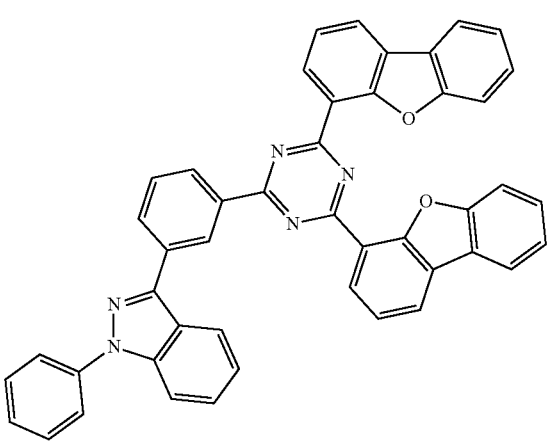
R8
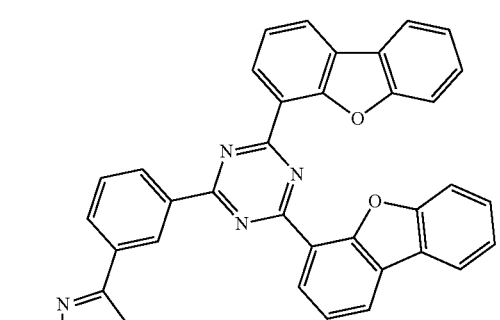
R9
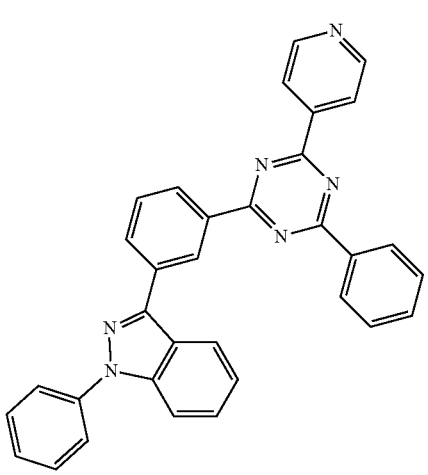

R10
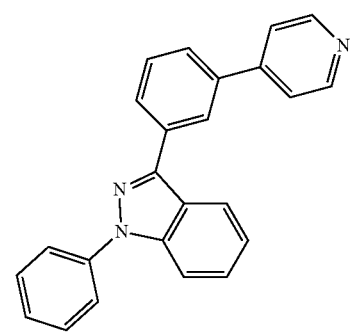
R11
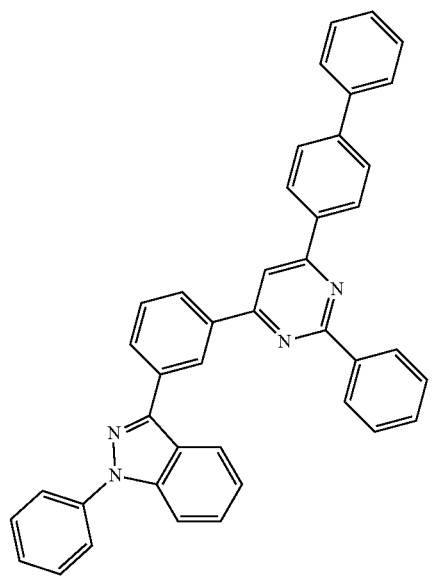
R12
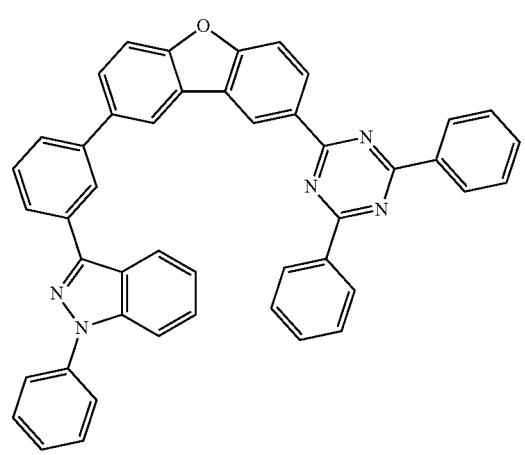
R13
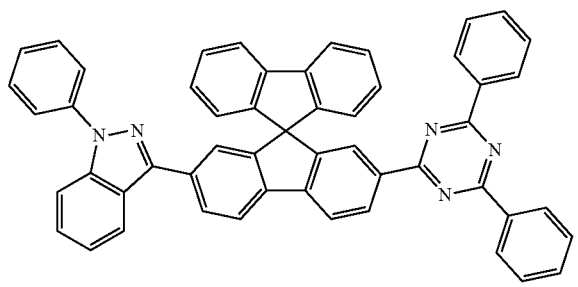
R14
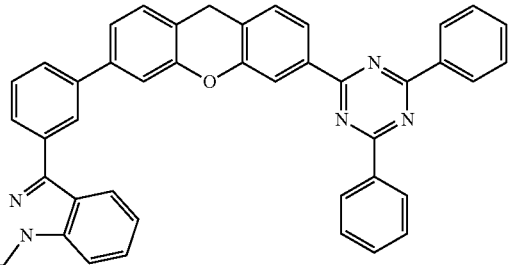
R15
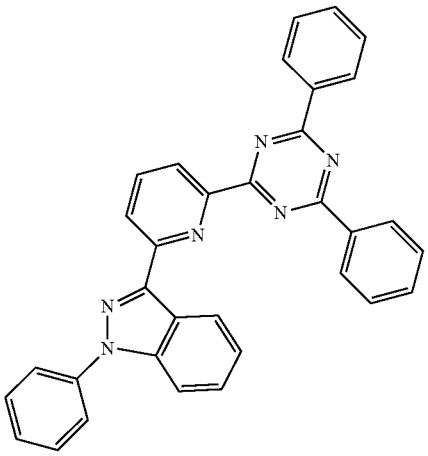
R16

25
-continued
R17
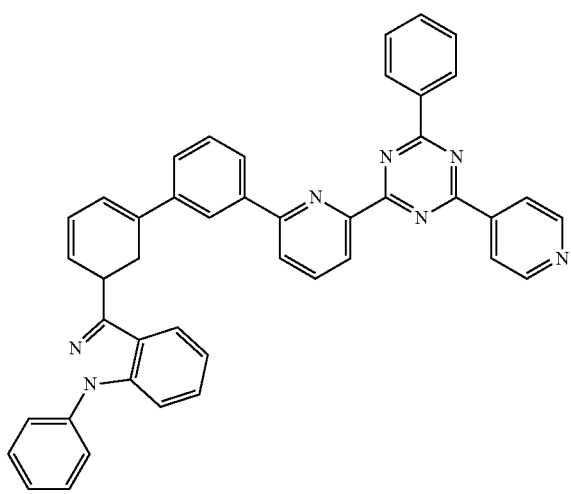
R18
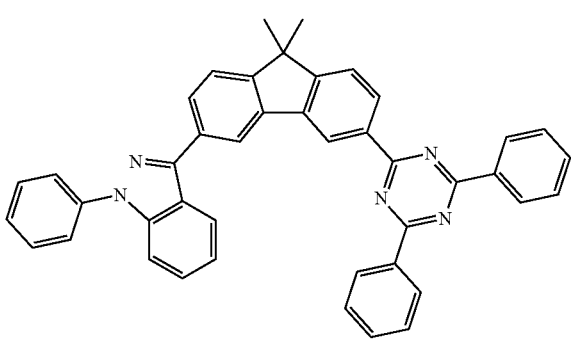
R19
26
-continued
R20
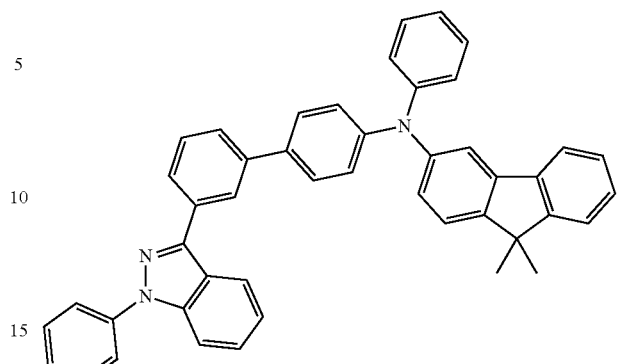
R21
R22
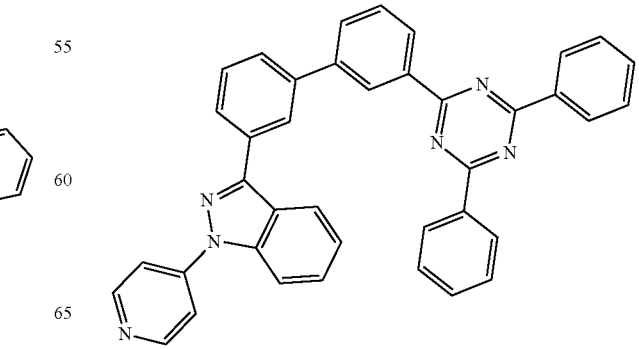

R23
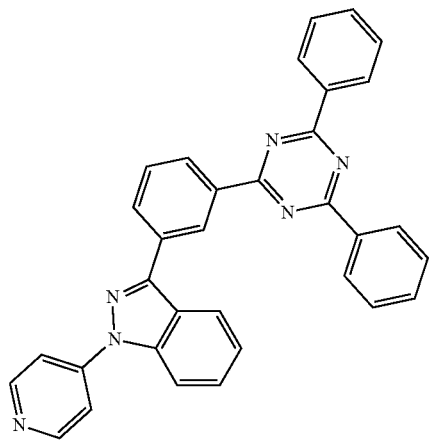
R24
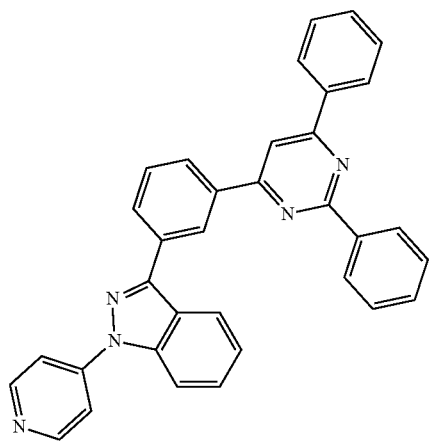
R25
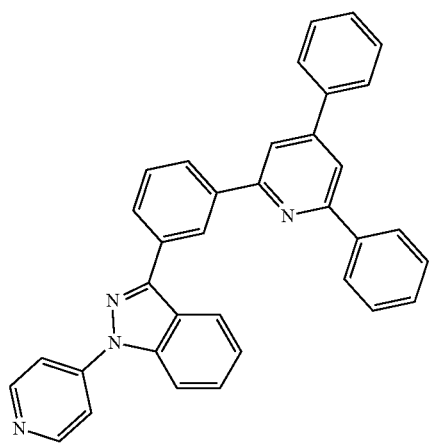
R26
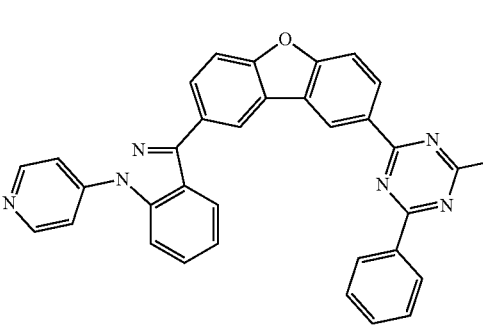
R27
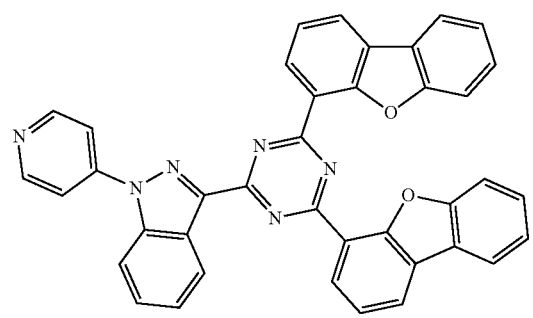
R28
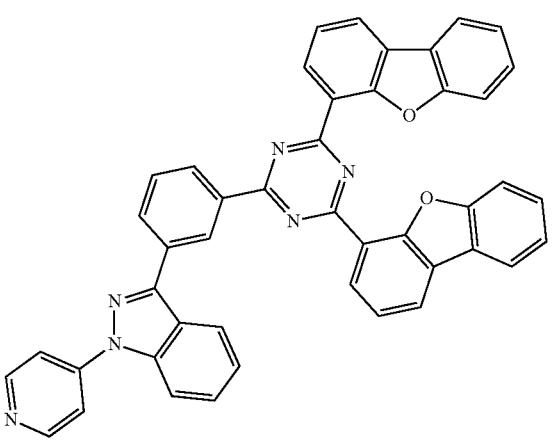
R29
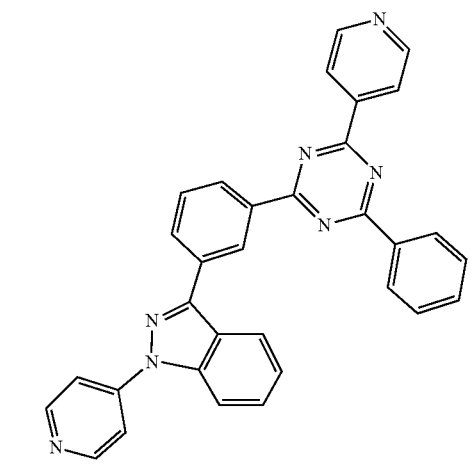
R30
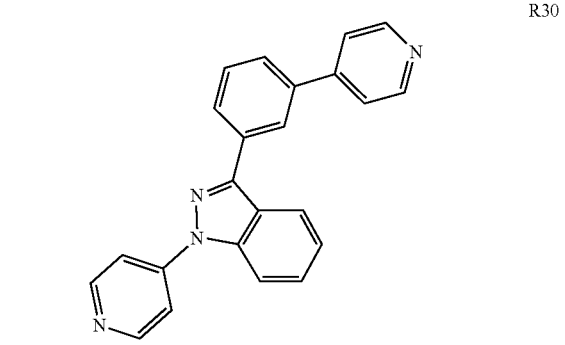

-continued
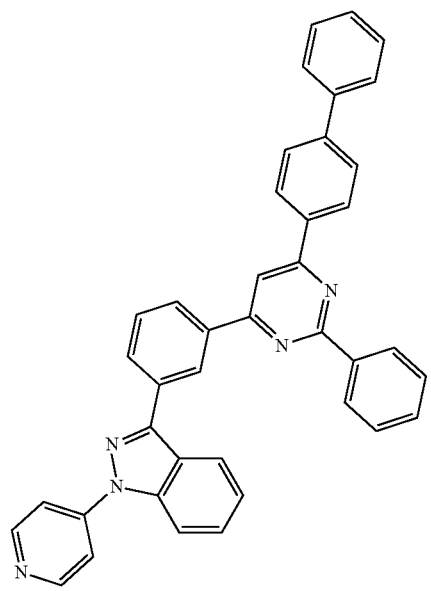
R31
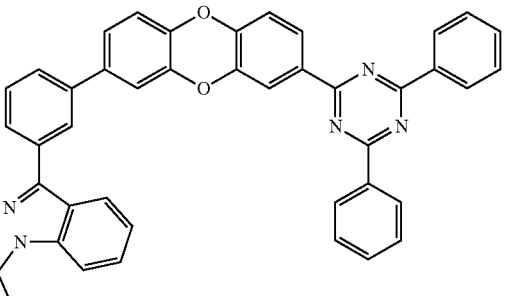
R35
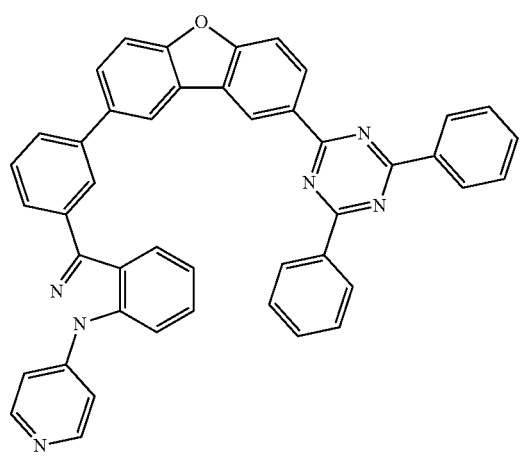
R32
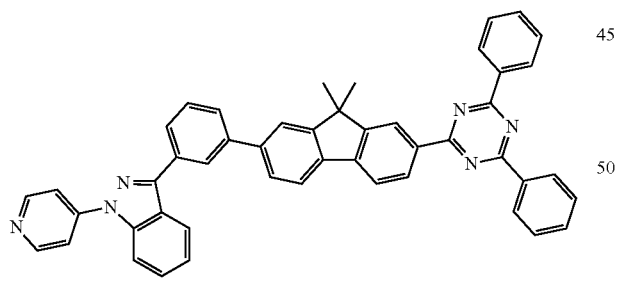
R33
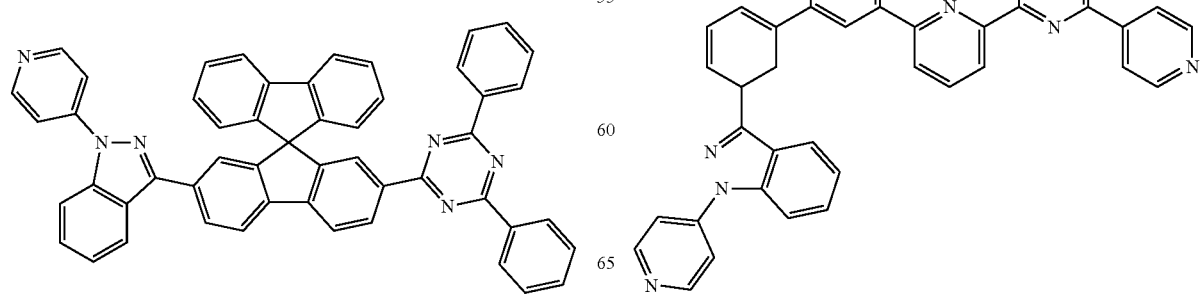

R38
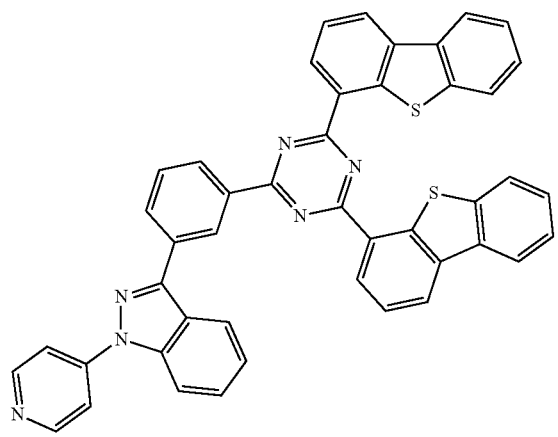
R39
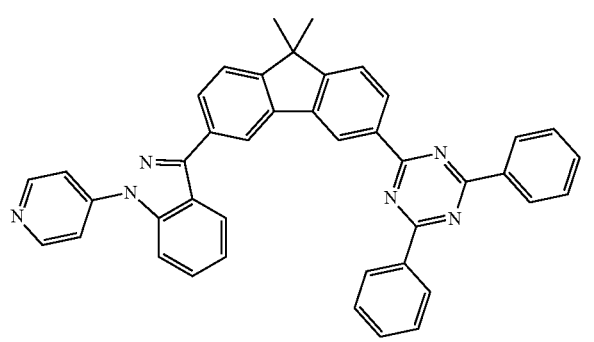
R40
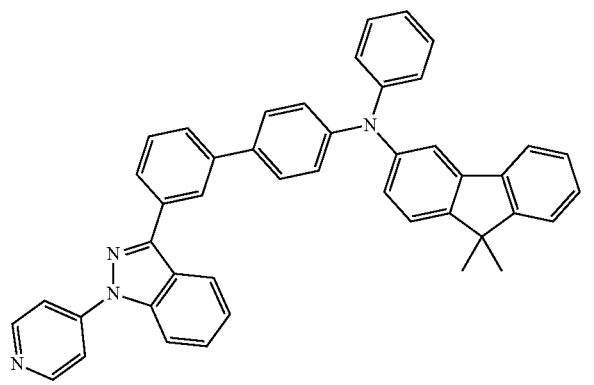
R41
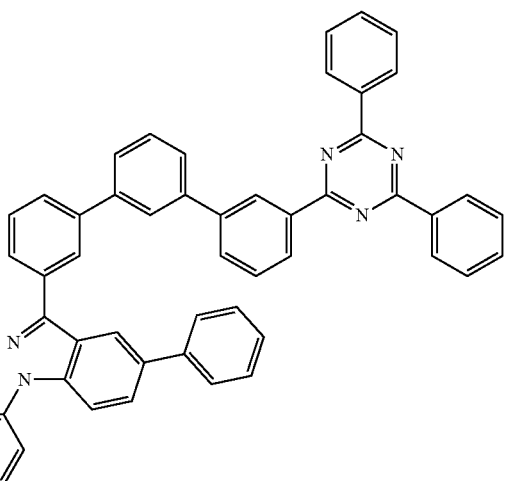
R42
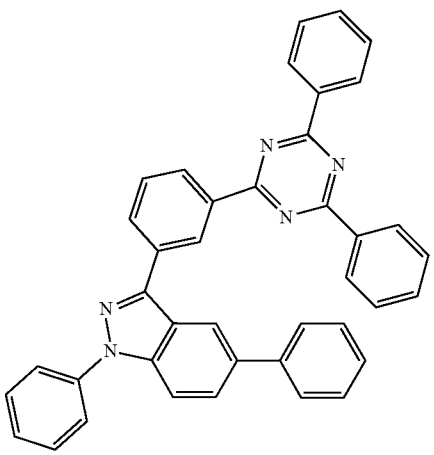
R43

R44
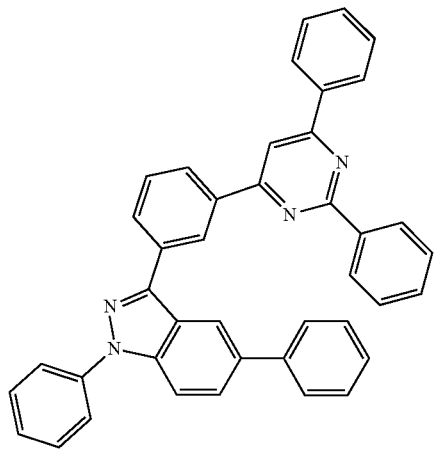
R45
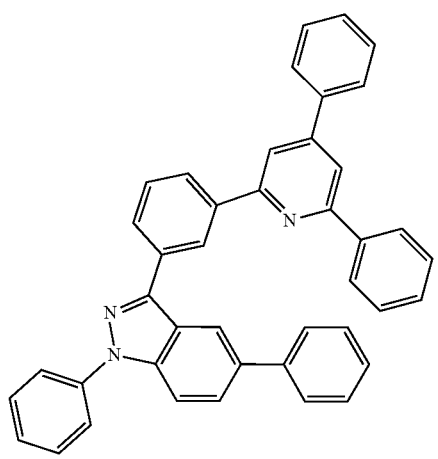
R46
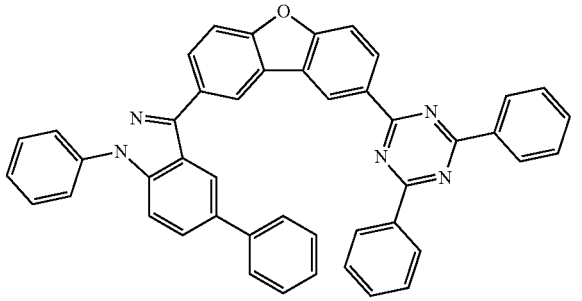
R47
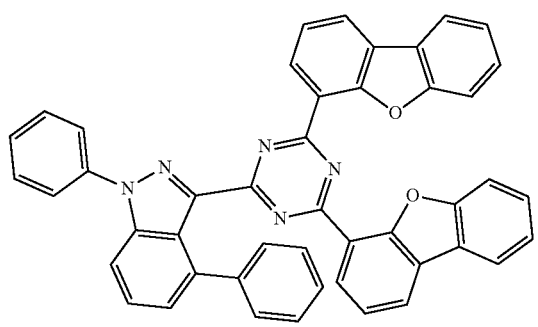
R48
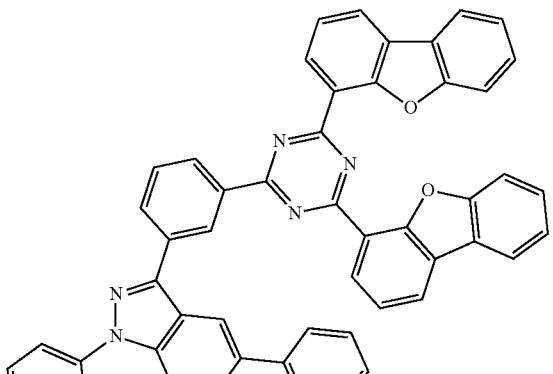
R49
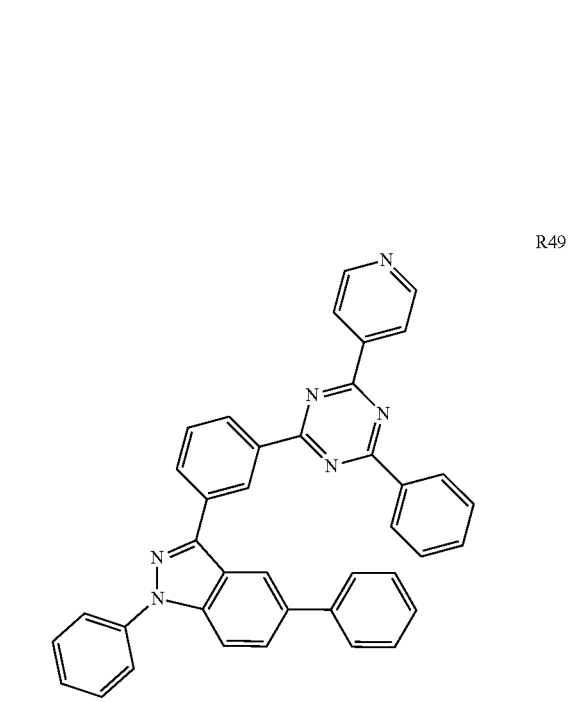
R50
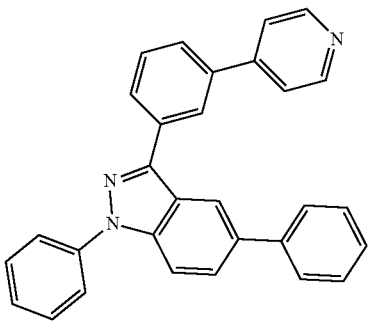

R51
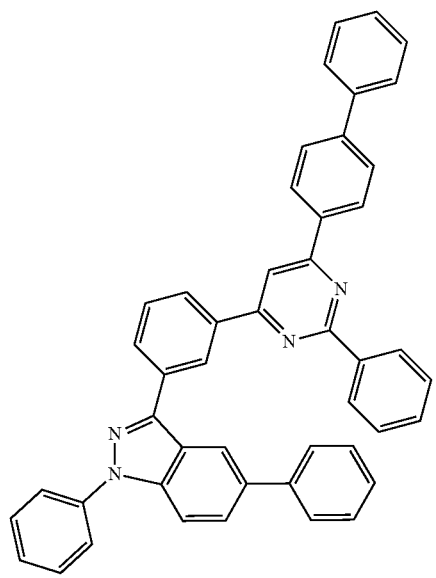
R54
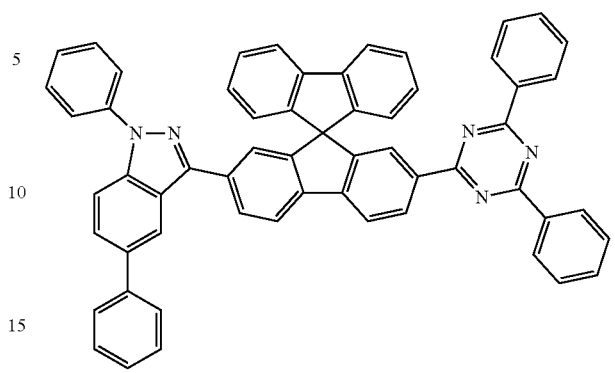
R52
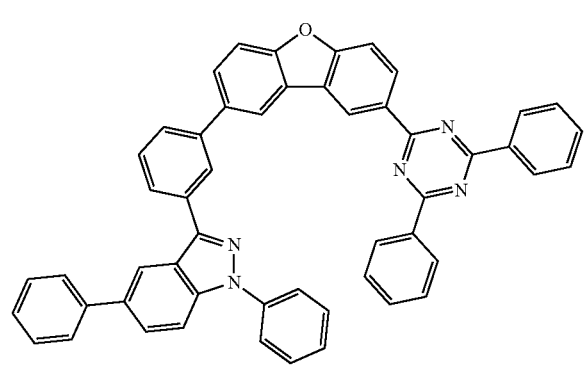
R55
R53
R56
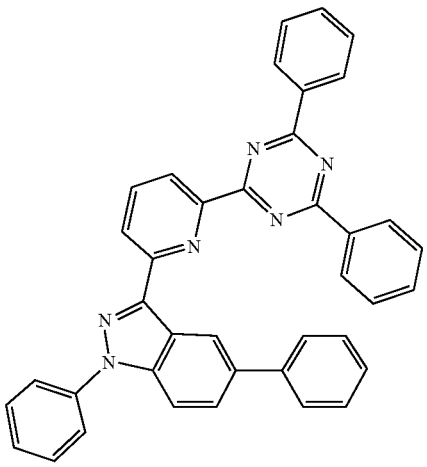

R57
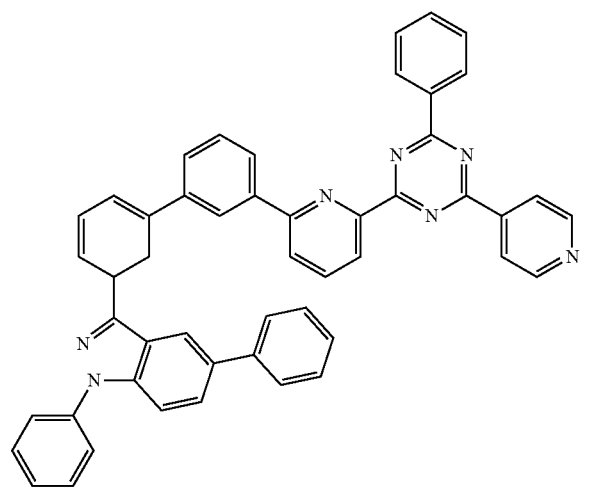
R60
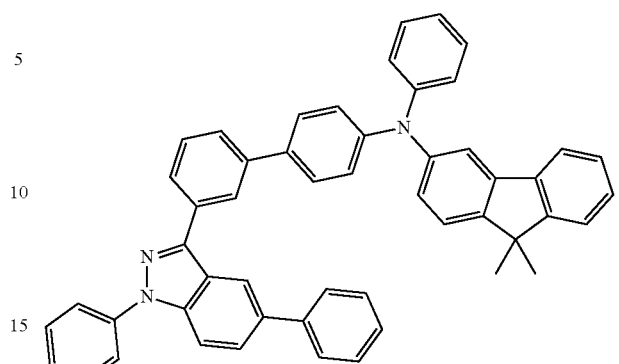
R58
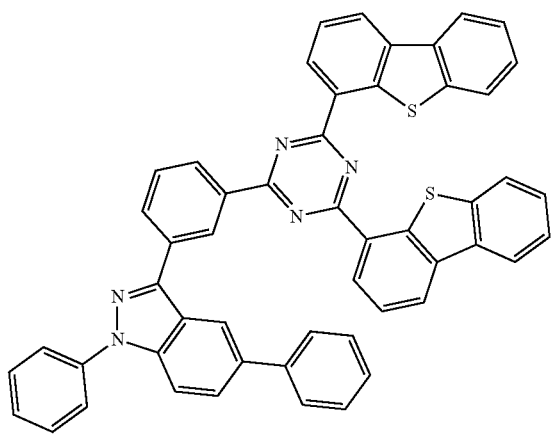
R61
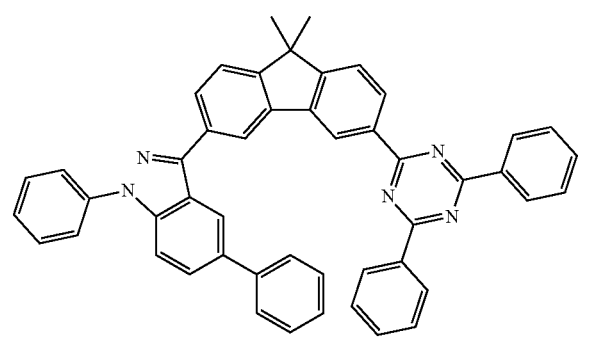
R59
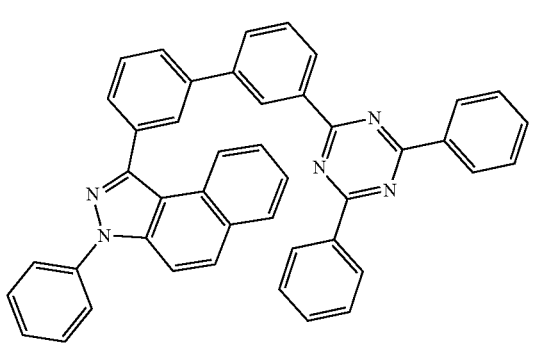
R62

R63
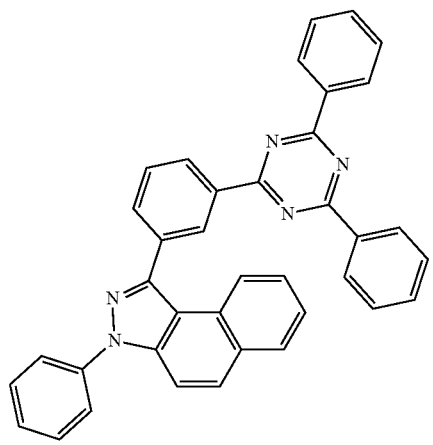
R64
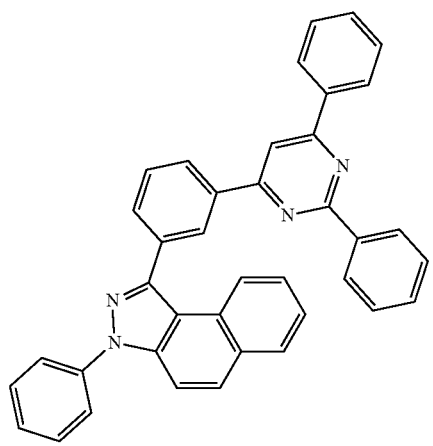
R65
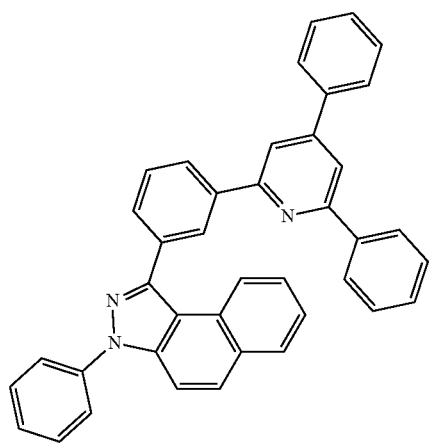
R66
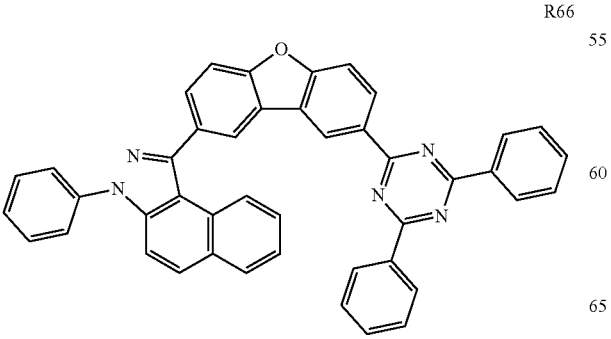
R67
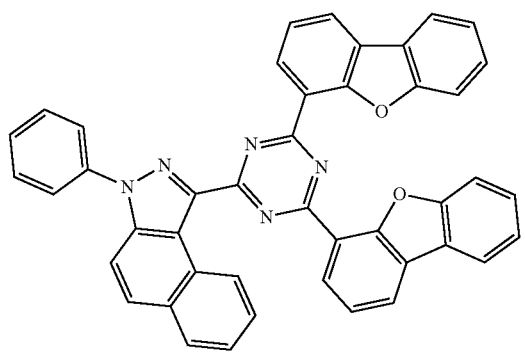
R68
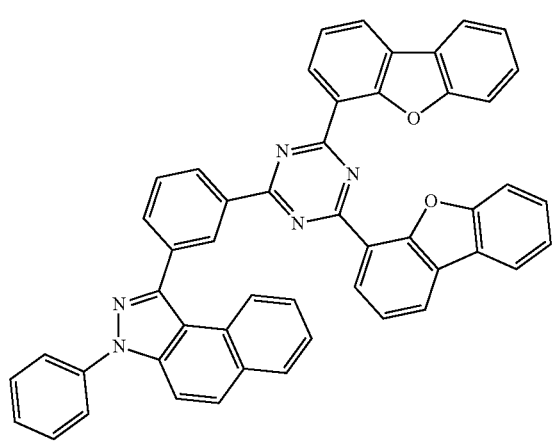
R69
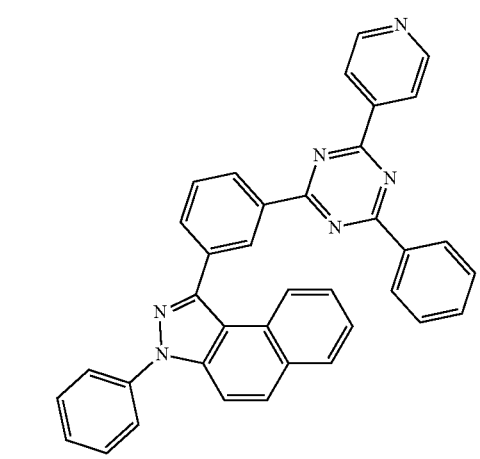
R70
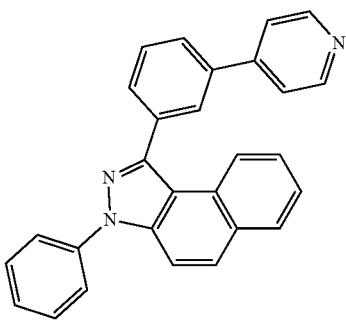

-continued
R71
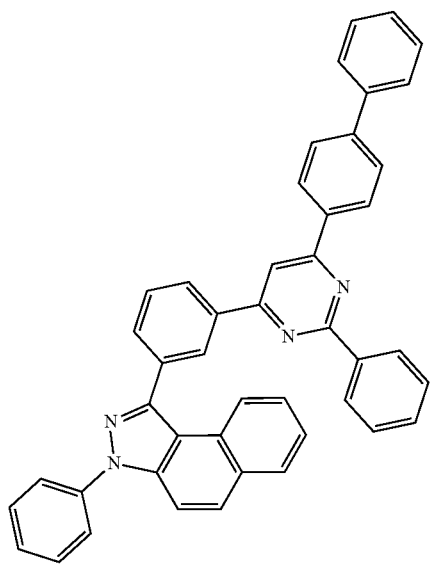
R72
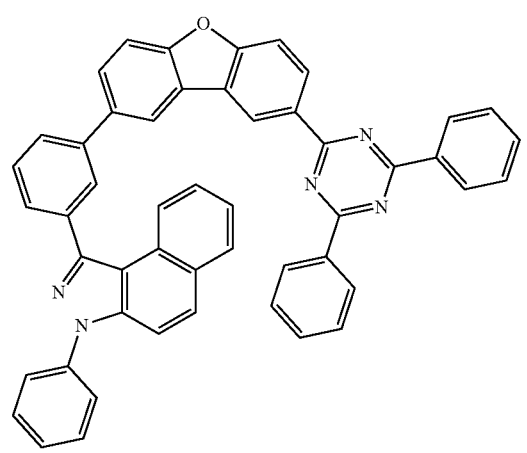
R73
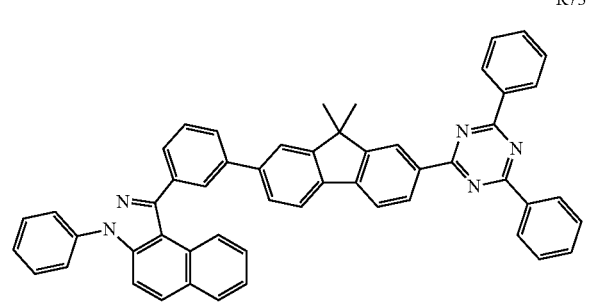
-continued
R74
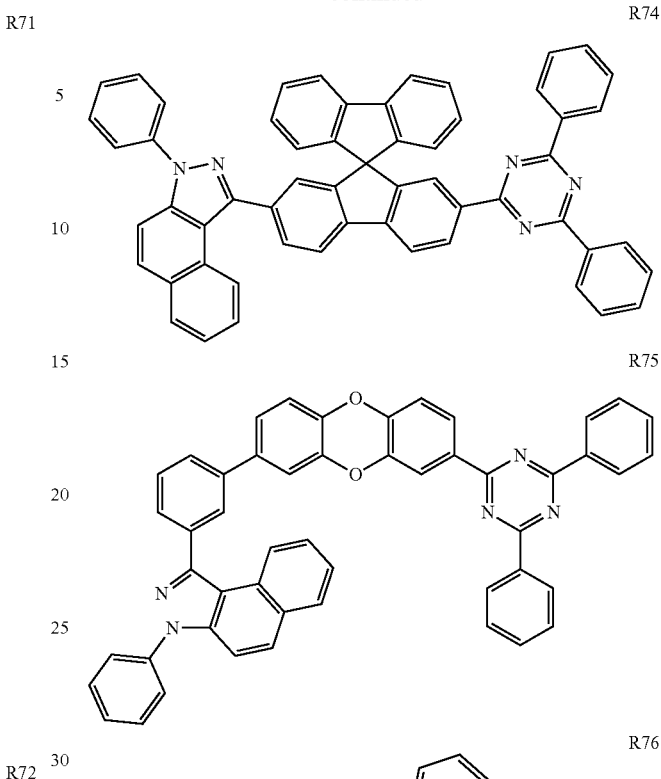
R75
R76
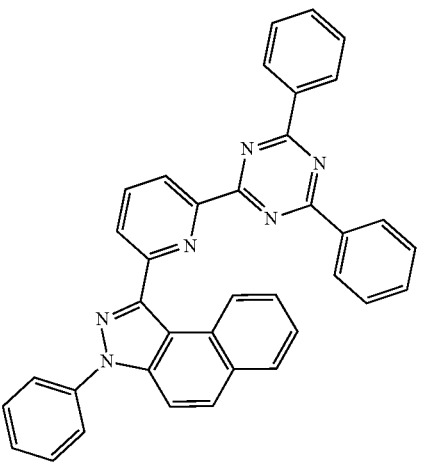
R77
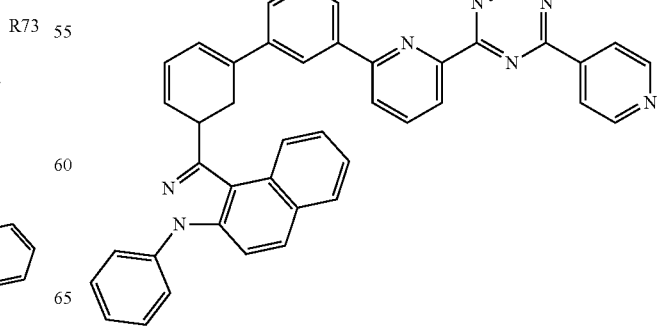

R78
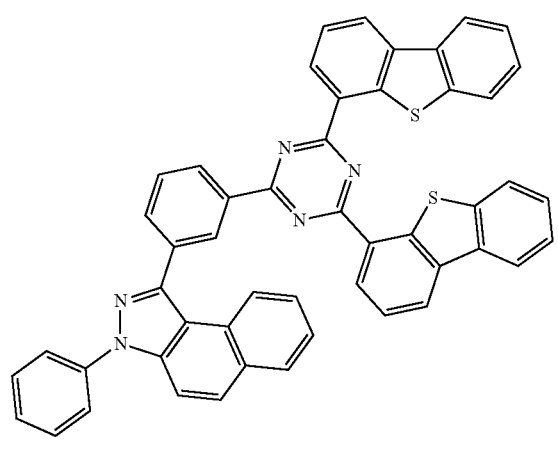
R79
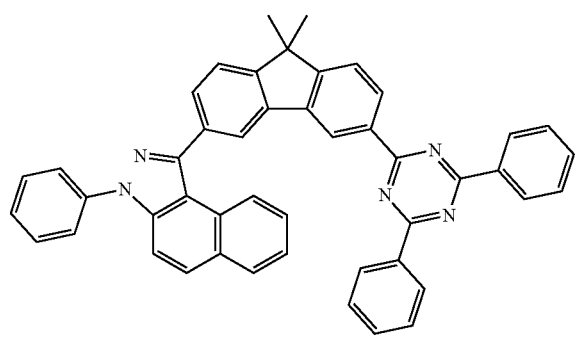
R80
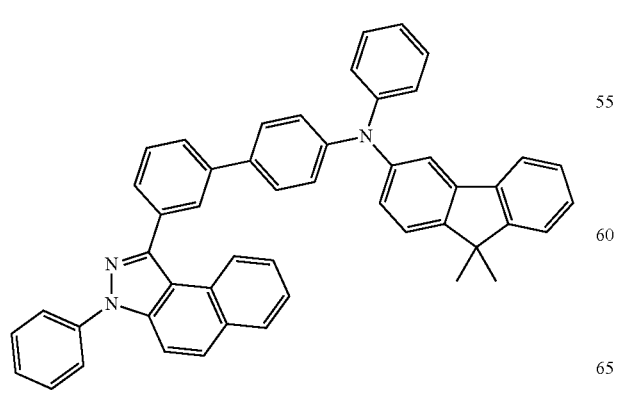
R101
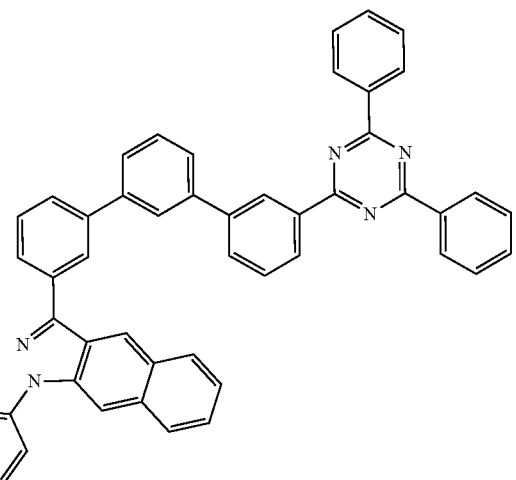
R102
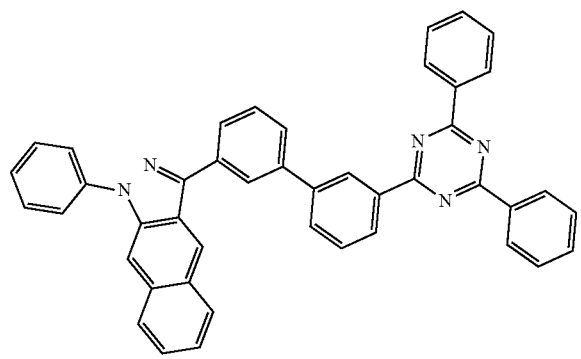
R103
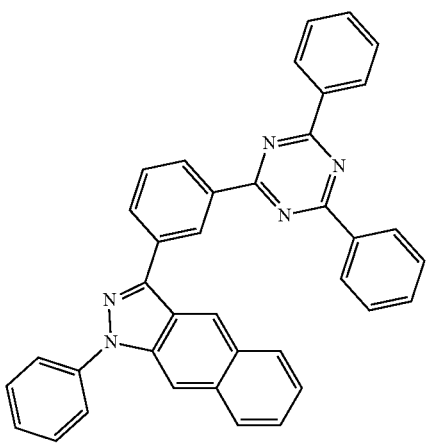

R104 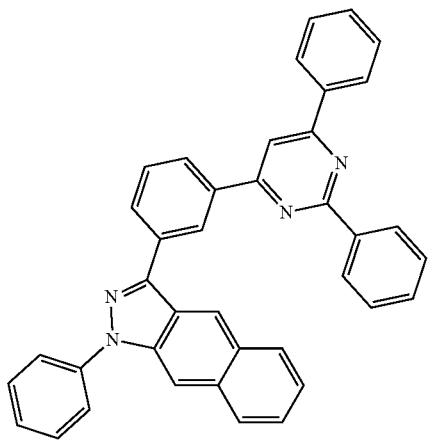
R105 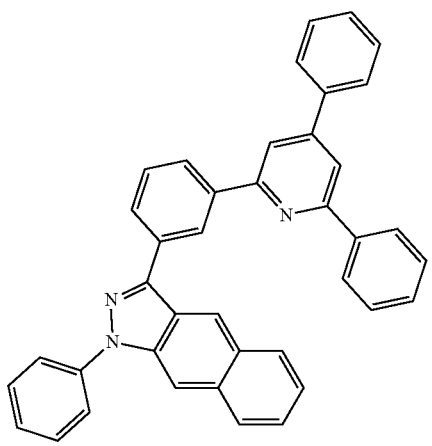
R106 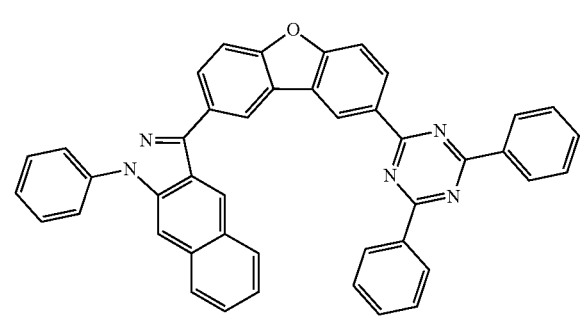
R107 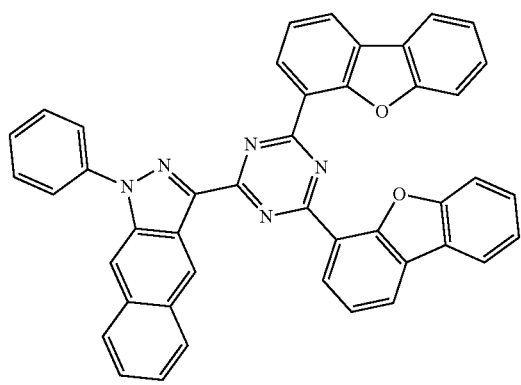
R108 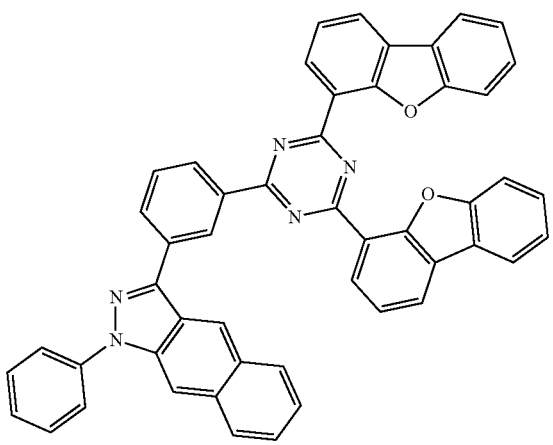
R109 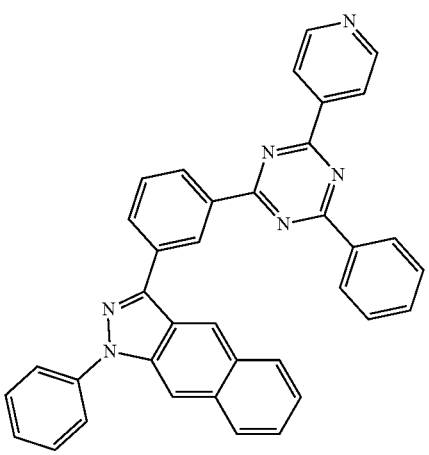
R110 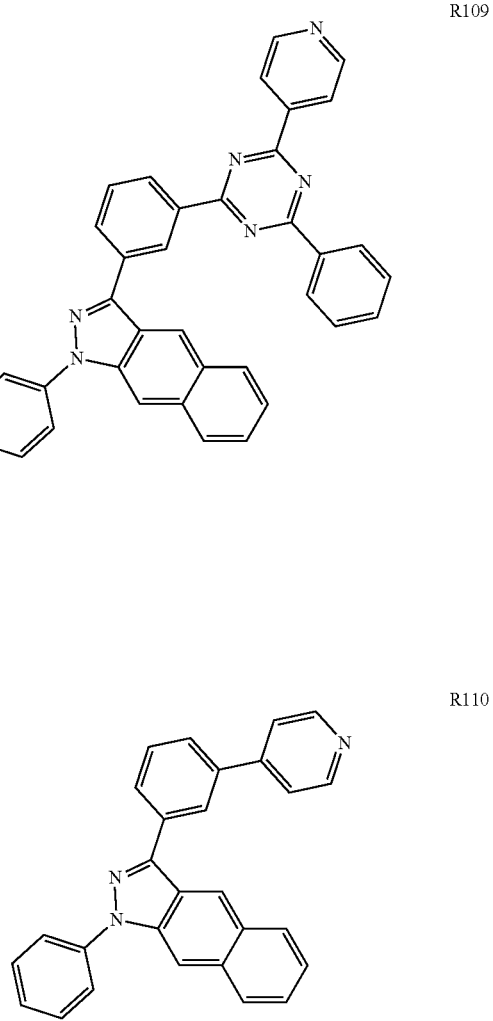

R111
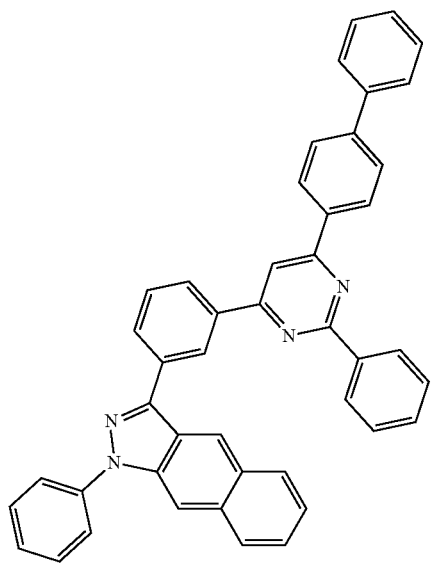
R112
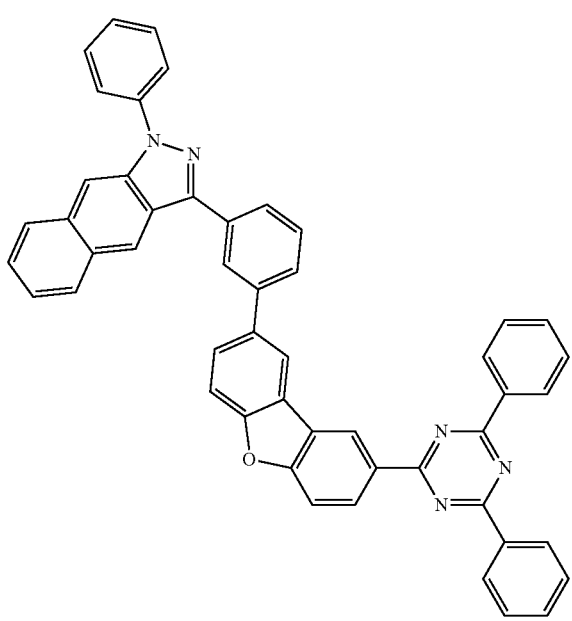
R113
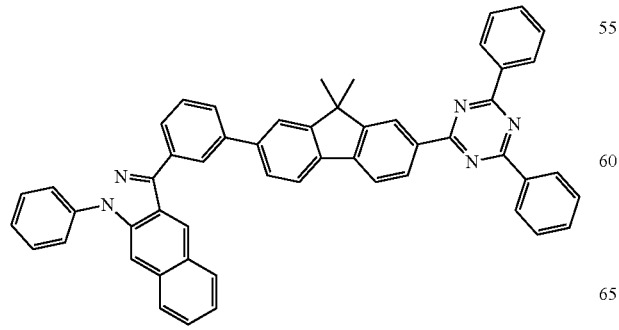
R114
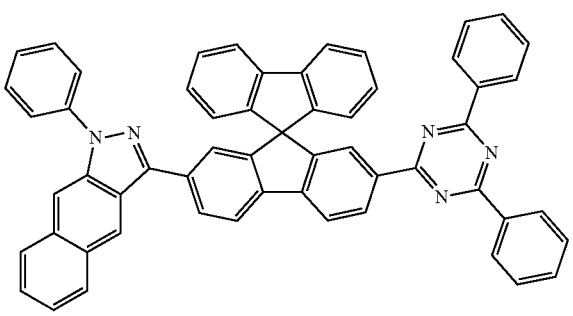
R115
R116

R117
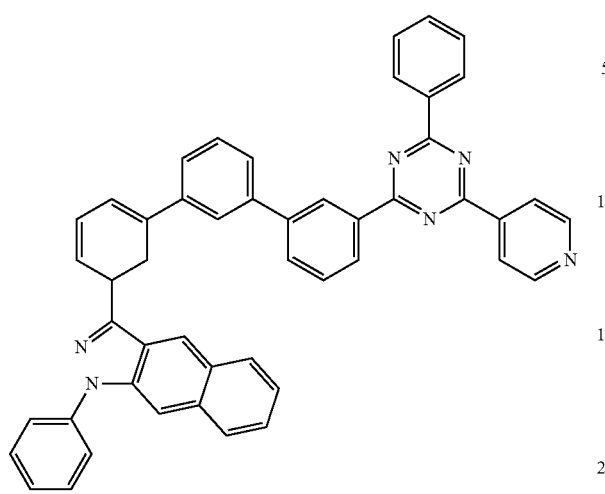
R118
R120
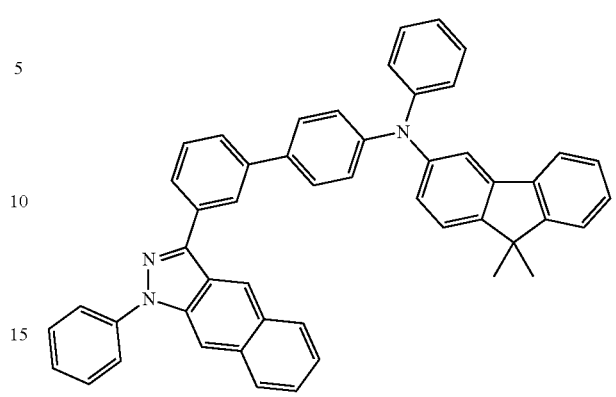
R121
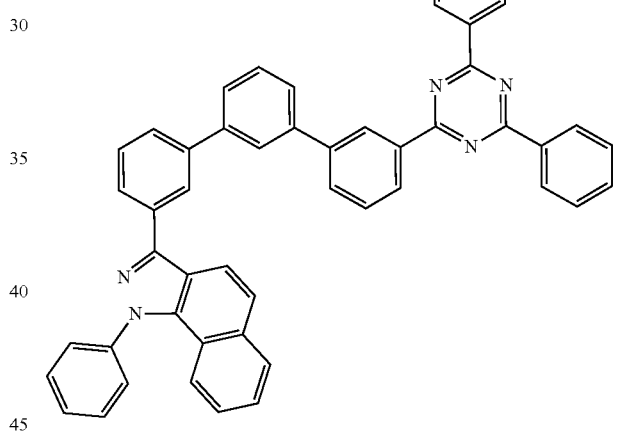
R119
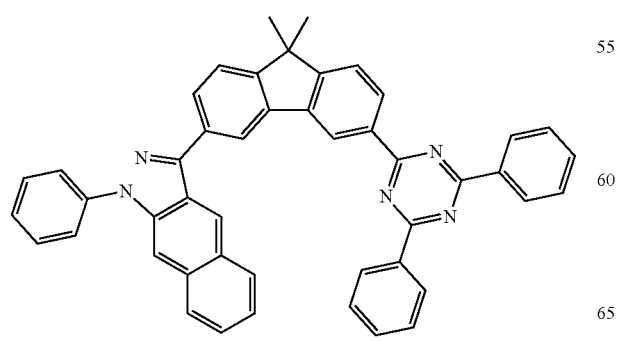
R122
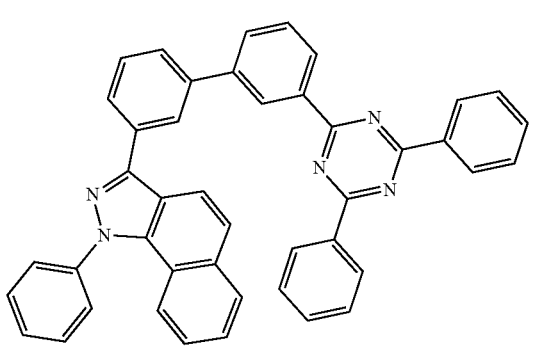

R123 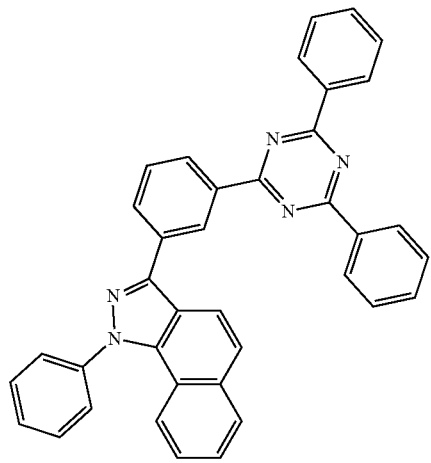
R124 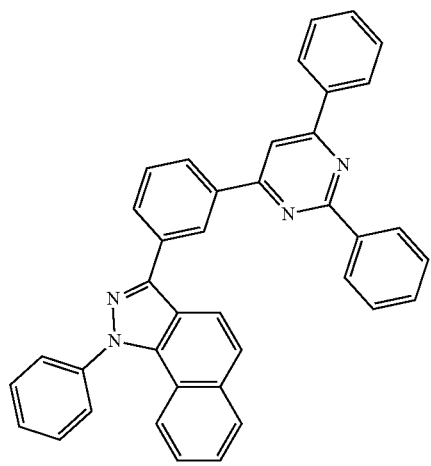
R125 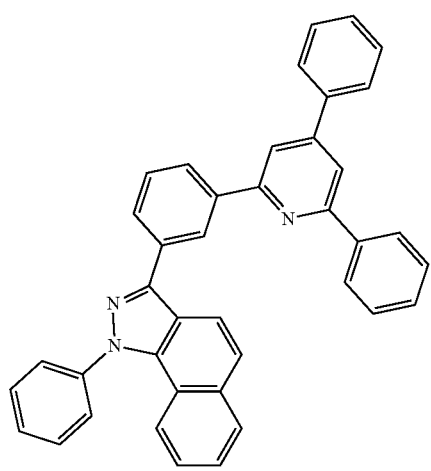
R126 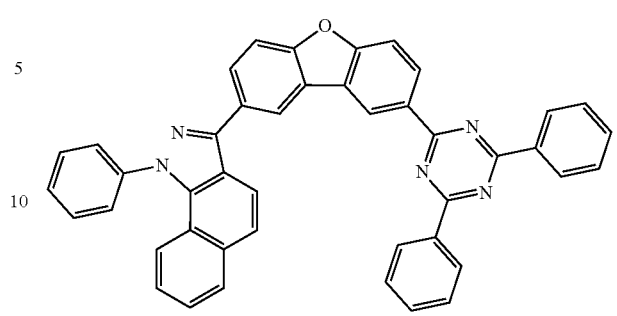
R127 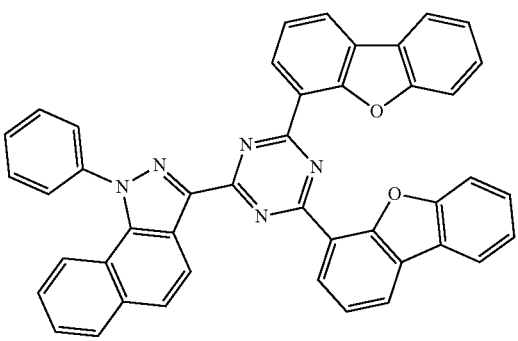
R128 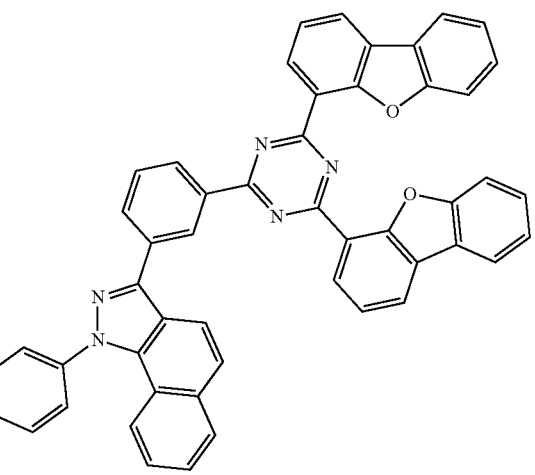
R129 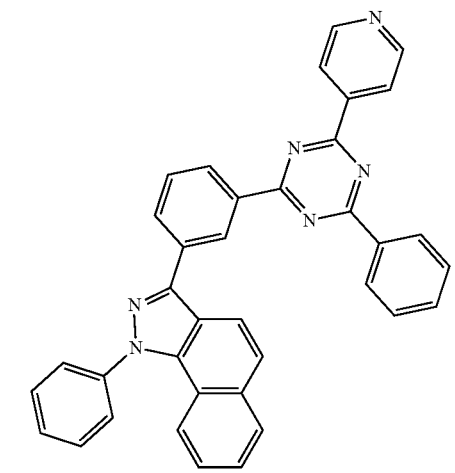

-continued
R130
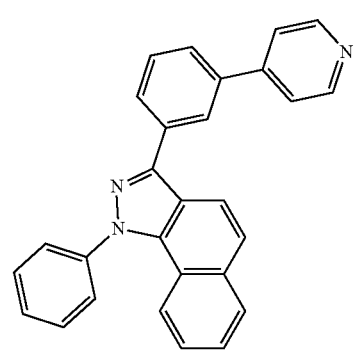
R131
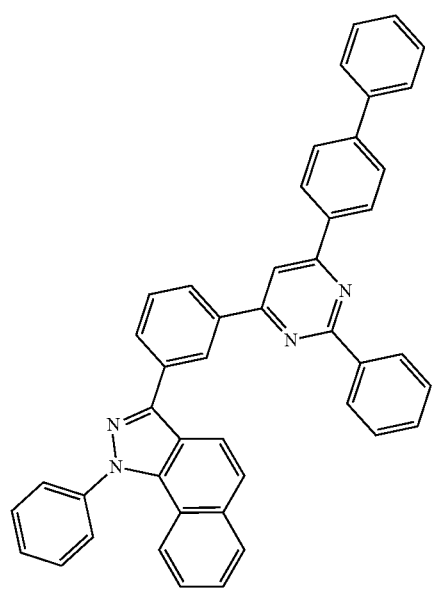
R132
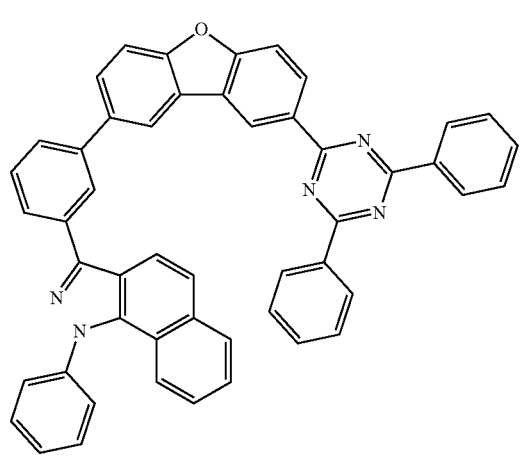
-continued
R133
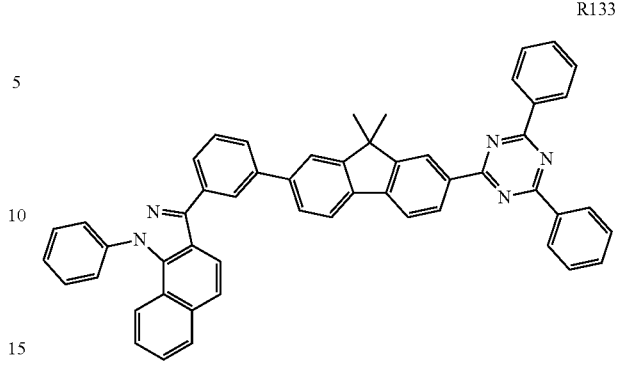
R134
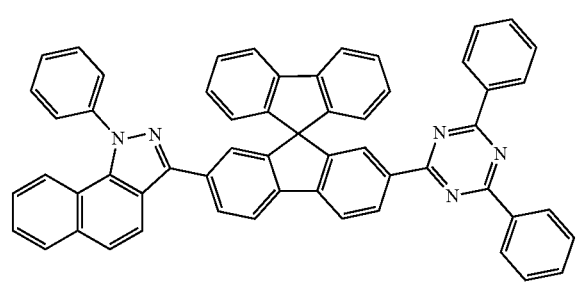
R135
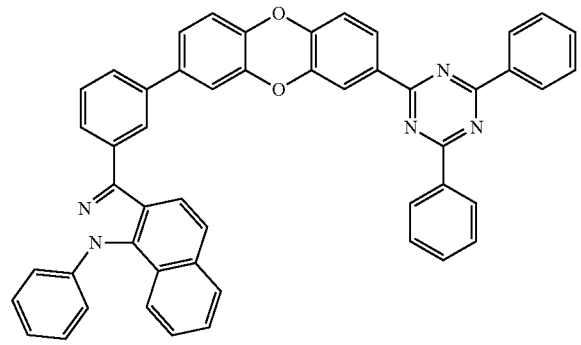
R136
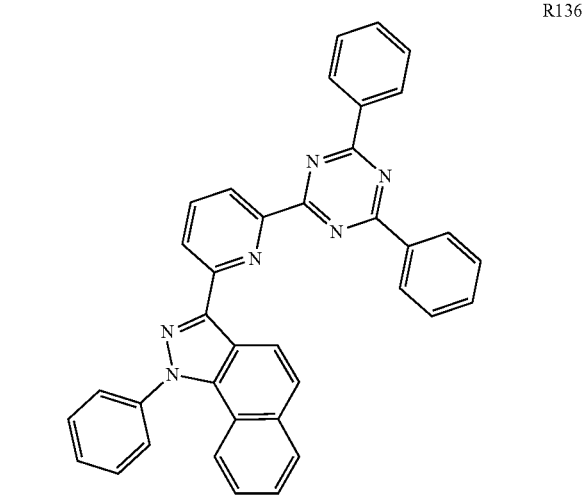

R137
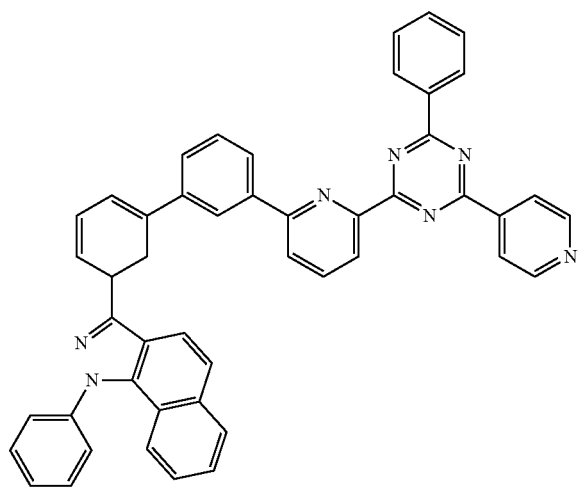
R140
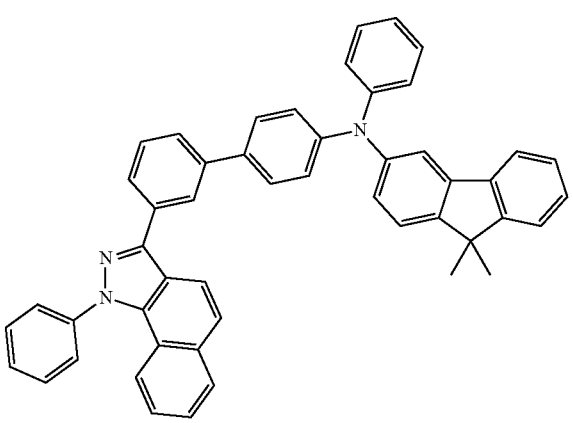
R138 R141
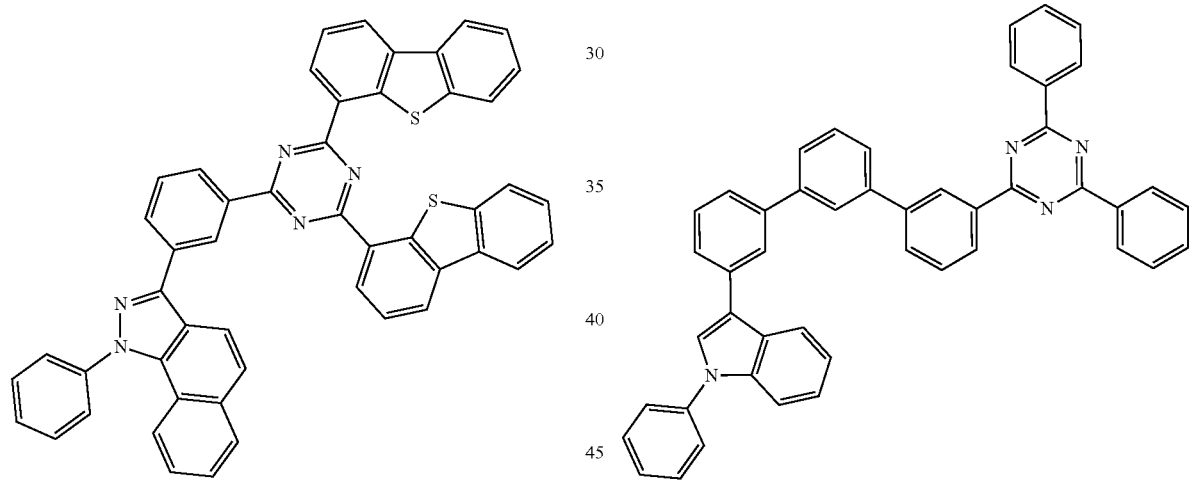
R139
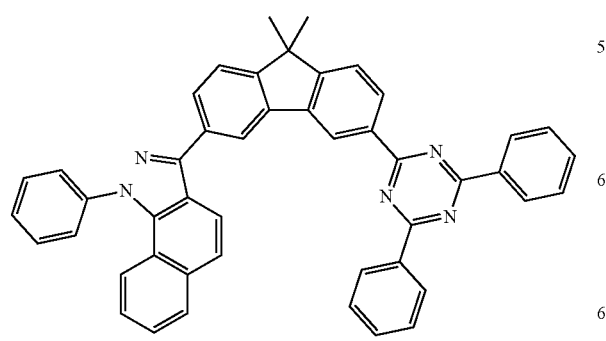
R142
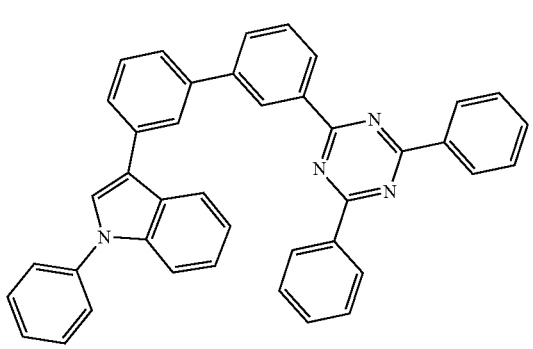

R143 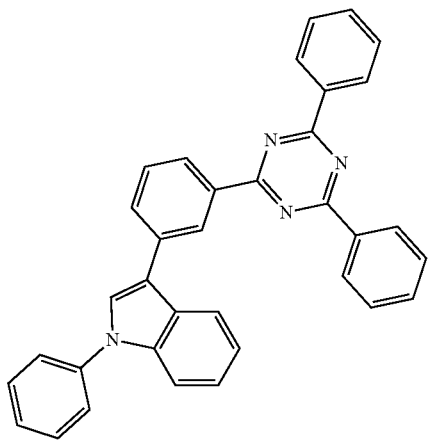
R144 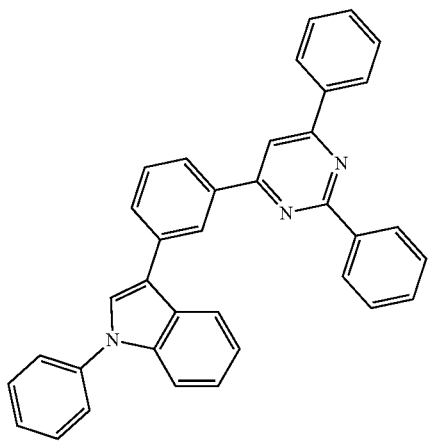
R145 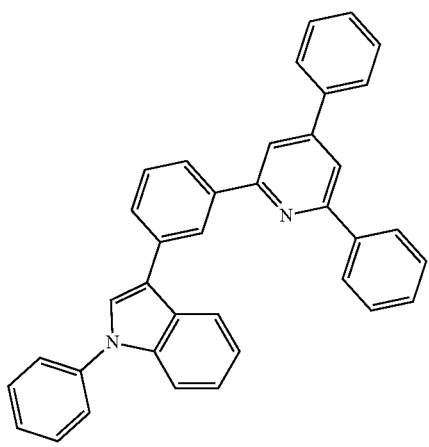
R146 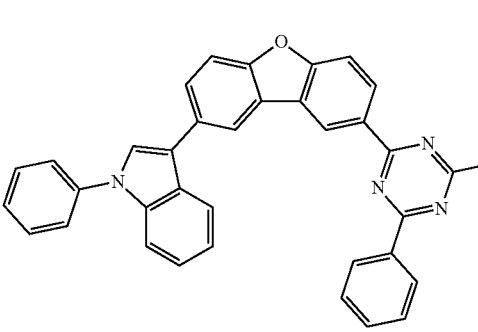
R147 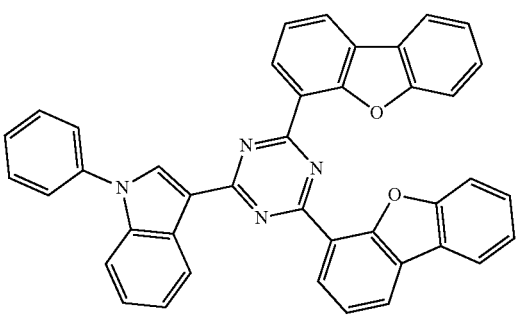
R148 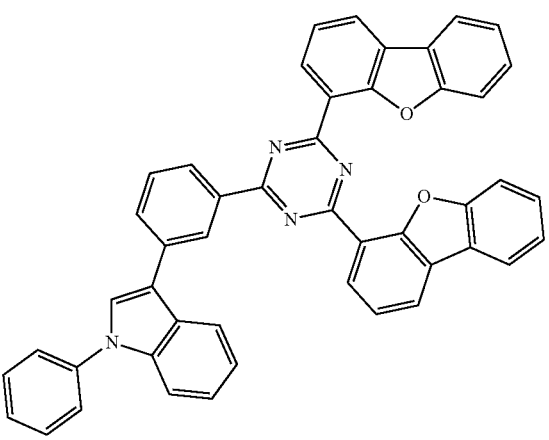
R149 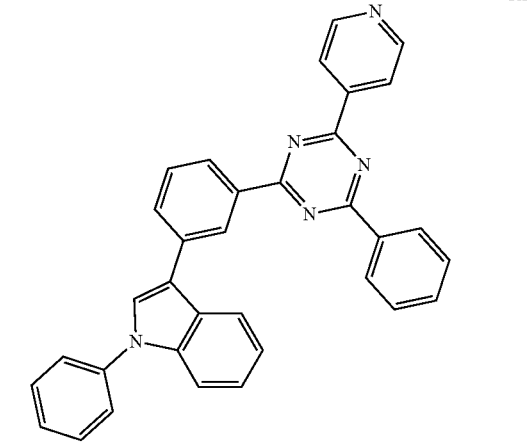
R150 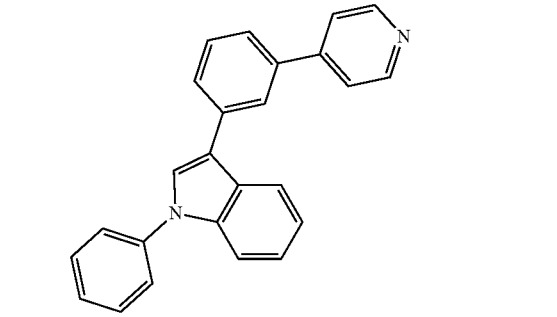

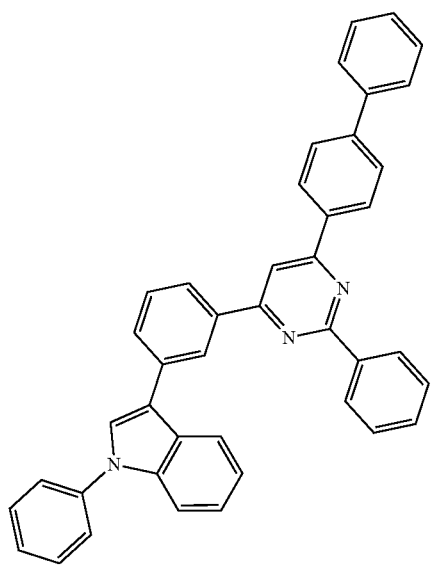
R151
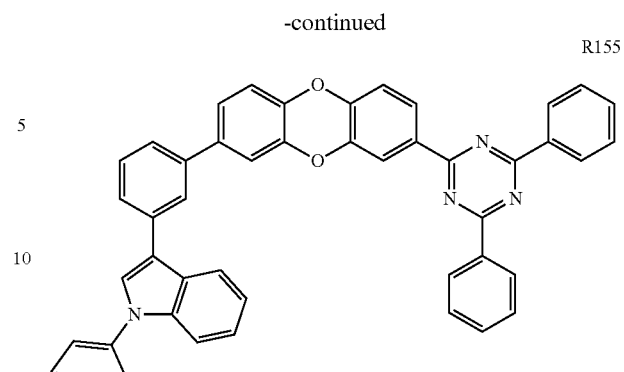
R155
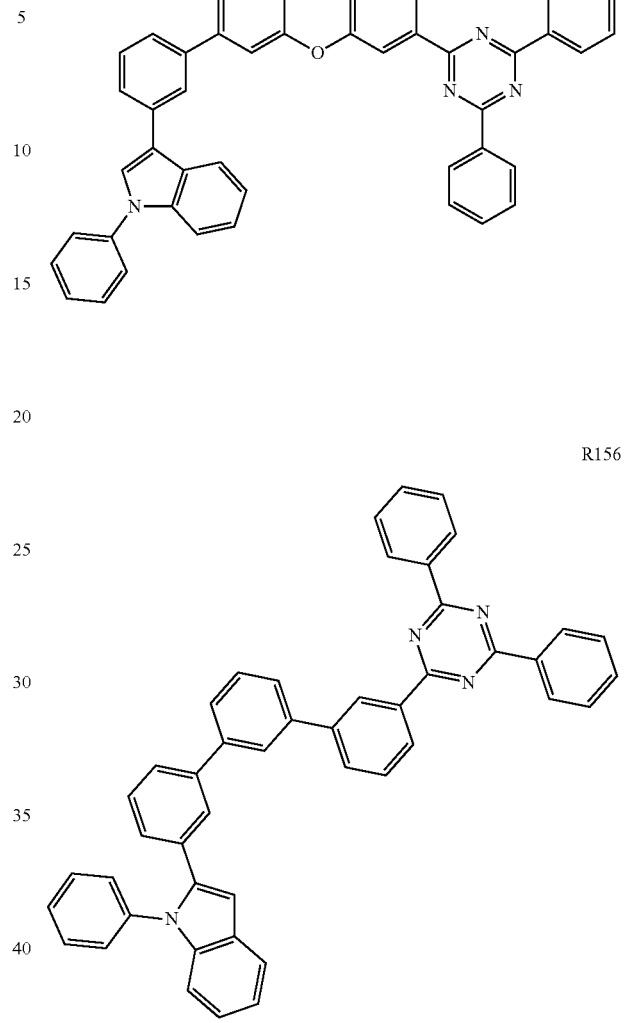
R152
R153
R154
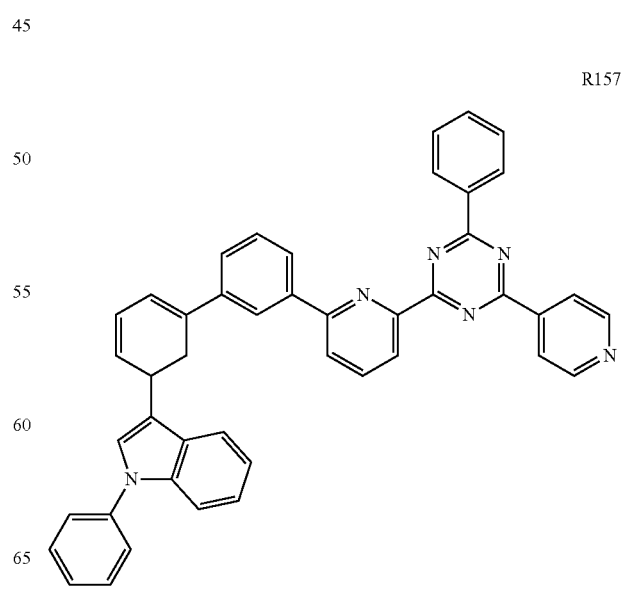
R156
R157

R158
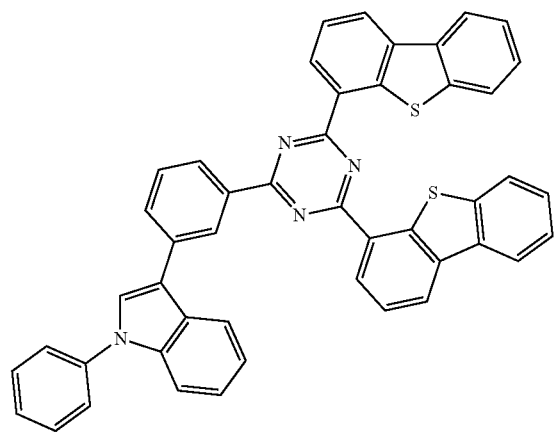
R161
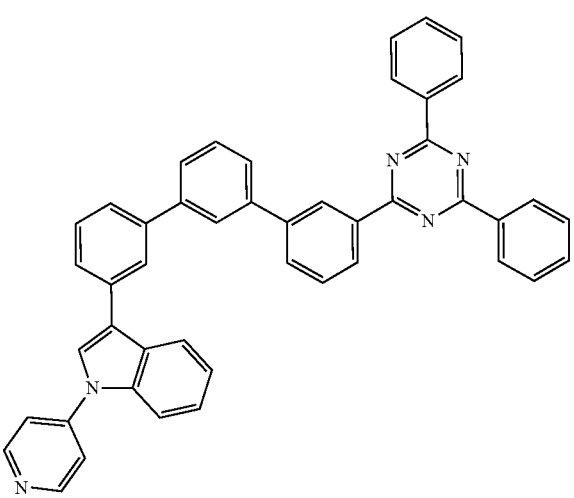
R159
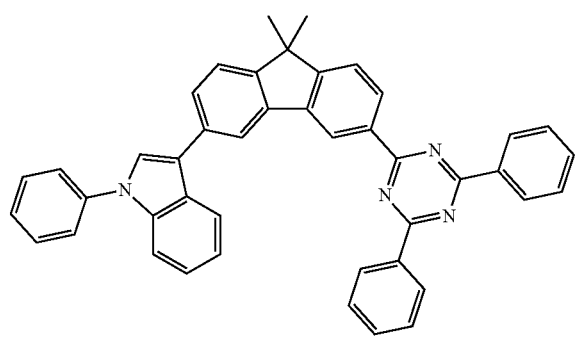
R162
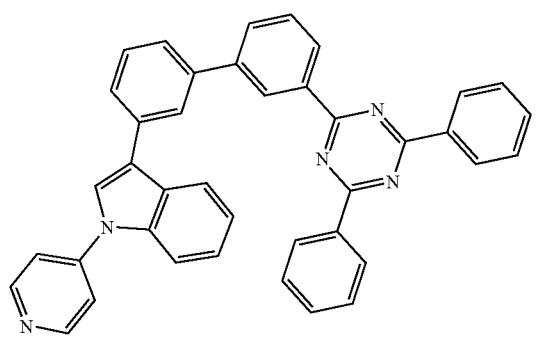
R160
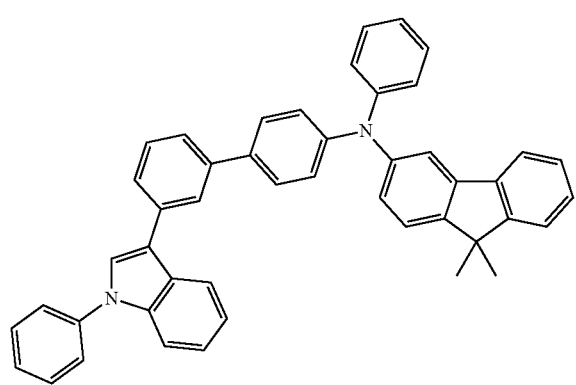
R163
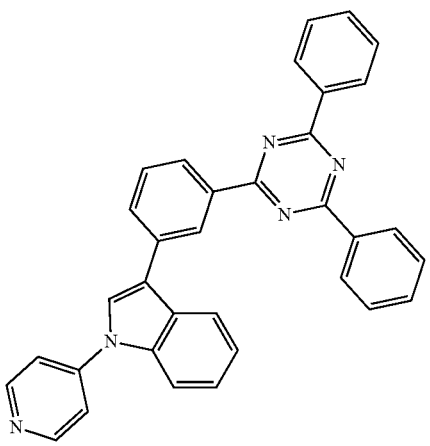

R164
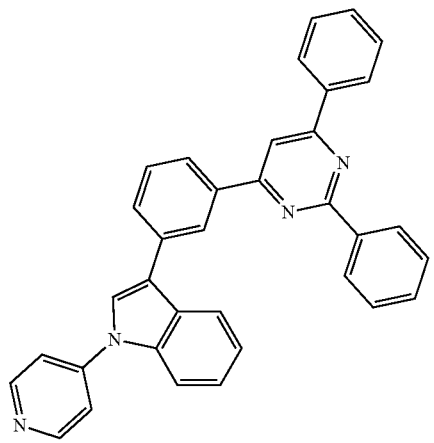
R165
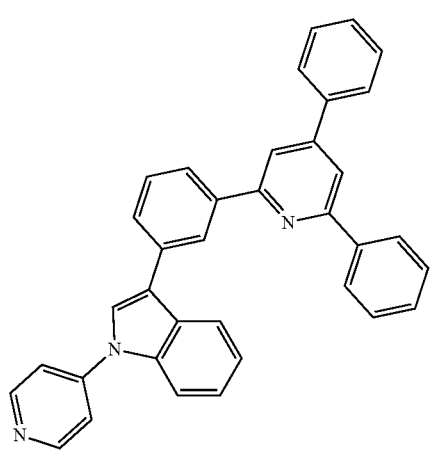
R166
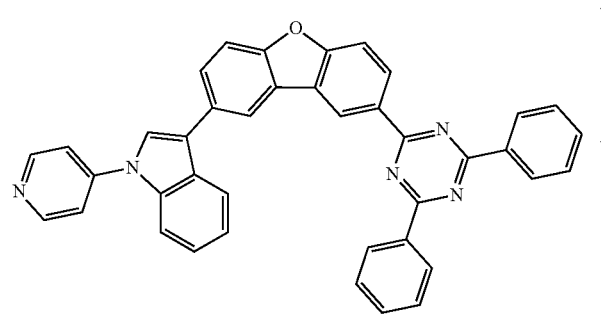
R167
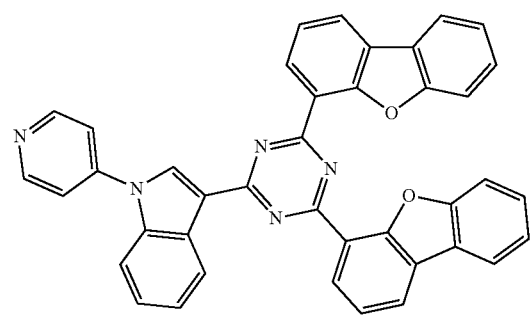
R168
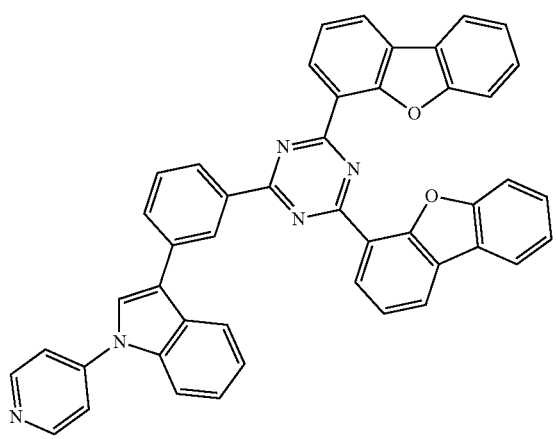
R169
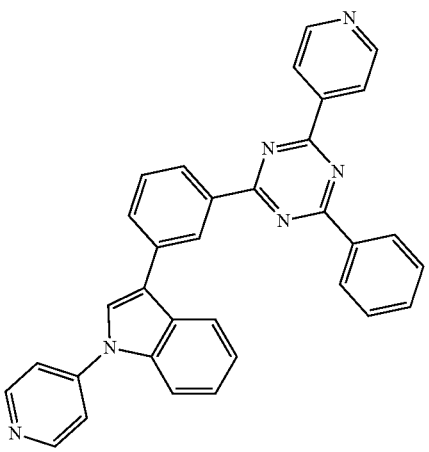
R170
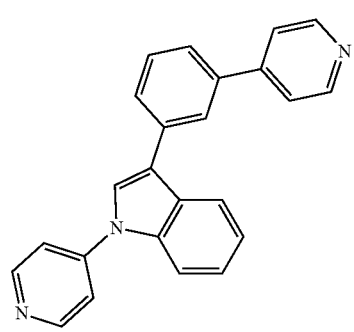

-continued
R171
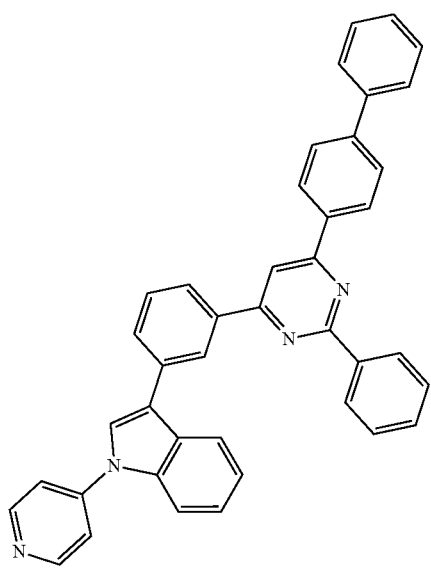
R172
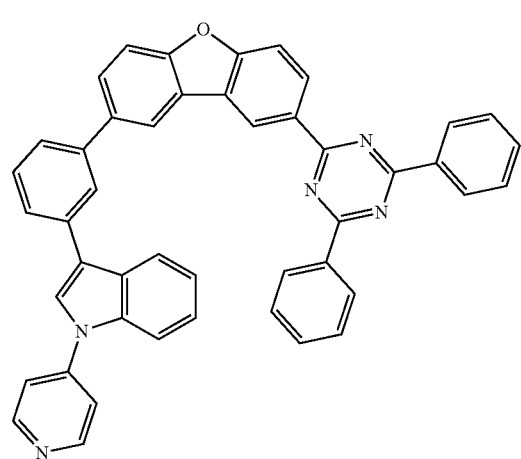
R173
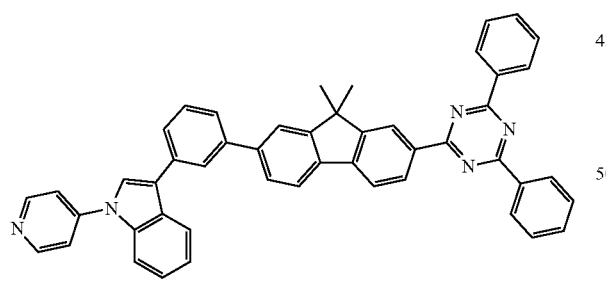
R174
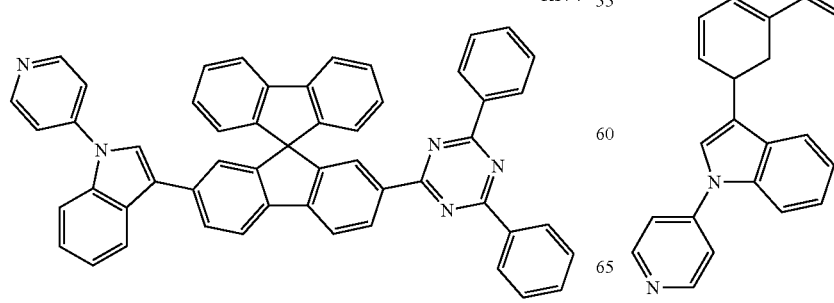
-continued
R175
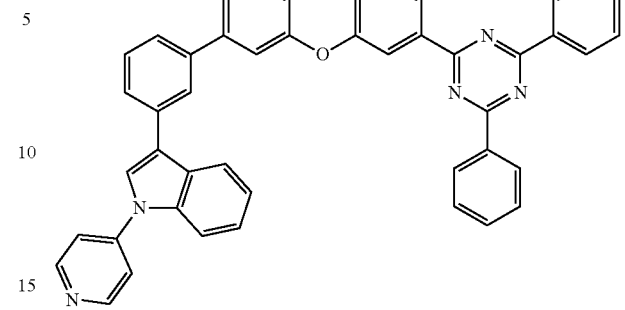
R176
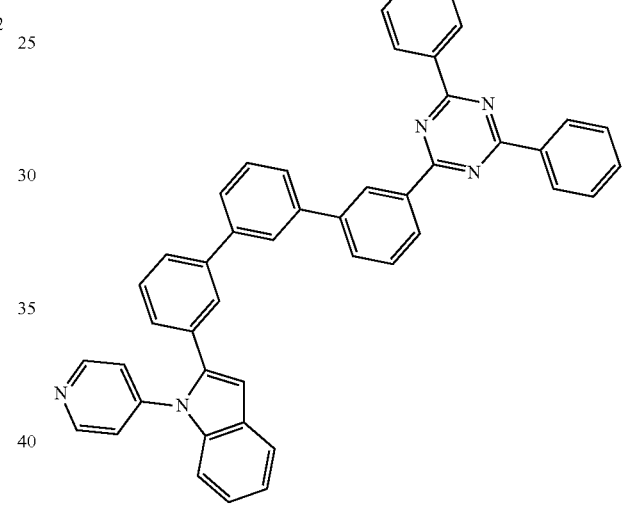
R177
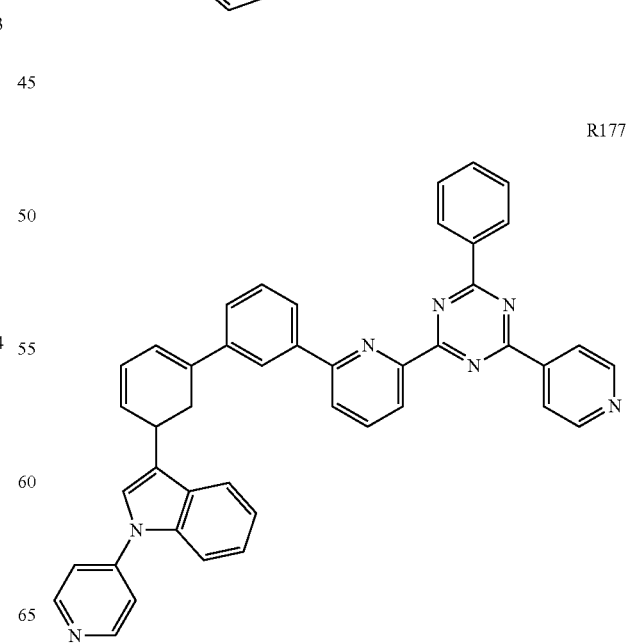

-continued
R178
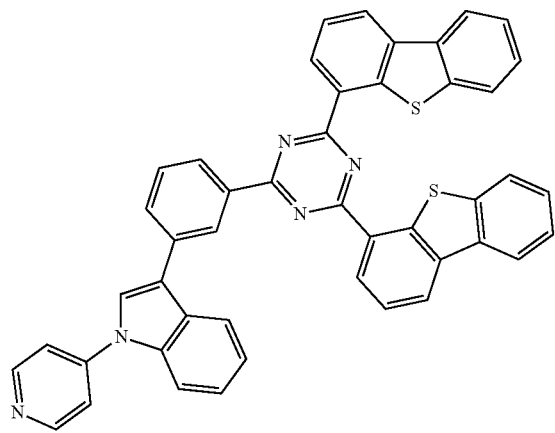
R179
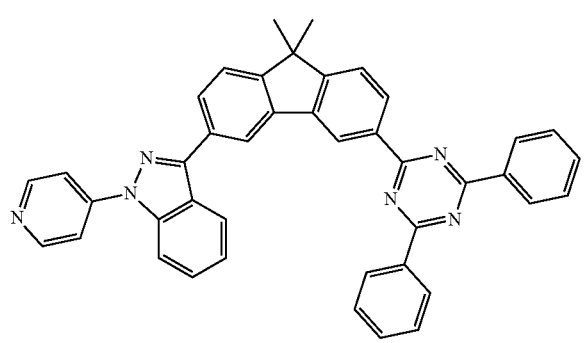
R180
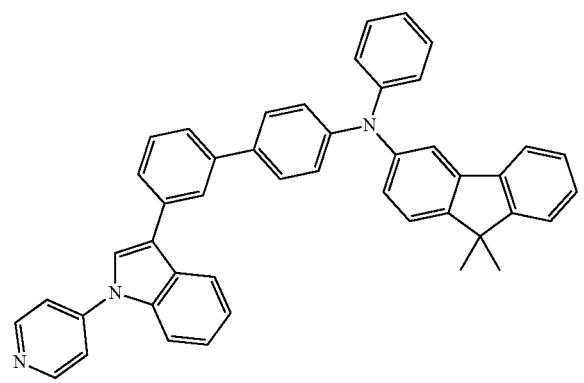
-continued
R181
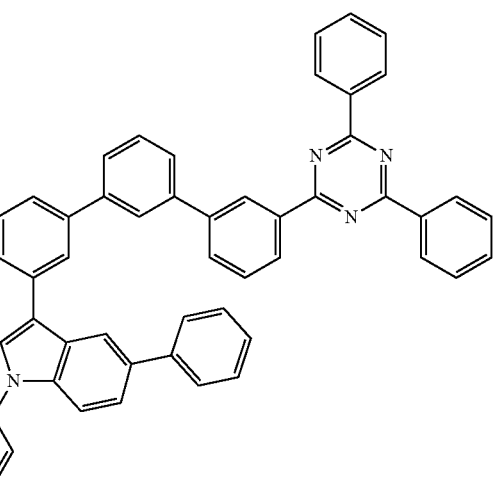
R182
R183
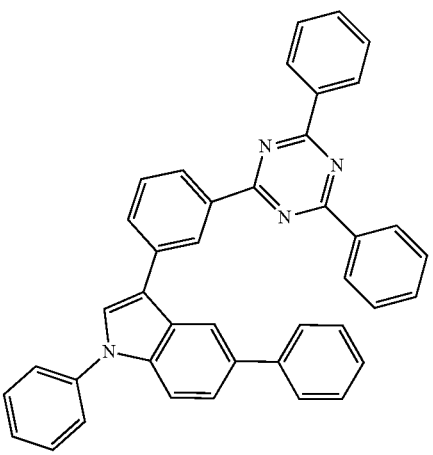

R184
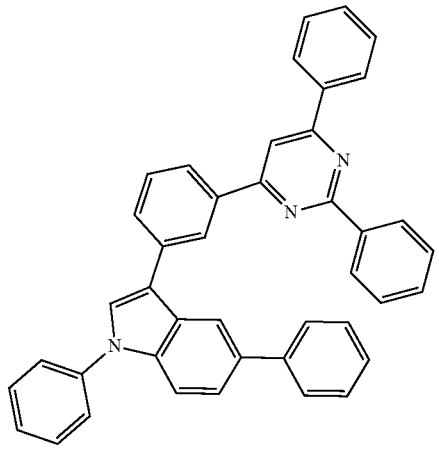
R185
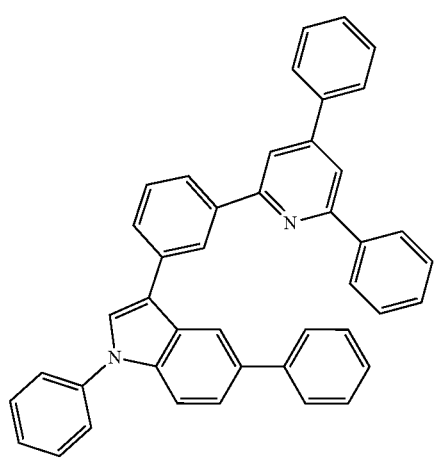
R186
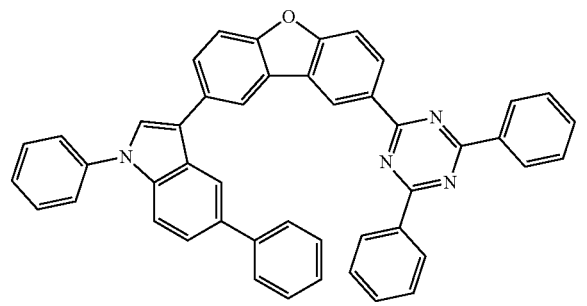
R187
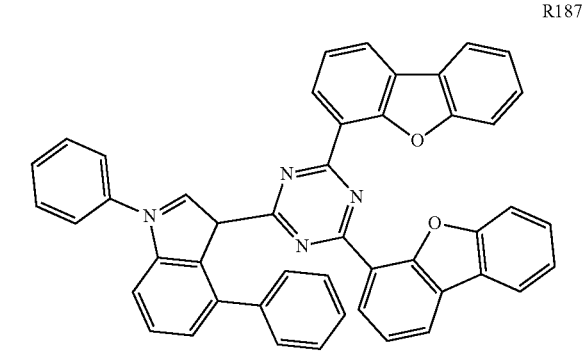
R188
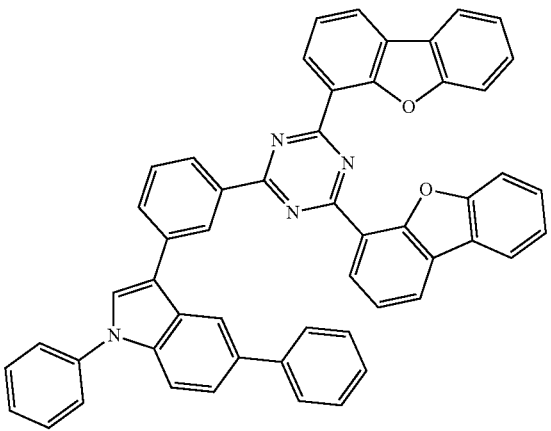
R189
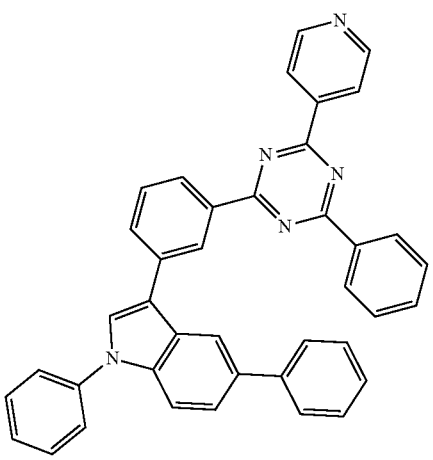
R190
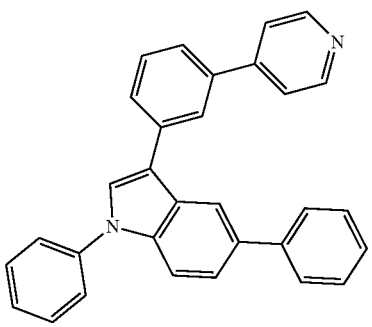

R191
R192
R193
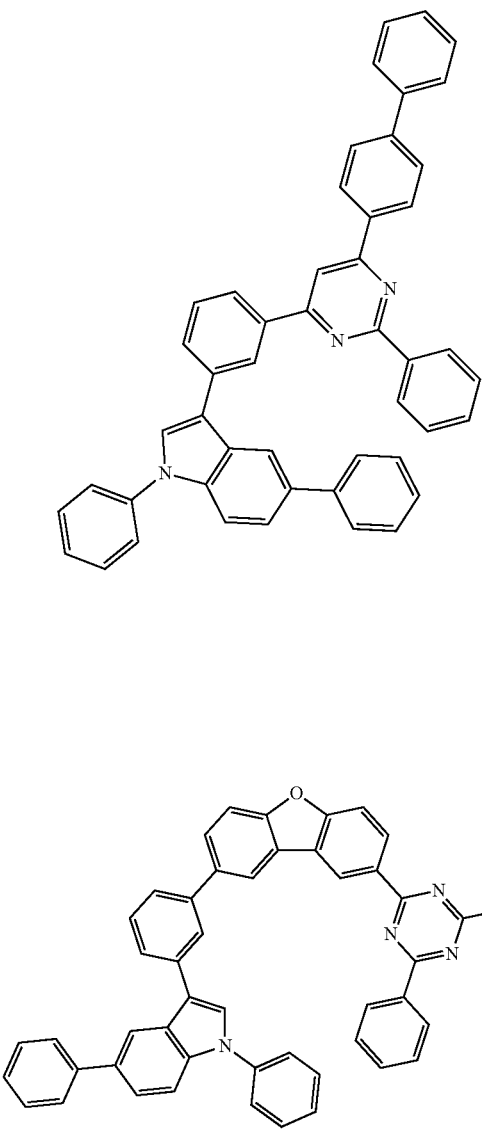
R194
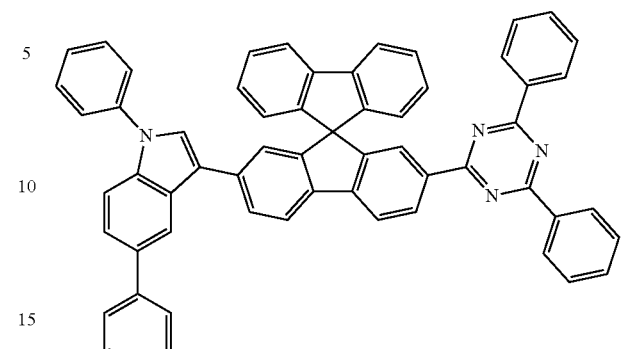
R195
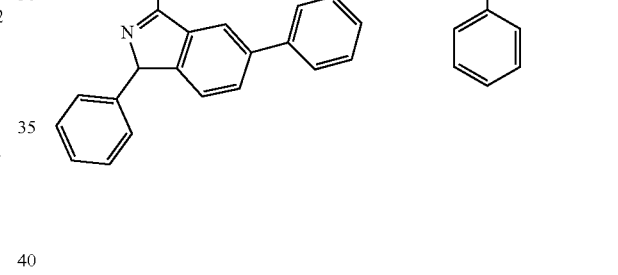
R196
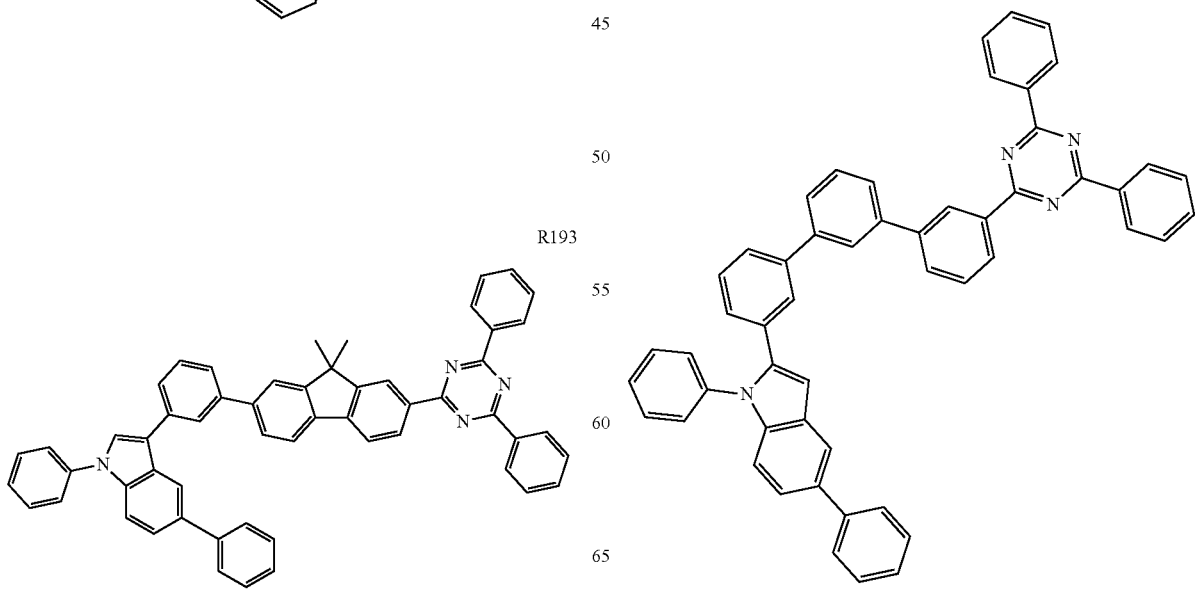

73
-continued
R197
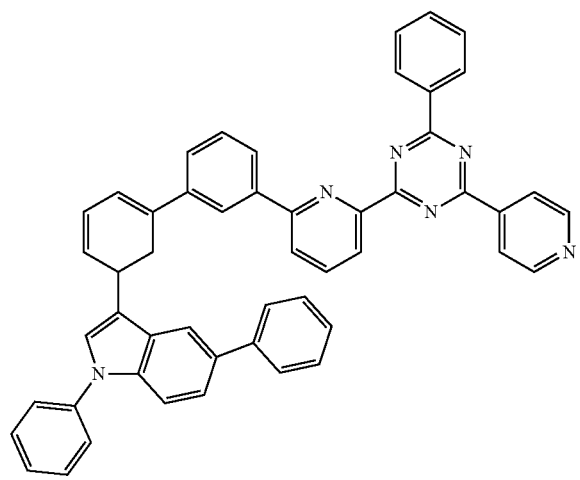
R198
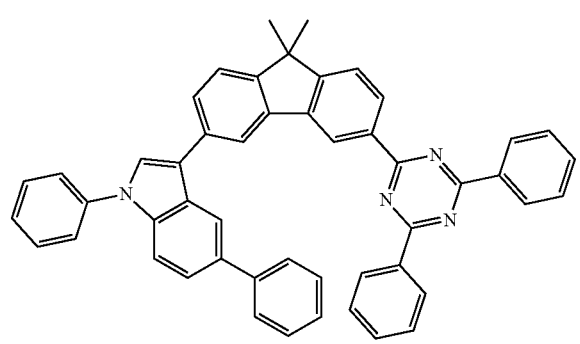
74
-continued
R200
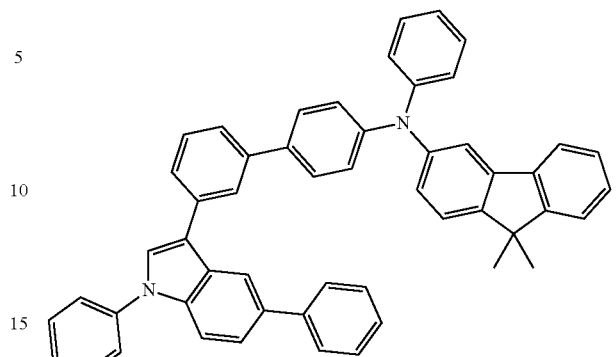
R201
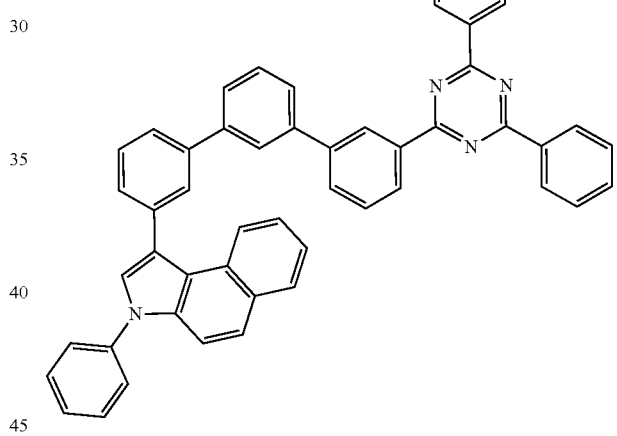
R199
R202
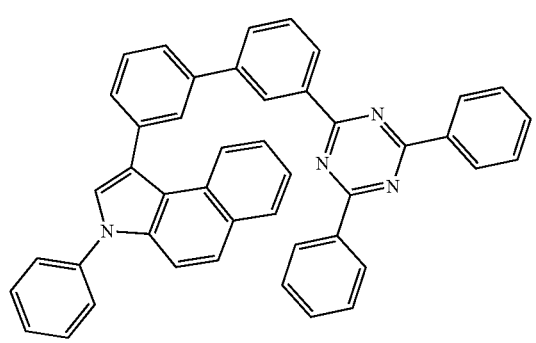

R203
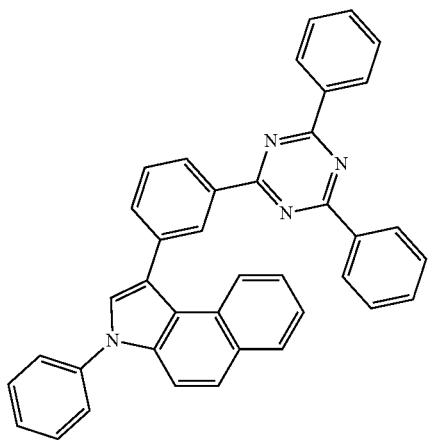
R204
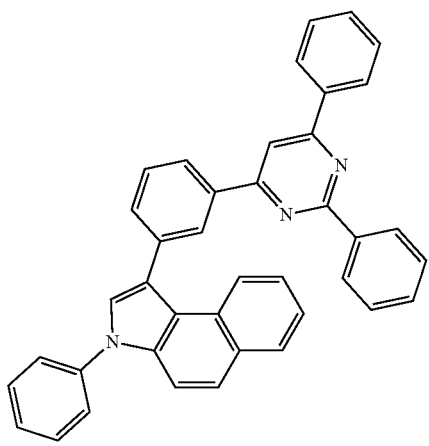
R205
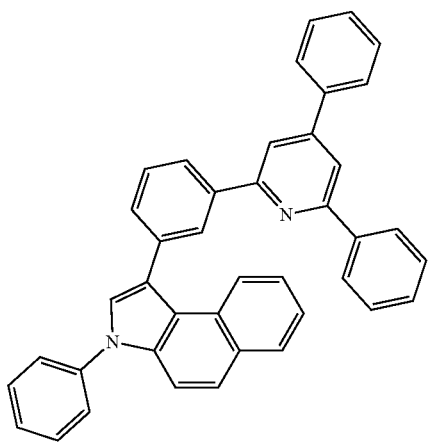
R206
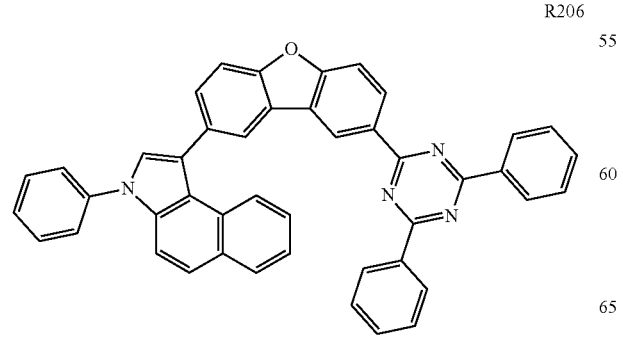
R207
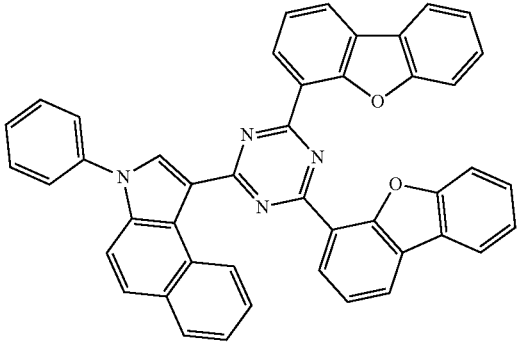
R208
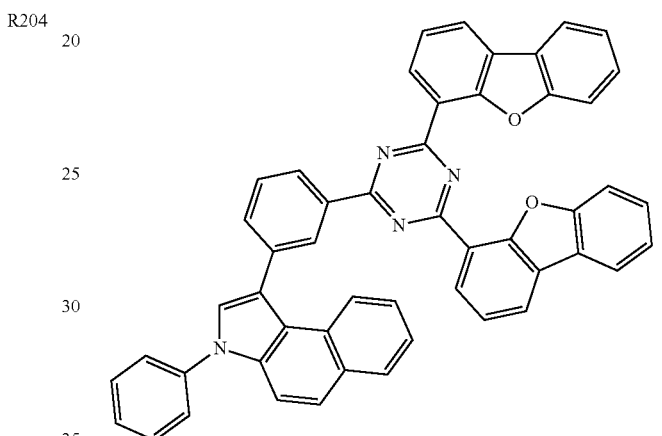
R209
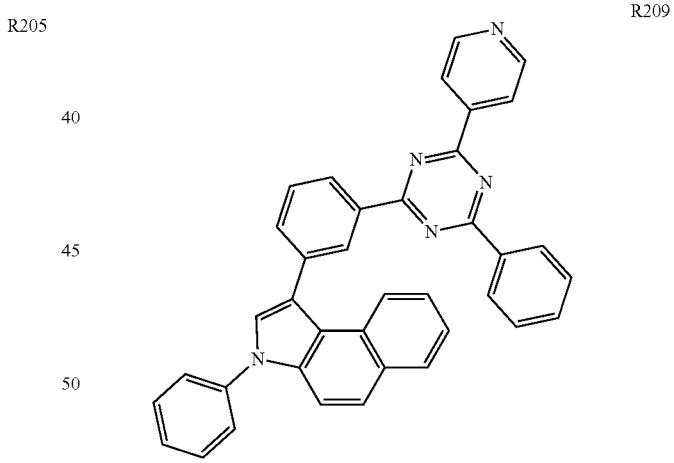
R210
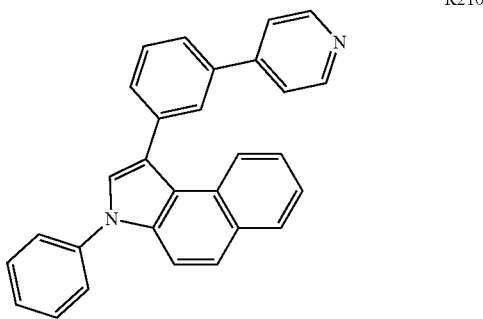

-continued
R211
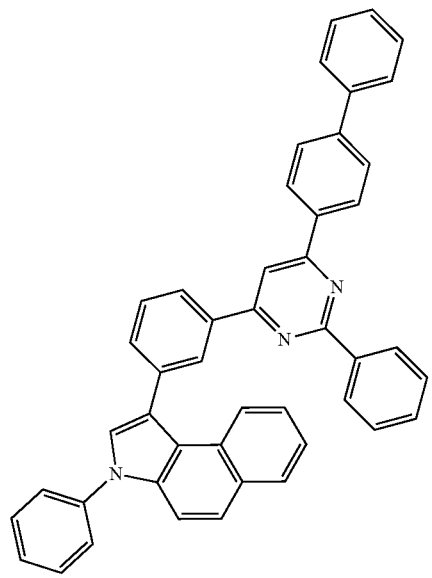
R212
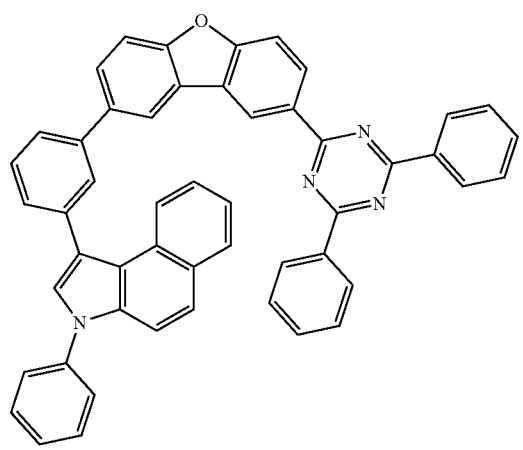
R213
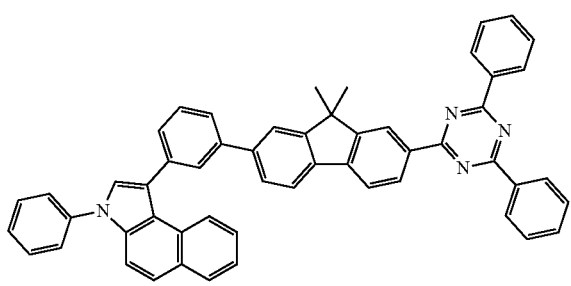
-continued
R214
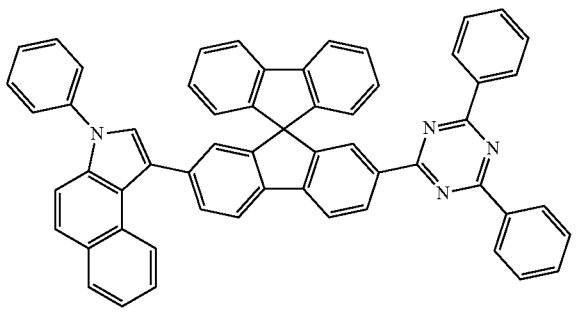
R215
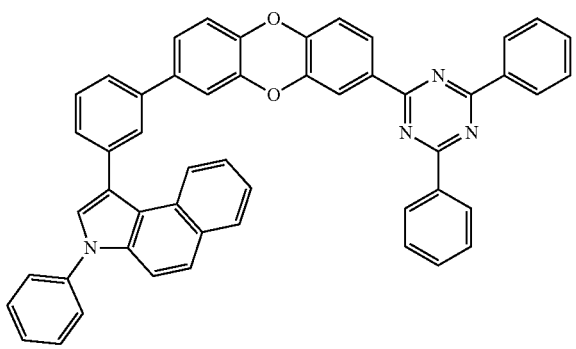
R216
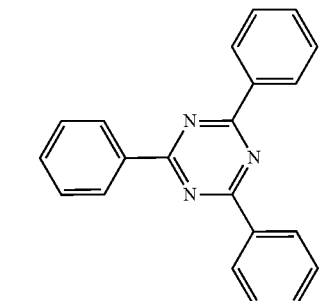
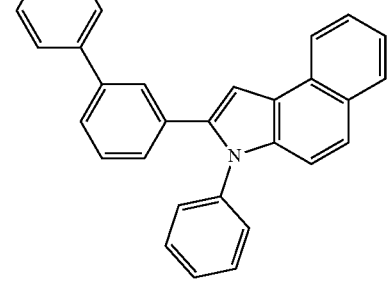

R217
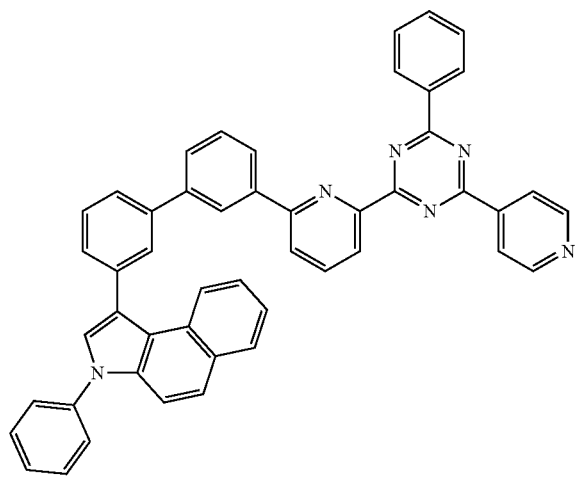
R218
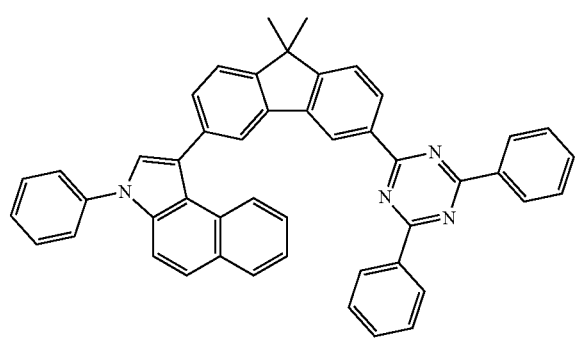
R219
R220
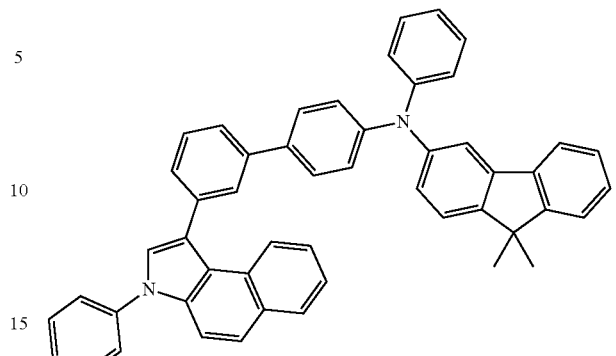
R221
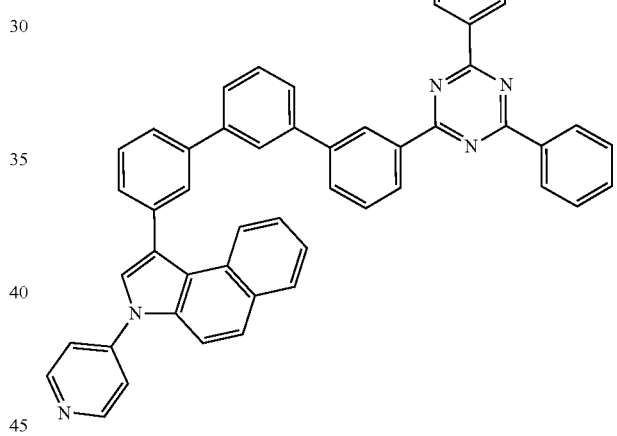
R222
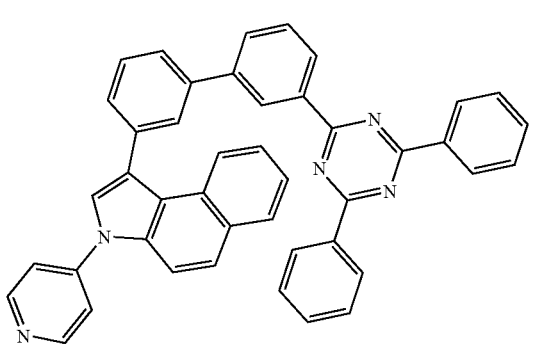

R223 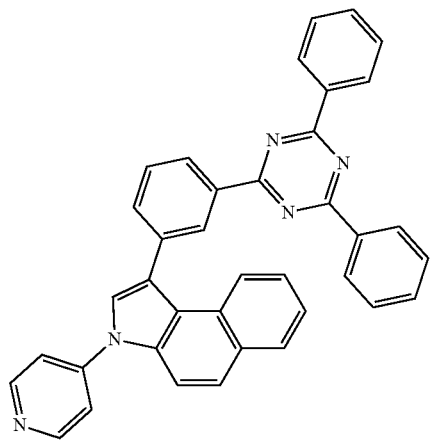
R224 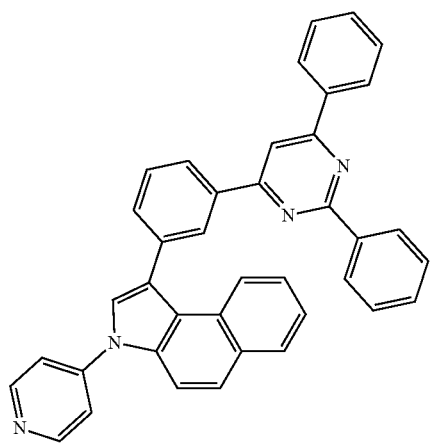
R225 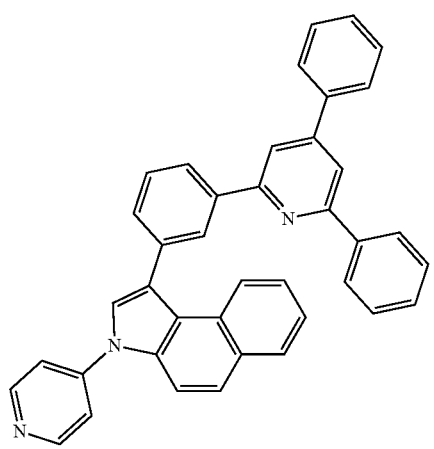
R226 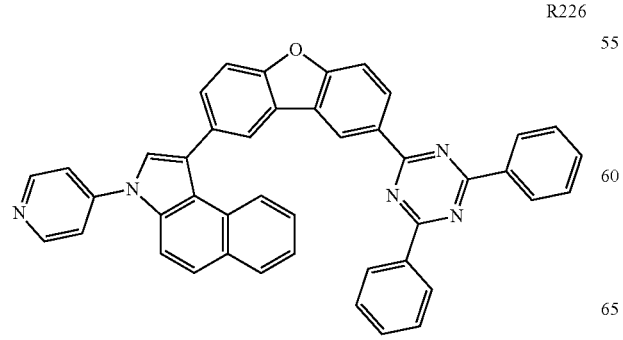
R227 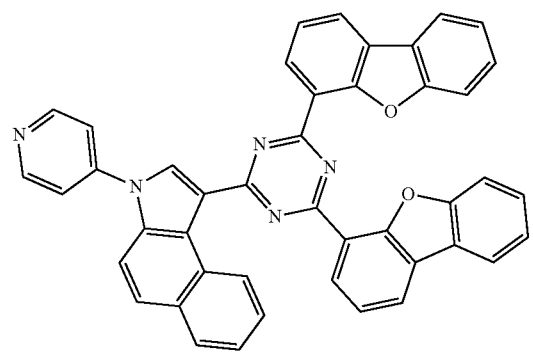
R228 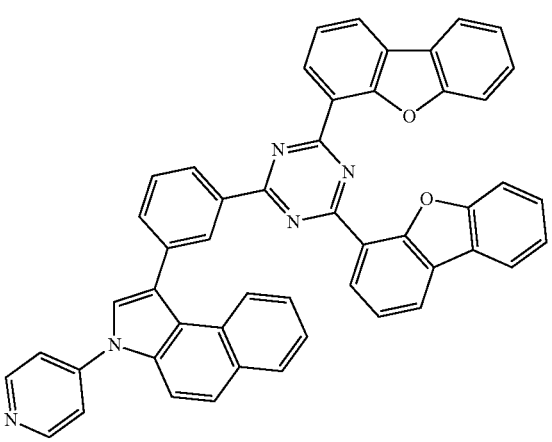
R229 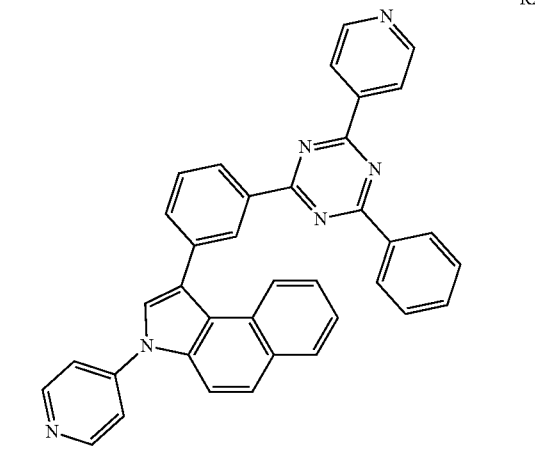
R230 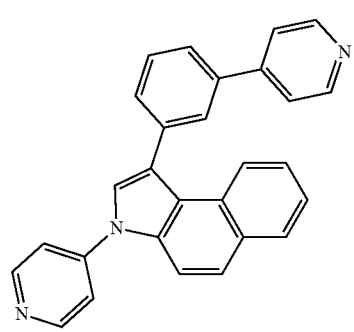

83
-continued
R231
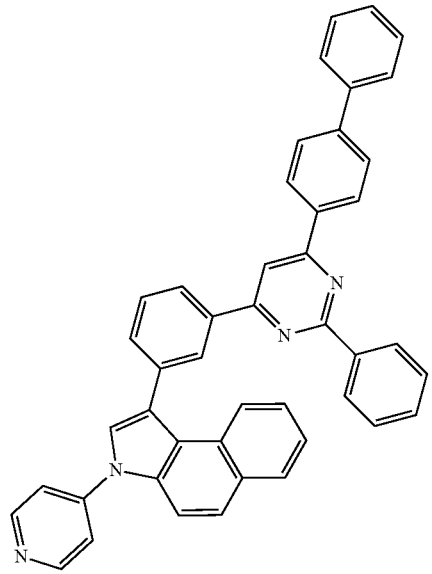
R232
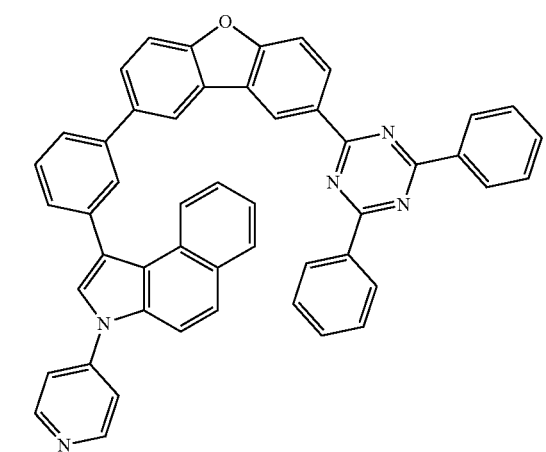
R233
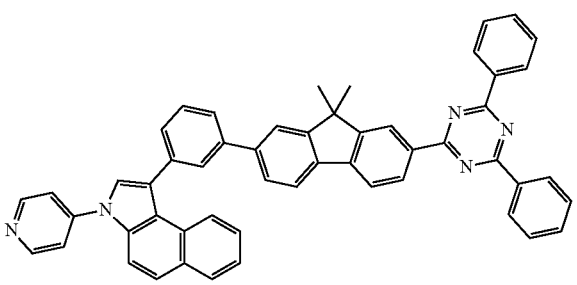
84
-continued
R234
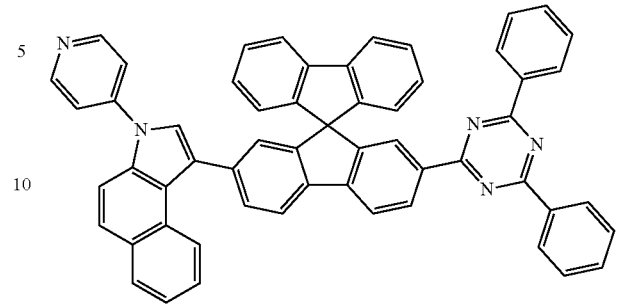
R235
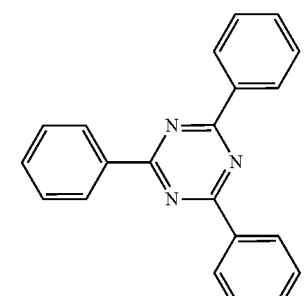
R236
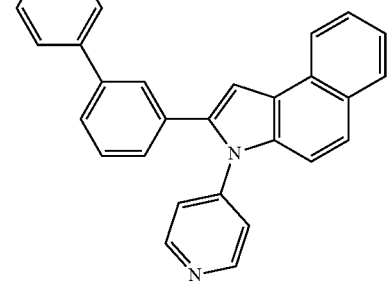

R237

R238

R239

R240

R241

R242

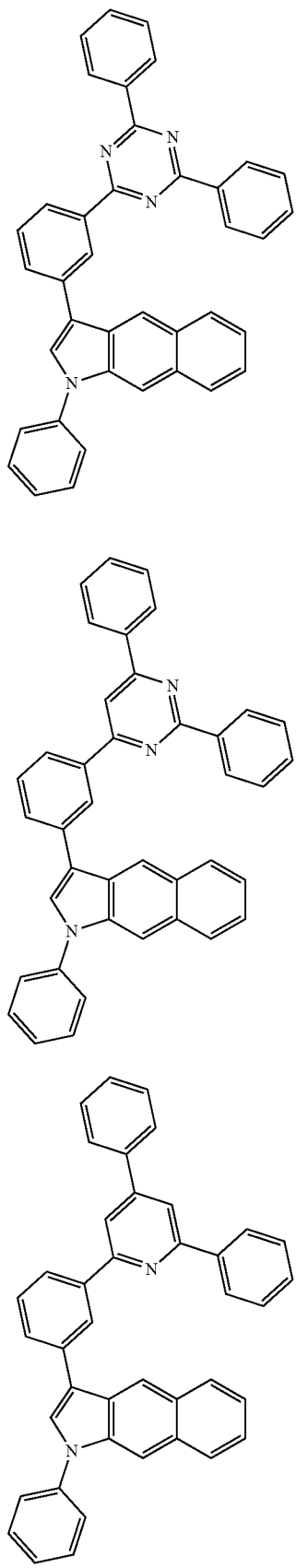
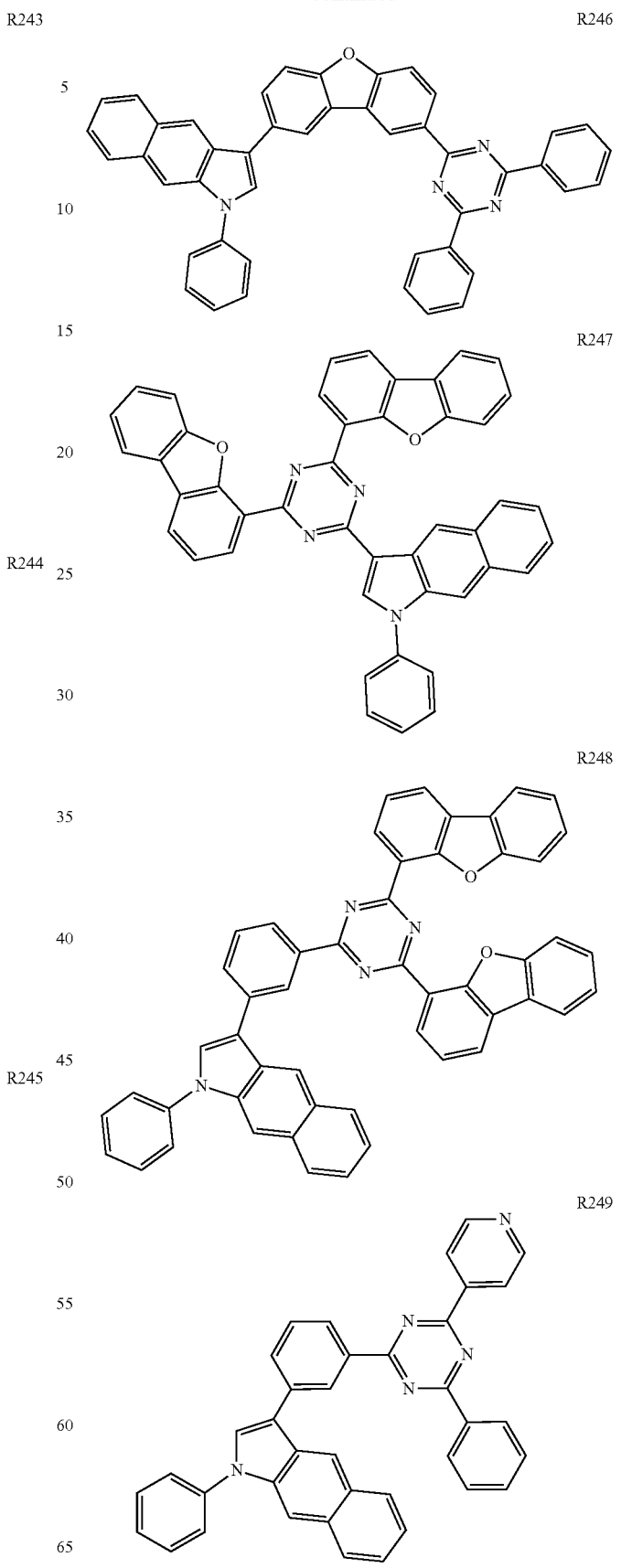

R250
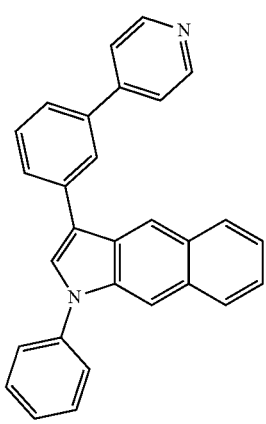
R254
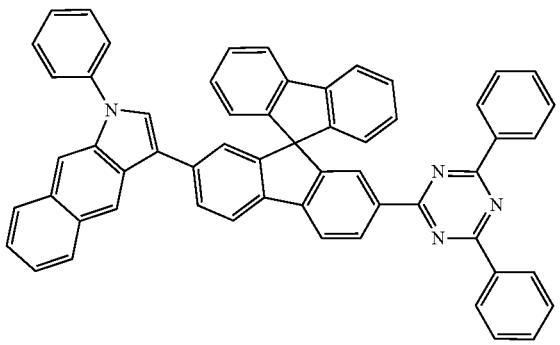
R251
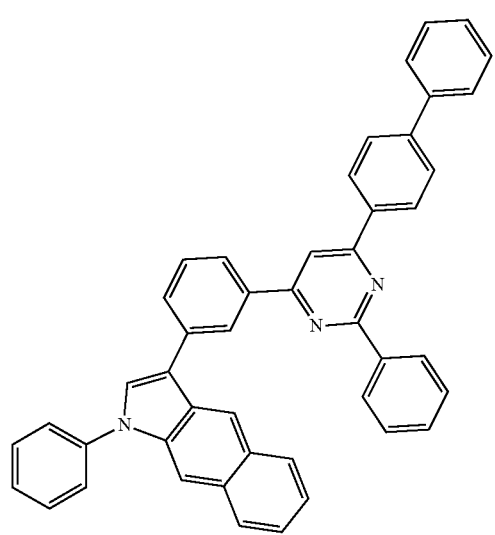
R255
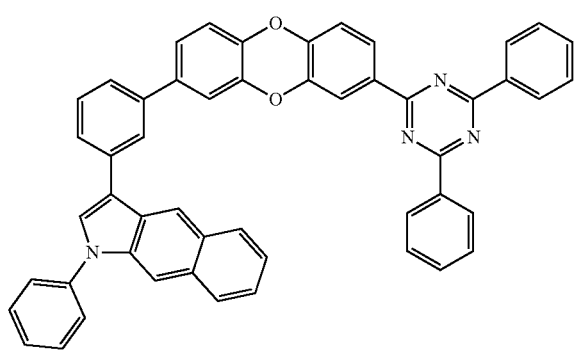
R252
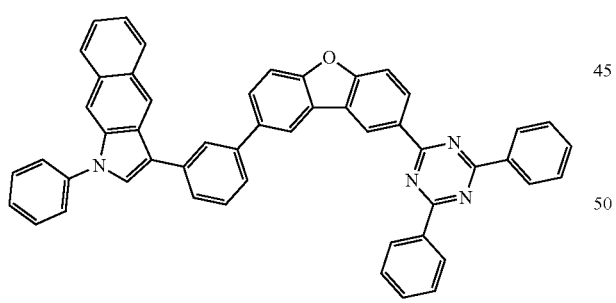
R253
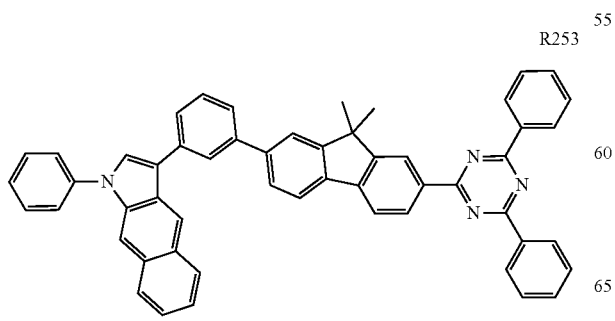
R256
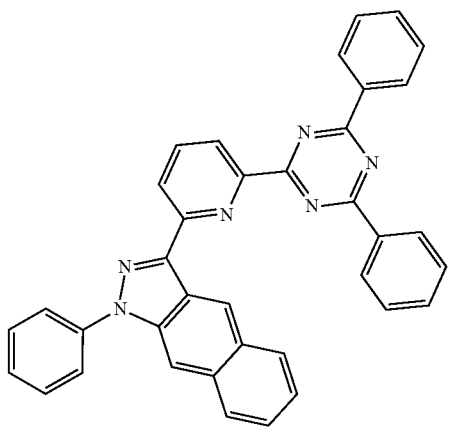

91
-continued
R257
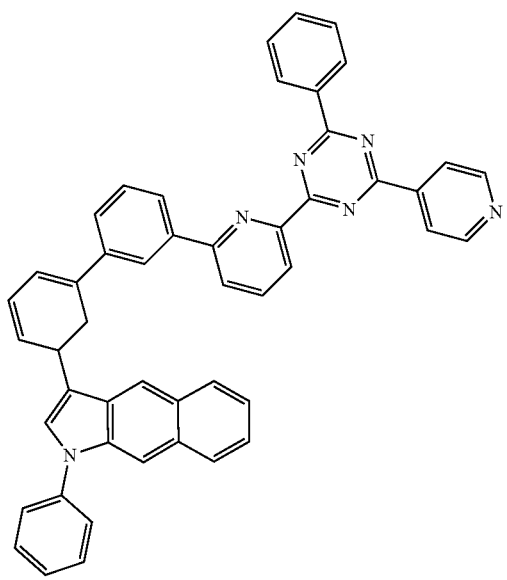
R258
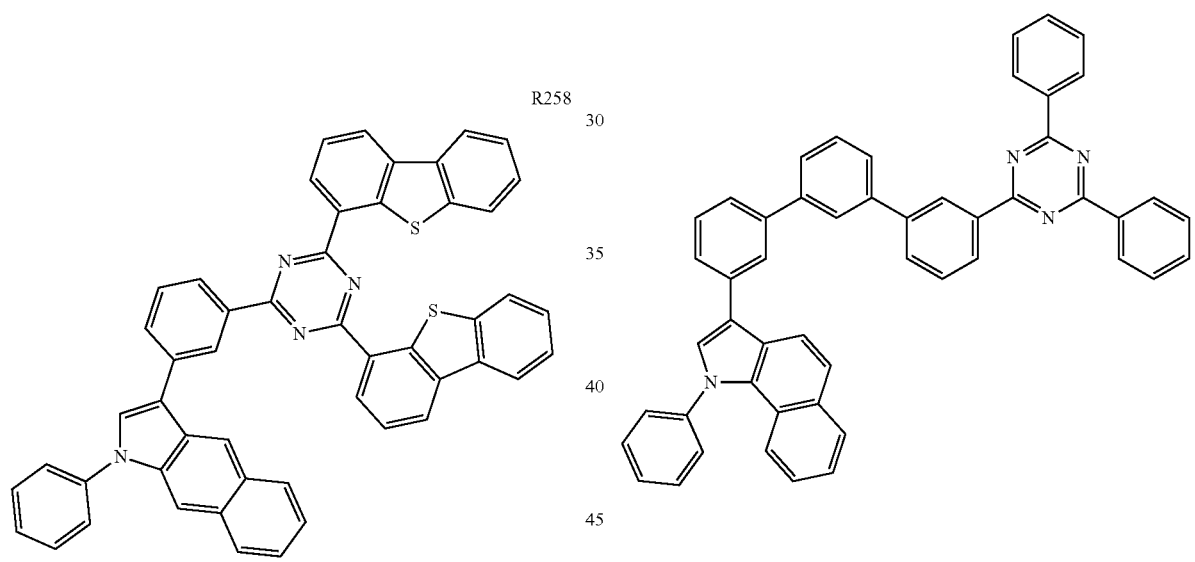
R259
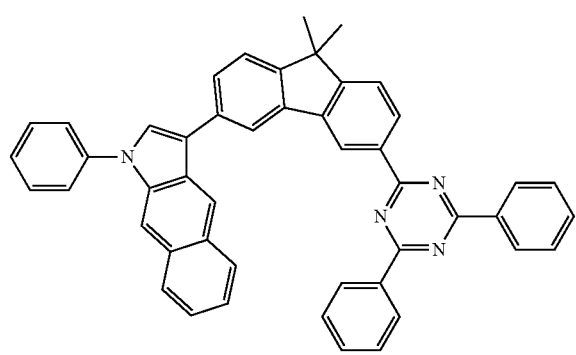
92
-continued
R260
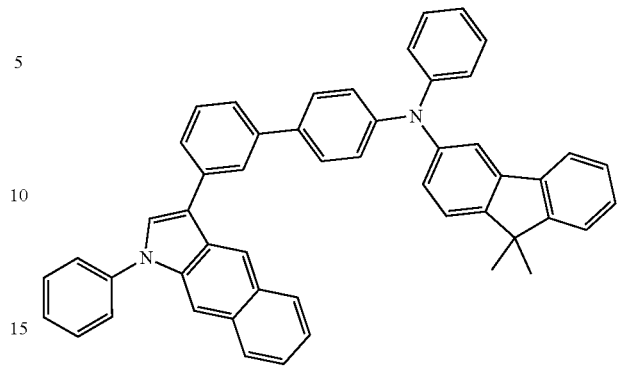
R261
R262
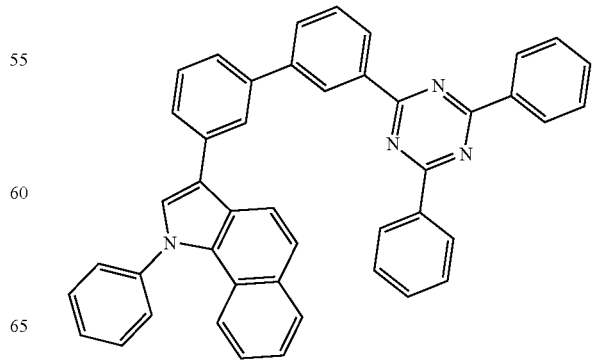

R263
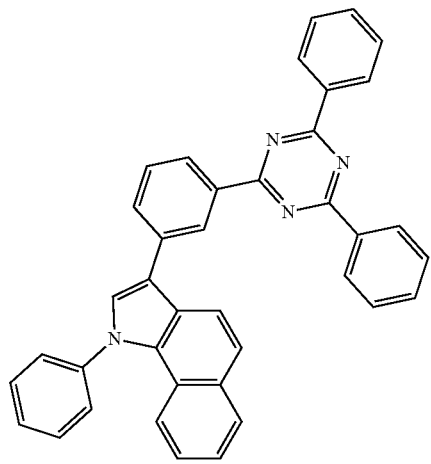
R264
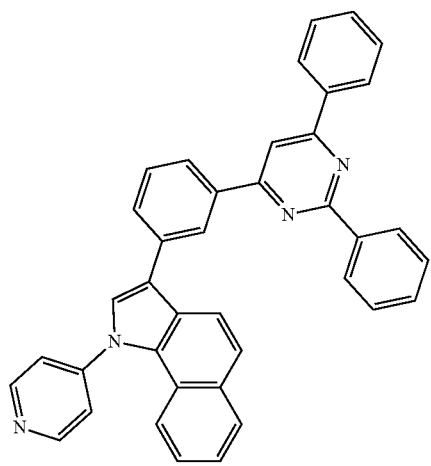
R265
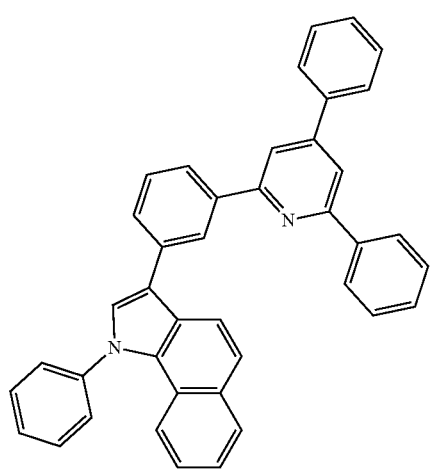
R266
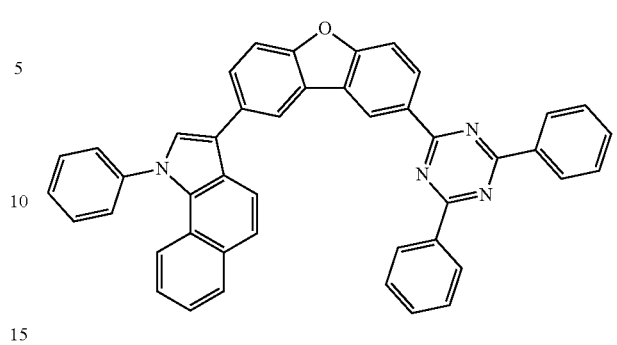
R267
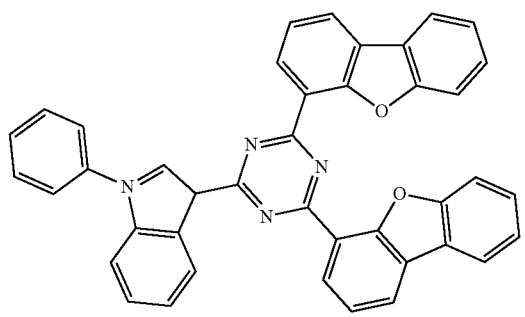
R268
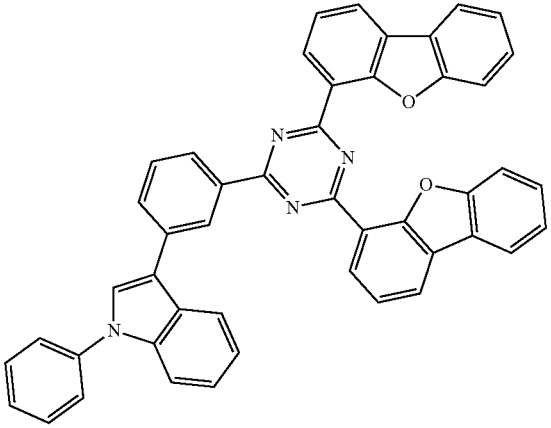
R269
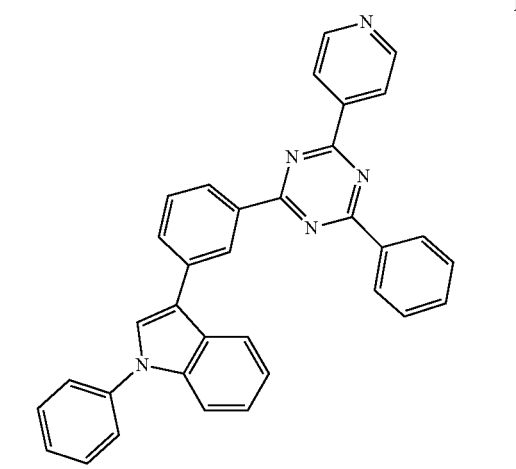

R270 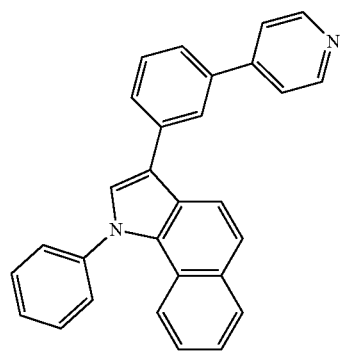
R273 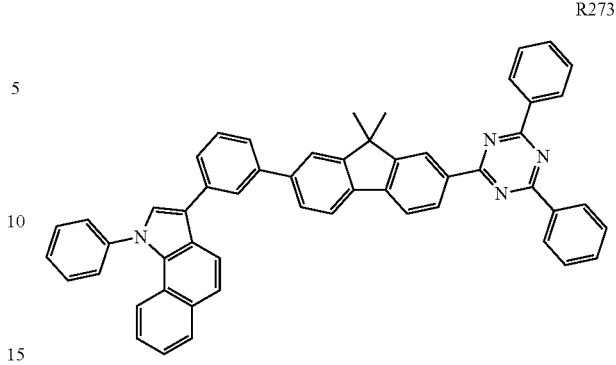
R271 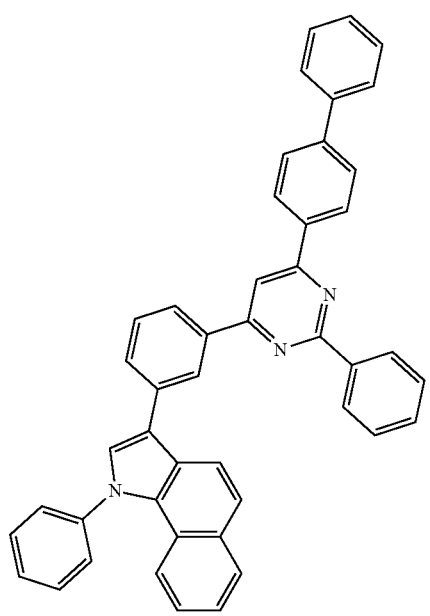
R274 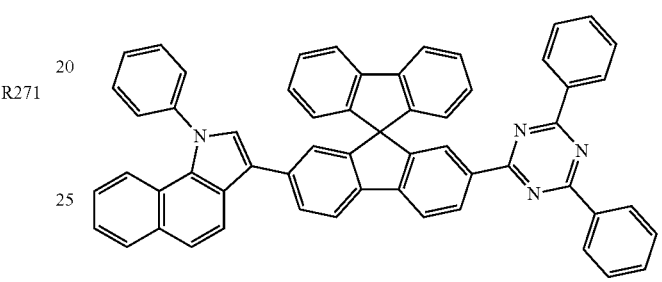
R275 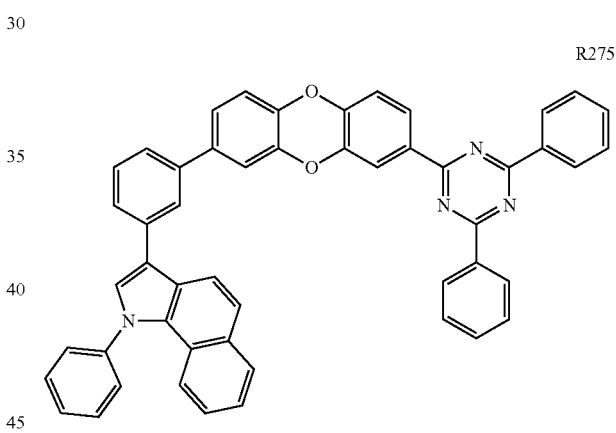
R272 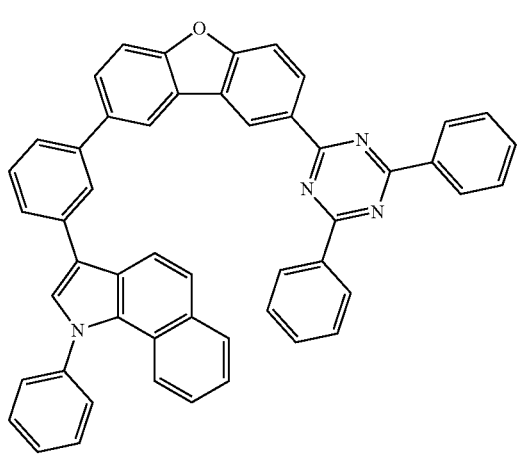
R276 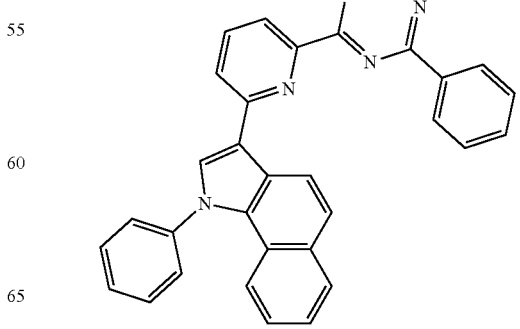

R277
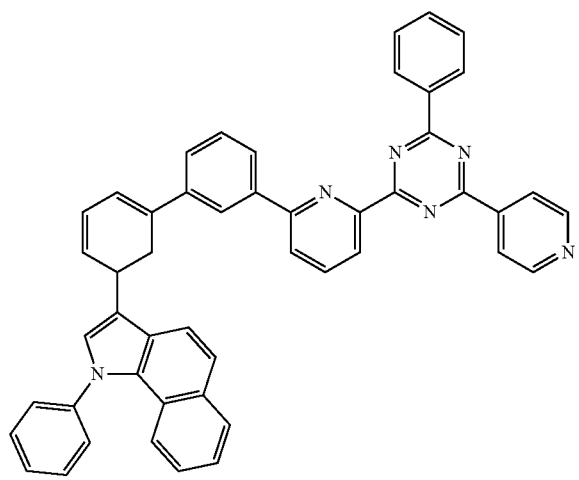
R278
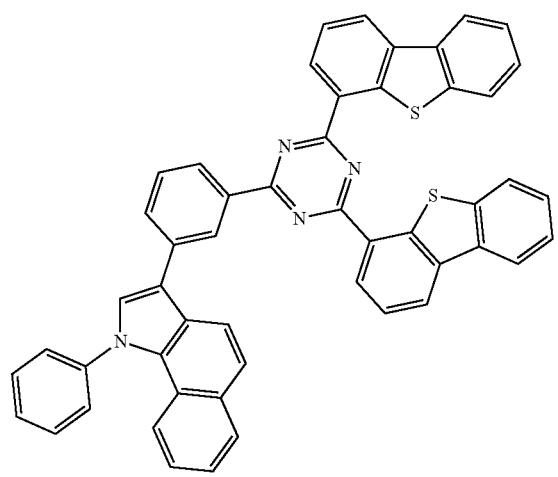
R279
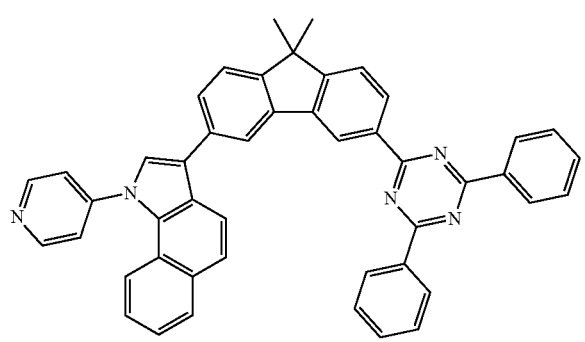
R280
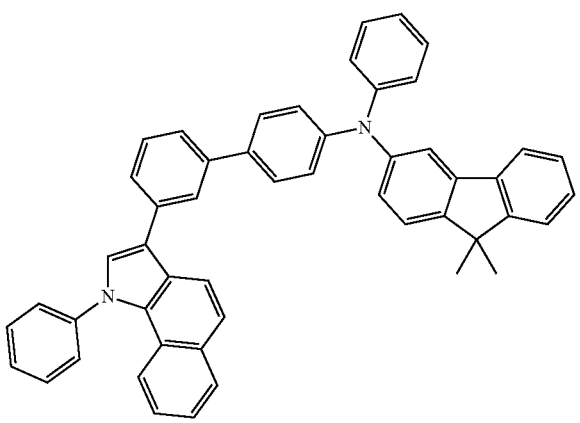
R281
R282
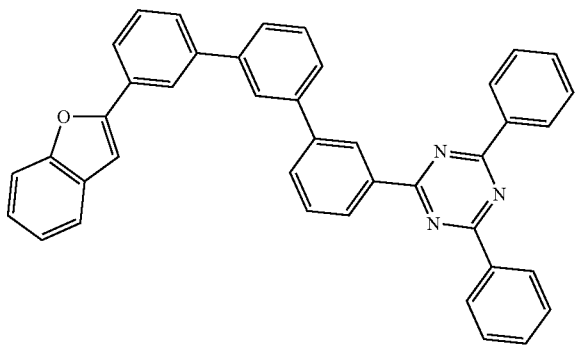

R283
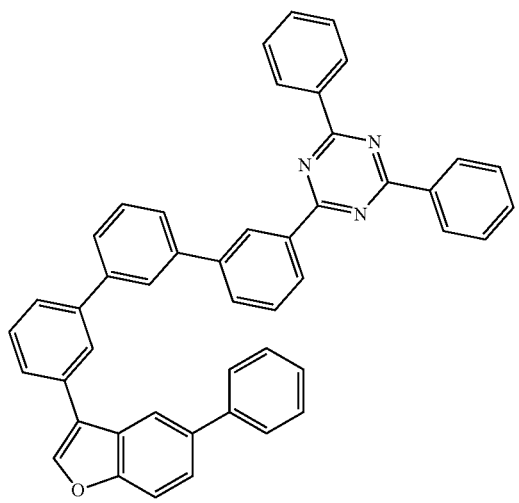
R284
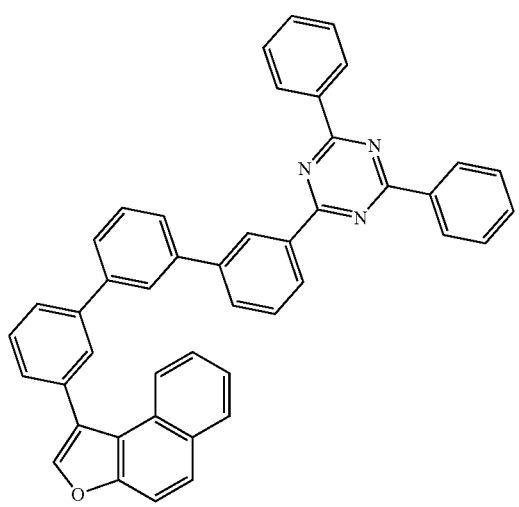
R285
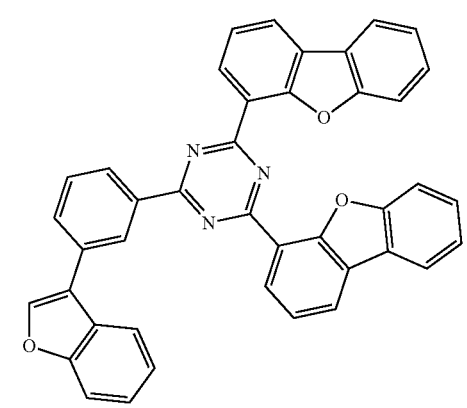
R286
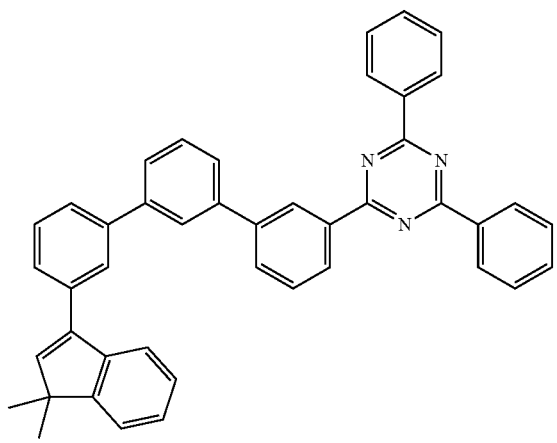
R287
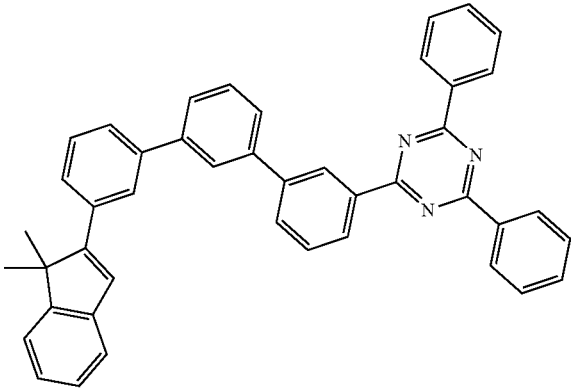
R288
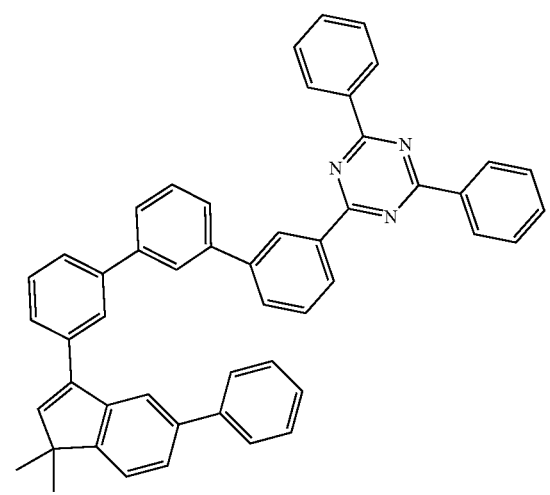

R289
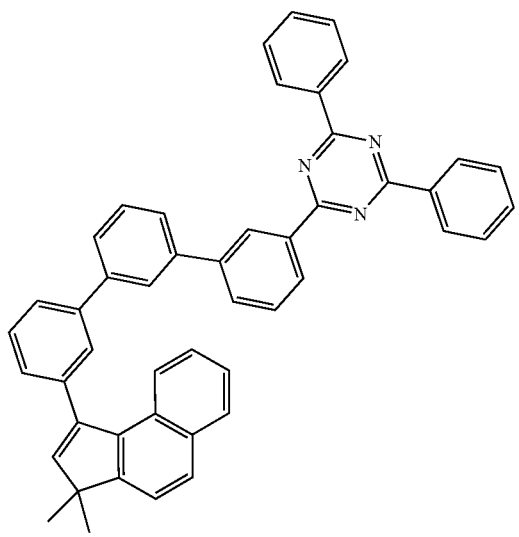
R290
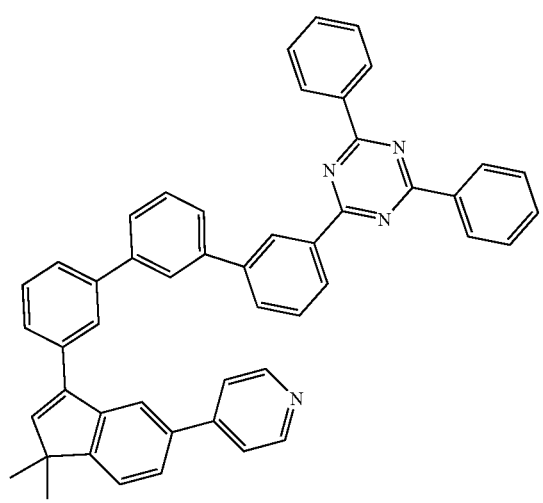
R291
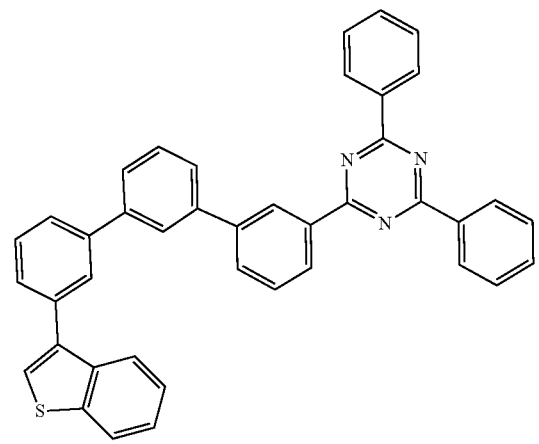
R292
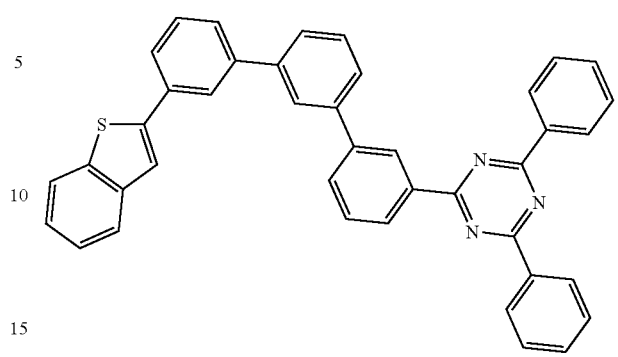
R293
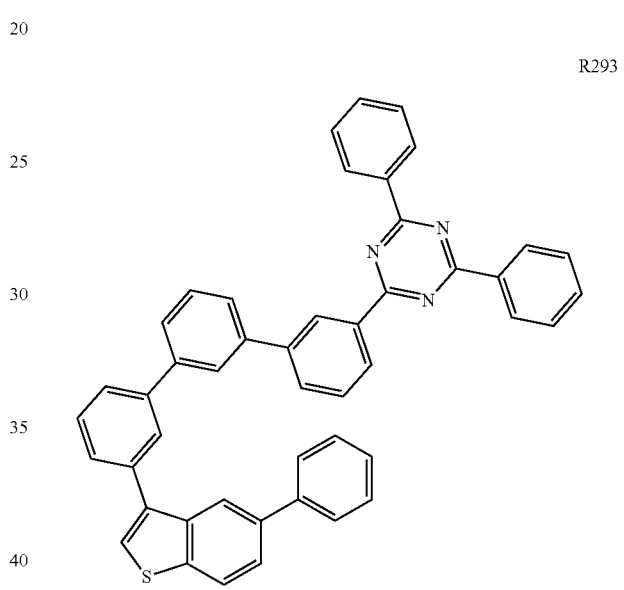
R294
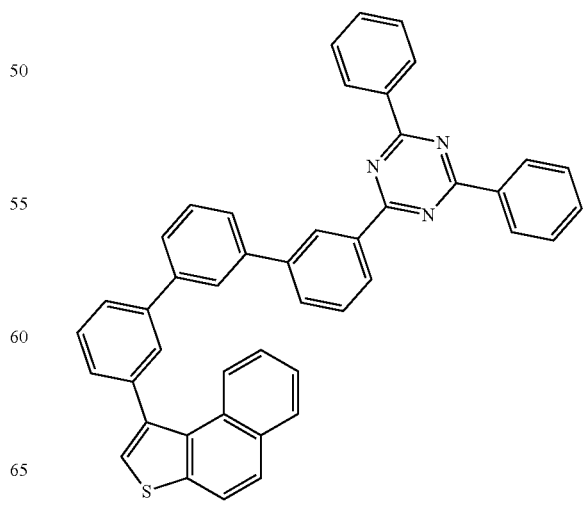

R295
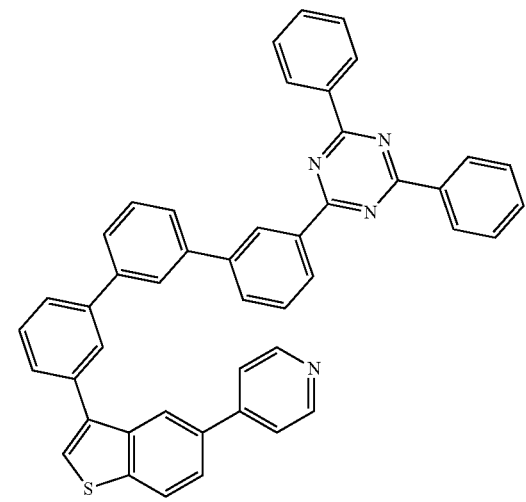
R296
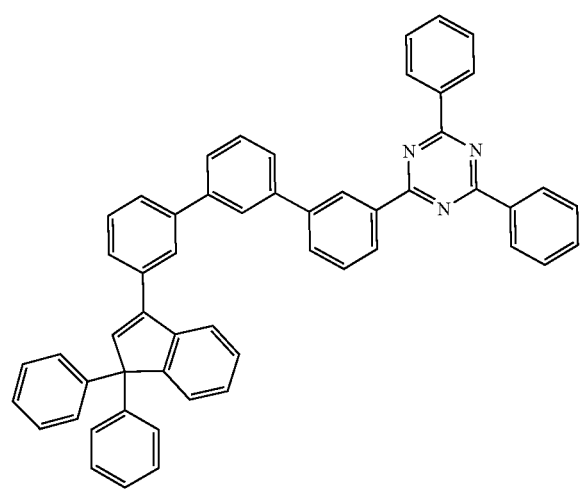
R297
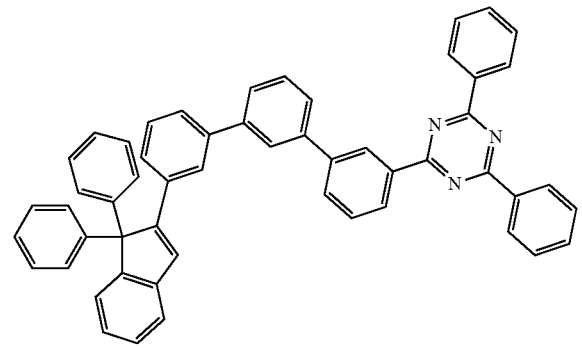
R298
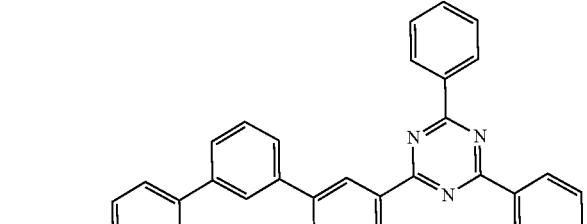
R299
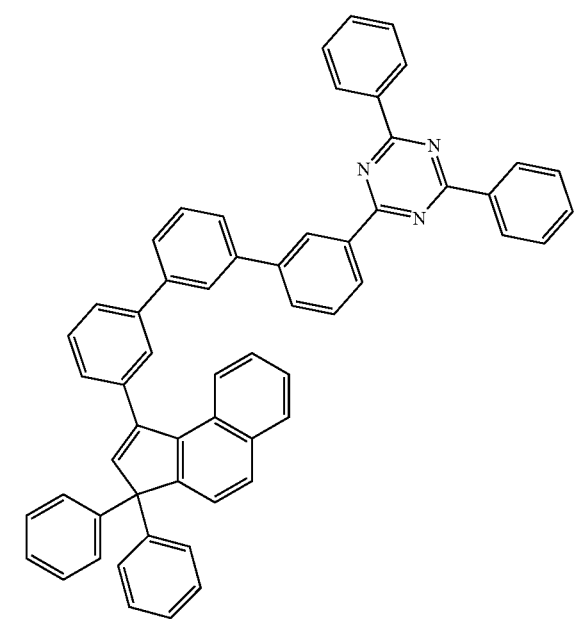
R300

The compound of Chemical Formula 1 of the present invention may be synthesized using general synthesis methods (refer to *Chem. Rev.,* 60:313 (1960); *J. Chem. SOC.* 4482 (1955); Chem. Rev. 95: 2457 (1995) or the like). Detailed synthesis processes of the compounds of the present invention will be specifically described in synthesis examples to be described later.

2. Organic Electroluminescent Device

Meanwhile, another aspect of the present invention relates to an organic electroluminescent device (organic EL device) including the compound represented by Chemical Formula 1 according to the present invention.

Specifically, the present invention relates to an organic electroluminescent device including an anode, a cathode, and one or more organic material layers provided between the anode and the cathode, and at least one of the one or more organic material layers includes the compound represented by Chemical Formula 1. Herein, the compound may be used either alone or as a mixture of two or more.

The one or more organic material layers may be any one or more of a hole injection layer, a hole transport layer, a light emitting layer, a light emitting auxiliary layer, a lifetime improving layer, an electron transport layer, an electron transport auxiliary layer and an electron injection layer, and at least one organic material layer among these may include the compound represented by Chemical Formula 1.

The structure of the organic electroluminescent device according to the present invention described above is not particularly limited, but, when referring to FIG. 1 as one example, includes an anode (10) and a cathode (20) facing each other, and an organic layer (30) located between the anode (10) and the cathode (20). Herein, the organic layer (30) may include a hole transport layer (31), a light emitting layer (32) and an electron transport layer (34). In addition, a hole transport auxiliary layer (33) may be included between the hole transport layer (31) and the light emitting layer (32), and an electron transport auxiliary layer (35) may be included between the electron transport layer (34) and the light emitting layer (32).

When referring to FIG. 2 as another example of the present invention, the organic layer (30) may further include a hole injection layer (37) between the hole transport layer (31) and the anode (10), and may further include an electron injection layer (36) between the electron transport layer (34) and the cathode (20).

The hole injection layer (37) laminated between the hole transport layer (31) and the anode (10) in the present invention is a layer having a function of, as well as improving interfacial properties between ITO used as the anode and an organic material used as the hole transport layer (31), smoothing the ITO surface by being coated on the top of the ITO of which surface is not smooth, and those commonly used in the art may be used without particular limit, and for example, amine compounds may be used. However, the hole injection layer is not limited thereto.

In addition, the electron injection layer (36) is a layer laminated on the top of the electron transport layer and having a function of facilitating electron injection from the cathode and eventually improving power efficiency, and is not particularly limited as long as it is commonly used in the art. For example, materials such as LiF, Liq, NaCl, CsF, $Li_2O$ or BaO may be used.

Although not shown in the drawings in the present invention, a light emitting auxiliary layer may be further included between the hole transport auxiliary layer (33) and the light emitting layer (32). The light emitting auxiliary layer may perform a role of adjusting a thickness of the organic layer (30) while performing a role of transporting holes to the light emitting layer (32). The light emitting auxiliary layer may include a hole transport material, and may be formed with the same material as the hole transport layer (31).

In addition, although not shown in the drawings in the present invention, a lifetime improving layer may be further included between the electron transport auxiliary layer (35) and the light emitting layer (32). Holes migrating to the light emitting layer (32) by getting on an ionization potential level in an organic light emitting device are not able to diffuse or migrate to the electron transport layer by being blocked by a high energy bather of the lifetime improving layer, and consequently, the lifetime improving layer has a function of limiting the holes in the light emitting layer. Such a function of limiting the holes in the light emitting layer prevents the holes from diffusing to the electron transport layer migrating electrons by reduction, and therefore, suppresses a lifetime decrease phenomenon caused through an irreversible decomposition reaction by oxidation, and thereby contributes to improving a lifetime of the organic light emitting device.

The compound represented by Chemical Formula 1 in the present invention has an EWG bonding to a 5-membered aromatic ring or a 5-membered aromatic heteroring such as indole, indazole, indene, benzofuran, benzothiophene or triazolo, and may be used as a host material since, by having a similar energy level with carbazole, the energy level may be adjusted to be higher than a dopant energy level. Particularly, benzofuran and benzothiophene moieties are electron abundant, and when used as an electron transport layer material of an organic electroluminescent device, mobility increases, and as a result, an increase in the luminous efficiency and a decrease in the driving voltage may be expected. In addition, the 5-membered aromatic ring or the 5-membered aromatic heteroring of the present invention has a smaller molecular weight compared to existing compounds, and therefore, may be deposited at a relatively lower deposition temperature when deposited compared to other materials, and favorable processability and enhanced thermal stability may be obtained.

Accordingly, the compound represented by Chemical Formula 1 of the present invention may be used as a material of any one of a hole injection layer, a hole transport layer, a light emitting layer, an electron transport layer and an electron injection layer, an organic material layer of an organic electroluminescent device, but may be preferably used as a material of any of a light emitting layer, an electron transport layer, and an electron transport auxiliary layer further laminated on the electron transport layer, and more preferably used as a material of an electron transport layer or an electron transport auxiliary layer.

In addition, when using the compound according to the present invention as a light emitting layer material, the compound represented by Chemical Formula 1 may be specifically used as a phosphorescent host, a fluorescent host or a dopant material of the light emitting layer, and may be preferably used as a phosphorescent host (blue, green and/or red phosphorescent host material).

In addition, the organic electroluminescent device in the present invention has, as described above, an anode, one or more organic material layers and a cathode consecutively laminated, and in addition thereto, may further include an insulating layer or an adhesive layer at an interface between the electrode and the organic material layer.

Except that at least one or more of the organic material layers (for example, electron transport auxiliary layer) are formed to include the compound represented by Chemical Formula 1, the organic electroluminescent device of the present invention may be manufactured by forming other organic material layers and electrodes using materials and methods known in the art.

The organic material layer may be formed using a vacuum deposition method or a solution coating method. Examples of the solution coating method may include spin coating, dip coating, doctor blading, inkjet printing, thermal transfer method or the like, but are not limited thereto.

A substrate capable of being used in the present invention is not particularly limited, and silicon wafers, quartz, glass plates, metal plates, plastic films, sheets and the like may be used.

The anode material may be prepared using, for example, a conductor having high work function so as to have smooth hole injection, and examples thereof may include metals such as vanadium, chromium, copper, zinc or gold, or alloys thereof; metal oxides such as zinc oxide, indium oxide, indium tin oxide (ITO) or indium zinc oxide (IZO); combinations of metals and oxides such as ZnO:Al or $SnO_2$:Sb; conductive polymers such as polythiophene, poly(3-methylthiophene), poly[3,4-(ethylene-1,2-dioxy)thiophene] (PEDT), polypyrrole or polyaniline; carbon black, and the like, but are not limited thereto.

The cathode material may be prepared using, for example, a conductor having low work function so as to have smooth electron injection, and examples thereof may include metals such as magnesium, calcium, sodium, potassium, titanium, indium, yttrium, lithium, gadolinium, aluminum, silver, tin or lead, or alloys thereof; and multilayer-structured materials such as LiF/Al or $LiO_2$/Al, but are not limited thereto.

Hereinafter, the present invention will be described in detail with reference to examples as follows. However, the following examples are for illustrative purposes only, and the present invention is not limited to the following examples.

[Preparation Example 1] Synthesis of A1

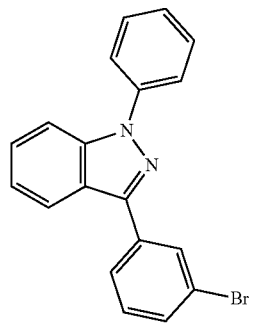

+

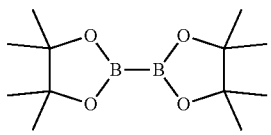 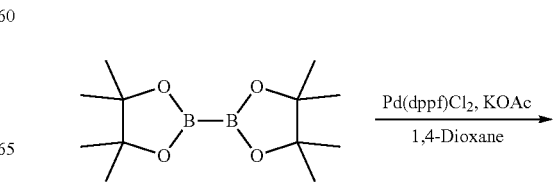

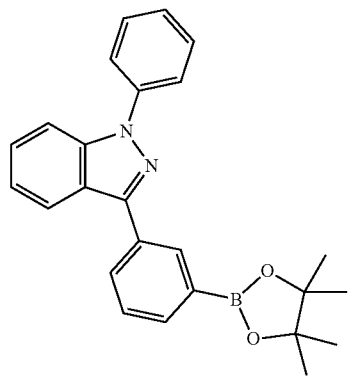

A1

Under a nitrogen stream, 3-(3-bromophenyl)-1-phenyl-1H-indazole (8.5 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol) and 1,4-dioxane (200 ml) were mixed, and stirred for 6 hours at 130° C.

After the reaction was finished, the result was extracted with ethyl acetate, the moisture was removed using MgSO$_4$, and the result was purified using column chromatography to obtain target Compound A1 (6.8 g, 17.1 mmol, yield 70%).

GC-Mass (theoretical value: 396.3 g/mol, measured value: 396 g/mol)

1H-NMR: δ 1.25 (s, 12H), 7.45~7.55 (m, 8H), 7.62 (s, 1H), 7.84~92 (m, 4H)

[Preparation Example 2] Synthesis of A2

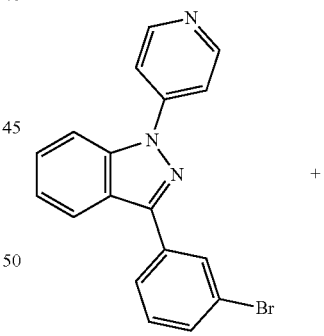

+

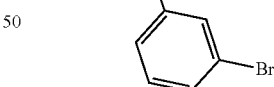 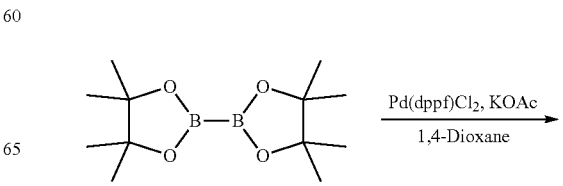

-continued

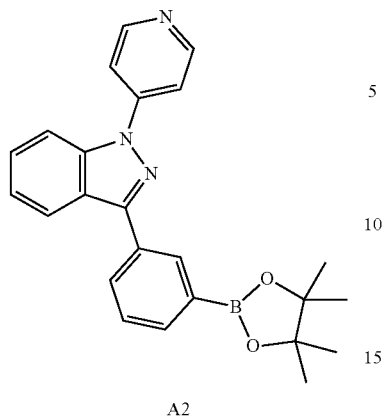

A2

A3

Under a nitrogen stream, 3-(3-bromophenyl)-1-(pyridin-4-yl)-1H-indazole (8.5 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g 73.1 mmol) and 1,4-dioxane (200 ml) were mixed, and stirred for 6 hours at 130° C.

After the reaction was finished, the result was extracted with ethyl acetate, the moisture was removed using MgSO$_4$, and the result was purified using column chromatography to obtain target Compound A2 (7.3 g, 18.3 mmol, yield 75%).

GC-Mass (theoretical value: 397.3 g/mol, measured value: 397 g/mol)

1H-NMR: δ 1.25 (s, 12H), 7.45~7.55 (m, 5H), 7.62 (s, 1H), 7.84~92 (m, 4H), 8.11~12 (d, 2H)

Under a nitrogen stream, 3-(3-bromophenyl)-1,5-diphenyl-1H-indazole (10.4 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g 73.1 mmol) and 1,4-dioxane (200 ml) were mixed, and stirred for 6 hours at 130° C.

After the reaction was finished, the result was extracted with ethyl acetate, the moisture was removed using MgSO$_4$, and the result was purified using column chromatography to obtain target Compound A3 (8.6 g, 18.3 mmol, yield 75%).

GC-Mass (theoretical value: 472.4 g/mol, measured value: 472 g/mol)

1H-NMR: δ 1.25 (s, 12H), 7.44~7.59 (m, 14H), 7.62 (s, 1H), 8.23~25 (d, 2H)

[Preparation Example 3] Synthesis of A3

[Preparation Example 4] Synthesis of A4

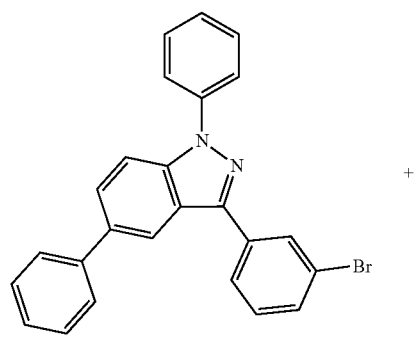 +

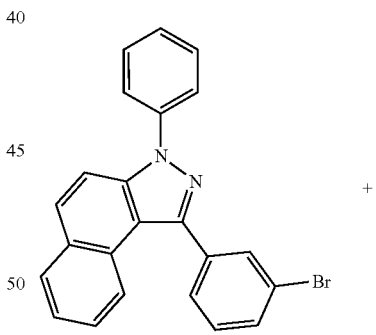 +

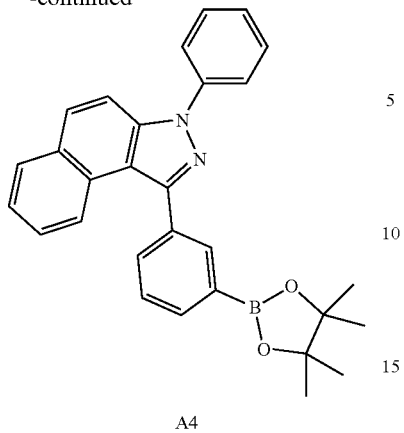

A4

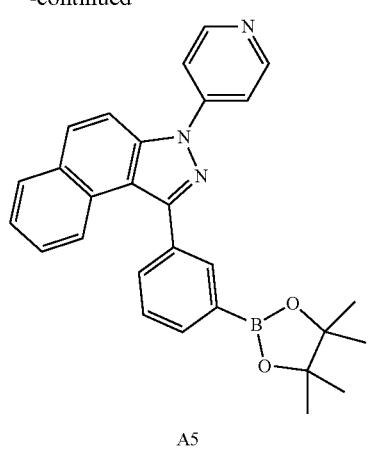

A5

Under a nitrogen stream, 1-(3-bromophenyl)-3-phenyl-3H-benzo[e]indazole (9.7 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g 73.1 mmol) and 1,4-dioxane (200 ml) were mixed, and stirred for 6 hours at 130° C.

After the reaction was finished, the result was extracted with ethyl acetate, the moisture was removed using MgSO$_4$, and the result was purified using column chromatography to obtain target Compound A4 (7.6 g, 17.1 mmol, yield 70%).

GC-Mass (theoretical value: 446.4 g/mol, measured value: 446 g/mol)

1H-NMR: δ 1.25 (s, 12H), 7.45~7.55 (m, 10H), 7.62 (s, 1H), 7.81~99 (m, 4H)

Under a nitrogen stream, 1-(3-bromophenyl)-3-(pyridin-4-yl)-3H-benzo[e]indazole (9.8 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol) and 1,4-dioxane (200 ml) were mixed, and stirred for 6 hours at 130° C.

After the reaction was finished, the result was extracted with ethyl acetate, the moisture was removed using MgSO$_4$, and the result was purified using column chromatography to obtain target Compound A5 (7.6 g, 17.1 mmol, yield 70%).

GC-Mass (theoretical value: 447.4 g/mol, measured value: 447 g/mol)

1H-NMR: δ 1.25 (s, 12H), 7.45~7.55 (m, 9H), 7.62 (s, 1H), 7.81~99 (m, 2H), 8.21~23 (d, 2H)

[Preparation Example 5] Synthesis of A5

[Preparation Example 6] Synthesis of A6

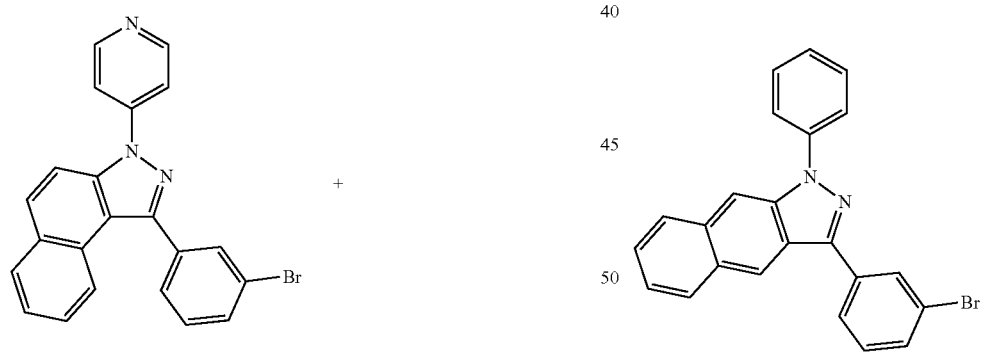

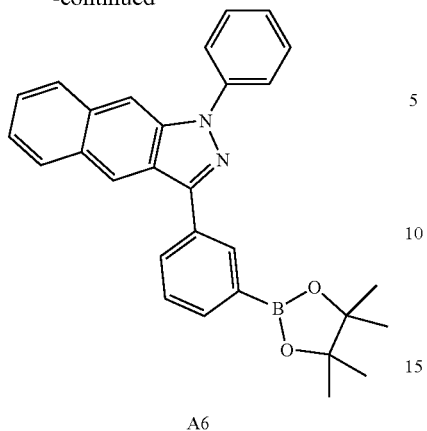

A6

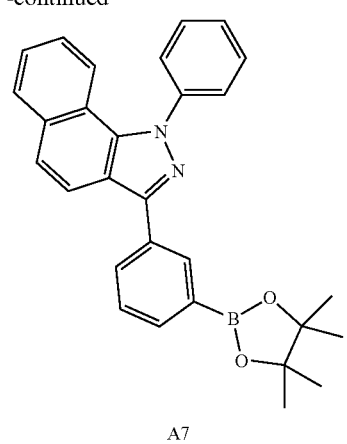

A7

Under a nitrogen stream, 3-(3-bromophenyl)-1-phenyl-1H-benzo[f]indazole (9.7 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol) and 1,4-dioxane (200 ml) were mixed, and stirred for 6 hours at 130° C.

After the reaction was finished, the result was extracted with ethyl acetate, the moisture was removed using MgSO$_4$, and the result was purified using column chromatography to obtain target Compound A6 (7.6 g, 17.1 mmol, yield 70%).

GC-Mass (theoretical value: 446.4 g/mol, measured value: 446 g/mol)

1H-NMR: δ 1.25 (s, 12H), 7.45~7.55 (m, 10H), 7.58 (s, 1H), 7.61 (s, 1H), 7.78 (s, 1H), 7.81~86 (m, 2H)

[Preparation Example 7] Synthesis of A7

Under a nitrogen stream, 3-(3-bromophenyl)-1-phenyl-1H-benzo[g]indazole (9.7 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol) and 1,4-dioxane (200 ml) were mixed, and stirred for 6 hours at 130° C.

After the reaction was finished, the result was extracted with ethyl acetate, the moisture was removed using MgSO$_4$, and the result was purified using column chromatography to obtain target Compound A7 (7.6 g, 17.1 mmol, yield 70%).

GC-Mass (theoretical value: 446.36 g/mol, measured value: 446 g/mol)

1H-NMR: δ 1.25 (s, 12H), 7.45~7.54 (m, 10H), 7.62 (s, 1H), 7.81~88 (m, 4H)

[Preparation Example 8] Synthesis of A8

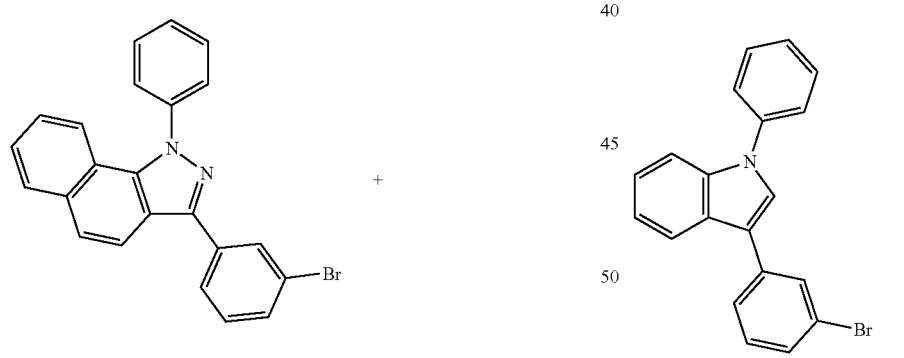

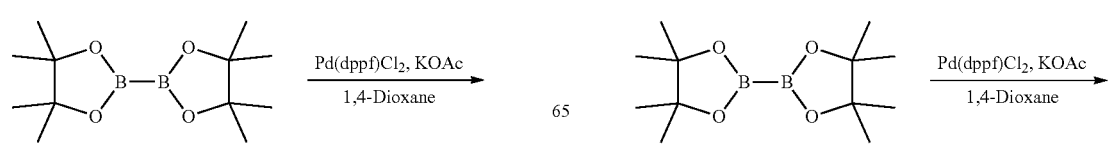

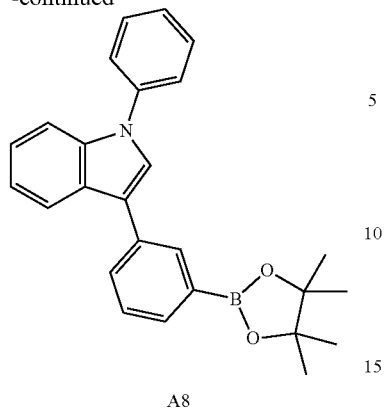

A8

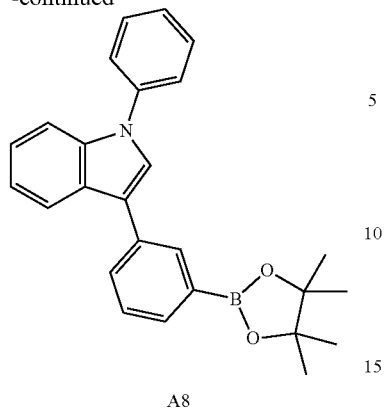

A9

Under a nitrogen stream, 3-(3-bromophenyl)-1-phenyl-1H-indole (8.5 g, 24.4 mmol), 4,4,4',4',5,5,5',5'-octamethyl-2,2'-bi(1,3,2-dioxaborolane) (7.4 g, 29.2 mmol), Pd(dppf)Cl₂ (0.6 g, 0.7 mmol), KOAc (7.2 g, 73.1 mmol) and 1,4-dioxane (200 ml) were mixed, and stirred for 6 hours at 130° C.

After the reaction was finished, the result was extracted with ethyl acetate, the moisture was removed using MgSO₄, and the result was purified using column chromatography to obtain target Compound A8 (6.7 g, 17.1 mmol, yield 70%).

GC-Mass (theoretical value: 395.3 g/mol, measured value: 395 g/mol)

1H-NMR: δ 1.25 (s, 12H), 7.43~7.55 (m, 9H), 7.62 (s, 1H), 7.84~92 (m, 4H)

Under a nitrogen stream, 3-(3-bromophenyl)-1-(pyridin-4-yl)-1H-indole (8.5 g 24.4 mmol), 4,4,4',4',5,5,5',5'-octamethyl-2,2'-bi(1,3,2-dioxaborolane) (7.4 g, 29.2 mmol), Pd(dppf)Cl₂ (0.6 g, 0.7 mmol), KOAc (7.2 g 73.1 mmol) and 1,4-dioxane (200 ml) were mixed, and stirred for 6 hours at 130° C.

After the reaction was finished, the result was extracted with ethyl acetate, the moisture was removed using MgSO₄, and the result was purified using column chromatography to obtain target Compound A9 (6.8 g, 17.1 mmol, yield 70%).

GC-Mass (theoretical value: 396.3 g/mol, measured value: 396 g/mol)

1H-NMR: δ 1.25 (s, 12H), 7.41~7.55 (m, 6H), 7.62 (s, 1H), 7.84~92 (m, 4H), 8.11~12 (d, 2H)

[Preparation Example 9] Synthesis of A9

[Preparation Example 10] Synthesis of A10

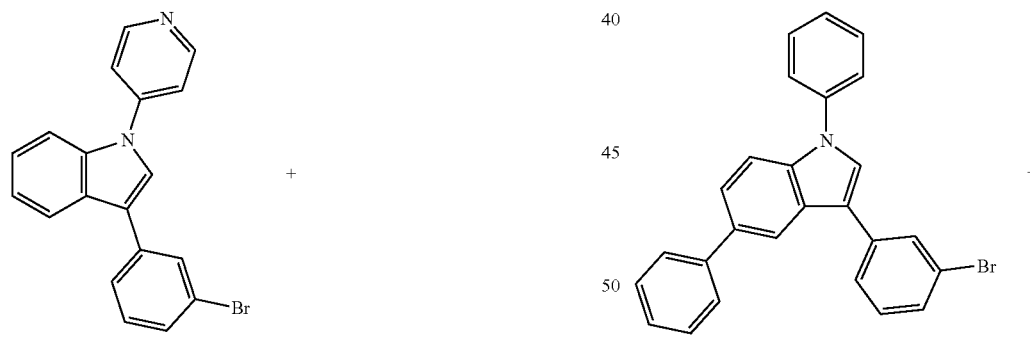

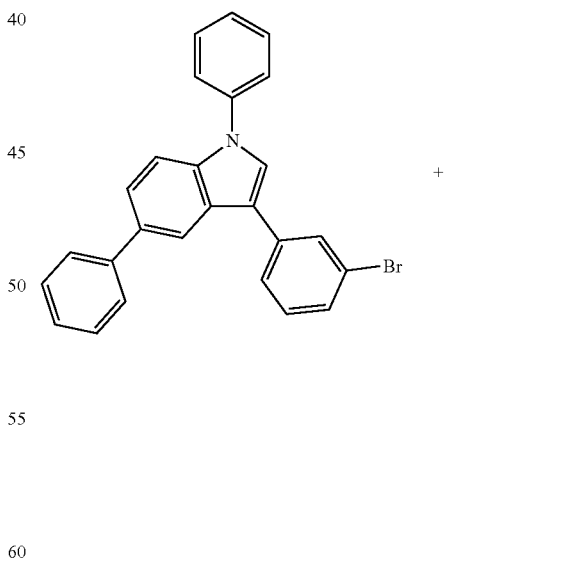

-continued

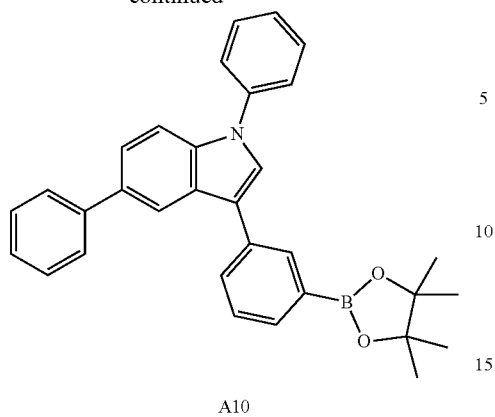

A10

Under a nitrogen stream, 3-(3-bromophenyl)-1,5-diphenyl-1H-indole (10.3 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol) and 1,4-dioxane (200 ml) were mixed, and stirred for 6 hours at 130° C.

After the reaction was finished, the result was extracted with ethyl acetate, the moisture was removed using MgSO$_4$, and the result was purified using column chromatography to obtain target Compound A10 (8.6 g, 18.3 mmol, yield 75%).

GC-Mass (theoretical value: 471.4 g/mol, measured value: 471 g/mol)

1H-NMR: δ 1.25 (s, 12H), 7.41~7.60 (m, 15H), 7.63 (s, 1H), 8.23~25 (d, 2H)

[Preparation Example 11] Synthesis of A11

-continued

A11

Under a nitrogen stream, 1-(3-bromophenyl)-3-phenyl-3H-benzo[e]indole (9.7 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g 73.1 mmol) and 1,4-dioxane (200 ml) were mixed, and stirred for 6 hours at 130° C.

After the reaction was finished, the result was extracted with ethyl acetate, the moisture was removed using MgSO$_4$, and the result was purified using column chromatography to obtain target Compound A11 (7.6 g, 17.1 mmol, yield 70%).

GC-Mass (theoretical value: 445.4 g/mol, measured value: 445 g/mol)

1H-NMR: δ 1.25 (s, 12H), 7.41~7.55 (m, 11H), 7.62 (s, 1H), 7.81·99 (m, 4H)

[Preparation Example 12] Synthesis of A12

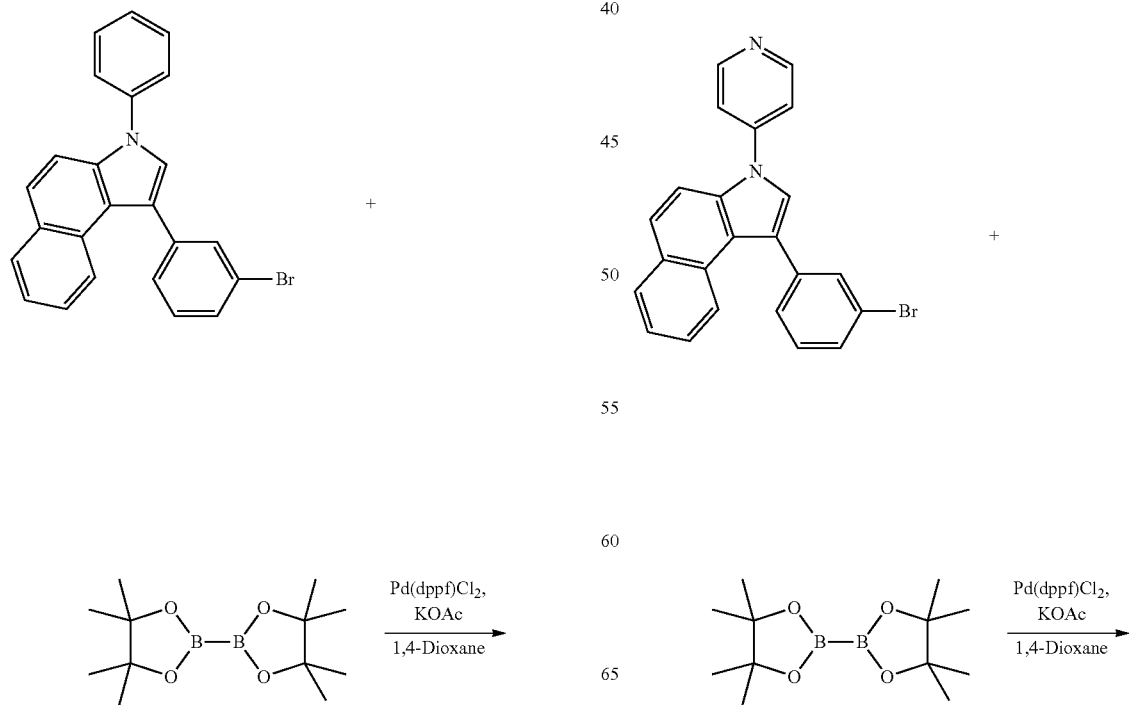

-continued

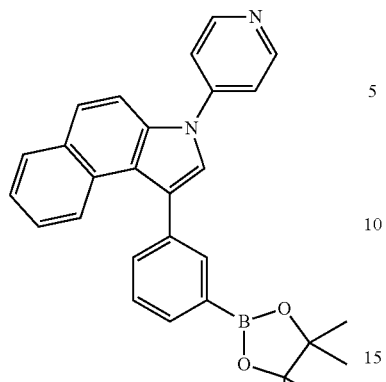

A12

Under a nitrogen stream, 1-(3-bromophenyl)-3-(pyridin-4-yl)-3H-benzo[e]indazole (9.7 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol) and 1,4-dioxane (200 ml) were mixed, and stirred for 6 hours at 130° C.

After the reaction was finished, the result was extracted with ethyl acetate, the moisture was removed using MgSO$_4$, and the result was purified using column chromatography to obtain target Compound A12 (7.6 g, 17.1 mmol, yield 70%).

GC-Mass (theoretical value: 446.4 g/mol, measured value: 446 g/mol)

1H-NMR: δ 1.25 (s, 12H), 7.42~7.55 (m, 10H), 7.62 (s, 1H), 7.81~99 (m, 2H), 8.21~23 (d, 2H)

[Preparation Example 13] Synthesis of A13

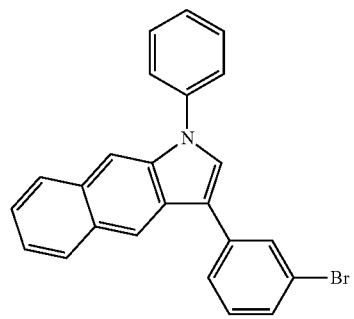

+

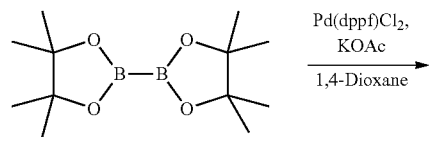

-continued

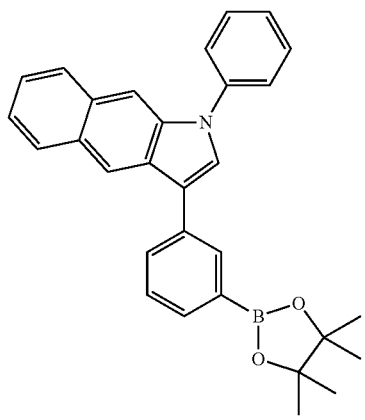

A13

Under a nitrogen stream, 3-(3-bromophenyl)-1-phenyl-1H-benzo[f]indole (9.7 g, 24.4 mmol), 4,4,4',4',5,5,5',5'-octamethyl-2,2'-bi(1,3,2-dioxaborolane) (7.4 g, 29.2 mmol), Pd(dppf)Cl$_2$ (0.6 g, 0.7 mmol), KOAc (7.2 g, 73.1 mmol) and 1,4-dioxane (200 ml) were mixed, and stirred for 6 hours at 130° C.

After the reaction was finished, the result was extracted with ethyl acetate, the moisture was removed using MgSO$_4$, and the result was purified using column chromatography to obtain target Compound A13 (7.6 g, 17.1 mmol, yield 70%).

GC-Mass (theoretical value: 445.4 g/mol, measured value: 445 g/mol)

1H-NMR: δ 1.25 (s, 12H), 7.42~7.55 (m, 11H), 7.58 (s, 1H), 7.61 (s, 1H), 7.78 (s, 1H), 7.81~85 (m, 2H)

[Preparation Example 14] Synthesis of A14

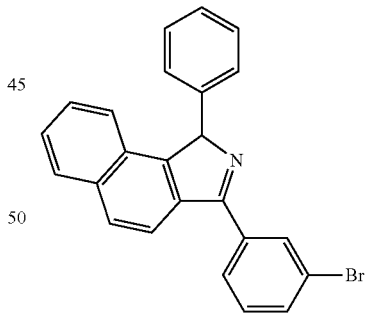

+

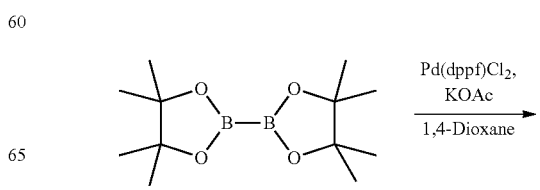

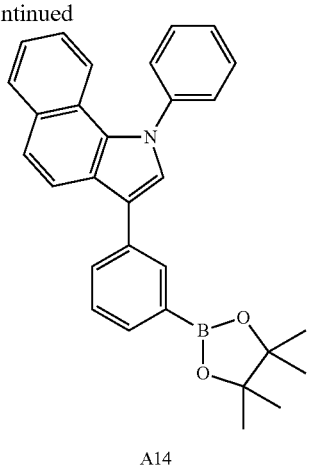

A14

Under a nitrogen stream, 3-(3-bromophenyl)-1-phenyl-1H-benzo[g]indazole (9.7 g, 24.4 mmol), 4,4,4',4',5,5,5',5'-octamethyl-2,2'-bi(1,3,2-dioxaborolane) (7.4 g 29.2 mmol), Pd(dppf)Cl₂ (0.6 g, 0.7 mmol), KOAc (7.2 g, 73.1 mmol) and 1,4-dioxane (200 ml) were mixed, and stirred for 6 hours at 130° C.

After the reaction was finished, the result was extracted with ethyl acetate, the moisture was removed using MgSO₄, and the result was purified using column chromatography to obtain target Compound A14 (7.6 g, 17.1 mmol, yield 70%).

GC-Mass (theoretical value: 445.37 g/mol, measured value: 445 g/mol)

1H-NMR: δ 1.25 (s, 12H), 7.42~7.54 (m, 11H), 7.62 (s, 1H), 7.82~89 (m, 4H)

[Preparation Example 15] Synthesis of A15

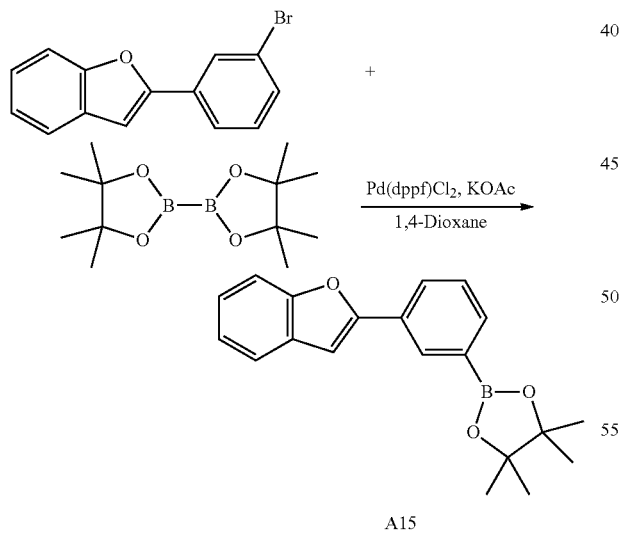

A15

Under a nitrogen stream, 2-(3-bromophenyl)benzofuran (6.7 g, 24.4 mmol), 4,4,4',4',5,5,5',5'-octamethyl-2,2'-bi(1,3,2-dioxaborolane) (7.4 g, 29.2 mmol), Pd(dppf)Cl₂ (0.6 g, 0.7 mmol), KOAc (7.2 g, 73.1 mmol) and 1,4-dioxane (200 ml) were mixed, and stirred for 6 hours at 130° C.

After the reaction was finished, the result was extracted with ethyl acetate, the moisture was removed using MgSO₄, and the result was purified using column chromatography to obtain target Compound A15 (5.5 g, 17.1 mmol, yield 70%).

GC-Mass (theoretical value: 320.2 g/mol, measured value: 320 g/mol)

1H NMR: δ 1.25 (s, 12H), 7.11 (s, 1H), 7.58 (s, 1H), 7.67~7.89 (m, 7H)

[Preparation Example 16] Synthesis of A16

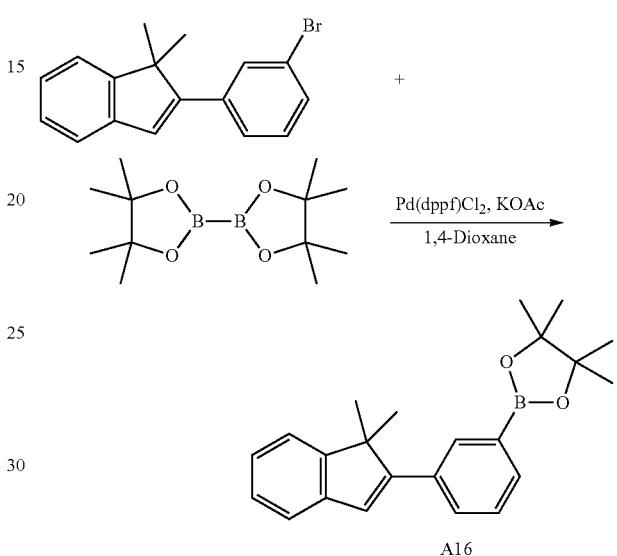

A16

Under a nitrogen stream, 2-(3-bromophenyl)-1,1-dimethyl-1H-indene (7.3 g, 24.4 mmol), 4,4,4',4',5,5,5',5'-octamethyl-2,2'-bi(1,3,2-dioxaborolane) (7.4 g, 29.2 mmol), Pd(dppf)Cl₂ 0.6 g, 0.7 mmol), KOAc (7.2 g, 73.1 mmol) and 1,4-dioxane (200 ml) were mixed, and stirred for 6 hours at 130° C.

After the reaction was finished, the result was extracted with ethyl acetate, the moisture was removed using MgSO₄, and the result was purified using column chromatography to obtain target Compound A16 (5.9 g, 17.1 mmol, yield 70%).

GC-Mass (theoretical value: 346.28 g/mol, measured value: 346 g/mol)

1H-NMR: δ 1.25 (s, 12H), 1.69 (s, 6H), 7.01 (s, 1H), 7.45 (s, 1H), 7.57~7.77 (m, 7H)

[Preparation Example 17] Synthesis of A17

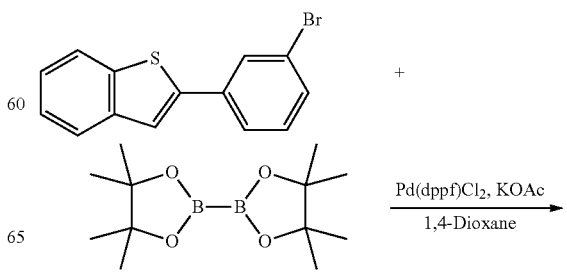

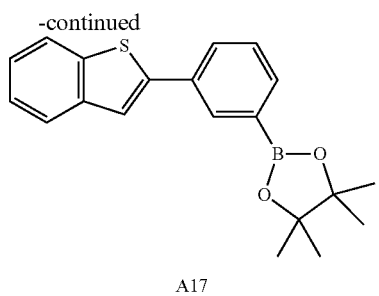

A17

Under a nitrogen stream, 2-(3-bromophenyl)benzo[b]thiophene (7.0 g, 24.4 mmol), 4,4,4',4',5,5,5',5'-octamethyl-2,2'-bi(1,3,2-dioxaborolane) (7.4 g, 29.2 mmol), Pd(dppf)Cl₂ (0.6 g, 0.7 mmol), KOAc (7.2 g, 73.1 mmol) and 1,4-dioxane (200 ml) were mixed, and stirred for 6 hours at 130° C.

After the reaction was finished, the result was extracted with ethyl acetate, the moisture was removed using MgSO₄, and the result was purified using column chromatography to obtain target Compound A17 (6.1 g, 18.3 mmol, yield 75%).

GC-Mass (theoretical value: 336.26 g/mol, measured value: 336 g/mol)

1H-NMR: δ 1.25 (s, 12H), 7.51 (s, 1H), 7.59 (s, 1H), 7.72~7.92 (m, 7H)

[Synthesis Example 1] Synthesis of R1

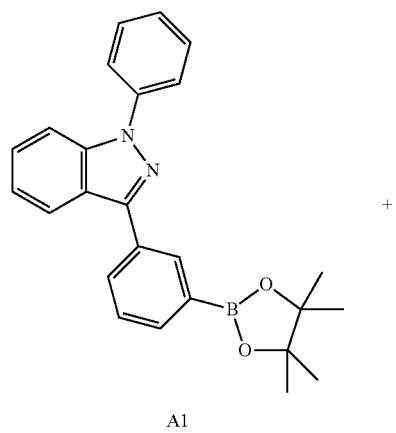

A1

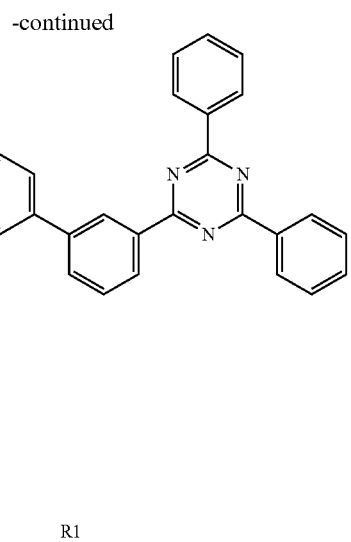

R1

Under a nitrogen stream, A1 (6.8 g, 17.1 mmol), 2-(3'-bromobiphenyl-3-yl)-4,6-diphenyl-1,3,5-triazine (8.7 g 18.8 mmol), Pd(PPh₃)₄ (1.0 g, 5 mol %), potassium carbonate (7.1 g, 51.2 mmol) and toluene/H₂O/ethanol (80 ml/40 ml/40 ml) were introduced, and stirred for 3 hours at 110° C.

After the reaction was finished, the organic layer was separated using methylene chloride, and water was removed using MgSO₄. After the solvent of the organic layer was removed, the result was purified using column chromatography to obtain target Compound R1 (8.4 g, 12.8 mmol, yield 75%).

GC-Mass (theoretical value: 653.8 g/mol, measured value: 653 g/mol)

[Synthesis Example 2] Synthesis of R8

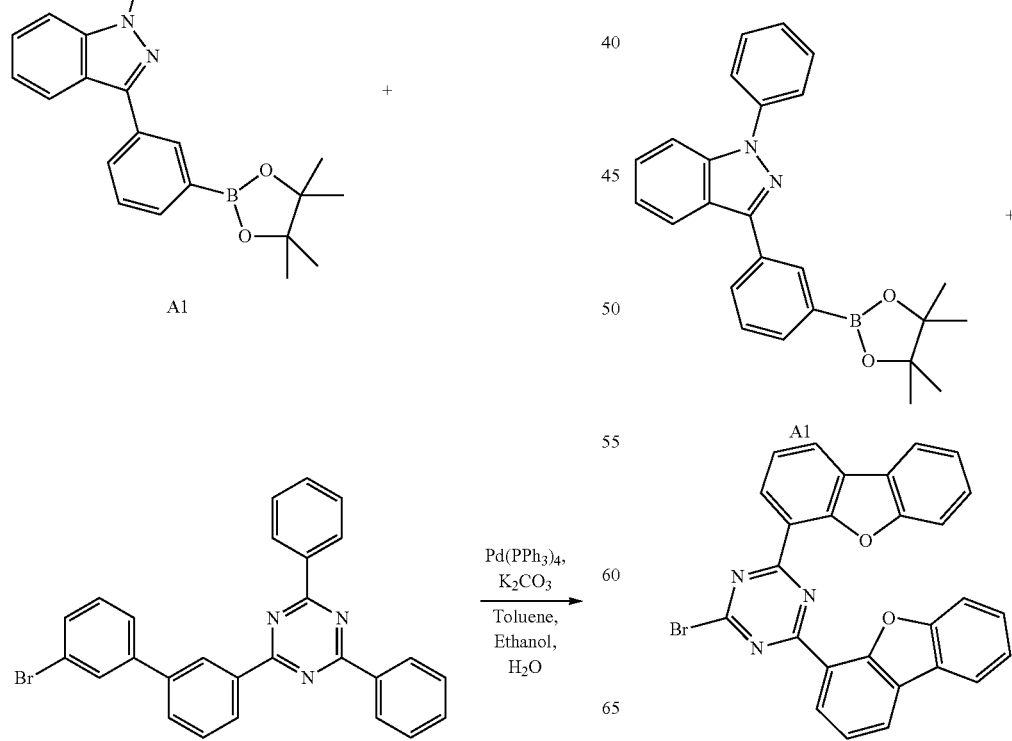

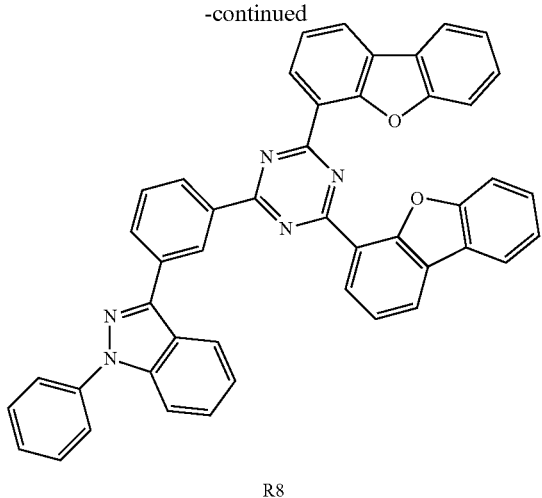

R8

Under a nitrogen stream, A1 (6.8 g 17.1 mmol), 2-bromo-4,6-bis(dibenzo[b,d]furan-4-yl)-1,3,5-triazine (9.2 g 18.8 mmol), Pd(PPh$_3$)$_4$ (1.0 g, 5 mol %), potassium carbonate (7.1 g, 51.2 mmol) and toluene/H$_2$O/ethanol (80 ml/40 ml/40 ml) were introduced, and stirred for 3 hours at 110° C.

After the reaction was finished, the organic layer was separated using methylene chloride, and water was removed using MgSO$_4$. After the solvent of the organic layer was removed, the result was purified using column chromatography to obtain target Compound R8 (9.0 g, 13.1 mmol, yield 77%).

GC-Mass (theoretical value: 681.8 g/mol, measured value: 682 g/mol)

[Synthesis Example 3] Synthesis of R21

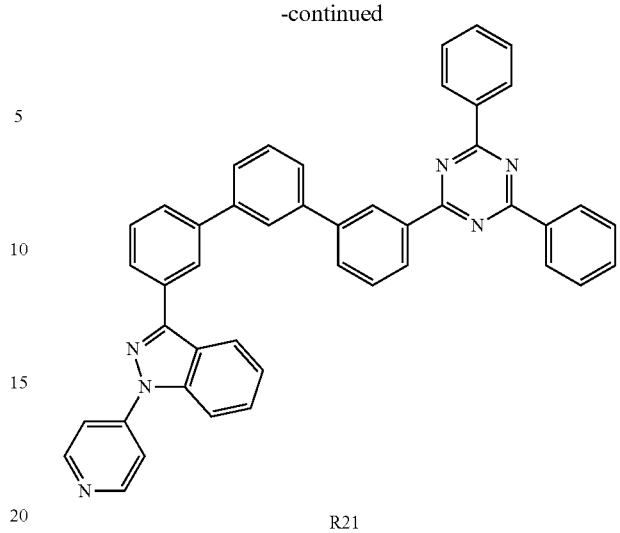

R21

Under a nitrogen stream, A2 (6.8 g, 17.1 mmol), 2-(3'-bromobiphenyl-3-yl)-4,6-diphenyl-1,3,5-triazine (8.7 g, 18.8 mmol), Pd(PPh$_3$)$_4$ (1.0 g, 5 mol %), potassium carbonate (7.1 g, 51.2 mmol) and toluene/H$_2$O/ethanol (80 ml/40 ml/40 ml) were introduced, and stirred for 3 hours at 110° C.

After the reaction was finished, the organic layer was separated using methylene chloride, and water was removed using MgSO$_4$. After the solvent of the organic layer was removed, the result was purified using column chromatography to obtain target Compound R21 (7.8 g, 11.9 mmol, yield 70%).

GC-Mass (theoretical value: 654.8 g/mol, measured value: 655 g/mol)

[Synthesis Example 4] Synthesis of R41

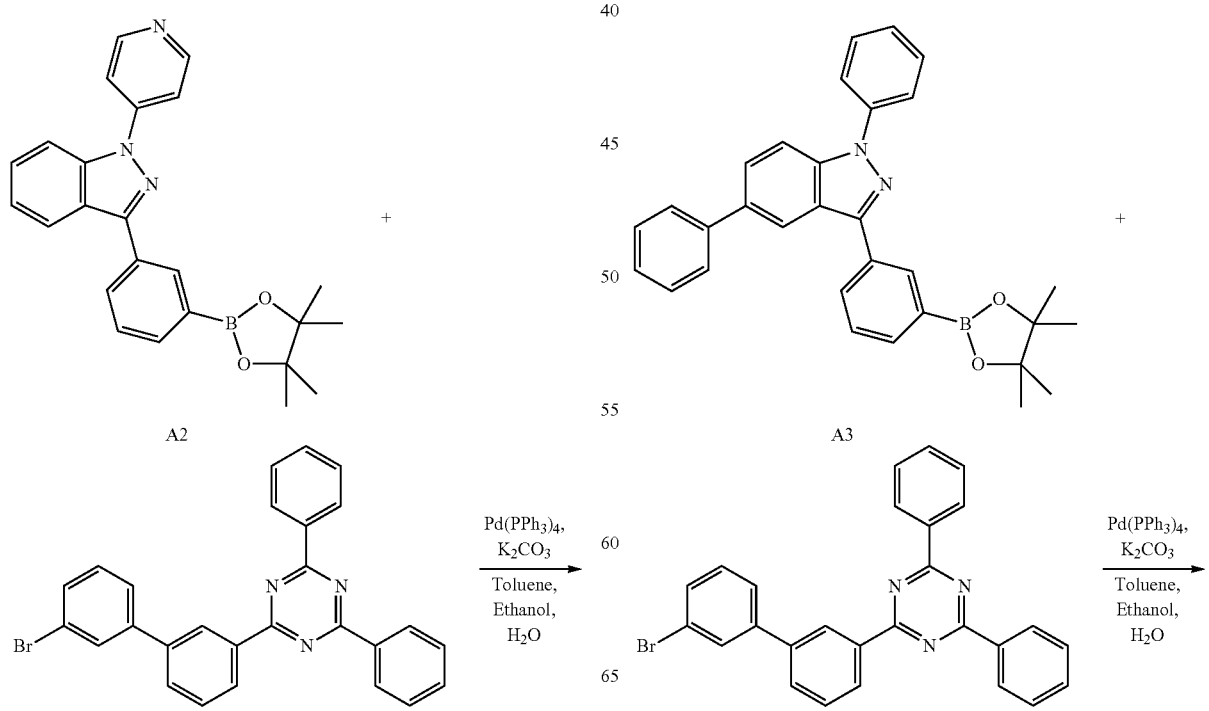

127
-continued

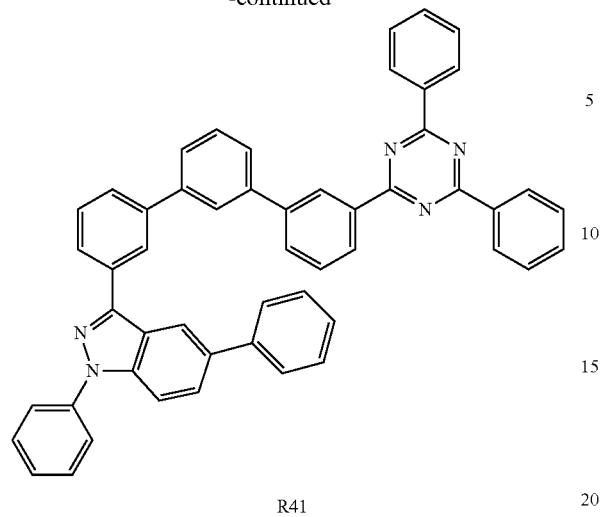

R41

Under a nitrogen stream, A3 (8.6 g, 18.3 mmol), 2-(3'-bromobiphenyl-3-yl)-4,6-diphenyl-1,3,5-triazine (9.3 g, 20.1 mmol), Pd(PPh$_3$)$_4$ (1.0 g, 5 mol %), potassium carbonate (7.1 g, 73.1 mmol) and toluene/H$_2$O/ethanol (80 ml/40 ml/40 ml) were introduced, and stirred for 3 hours at 110° C.

After the reaction was finished, the organic layer was separated using methylene chloride, and water was removed using MgSO$_4$. After the solvent of the organic layer was removed, the result was purified using column chromatography to obtain target Compound R41 (10.0 g, 13.7 mmol, yield 75%).

GC-Mass (theoretical value: 729.9 g/mol, measured value: 730 g/mol)

[Synthesis Example 5] Synthesis of R61

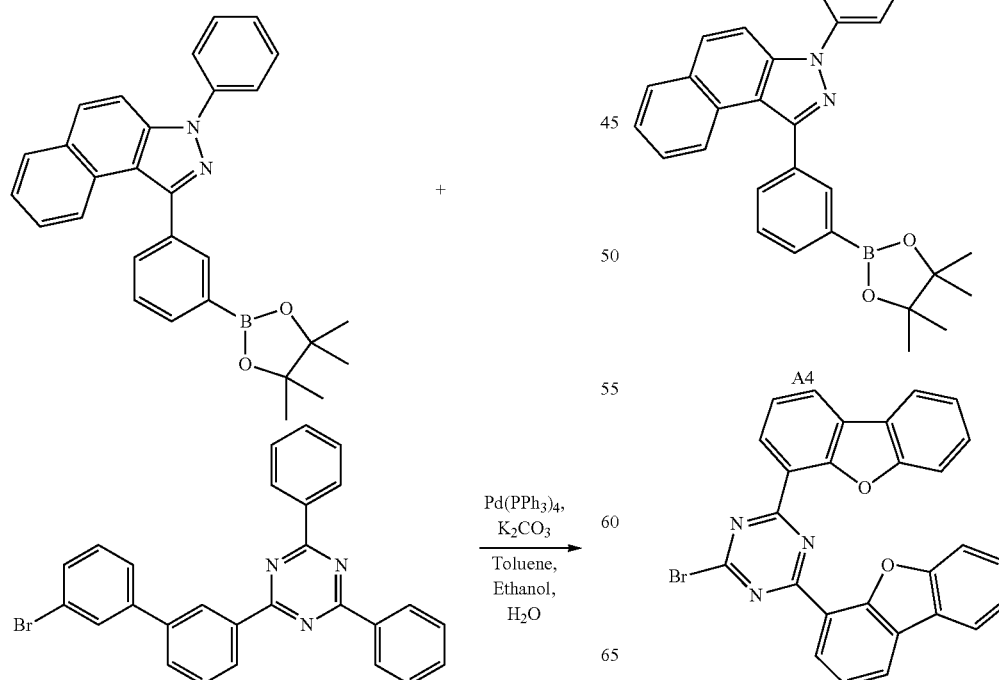

128
-continued

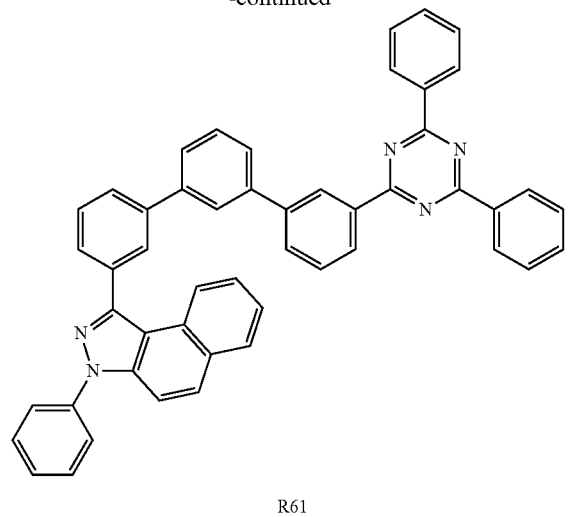

R61

Under a nitrogen stream, A4 (7.6 g, 17.1 mmol), 2-(3'-bromobiphenyl-3-yl)-4,6-diphenyl-1,3,5-triazine (8.7 g, 18.8 mmol), Pd(PPh$_3$)$_4$ (1.0 g, 5 mol %), potassium carbonate (7.1 g, 51.2 mmol) and toluene/H$_2$O/ethanol (80 ml/40 ml/40 ml) were introduced, and stirred for 3 hours at 110° C.

After the reaction was finished, the organic layer was separated using methylene chloride, and water was removed using MgSO$_4$. After the solvent of the organic layer was removed, the result was purified using column chromatography to obtain target Compound R61 (9.0 g, 12.8 mmol, yield 75%).

GC-Mass (theoretical value: 703.9 g/mol, measured value: 703 g/mol)

[Synthesis Example 6] Synthesis of R68

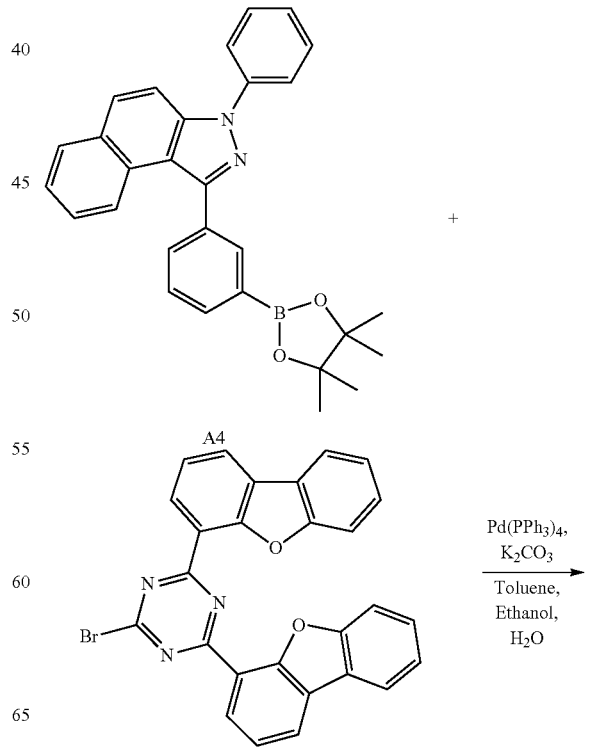

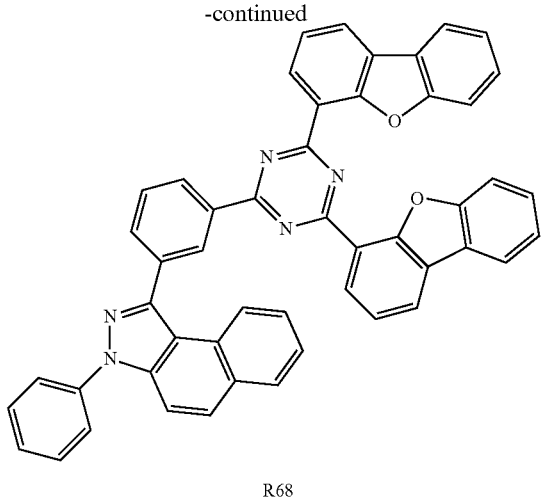

R68

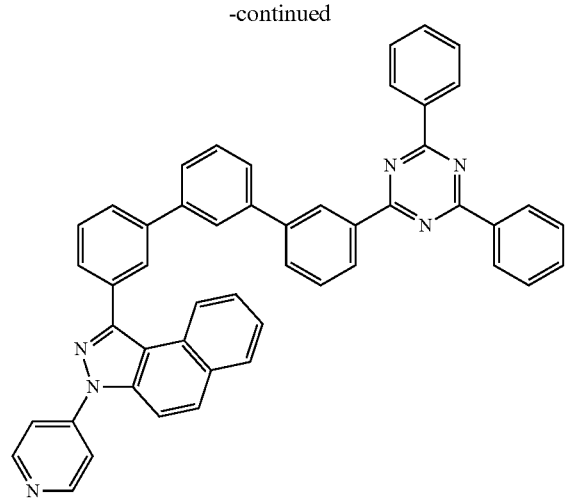

R81

Under a nitrogen stream, A4 (7.6 g, 17.1 mmol), 2-bromo-4,6-bis(dibenzo[b,d]furan-4-yl)-1,3,5-triazine (9.2 g, 18.8 mmol), Pd(PPh$_3$)$_4$ (1.0 g, 5 mol %), potassium carbonate (7.1 g, 51.2 mmol) and toluene/H$_2$O/ethanol (80 ml/40 ml/40 ml) were introduced, and stirred for 3 hours at 110° C.

After the reaction was finished, the organic layer was separated using methylene chloride, and water was removed using MgSO$_4$. After the solvent of the organic layer was removed, the result was purified using column chromatography to obtain target Compound R68 (9.4 g, 12.8 mmol, yield 75%).

GC-Mass (theoretical value: 731.8 g/mol, measured value: 731 g/mol)

[Synthesis Example 7] Synthesis of R81

Under a nitrogen stream, A5 (7.6 g, 17.1 mmol), 2-(3'-bromobiphenyl-3-yl)-4,6-diphenyl-1,3,5-triazine (8.7 g 18.8 mmol), Pd(PPh$_3$)$_4$ (1.0 g, 5 mol %), potassium carbonate (7.1 g, 51.2 mmol) and toluene/H$_2$O/ethanol (80 ml/40 ml/40 ml) were introduced, and stirred for 3 hours at 110° C.

After the reaction was finished, the organic layer was separated using methylene chloride, and water was removed using MgSO$_4$. After the solvent of the organic layer was removed, the result was purified using column chromatography to obtain target Compound R81 (8.9 g 12.6 mmol, yield 74%).

GC-Mass (theoretical value: 703.9 g/mol, measured value: 704 g/mol)

[Synthesis Example 8] Synthesis of R101

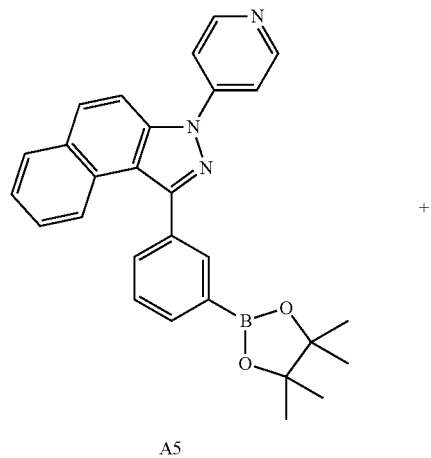

A5

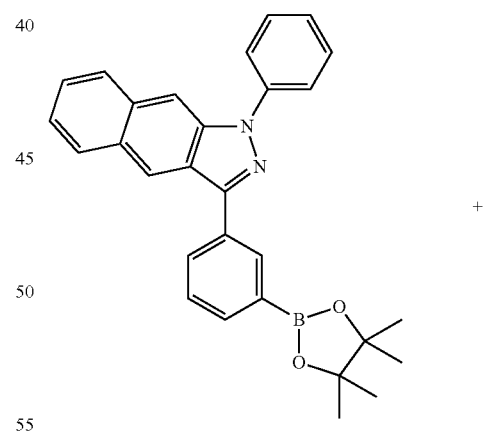

A6

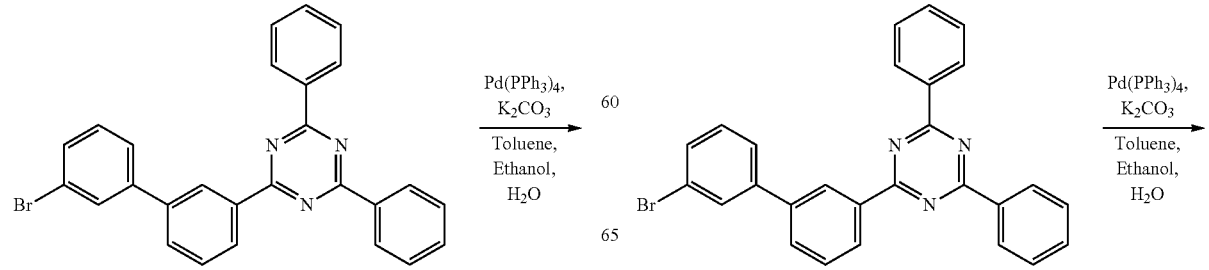

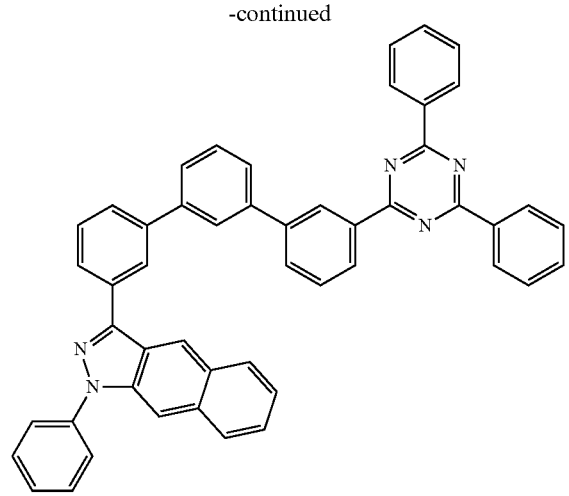

R101

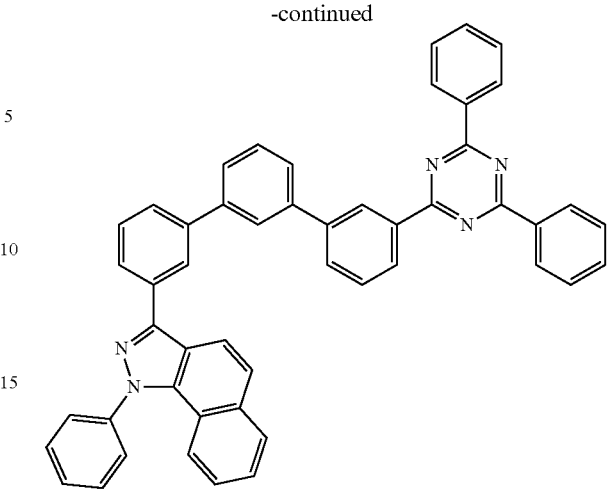

R121

Under a nitrogen stream, A6 (7.6 g, 17.1 mmol), 2-(3'-bromobiphenyl-3-yl)-4,6-diphenyl-1,3,5-triazine (8.7 g 18.8 mmol), Pd(PPh$_3$)$_4$ (1.0 g, 5 mol %), potassium carbonate (7.1 g, 51.2 mmol) and toluene/H$_2$O/ethanol (80 ml/40 ml/40 ml) were introduced, and stirred for 3 hours at 110° C.

After the reaction was finished, the organic layer was separated using methylene chloride, and water was removed using MgSO$_4$. After the solvent of the organic layer was removed, the result was purified using column chromatography to obtain target Compound R101 (9.0 g, 12.8 mmol, yield 75%).

GC-Mass (theoretical value: 703.9 g/mol, measured value: 703 g/mol)

[Synthesis Example 9] Synthesis of R121

Under a nitrogen stream, A7 (7.6 g, 17.1 mmol), 2-(3'-bromobiphenyl-3-yl)-4,6-diphenyl-1,3,5-triazine (8.7 g, 18.8 mmol), Pd(PPh$_3$)$_4$ (1.0 g, 5 mol %), potassium carbonate (7.1 g, 51.2 mmol) and toluene/H$_2$O/ethanol (80 ml/40 ml/40 ml) were introduced, and stirred for 3 hours at 110° C.

After the reaction was finished, the organic layer was separated using methylene chloride, and water was removed using MgSO$_4$. After the solvent of the organic layer was removed, the result was purified using column chromatography to obtain target Compound R121 (8.9 g, 12.0 mmol, yield 74%).

GC-Mass (theoretical value: 703.9 g/mol, measured value: 703 g/mol)

[Synthesis Example 10] Synthesis of R141

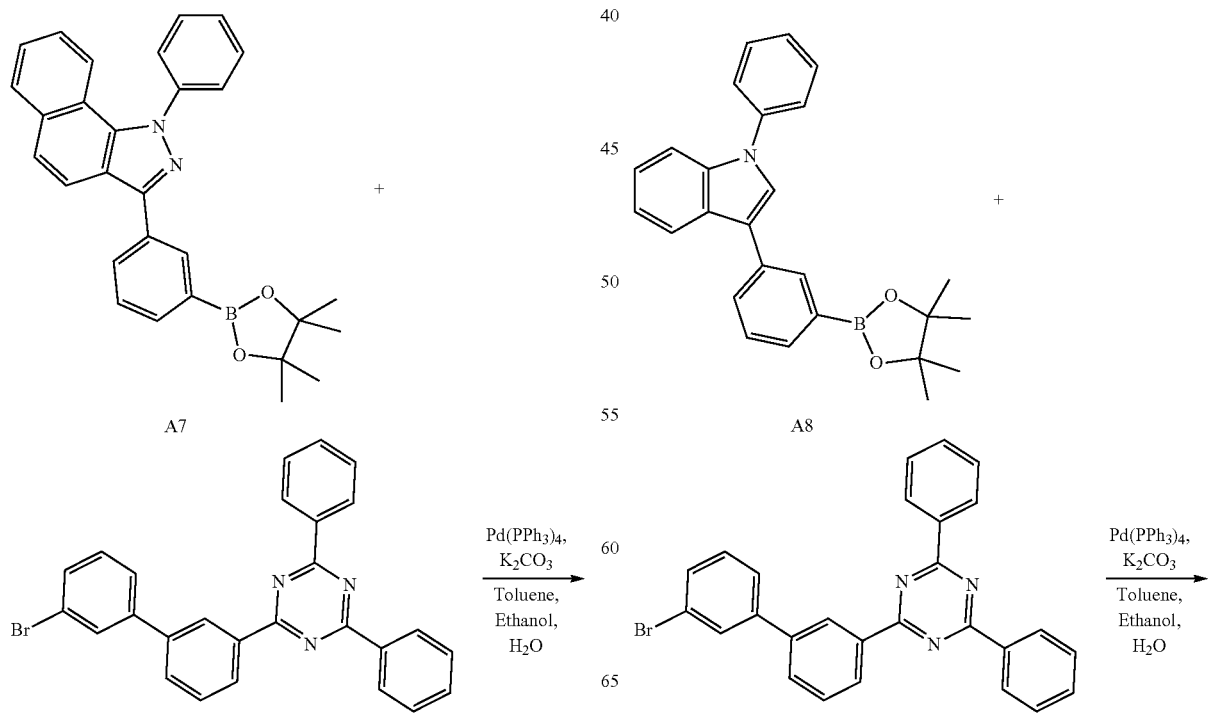

-continued

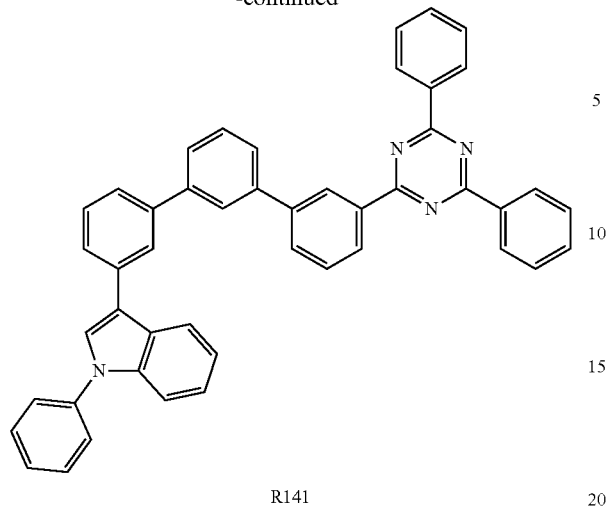

R141

Under a nitrogen stream, A8 (6.7 g, 17.1 mmol), 2-(3'-bromobiphenyl-3-yl)-4,6-diphenyl-1,3,5-triazine (8.7 g, 18.8 mmol), Pd(PPh$_3$)$_4$ (1.0 g, 5 mol %), potassium carbonate (7.1 g, 51.2 mmol) and toluene/H$_2$O/ethanol (80 ml/40 ml/40 ml) were introduced, and stirred for 3 hours at 110° C.

After the reaction was finished, the organic layer was separated using methylene chloride, and water was removed using MgSO$_4$. After the solvent of the organic layer was removed, the result was purified using column chromatography to obtain target Compound R141 (8.3 g, 12.8 mmol, yield 75%).

GC-Mass (theoretical value: 652.8 g/mol, measured value: 653 g/mol)

[Synthesis Example 11] Synthesis of R148

-continued

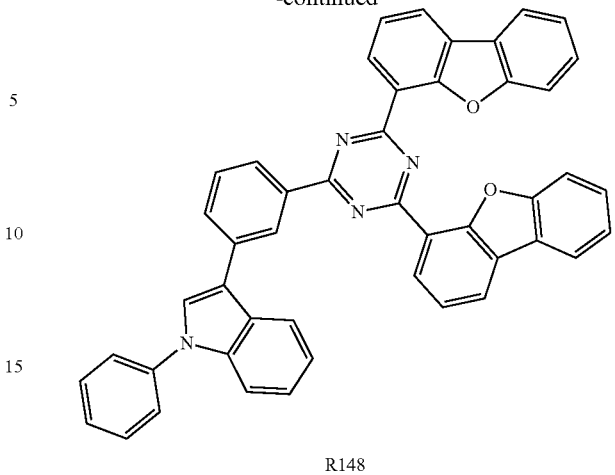

R148

Under a nitrogen stream, A8 (6.7 g, 17.1 mmol), 2-bromo-4,6-bis(dibenzo[b,d]furan-4-yl)-1,3,5-triazine (9.2 g, 18.8 mmol), Pd(PPh$_3$)$_4$ (1.0 g, 5 mol %), potassium carbonate (7.1 g, 51.2 mmol) and toluene/H$_2$O/ethanol (80 ml/40 ml/40 ml) were introduced, and stirred for 3 hours at 110° C.

After the reaction was finished, the organic layer was separated using methylene chloride, and water was removed using MgSO$_4$. After the solvent of the organic layer was removed, the result was purified using column chromatography to obtain target Compound R148 (8.7 g, 12.8 mmol, yield 75%).

GC-Mass (theoretical value: 680.8 g/mol, measured value: 681 g/mol)

[Synthesis Example 12] Synthesis of R161

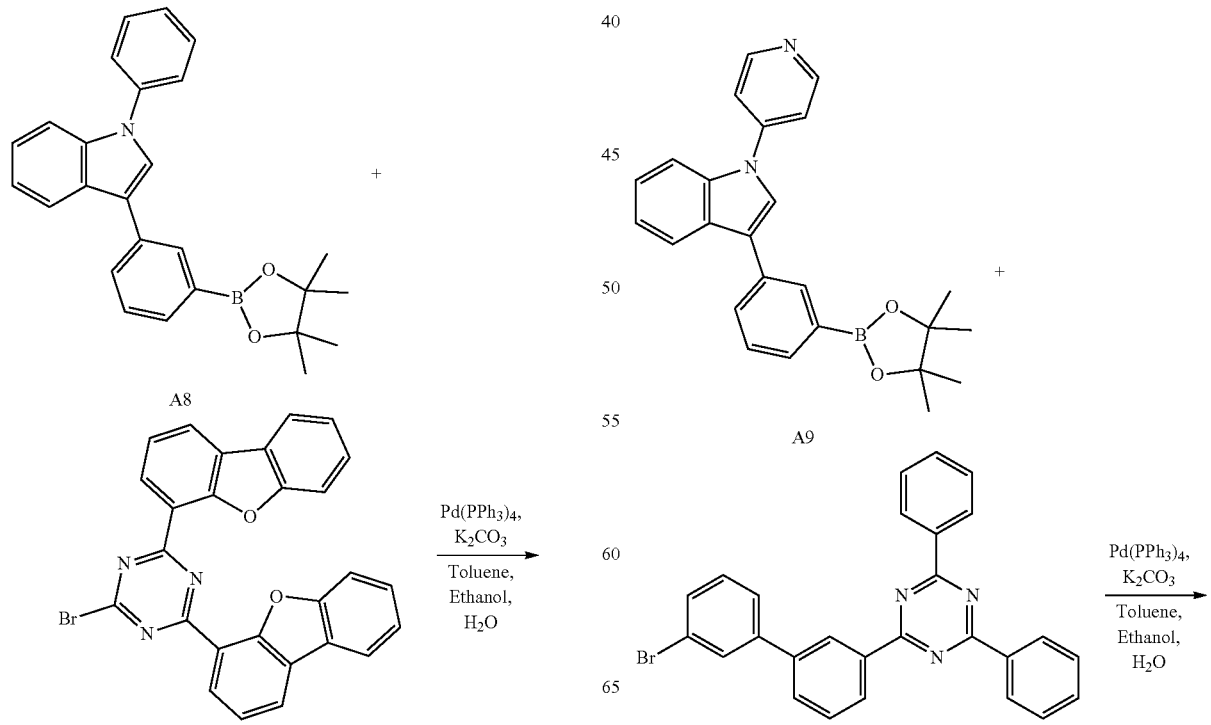

-continued

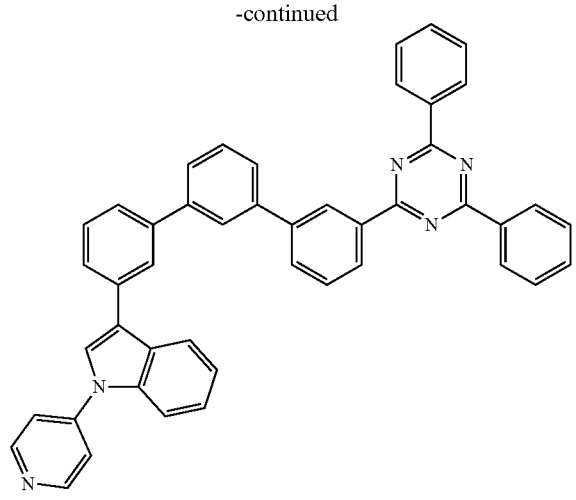

R161

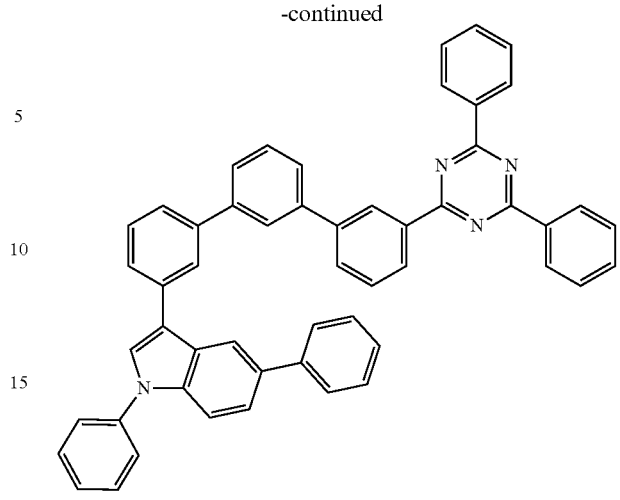

R181

Under a nitrogen stream, A9 (6.8 g, 17.1 mmol), 2-(3'-bromobiphenyl-3-yl)-4,6-diphenyl-1,3,5-triazine (8.7 g, 18.8 mmol), Pd(PPh$_3$)$_4$ (1.0 g, 5 mol %), potassium carbonate (7.1 g, 51.2 mmol) and toluene/H$_2$O/ethanol (80 ml/40 ml/40 ml) were introduced, and stirred for 3 hours at 110° C.

After the reaction was finished, the organic layer was separated using methylene chloride, and water was removed using MgSO$_4$. After the solvent of the organic layer was removed, the result was purified using column chromatography to obtain target Compound R161 (7.9 g, 11.1 mmol, yield 71%).

GC-Mass (theoretical value: 653.8 g/mol, measured value: 654 g/mol)

[Synthesis Example 13] Synthesis of R181

Under a nitrogen stream, A10 (8.6 g, 18.3 mmol), 2-(3'-bromobiphenyl-3-yl)-4,6-diphenyl-1,3,5-triazine (9.3 g, 20.1 mmol), Pd(PPh$_3$)$_4$ (1.0 g, 5 mol %), potassium carbonate (7.1 g, 73.1 mmol) and toluene/H$_2$O/ethanol (80 ml/40 ml/40 ml) were introduced, and stirred for 3 hours at 110° C.

After the reaction was finished, the organic layer was separated using methylene chloride, and water was removed using MgSO$_4$. After the solvent of the organic layer was removed, the result was purified using column chromatography to obtain target Compound R181 (10.0 g, 13.7 mmol, yield 75%).

GC-Mass (theoretical value: 729.9 g/mol, measured value: 730 g/mol)

[Synthesis Example 14] Synthesis of R201

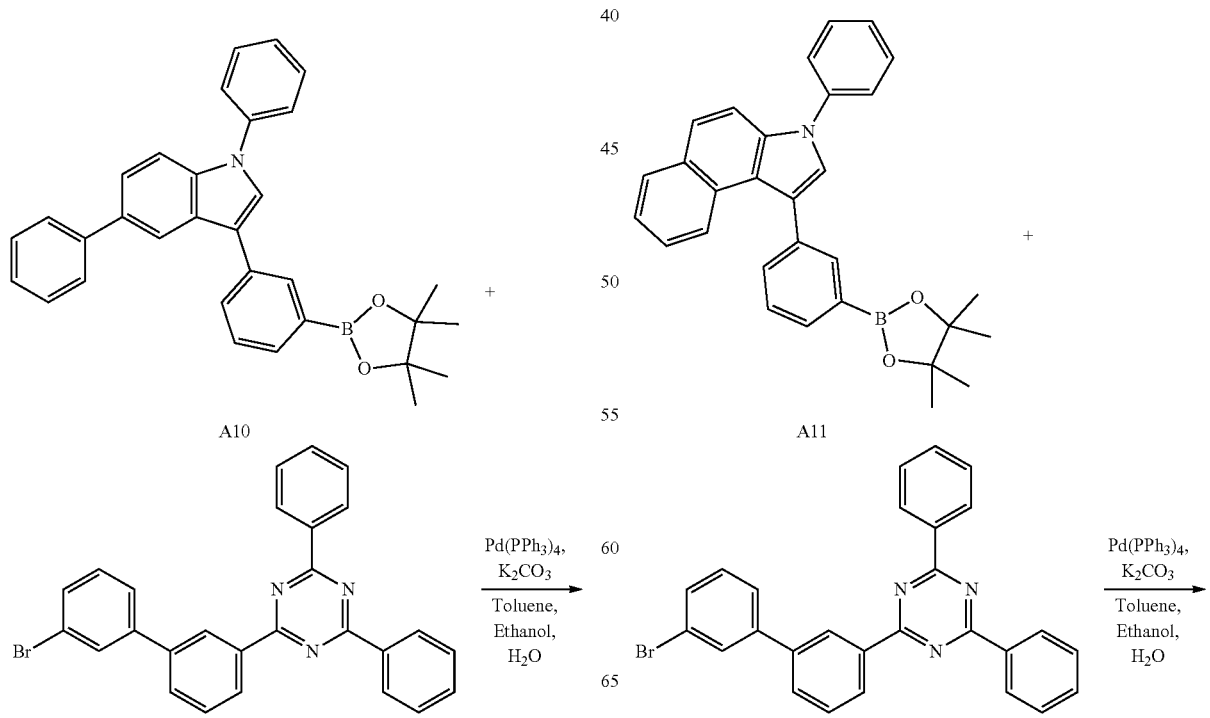

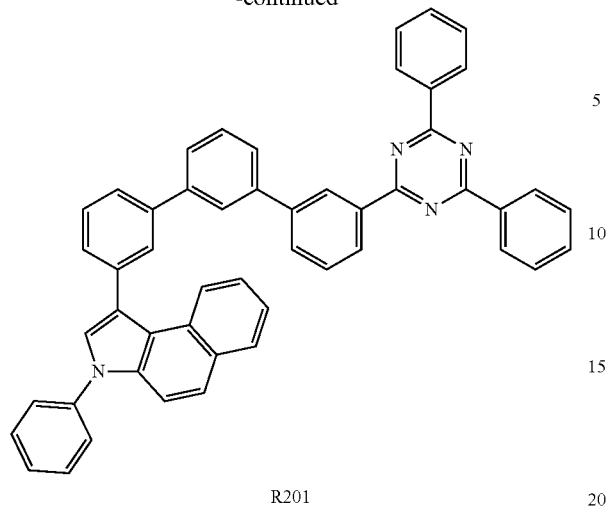

R201

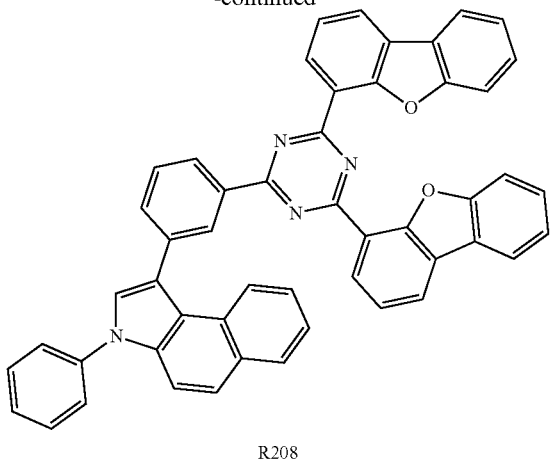

R208

Under a nitrogen stream, A11 (7.6 g, 17.1 mmol), 2-(3'-bromobiphenyl-3-yl)-4,6-diphenyl-1,3,5-triazine (8.7 g, 18.8 mmol), Pd(PPh$_3$)$_4$ (1.0 g, 5 mol %), potassium carbonate (7.1 g, 51.2 mmol) and toluene/H$_2$O/ethanol (80 ml/40 ml/40 ml) were introduced, and stirred for 3 hours at 110° C.

After the reaction was finished, the organic layer was separated using methylene chloride, and water was removed using MgSO$_4$. After the solvent of the organic layer was removed, the result was purified using column chromatography to obtain target Compound R201 (9.0 g, 12.8 mmol, yield 75%).

GC-Mass (theoretical value: 703.9 g/mol, measured value: 703 g/mol)

[Synthesis Example 15] Synthesis of R208

Under a nitrogen stream, A11 (7.6 g 17.1 mmol), 2-bromo-4,6-bis(dibenzo[b,d]furan-4-yl)-1,3,5-triazine (9.2 g 18.8 mmol), Pd(PPh$_3$)$_4$ (1.0 g, 5 mol %), potassium carbonate (7.1 g, 51.2 mmol) and toluene/H$_2$O/ethanol (80 ml/40 ml/40 ml) were introduced, and stirred for 3 hours at 110° C.

After the reaction was finished, the organic layer was separated using methylene chloride, and water was removed using MgSO$_4$. After the solvent of the organic layer was removed, the result was purified using column chromatography to obtain target Compound R208 (9.4 g, 12.8 mmol, yield 75%).

GC-Mass (theoretical value: 731.8 g/mol, measured value: 731 g/mol)

[Synthesis Example 16] Synthesis of R221

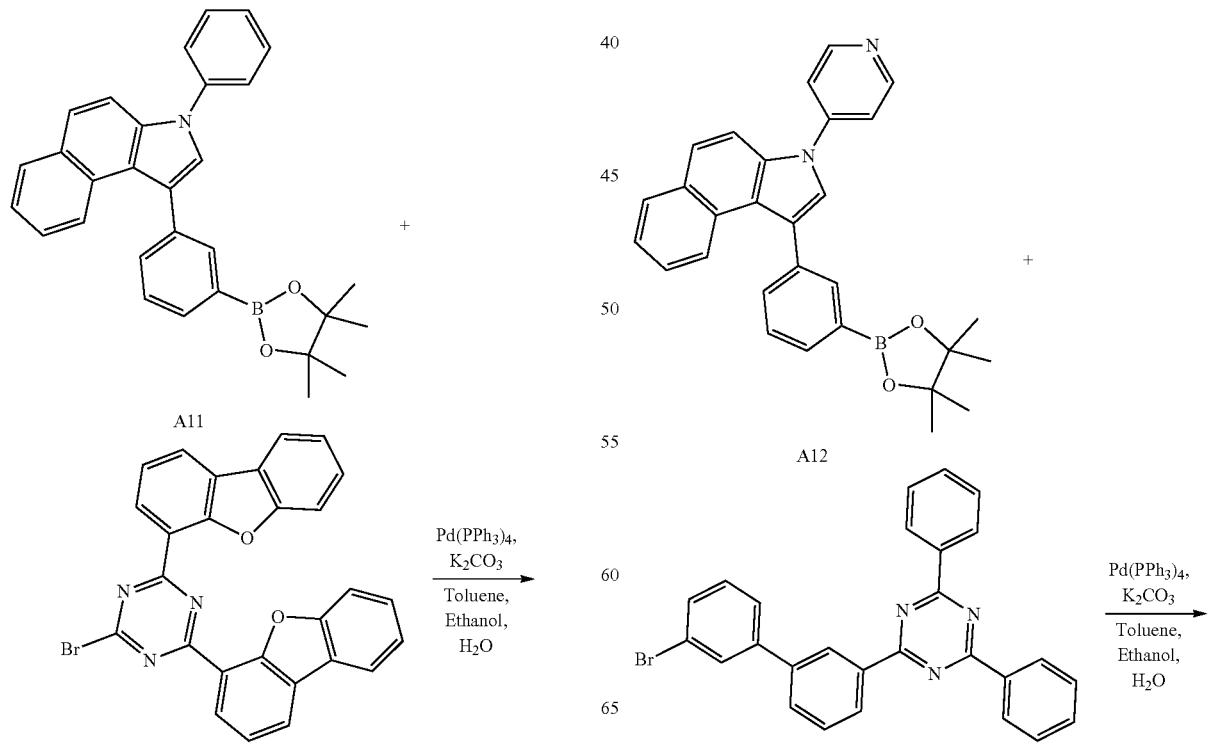

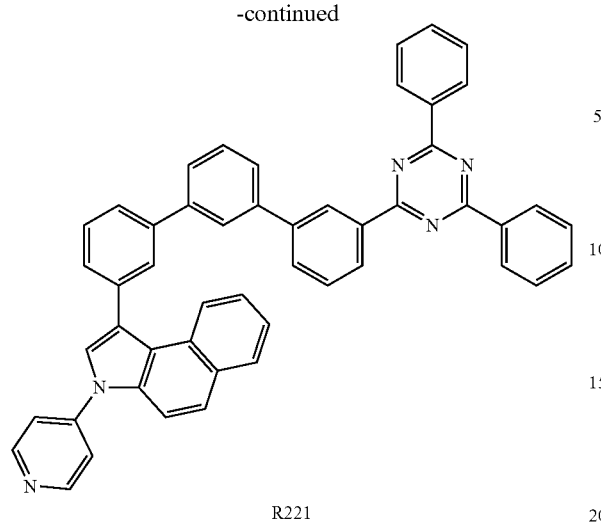

R221

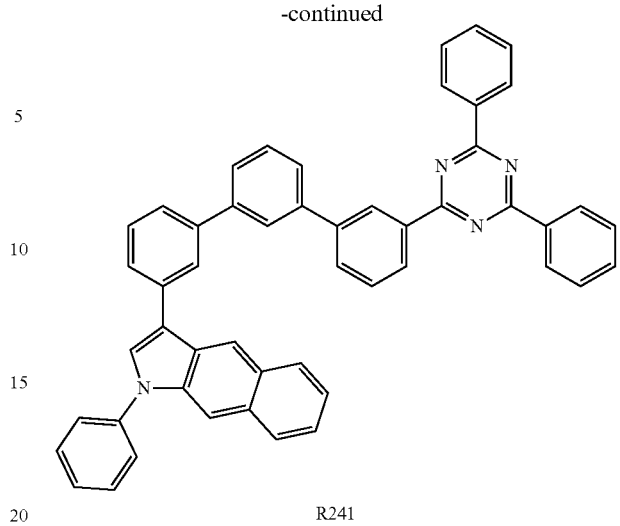

R241

Under a nitrogen stream, A12 (7.6 g, 17.1 mmol), 2-(3'-bromobiphenyl-3-yl)-4,6-diphenyl-1,3,5-triazine (8.7 g, 18.8 mmol), Pd(PPh$_3$)$_4$ (1.0 g, 5 mol %), potassium carbonate (7.1 g, 51.2 mmol) and toluene/H$_2$O/ethanol (80 ml/40 ml/40 ml) were introduced, and stirred for 3 hours at 110° C.

After the reaction was finished, the organic layer was separated using methylene chloride, and water was removed using MgSO$_4$. After the solvent of the organic layer was removed, the result was purified using column chromatography to obtain target Compound R221 (8.9 g, 12.6 mmol, yield 74%).

GC-Mass (theoretical value: 703.9 g/mol, measured value: 704 g/mol)

[Synthesis Example 17] Synthesis of R241

Under a nitrogen stream, A13 (7.6 g, 17.1 mmol), 2-(3'-bromobiphenyl-3-yl)-4,6-diphenyl-1,3,5-triazine (8.7 g, 18.8 mmol), Pd(PPh$_3$)$_4$ (1.0 g, 5 mol %), potassium carbonate (7.1 g, 51.2 mmol) and toluene/H$_2$O/ethanol (80 ml/40 ml/40 ml) were introduced, and stirred for 3 hours at 110° C.

After the reaction was finished, the organic layer was separated using methylene chloride, and water was removed using MgSO$_4$. After the solvent of the organic layer was removed, the result was purified using column chromatography to obtain target Compound R241 (9.0 g, 12.8 mmol, yield 75%).

GC-Mass (theoretical value: 702.9 g/mol, measured value: 703 g/mol)

[Synthesis Example 18] Synthesis of R261

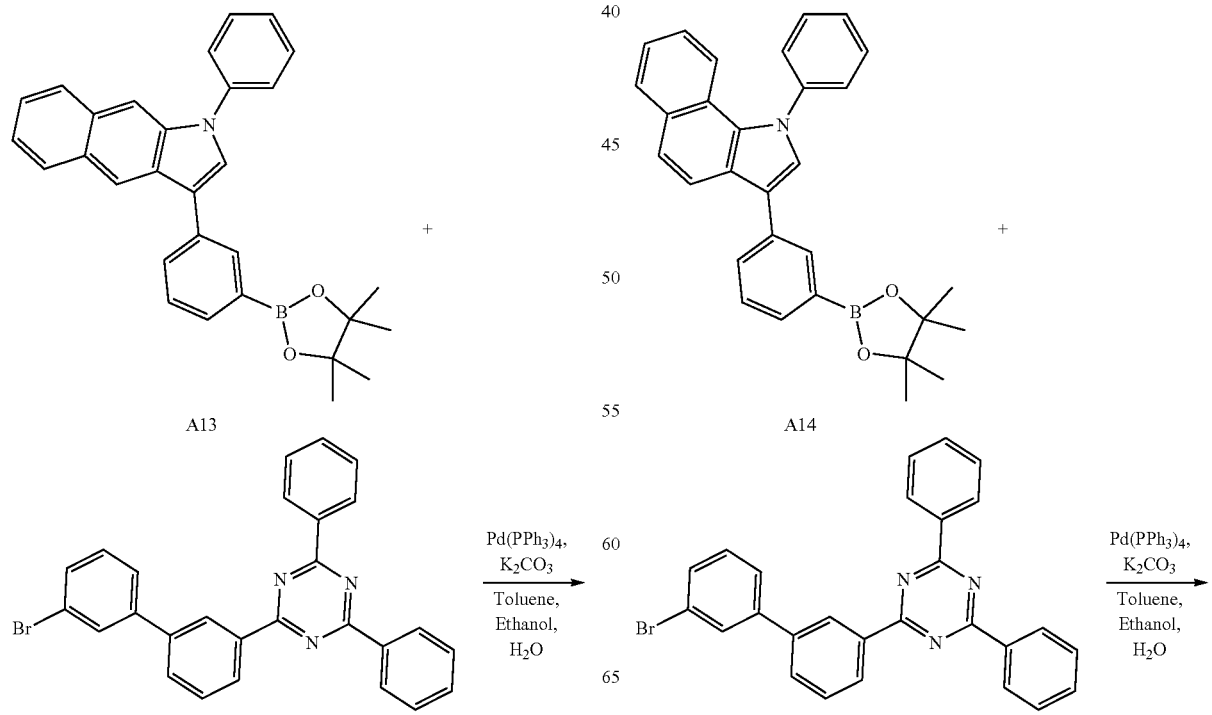

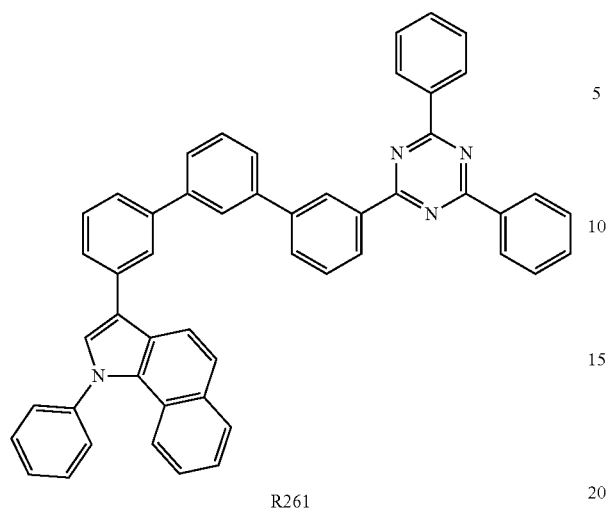

R261

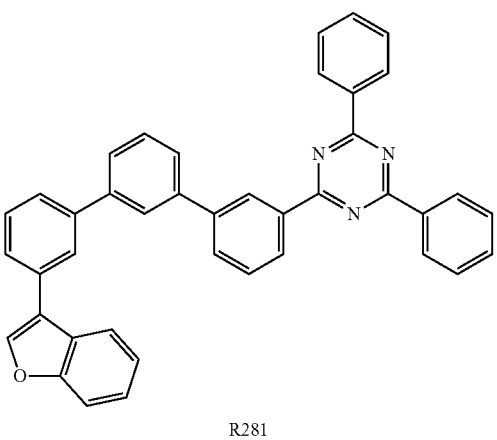

R281

Under a nitrogen stream, A14 (7.6 g, 17.1 mmol), 2-(3'-bromobiphenyl-3-yl)-4,6-diphenyl-1,3,5-triazine (8.7 g, 18.8 mmol), Pd(PPh$_3$)$_4$ (1.0 g, 5 mol %), potassium carbonate (7.1 g, 51.2 mmol) and toluene/H$_2$O/ethanol (80 ml/40 ml/40 ml) were introduced, and stirred for 3 hours at 110° C.

After the reaction was finished, the organic layer was separated using methylene chloride, and water was removed using MgSO$_4$. After the solvent of the organic layer was removed, the result was purified using column chromatography to obtain target Compound R261 (8.9 g, 12.0 mmol, yield 74%).

GC-Mass (theoretical value: 702.9 g/mol, measured value: 703 g/mol)

[Synthesis Example 19] Synthesis of R281

Under a nitrogen stream, A15 (5.5 g, 17.1 mmol), 2-(3'-bromobiphenyl-3-yl)-4,6-diphenyl-1,3,5-triazine (8.7 g, 18.8 mmol), Pd(PPh$_3$)$_4$ (1.0 g, 5 mol %), potassium carbonate (7.1 g, 51.2 mmol) and toluene/H$_2$O/ethanol (80 ml/40 ml/40 ml) were introduced, and stirred for 3 hours at 110° C.

After the reaction was finished, the organic layer was separated using methylene chloride, and water was removed using MgSO$_4$. After the solvent of the organic layer was removed, the result was purified using column chromatography to obtain target Compound R281 (9.9 g, 12.8 mmol, yield 75%).

GC-Mass (theoretical value: 577.7 g/mol, measured value: 578 g/mol)

[Synthesis Example 20] Synthesis of R285

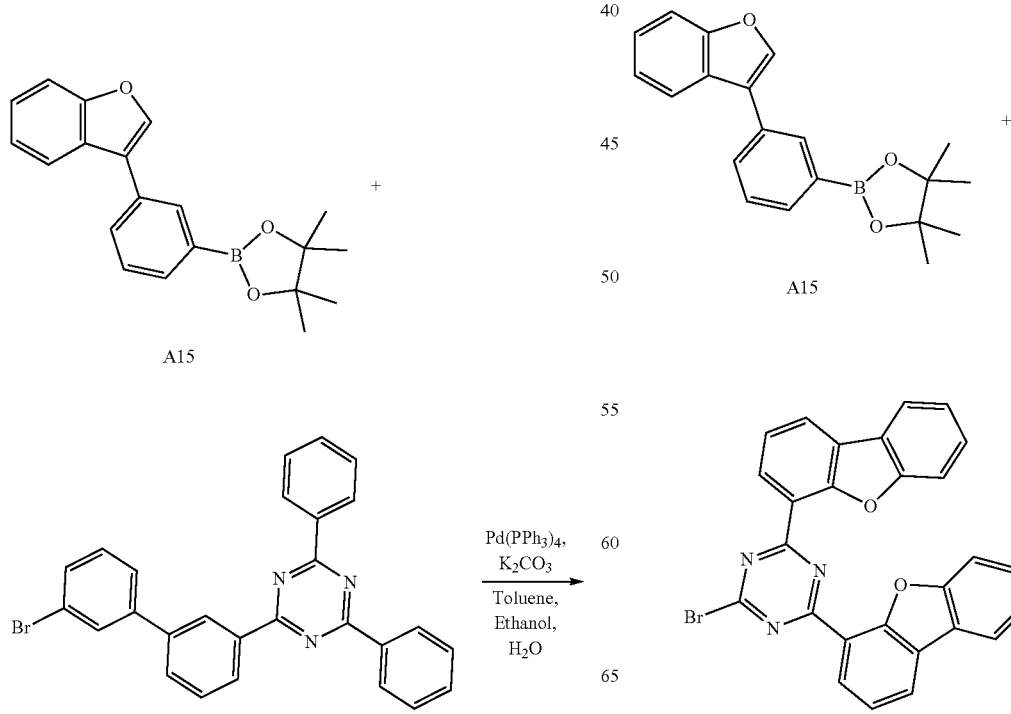

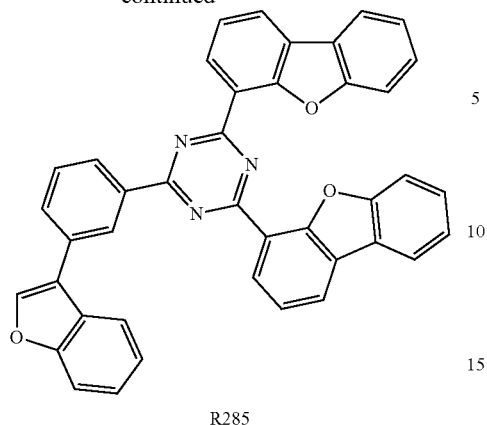

R285

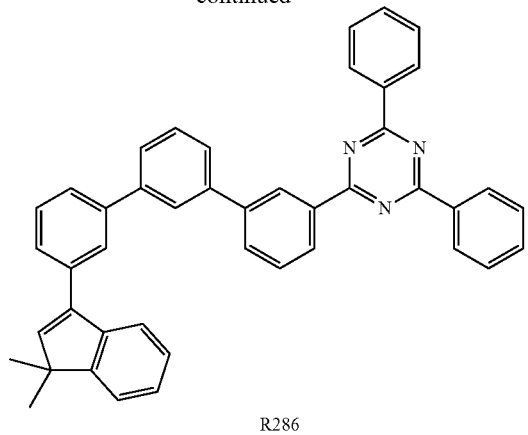

R286

Under a nitrogen stream, A15 (5.5 g 17.1 mmol), 2-bromo-4,6-bis(dibenzo[b,d]furan-4-yl)-1,3,5-triazine (9.2 g 18.8 mmol), Pd(PPh$_3$)$_4$ (1.0 g, 5 mol %), potassium carbonate (7.1 g, 51.2 mmol) and toluene/H$_2$O/ethanol (80 ml/40 ml/40 ml) were introduced, and stirred for 3 hours at 110° C.

After the reaction was finished, the organic layer was separated using methylene chloride, and water was removed using MgSO$_4$. After the solvent of the organic layer was removed, the result was purified using column chromatography to obtain target Compound R285 (8.0 g, 13.1 mmol, yield 77%).

GC-Mass (theoretical value: 605.7 g/mol, measured value: 606 g/mol)

[Synthesis Example 21] Synthesis of R286

Under a nitrogen stream, A16 (5.9 g, 17.1 mmol), 2-(3'-bromobiphenyl-3-yl)-4,6-diphenyl-1,3,5-triazine (8.7 g, 18.8 mmol), Pd(PPh$_3$)$_4$ (1.0 g, 5 mol %), potassium carbonate (7.1 g, 51.2 mmol) and toluene/H$_2$O/ethanol (80 ml/40 ml/40 ml) were introduced, and stirred for 3 hours at 110° C.

After the reaction was finished, the organic layer was separated using methylene chloride, and water was removed using MgSO$_4$. After the solvent of the organic layer was removed, the result was purified using column chromatography to obtain target Compound R286 (7.2 g, 11.9 mmol, yield 70%).

GC-Mass (theoretical value: 603.8 g/mol, measured value: 604 g/mol)

[Synthesis Example 22] Synthesis of R291

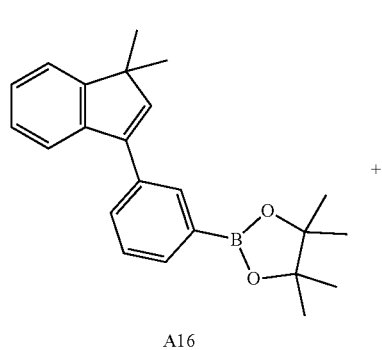

A16

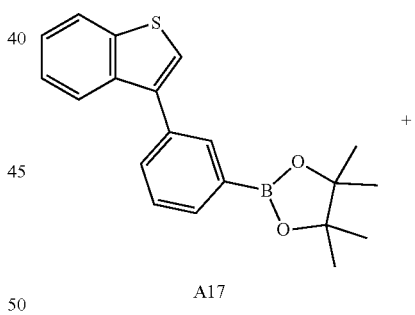

A17

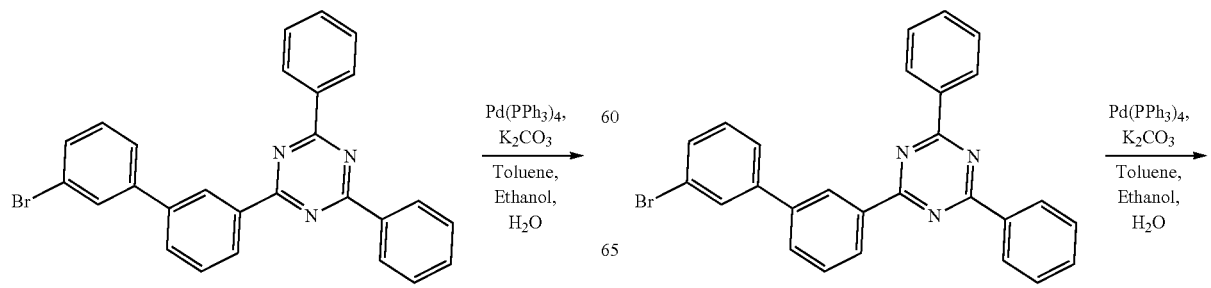

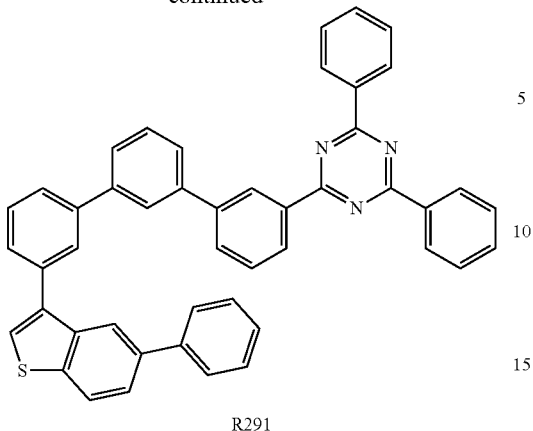

R291

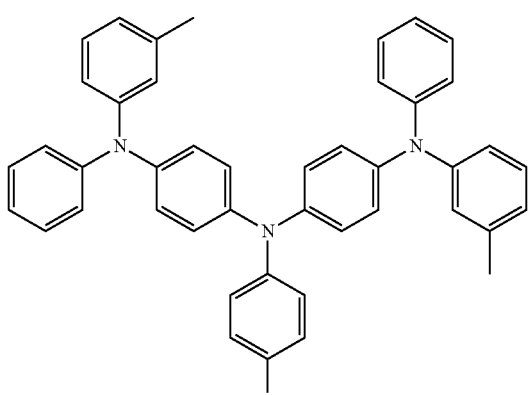

m-MTDATA

Under a nitrogen stream, A17 (6.1 g, 18.3 mmol), 2-(3'-bromobiphenyl-3-yl)-4,6-diphenyl-1,3,5-triazine (9.3 g, 20.1 mmol), Pd(PPh$_3$)$_4$ (1.0 g, 5 mol %), potassium carbonate (7.6 g, 73.1 mmol) and toluene/H$_2$O/ethanol (80 ml/40 ml/40 ml) were introduced, and stirred for 3 hours at 110° C.

After the reaction was finished, the organic layer was separated using methylene chloride, and water was removed using MgSO$_4$. After the solvent of the organic layer was removed, the result was purified using column chromatography to obtain target Compound R291 (9.2 g, 13.7 mmol, yield 75%).

GC-Mass (theoretical value: 669.9 g/mol, measured value: 670 g/mol)

Examples 1 to 6 Manufacture of Green Organic Electroluminescent Device

After high purity sublimation purifying the compounds synthesized in the synthesis examples using commonly known methods, green organic electroluminescent devices were manufactured using the following procedure.

First, a glass substrate on which indium tin oxide (ITO) was coated as a thin film to a thickness of 1500 Å was ultrasonic cleaned using distilled water. After the cleaning with distilled water was finished, the substrate was ultrasonic cleaned with solvents of isopropyl alcohol, acetone, methanol and the like, dried, then transferred to a UV OZONE washer (Power sonic 405, manufactured by Hwashin Tech. Co., Ltd.), and then, after cleaning the substrate for 5 minutes using UV, the substrate was transferred to a vacuum deposition apparatus.

On the transparent ITO electrode prepared as above, m-MTDATA (60 nm)/TCTA (80 nm)/each compound of R1, R8, R141, R148, R201 and R208+10% Ir(ppy)$_3$ (300 nm)/BCP (10 nm)/Alq$_3$ (30 nm)/LiF (1 nm)/Al (200 nm) were laminated in this order to manufacture an organic electroluminescent device.

Structures of m-MTDATA, TCTA, Ir(ppy)$_3$, CBP and BCP are as follows.

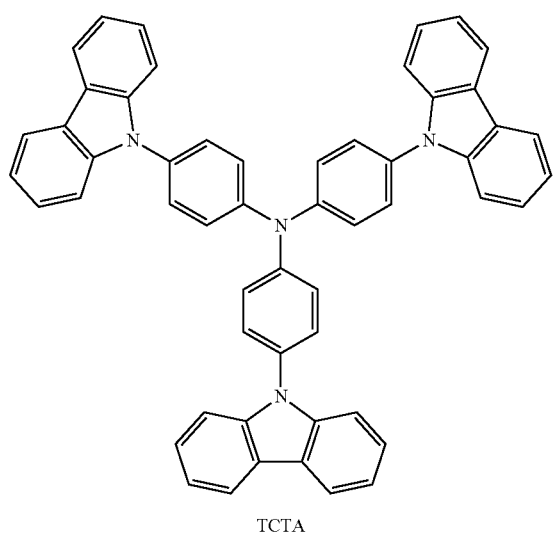

TCTA

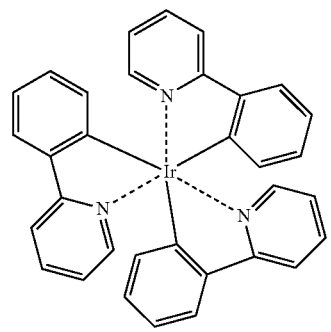

Ir(ppy)$_3$

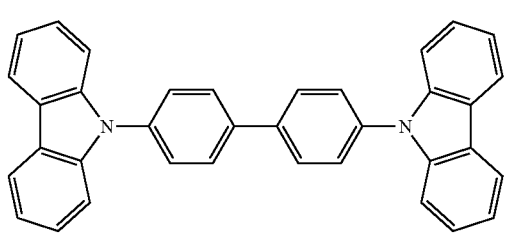

CBP

-continued

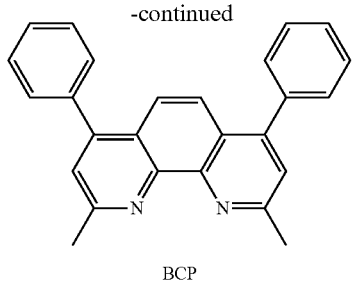

BCP

Comparative Example 1 Manufacture of Green Organic Electroluminescent Device A green organic electroluminescent device was manufactured in the same manner as in Example 1 except that CBP was used instead of Compound R141 as the light emitting host material when forming the light emitting layer.

Evaluation Example 1

For each of the green organic electroluminescent devices manufactured in Examples 1 to 6 and Comparative Example 2, driving voltage, current efficiency and light emission peak at current density of (10) mA/cm$^2$ were measured, and the results are shown in the following Table 1.

TABLE 1

| Sample | Host | Driving Voltage (V) | EL Peak (nm) | Current Efficiency (cd/A) |
|---|---|---|---|---|
| Example 1 | R1 | 5.2 | 515 | 12.5 |
| Example 2 | R8 | 4.3 | 515 | 11.4 |
| Example 3 | R141 | 5.1 | 515 | 12.3 |
| Example 4 | R148 | 4.2 | 515 | 11.1 |
| Example 5 | R201 | 5.4 | 515 | 12.2 |
| Example 6 | R208 | 4.4 | 515 | 10.8 |
| Comparative Example 1 | CBP | 7.1 | 516 | 7.2 |

As shown in Table 1, it was seen that using the compound (R1, R8, R141, R148, R201, R208) according to the present invention in a light emitting layer of the green organic EL device (Examples 1 to 6) resulted in more superior performance in terms of efficiency and driving voltage compared to the green organic EL device using existing CBP (Comparative Example 1).

Examples 7 to 28 Manufacture of Blue Organic Electroluminescent Device

After high purity sublimation purifying the compounds synthesized in the synthesis examples using commonly known methods, blue organic electroluminescent devices were manufactured using the following procedure.

First, a glass substrate on which indium tin oxide (ITO) was coated as a thin film to a thickness of 1500 Å was ultrasonic cleaned using distilled water. After the cleaning with distilled water was finished, the substrate was ultrasonic cleaned with solvents of isopropyl alcohol, acetone, methanol and the like, dried, then transferred to a UV OZONE washer (Power sonic 405, manufactured by Hwashin Tech. Co., Ltd), and then, after cleaning the substrate for 5 minutes using UV, the substrate was transferred to a vacuum deposition apparatus.

On the transparent ITO electrode prepared as above, DS-205 (Doosan Corporation Electro-Materials, 80 nm)/NPB (15 nm)/ADN+5% DS-405 (Doosan Corporation Electro-Materials, 30 nm)/each compound of R1, R8, R21, R41, R61, R68, R81, R101, R121, R141, R141, R148, R161, R181, R201, R208, R221, R241, R261, R281, R285, R286 and R291 (5 nm)/Alq$_3$ (25 nm)/LiF (1 nm)/Al (200 nm) were laminated in this order to manufacture an organic electroluminescent device.

Comparative Example 2 Manufacture of Blue Organic Electroluminescent Device

A blue organic electroluminescent device was manufactured in the same manner as in Example 6 except that R1 was not used as the electron transport auxiliary layer material, and Alq$_3$, the electron transport layer material, was deposited to 30 nm instead of 25 nm.

Structures of NPB, AND and Alq$_3$ used in Examples 6 to 28 and Comparative Example 2 are as follows.

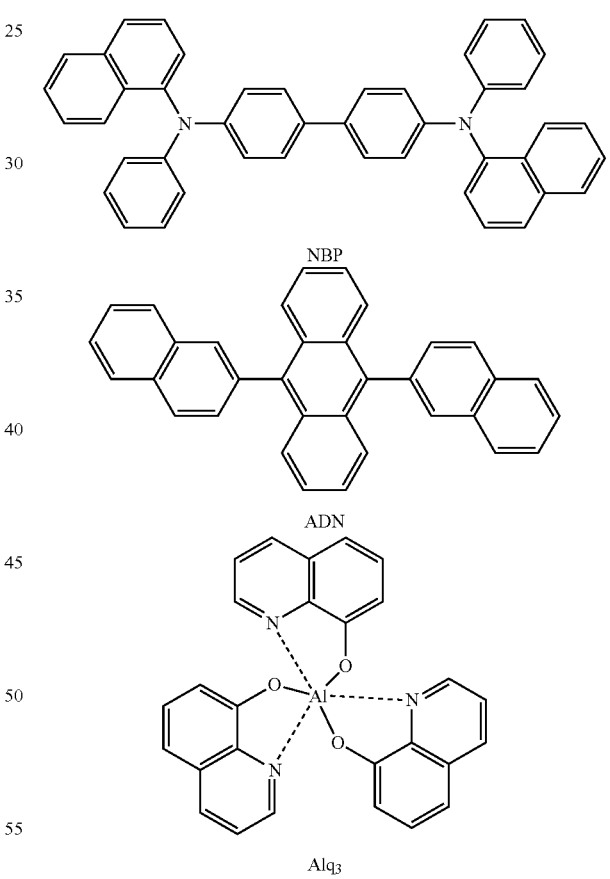

Comparative Example 3 Manufacture of Blue Organic Electroluminescent Device

A blue organic electroluminescent device was manufactured in the same manner as in Example 6 except that A1 of the following structural formula was used instead of R1 as the electron transport auxiliary layer material.

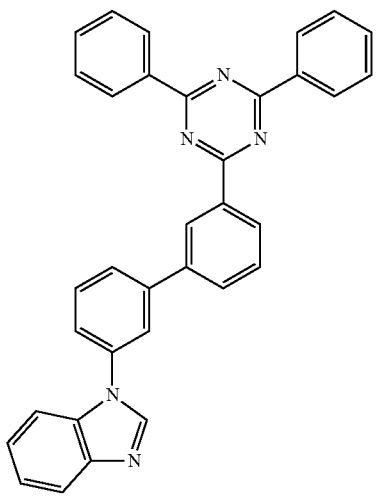

A1

Evaluation Example 2

For each of the organic electroluminescent devices manufactured in Examples 7 to 28 and Comparative Examples 2 and 3, driving voltage, light emission wavelength and current efficiency at current density of 10 mA/cm² were measured, and the results are shown in the following Table 2.

TABLE 2

| Sample | Electron Transport Auxiliary Layer | Driving Voltage (V) | Light Emission Peak (nm) | Current Efficiency (cd/A) |
|---|---|---|---|---|
| Example 7 | R1 | 4.4 | 458 | 8.3 |
| Example 8 | R8 | 3.9 | 458 | 7.5 |
| Example 9 | R21 | 4.4 | 458 | 8.0 |
| Example 10 | R41 | 4.4 | 458 | 8.2 |
| Example 11 | R61 | 4.4 | 458 | 8.1 |
| Example 12 | R68 | 4.4 | 458 | 8.2 |
| Example 13 | R81 | 4.4 | 458 | 8.3 |
| Example 14 | R101 | 4.4 | 458 | 8.0 |
| Example 15 | R121 | 4.4 | 458 | 8.2 |
| Example 16 | R141 | 4.3 | 458 | 7.8 |
| Example 17 | R148 | 3.5 | 458 | 7.1 |
| Example 18 | R161 | 4.4 | 458 | 7.3 |
| Example 19 | R181 | 4.5 | 458 | 7.4 |
| Example 20 | R201 | 4.1 | 458 | 7.5 |
| Example 21 | R208 | 3.9 | 458 | 7.0 |
| Example 22 | R221 | 4.2 | 458 | 7.5 |
| Example 23 | R241 | 4.1 | 458 | 7.6 |
| Example 24 | R261 | 4.5 | 458 | 7.3 |
| Example 25 | R281 | 3.8 | 458 | 6.9 |
| Example 26 | R285 | 3.4 | 458 | 6.8 |
| Example 27 | R286 | 4.7 | 458 | 7.2 |
| Example 28 | R291 | 3.8 | 458 | 6.9 |
| Comparative Example 2 | Alq$_3$ | 4.8 | 458 | 6.2 |
| Comparative Example 3 | A1 | 4.7 | 457 | 6.5 |

As shown in Table 2, it was seen that the blue organic electroluminescent devices using the compound of the present invention in an electron transport auxiliary layer (Examples 6 to 28) exhibited superior performance in terms of current efficiency, light emission peak and driving voltage compared to the blue organic electroluminescent devices without an electron transport auxiliary layer (Comparative Examples 2 and 3).

Examples 29 to 32 Manufacture of Blue Organic Electroluminescent Device

After high purity sublimation purifying the compounds synthesized in the synthesis examples using commonly known methods, blue organic electroluminescent devices were manufactured using the following procedure.

First, a glass substrate on which indium tin oxide (ITO) was coated as a thin film to a thickness of 1500 Å was ultrasonic cleaned using distilled water. After the cleaning with distilled water was finished, the substrate was ultrasonic cleaned with solvents of isopropyl alcohol, acetone, methanol and the like, dried, then transferred to a UV OZONE washer (Power sonic 405, manufactured by Hwashin Tech. Co., Ltd.), and then, after cleaning the substrate for 5 minutes using UV, the substrate was transferred to a vacuum deposition apparatus.

On the transparent ITO electrode prepared as above, DS-205 (Doosan Corporation Electro-Materials, 80 nm)/NPB (15 nm)/ADN+5% DS-405 (Doosan Corporation Electro-Materials, 30 nm)/each compound of R1, R8, R21 and R41 (30 nm)/LiF (1 nm)/Al (200 nm) were laminated in this order to manufacture an organic electroluminescent device.

Comparative Example 4 Manufacture of Blue Organic Electroluminescent Device

A blue organic electroluminescent device was manufactured in the same manner as in Example 29 except that Alq$_3$ was used instead of R1 as the electron transport layer material.

Comparative Example 5 Manufacture of Blue Organic Electroluminescent Device

A blue organic electroluminescent device was manufactured in the same manner as in Example 29 except that R1 was not used as the electron transport layer material.

Evaluation Example 3

For each of the blue organic electroluminescent devices manufactured in Examples 29 to 32 and Comparative Examples 2 and 3, driving voltage, current efficiency and light emission wavelength at current density of 10 mA/cm² were measured, and the results are shown in the following Table 3.

TABLE 3

| Sample | Electron Transport Layer | Driving Voltage (V) | Light Emission Peak (nm) | Current Efficiency (cd/A) |
|---|---|---|---|---|
| Example 29 | R1 | 4.5 | 455 | 8.7 |
| Example 30 | R8 | 3.9 | 455 | 7.8 |
| Example 31 | R21 | 4.4 | 455 | 8.4 |
| Example 32 | R41 | 4.2 | 455 | 9.3 |
| Comparative Example 4 | Alq$_3$ | 4.7 | 458 | 5.5 |
| Comparative Example 5 | — | 4.8 | 460 | 6.2 |

As shown in Table 3, it was seen that the blue organic electroluminescent devices using the compound of the present invention in an electron transport layer (Examples 29 to 32) exhibited superior performance in terms of driving voltage, light emission peak and current efficiency compared to the blue organic electroluminescent device using existing Alq₃ in an electron transport layer (Comparative Example 4), and the blue organic electroluminescent device without an electron transport layer (Comparative Example 5).

REFERENCE NUMERAL

10: Anode
20: Cathode
30: Organic Layer
31: Hole Transport Layer
32: Light Emitting Layer
33: Hole Transport Auxiliary Layer
34: Electron Transport Layer
35: Electron Transport Auxiliary Layer
36: Electron Injection Layer
37: Hole Injection Layer

The invention claimed is:
1. A compound selected from the group consisting of the following compounds:

R6

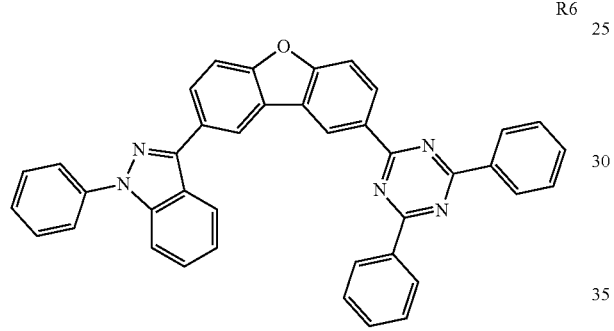

R7

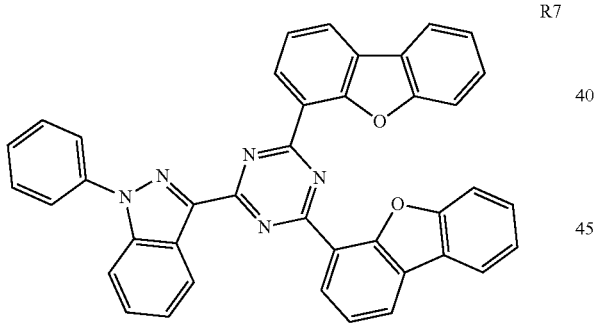

R8

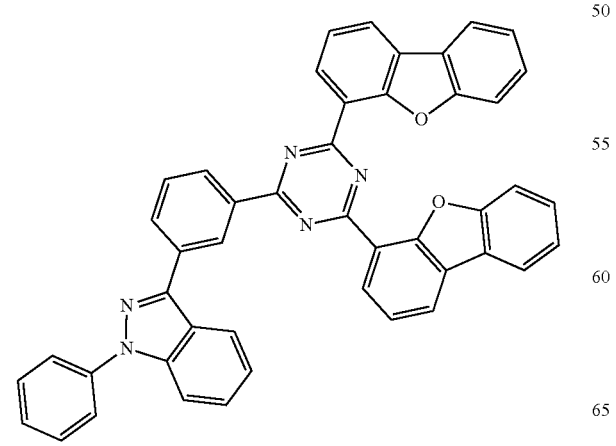

-continued

R9

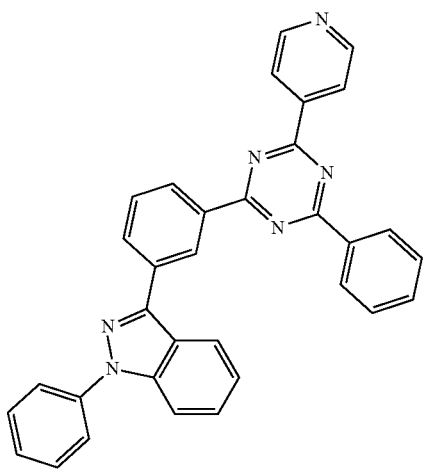

R11

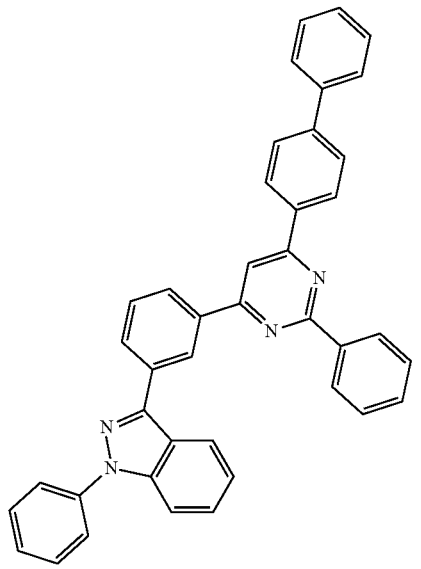

R12

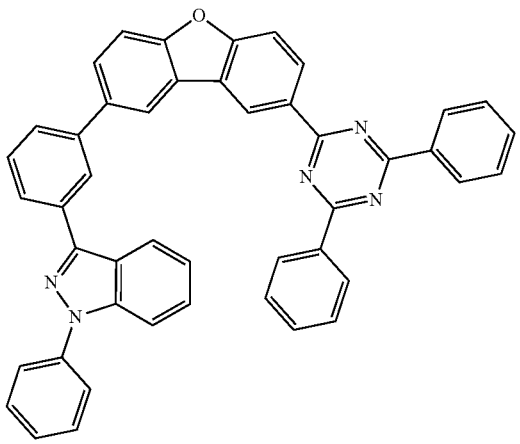

R13
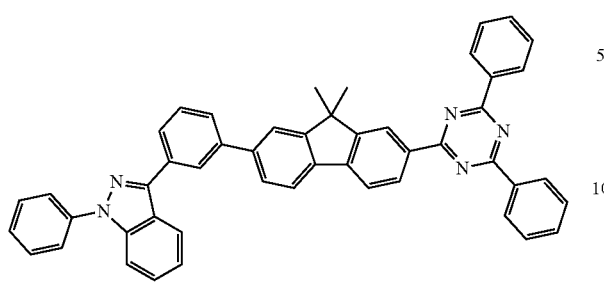
R14
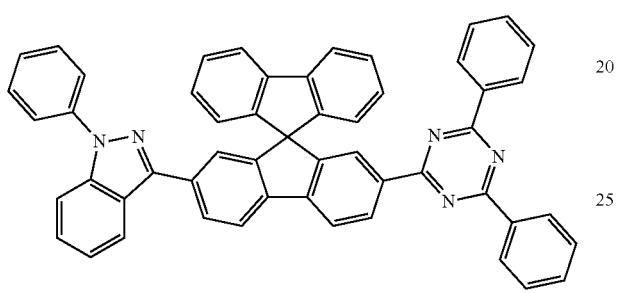
R15
R16
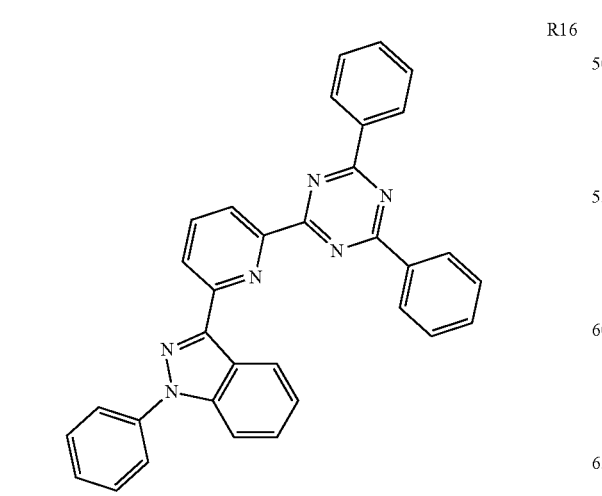
R17
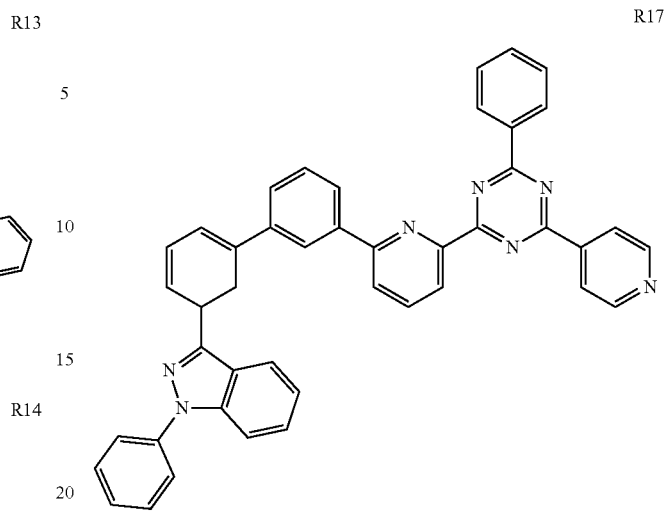
R18
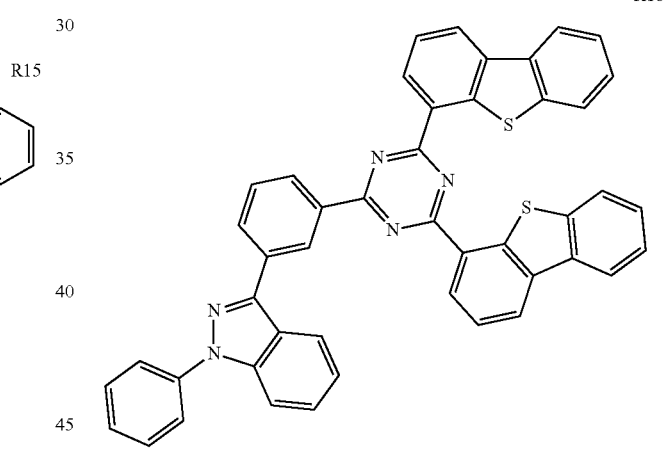
R19
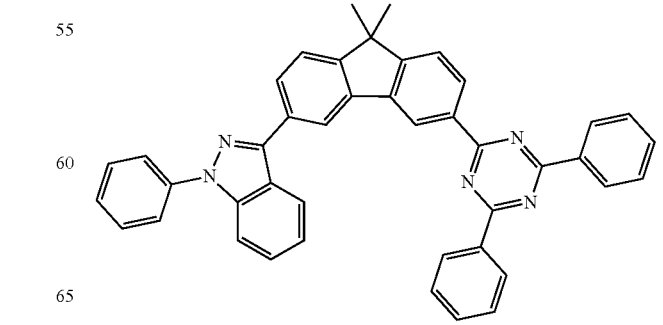

155
-continued
R20
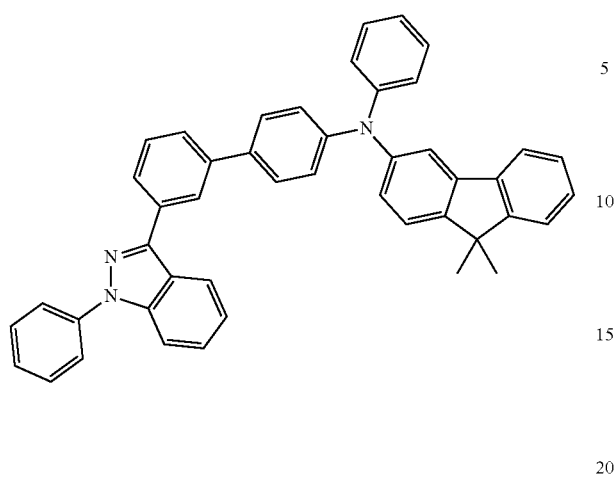
R21
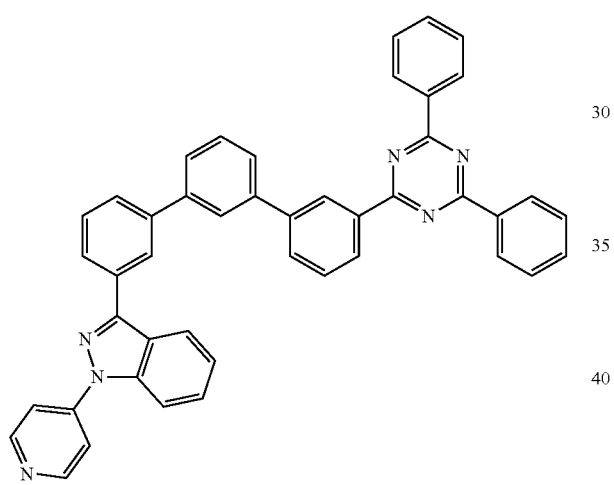
R22
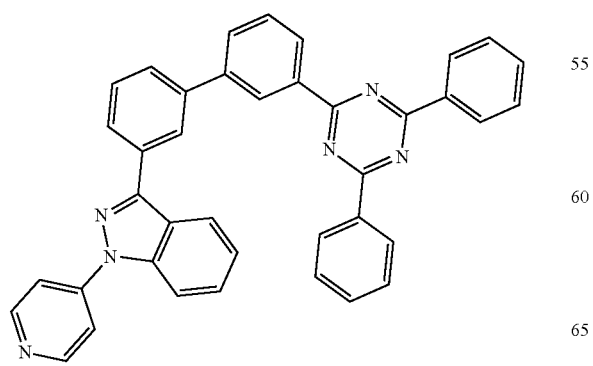
156
-continued
R23
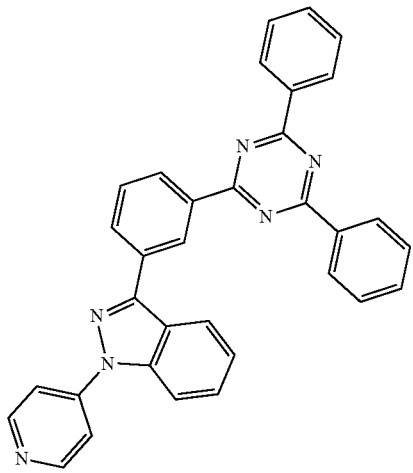
R24
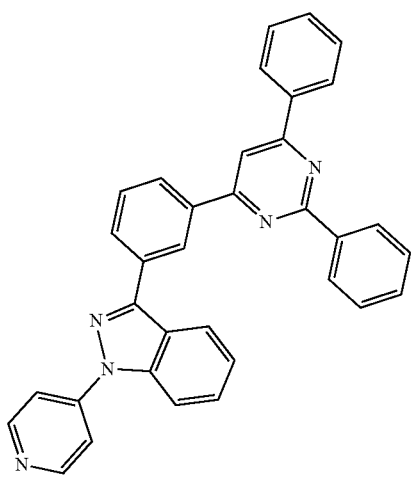
R26
(image on right, middle)
R27
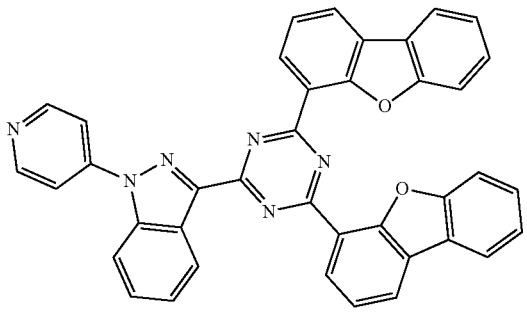

R28
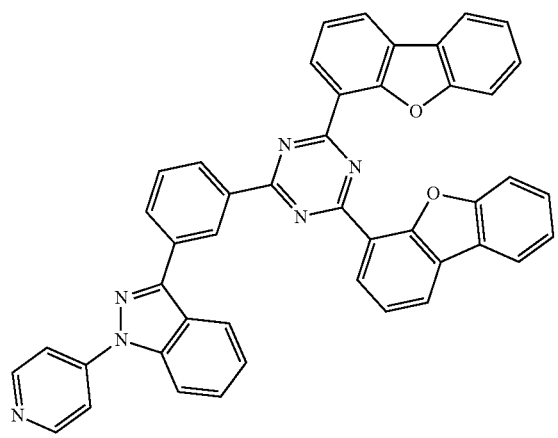
R29
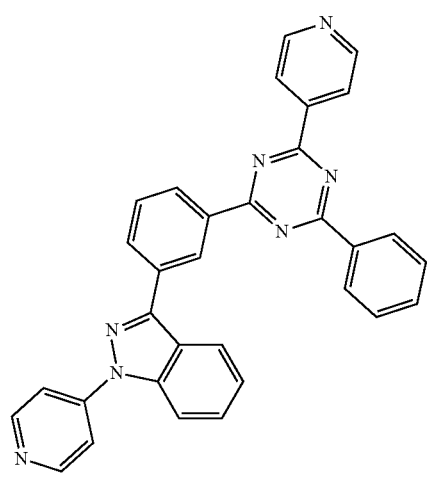
R31
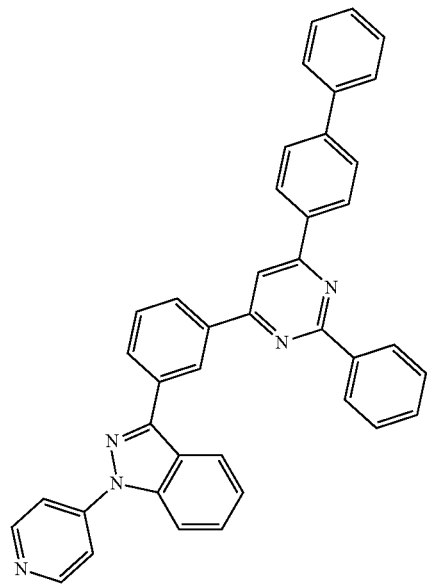
R32
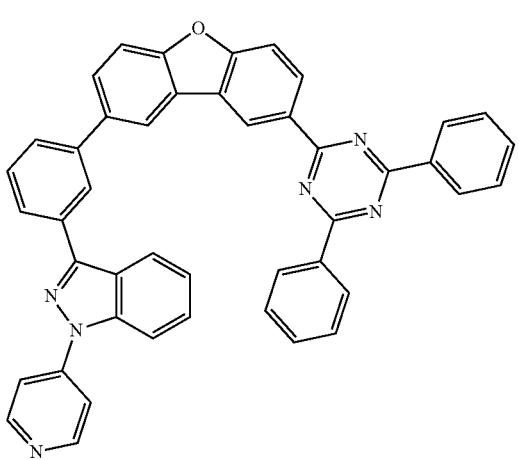
R33
R34
R35
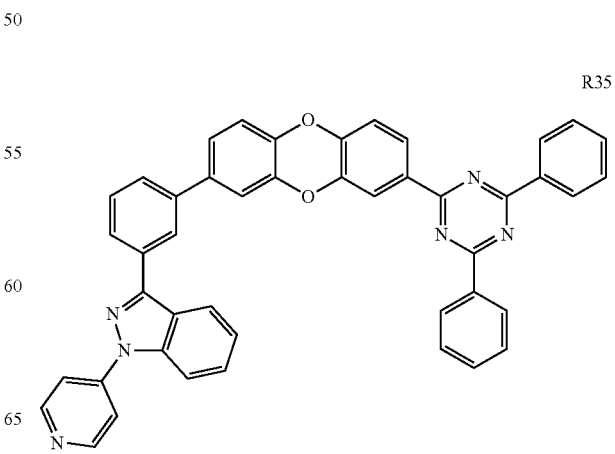

159
-continued
R36
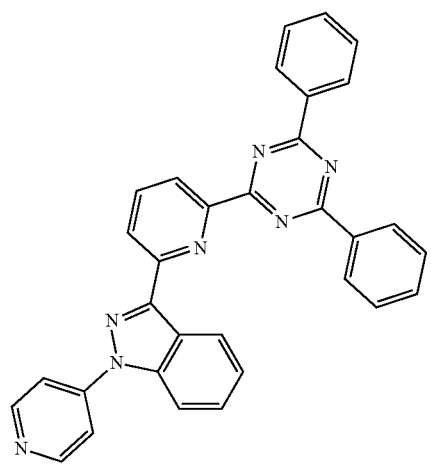
R37
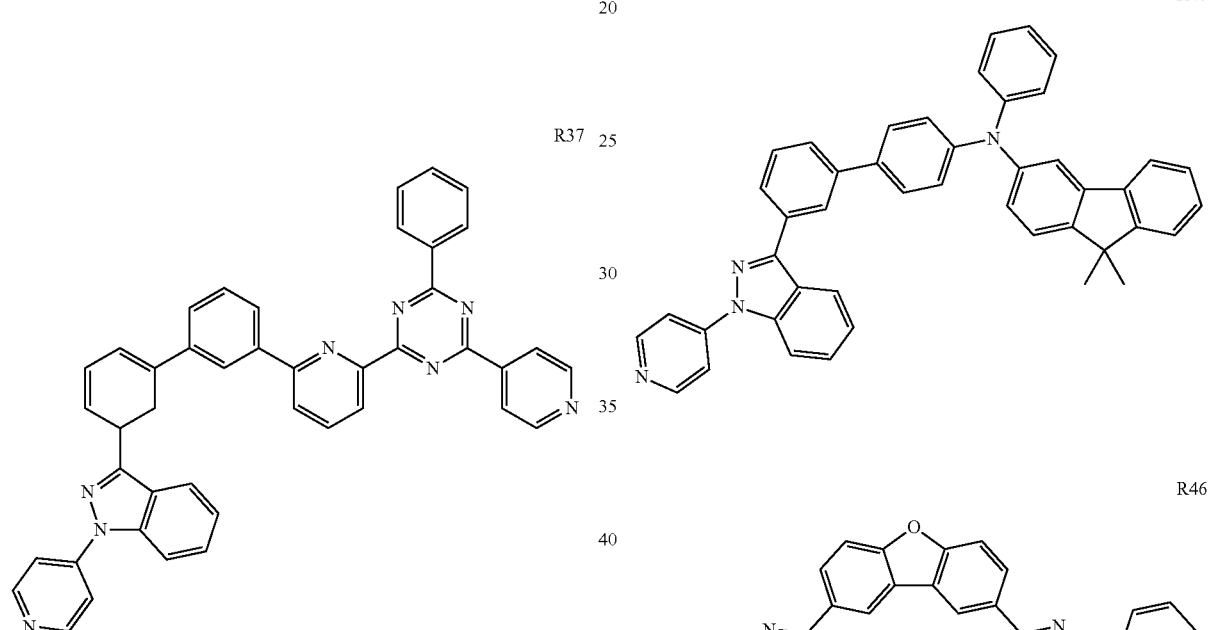
R38
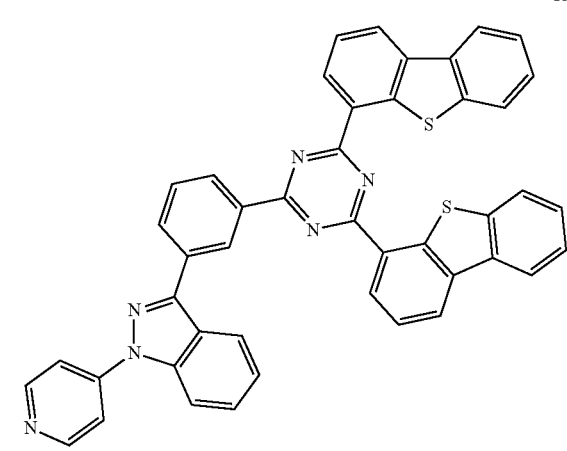
160
-continued
R39
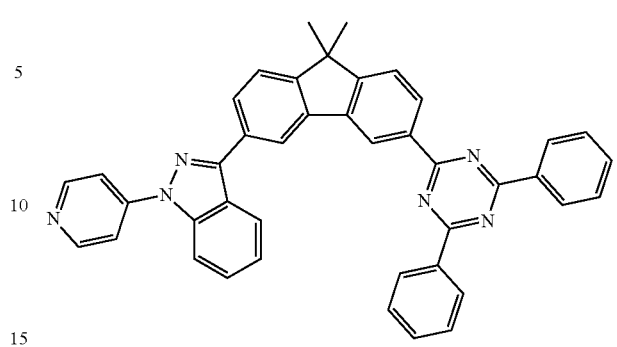
R40
R46
R47
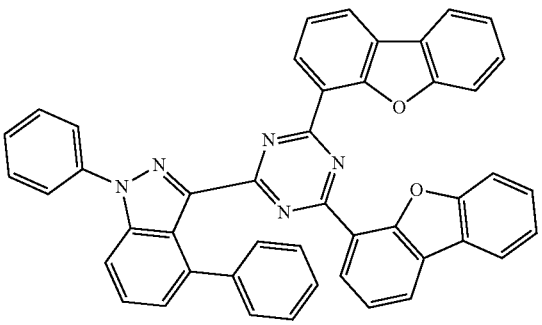

-continued
R48
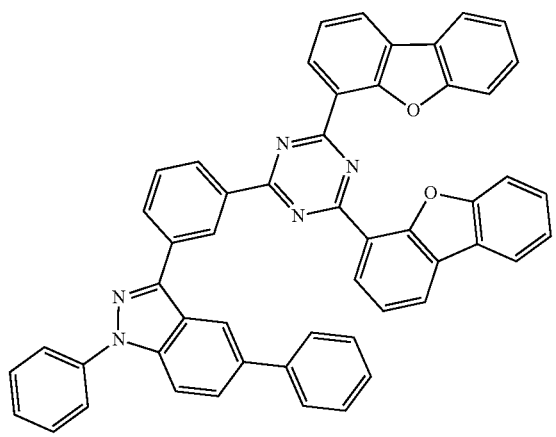
R49
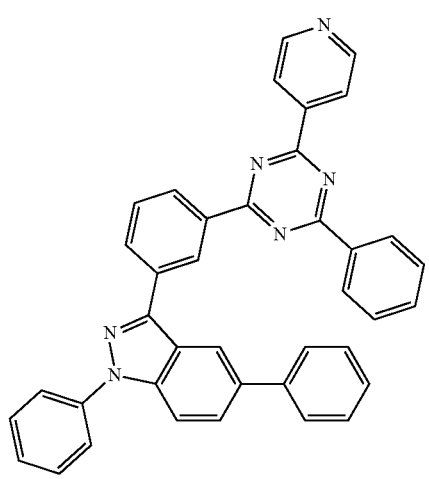
R51
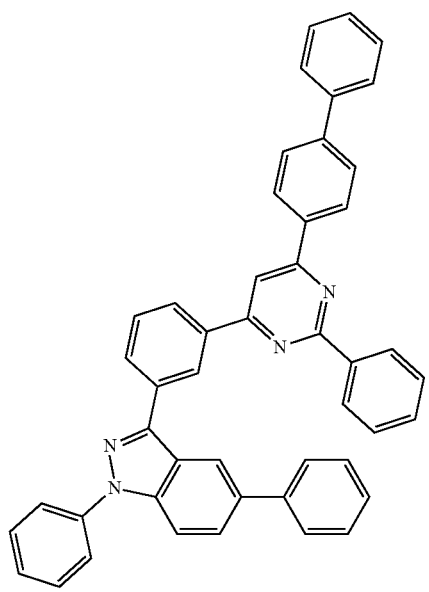
-continued
R52
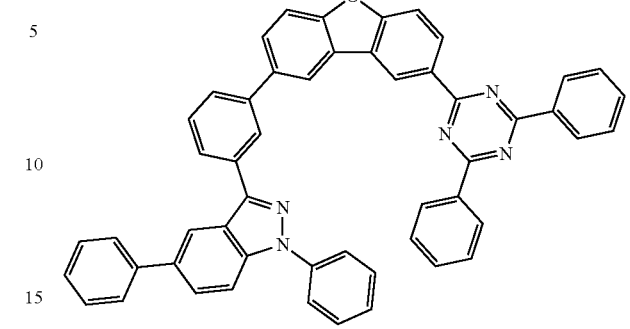
R53
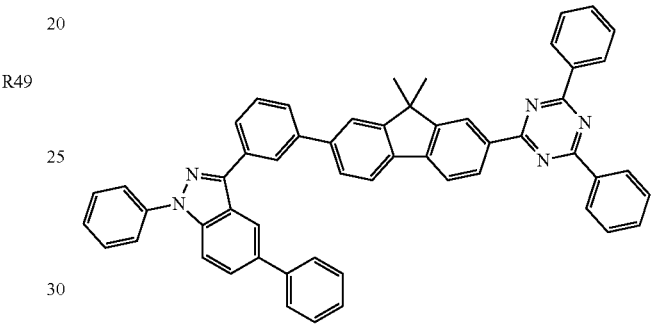
R54
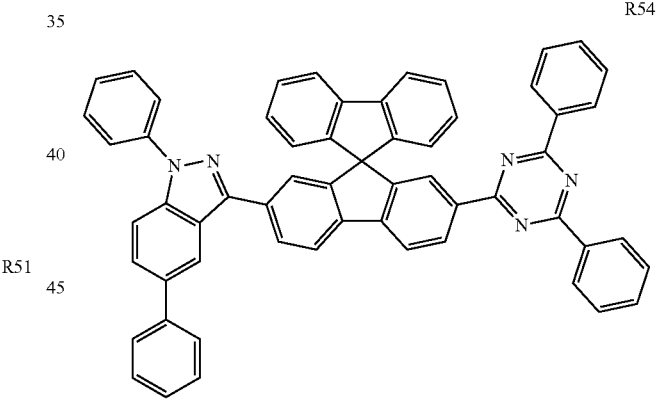
R55
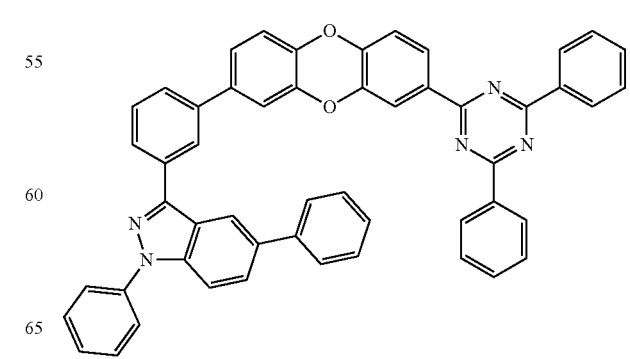

-continued
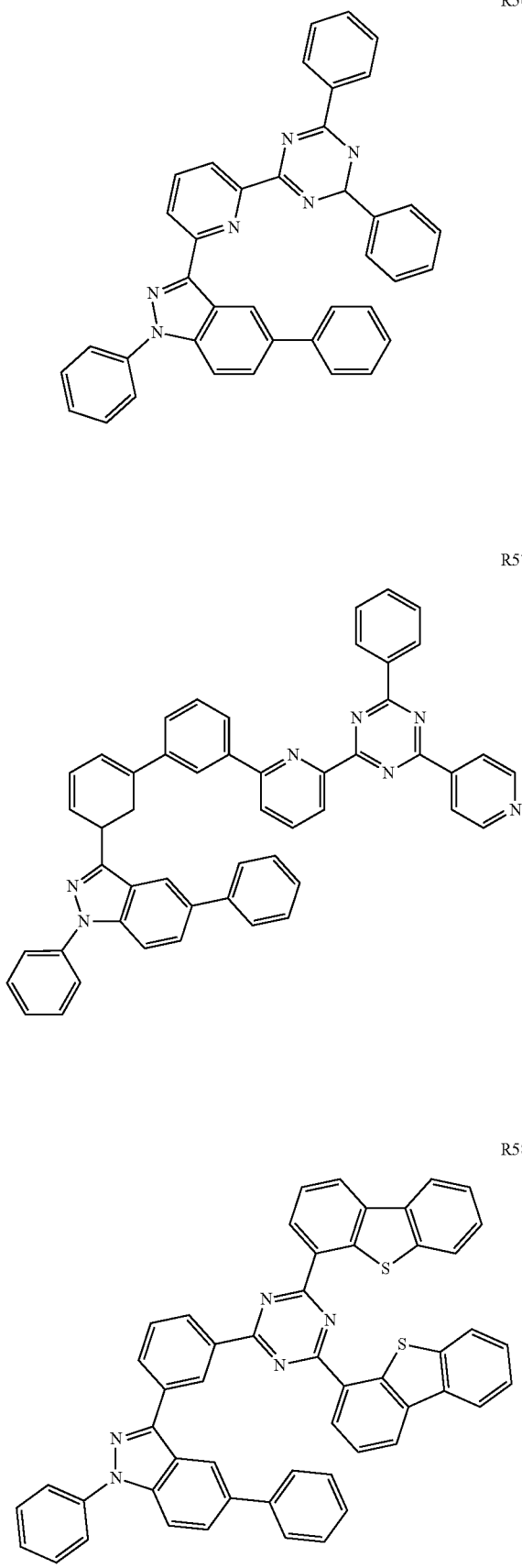
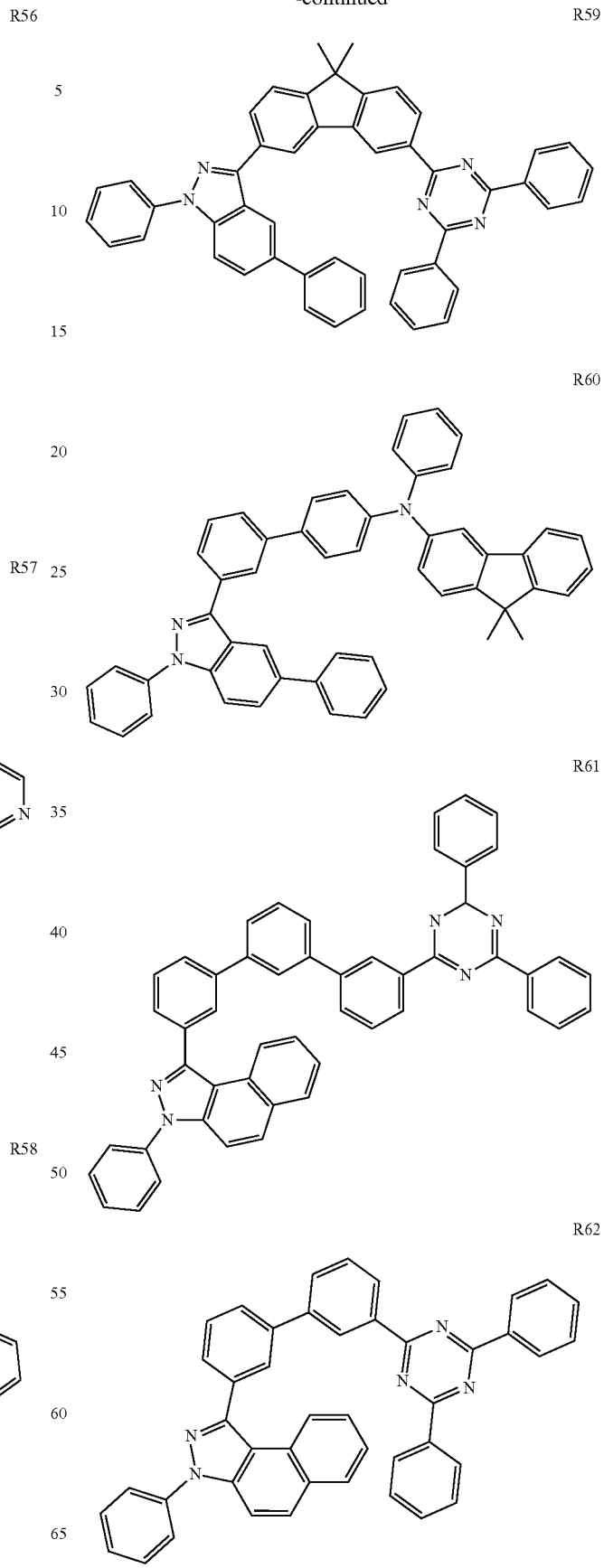

R63 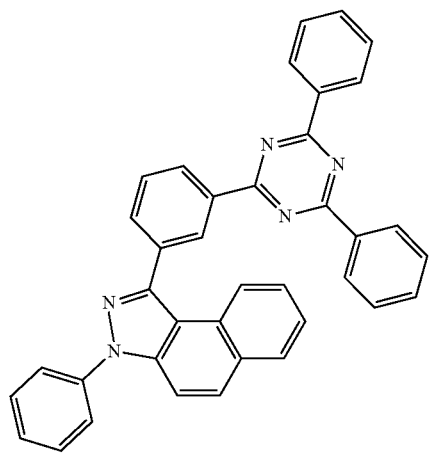
R64 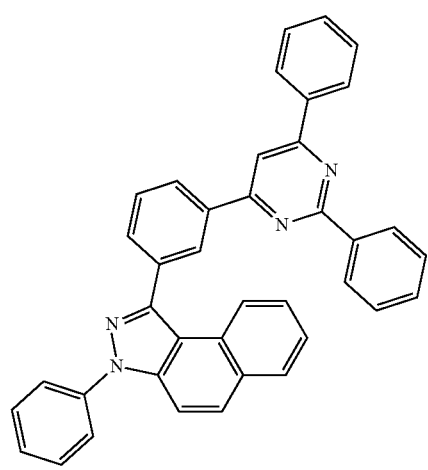
R65 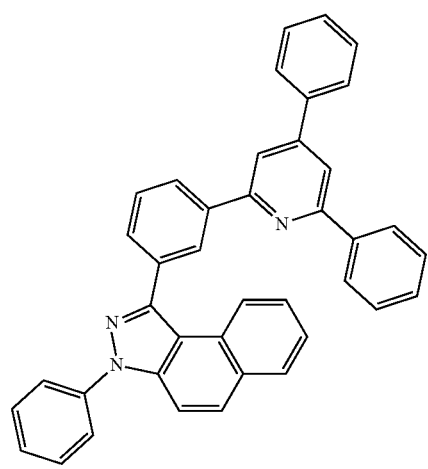
R66 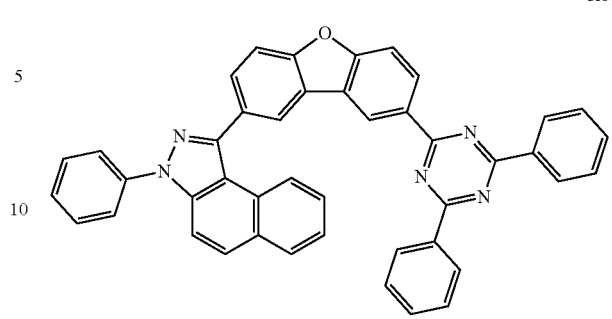
R67 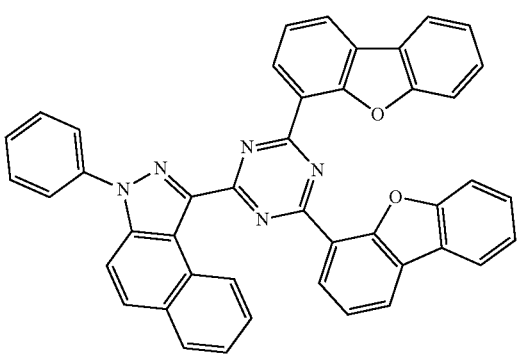
R68 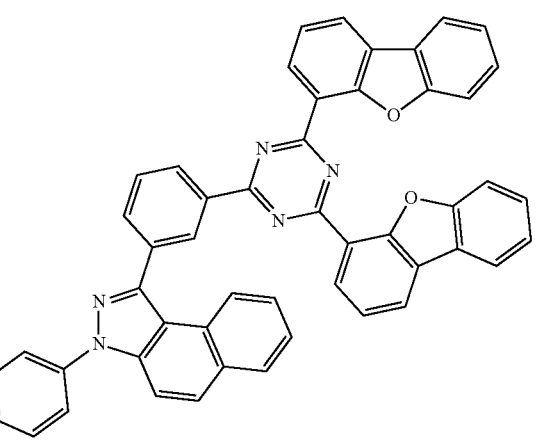
R69 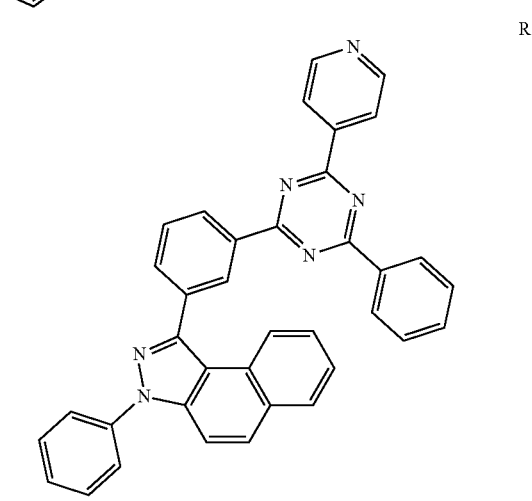

R70
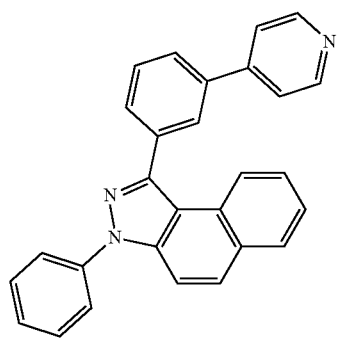
R71
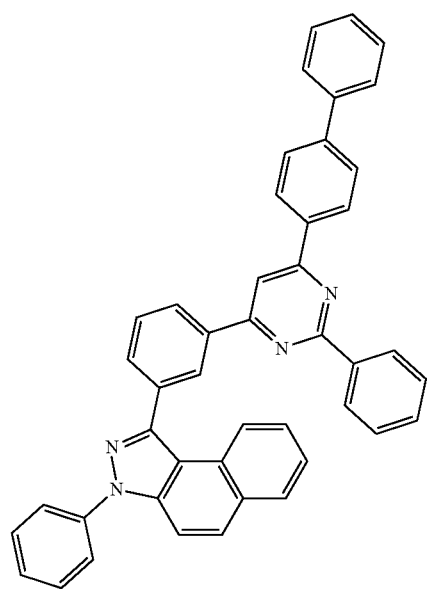
R72
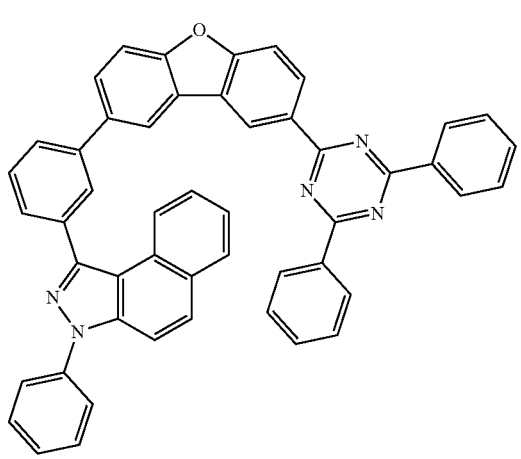
R73
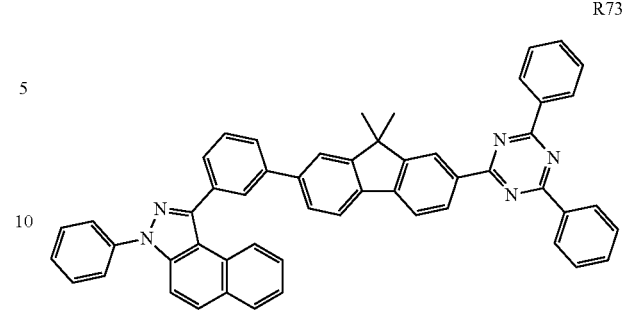
R74
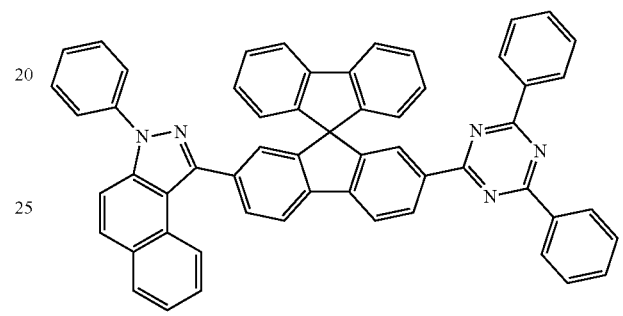
R75
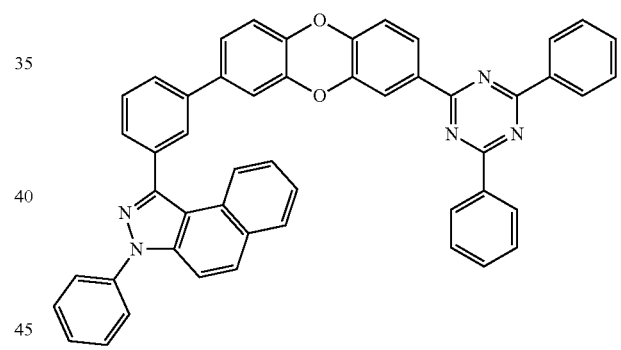
R76
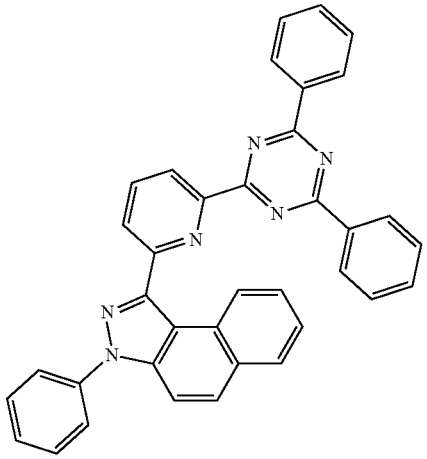

R77
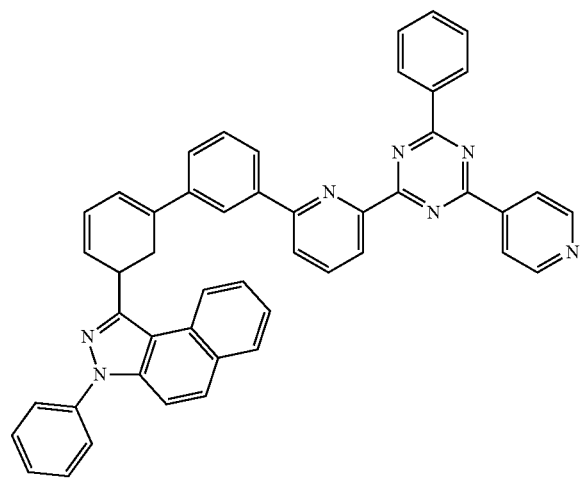
R78
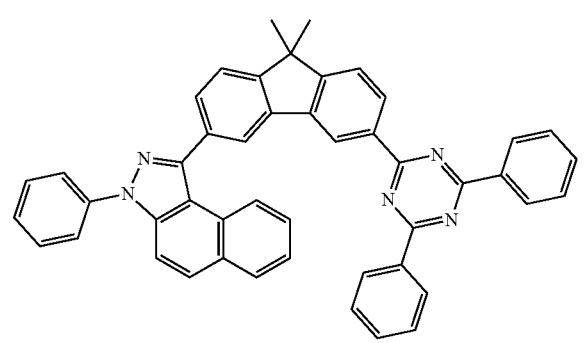
R80
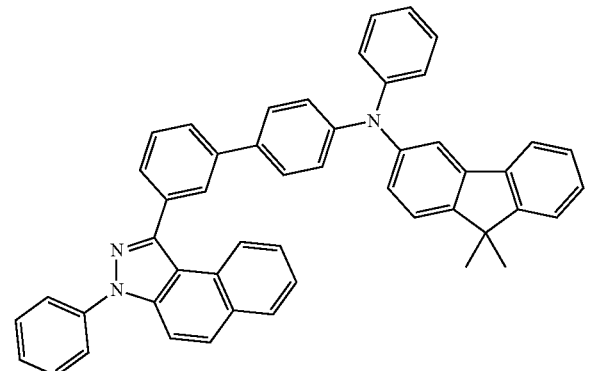
R81
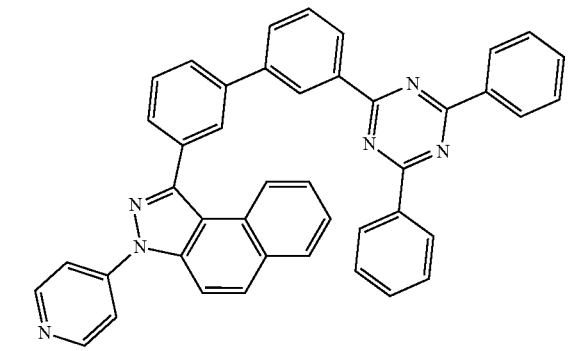

-continued
R83
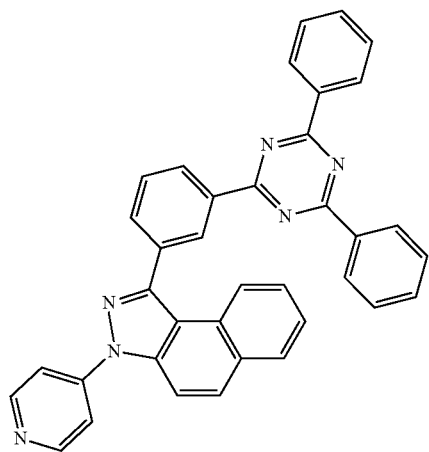
R84
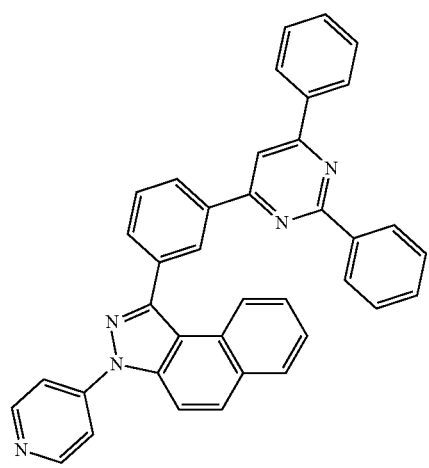
R85
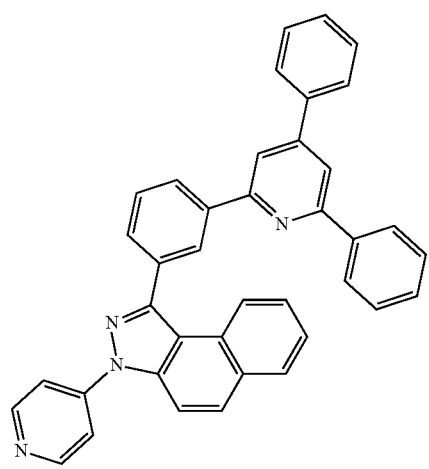
-continued
R86
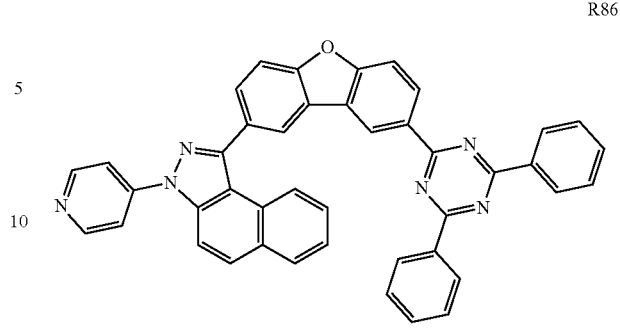
R87
R88
R89
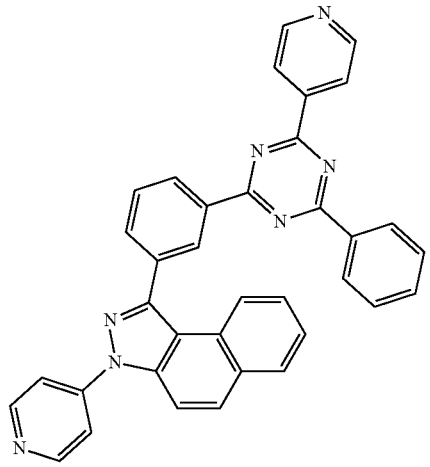

-continued
R90
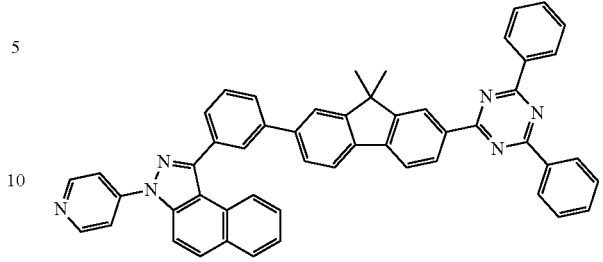
R91
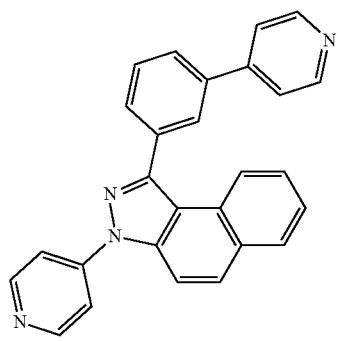
R93
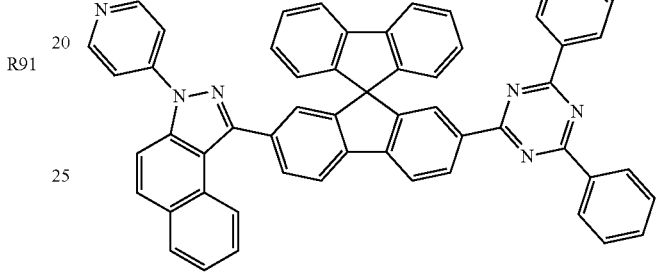
R94
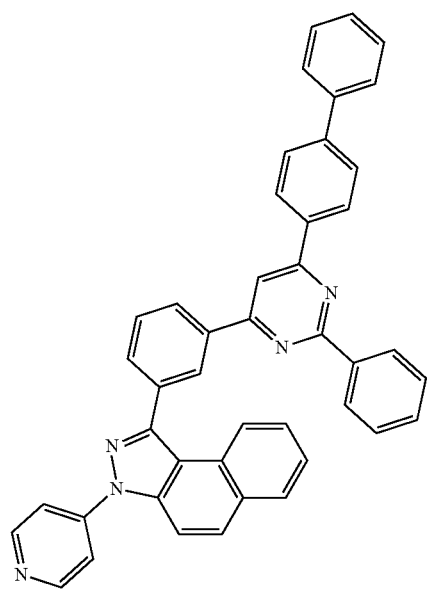
R95
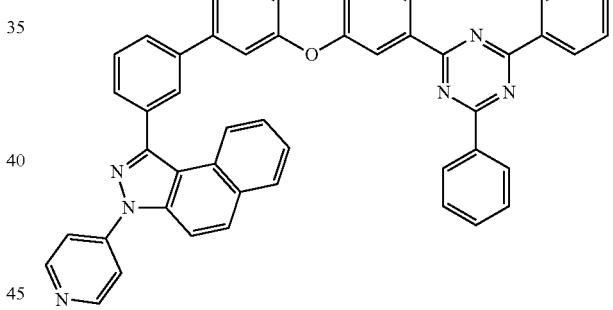
R92
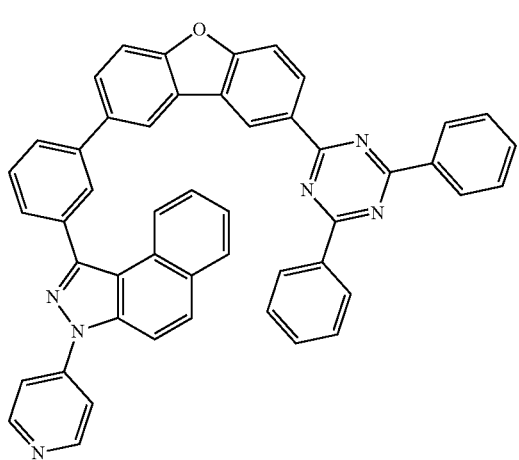
R96
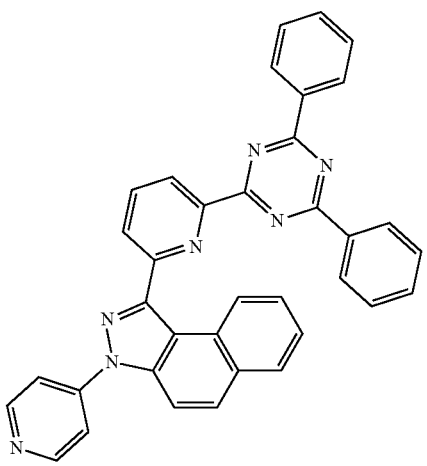

-continued
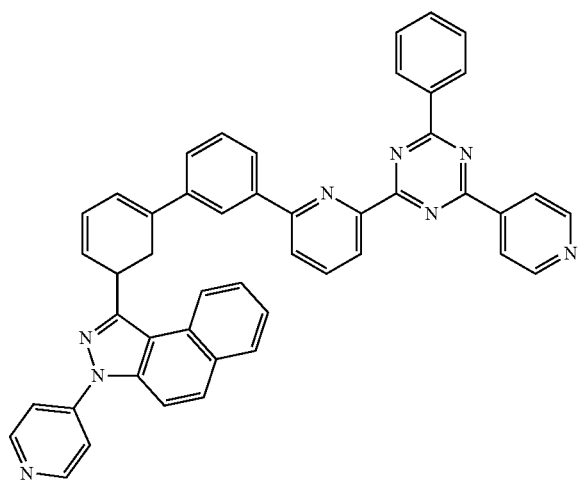
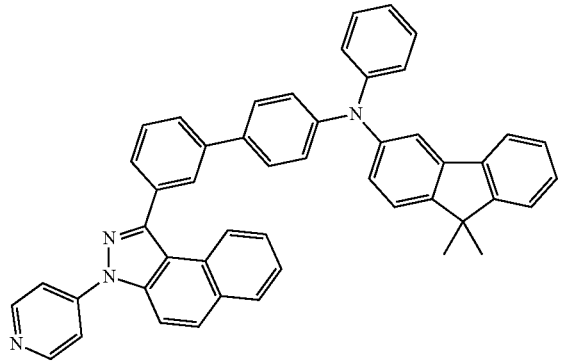
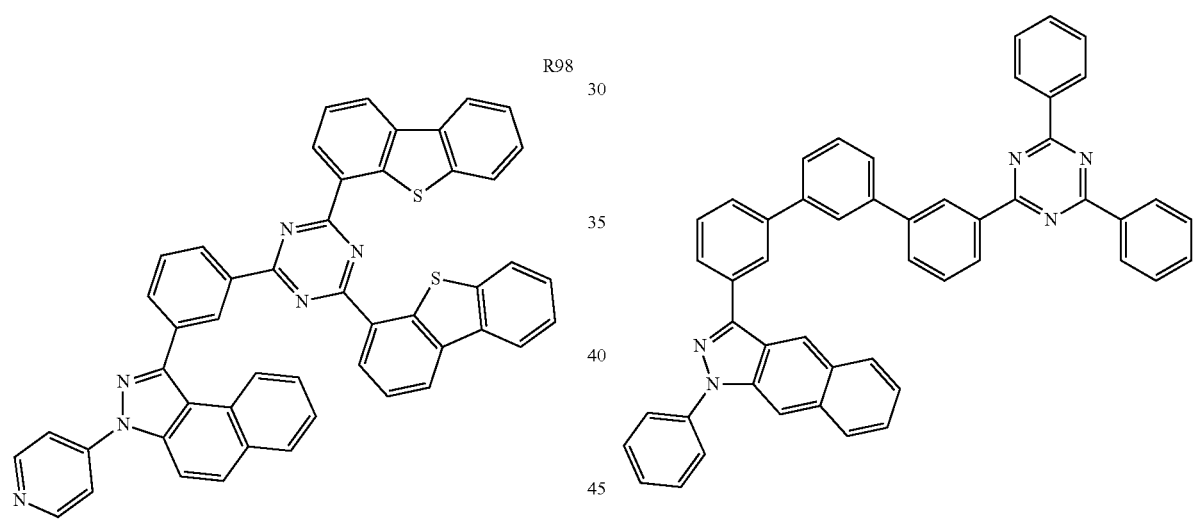
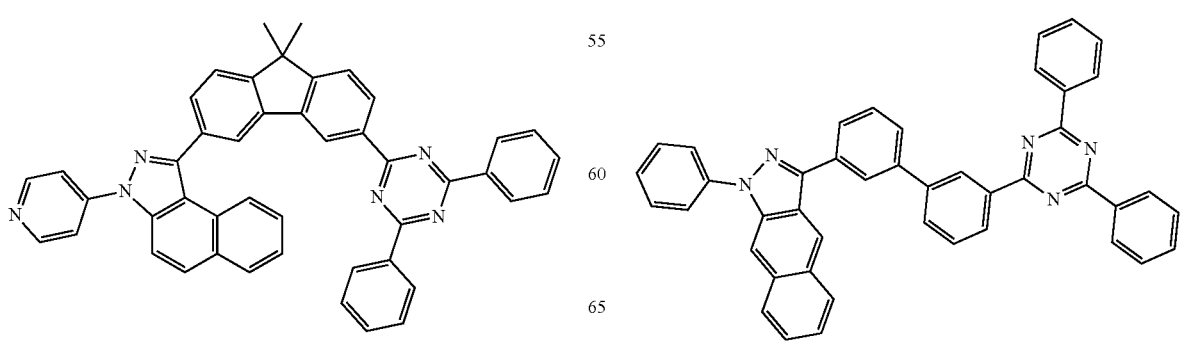

-continued
R103
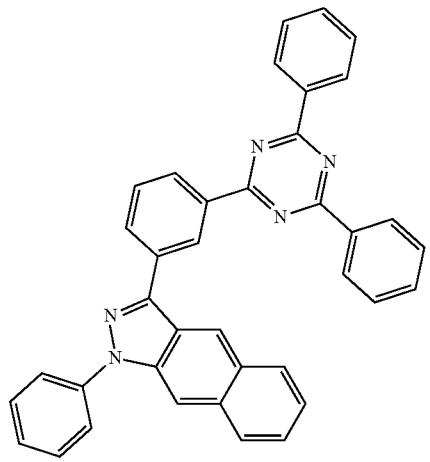
R104
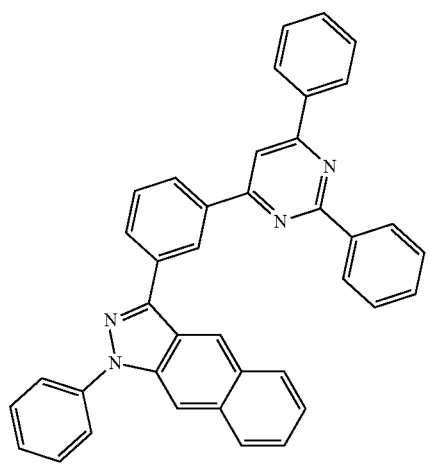
R105
-continued
R106
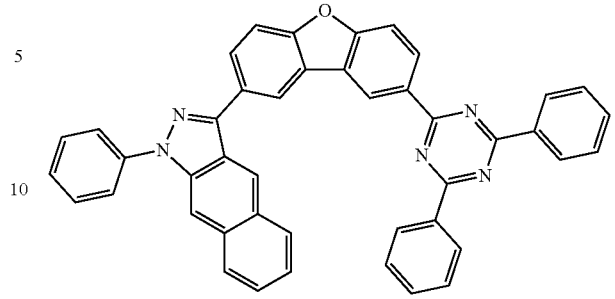
R107
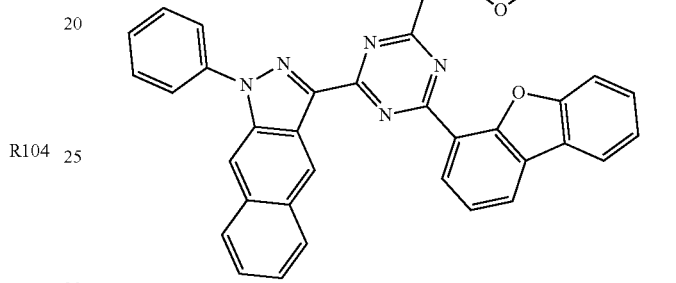
R108
R109
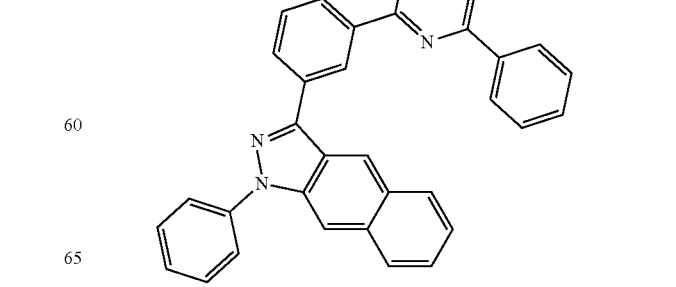

R110 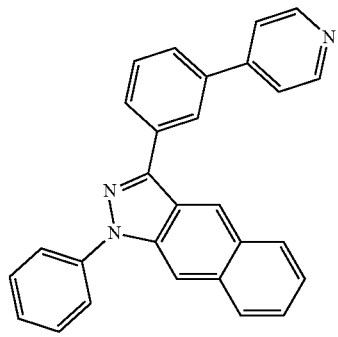
R113 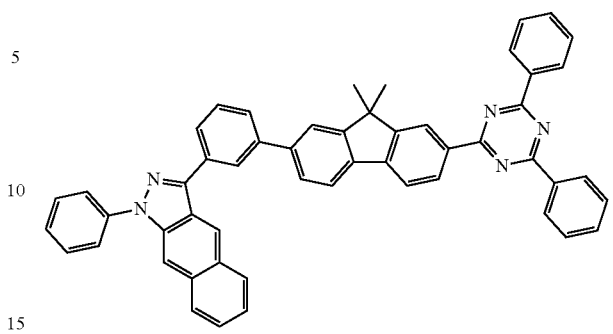
R111 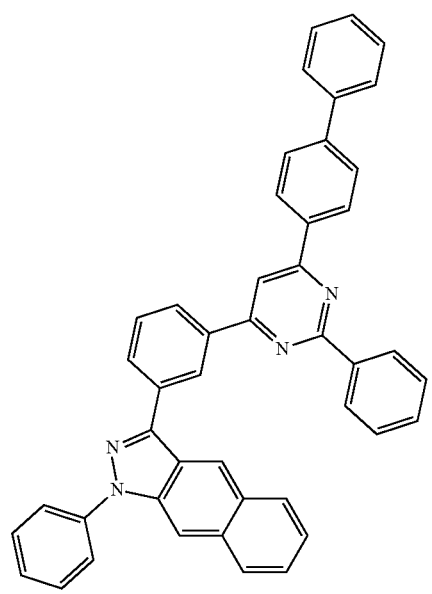
R114 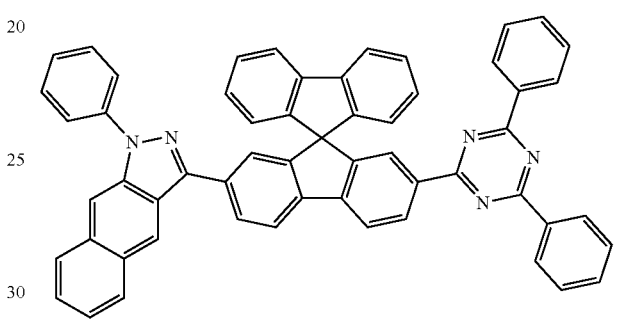
R115 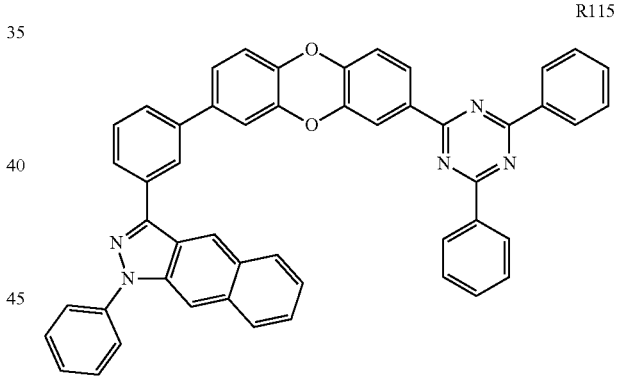
R112 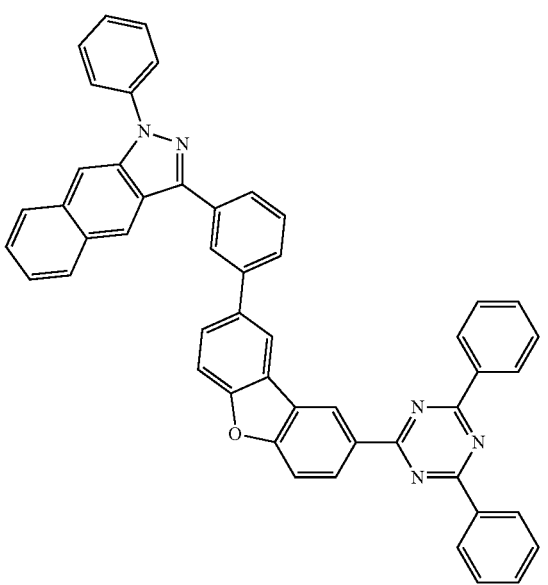
R116 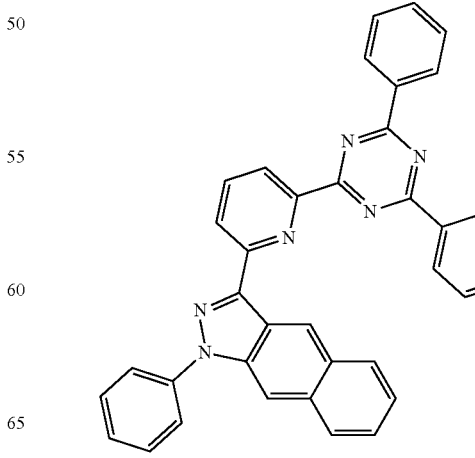

R117
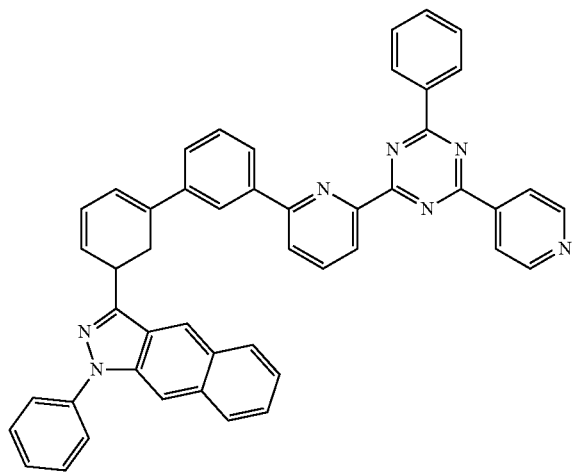
R120
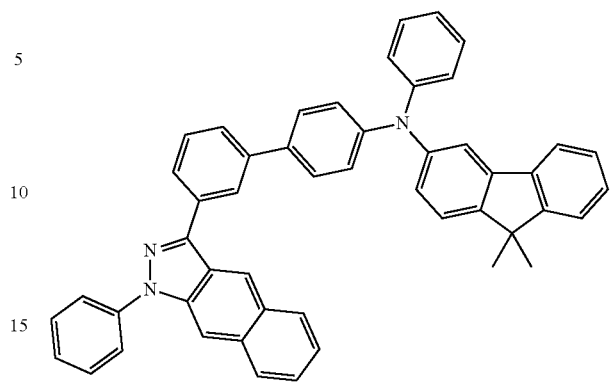
R118
R121
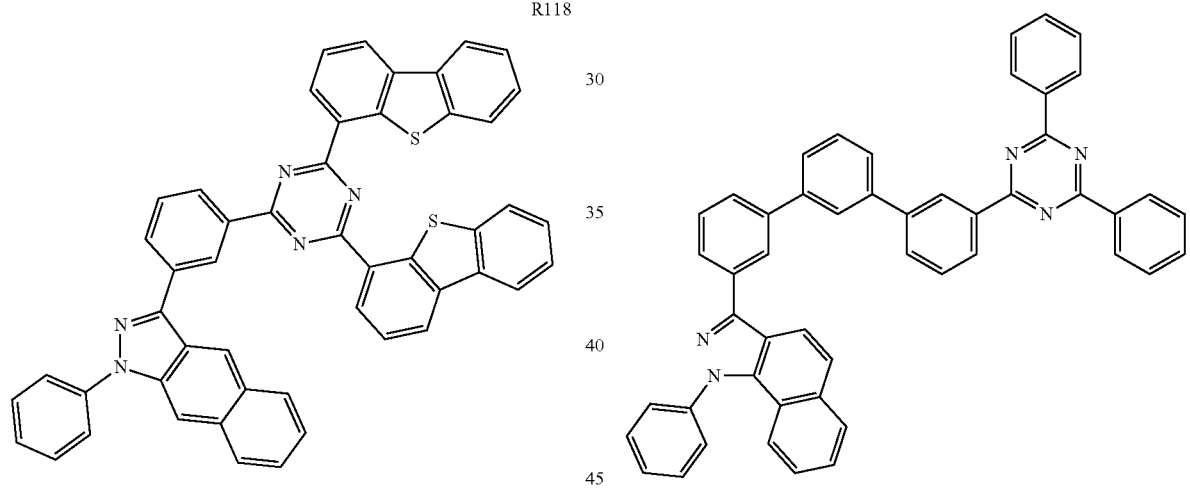
R119
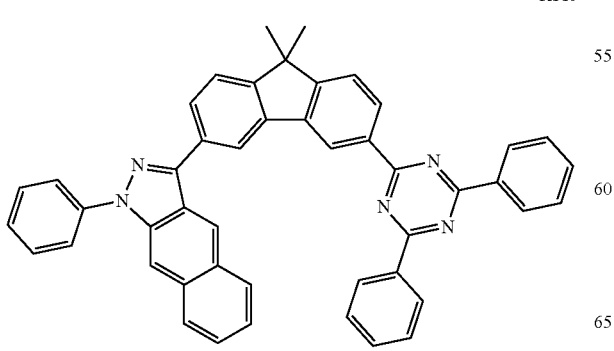
R122
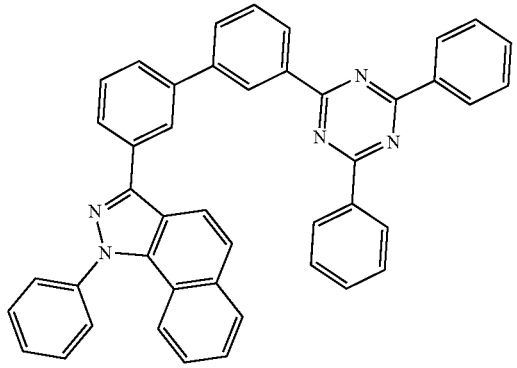

R123
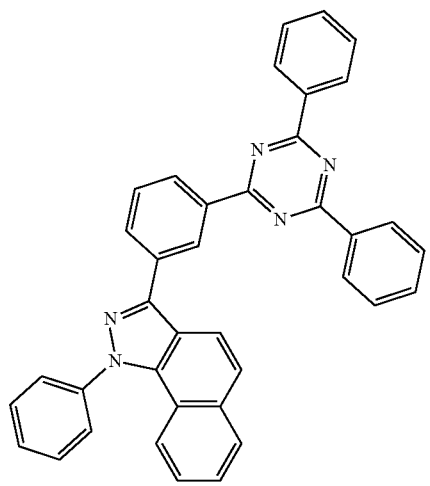
R124
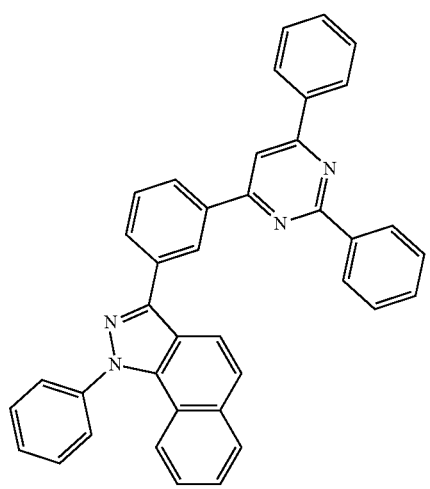
R125
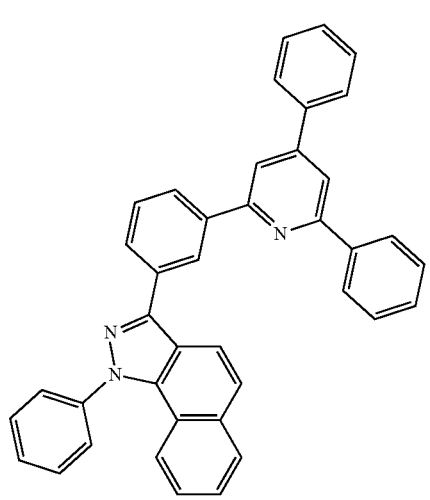
R126
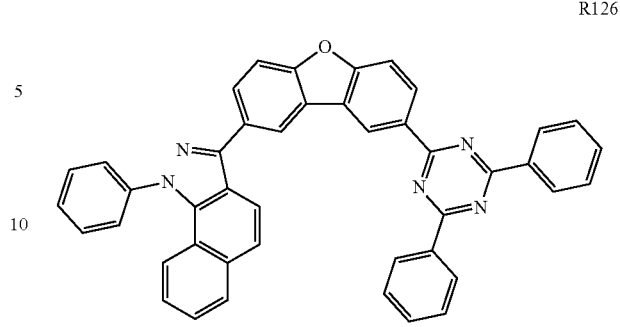
R127
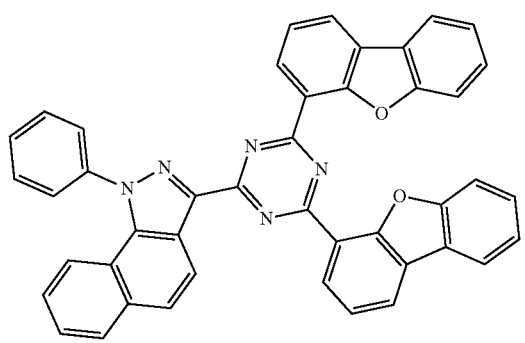
R128
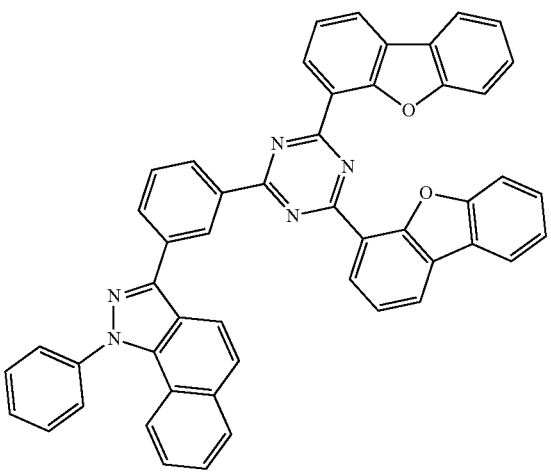
R129
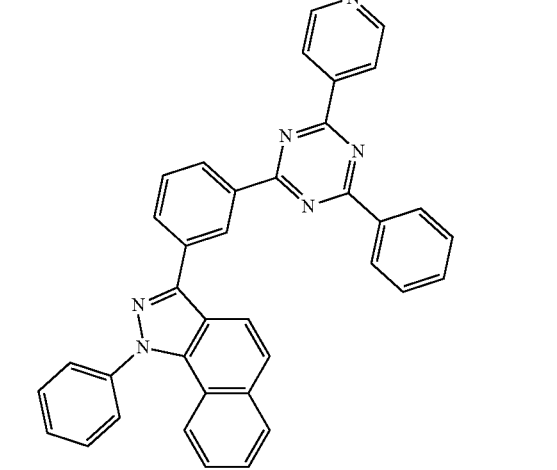

R130
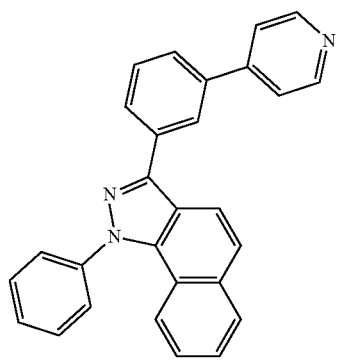
R133
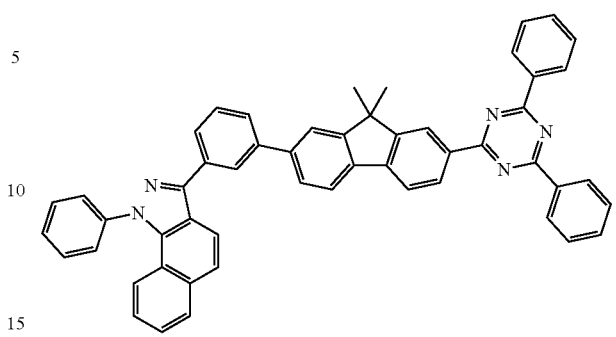
R131
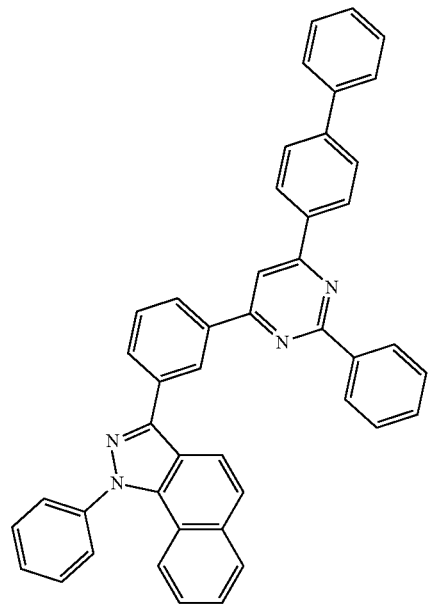
R134
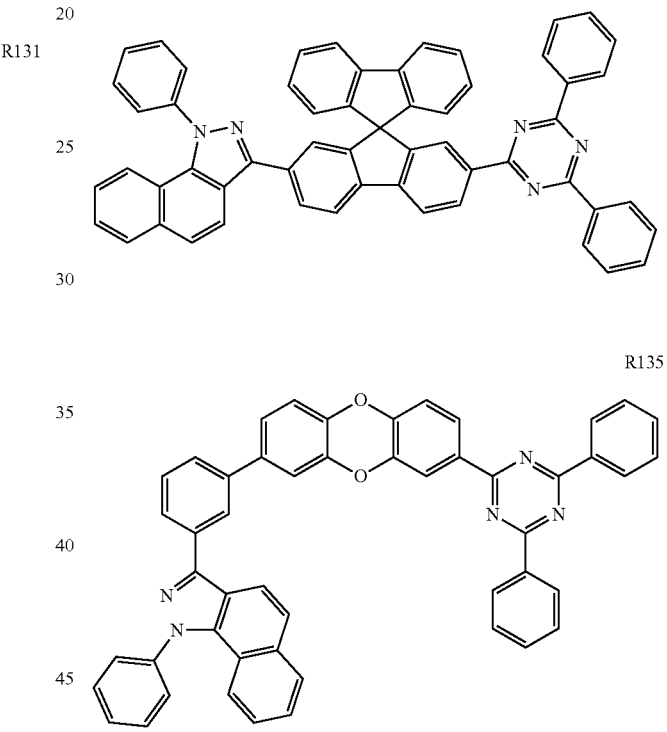
R135
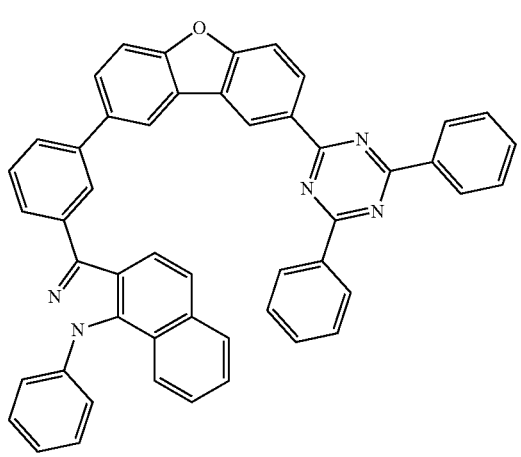
R132
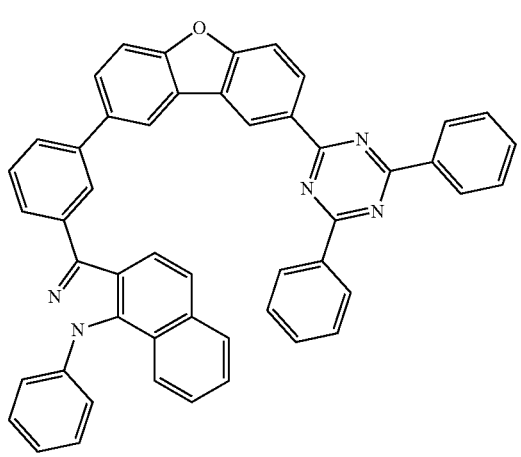
R136
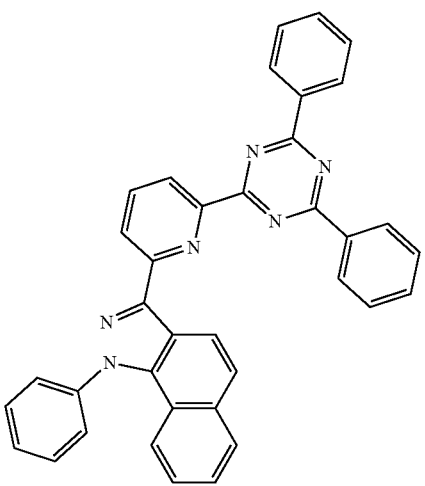

-continued
R137
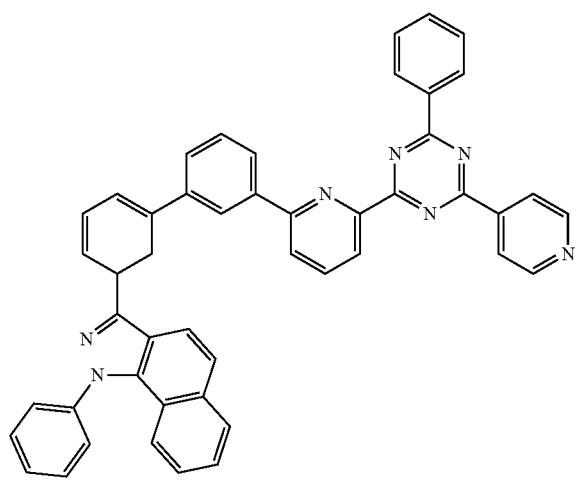
R138
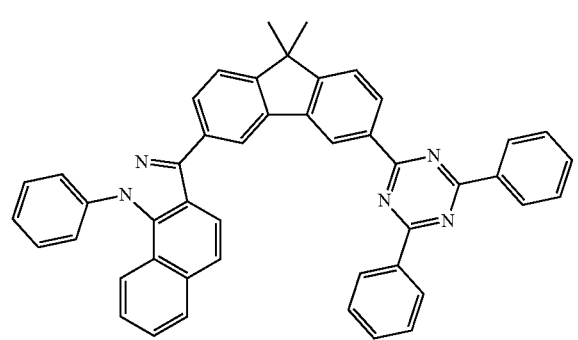
R139
-continued
R140
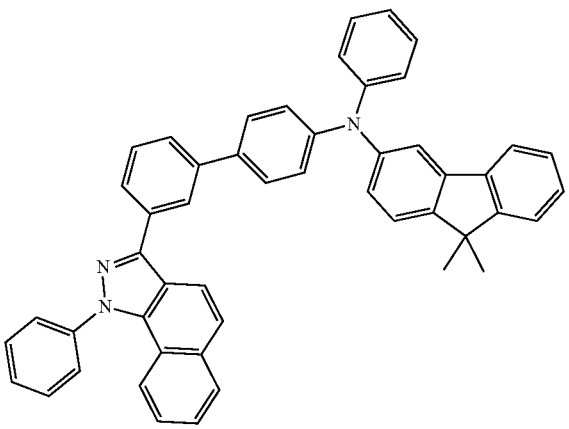
R146
R154
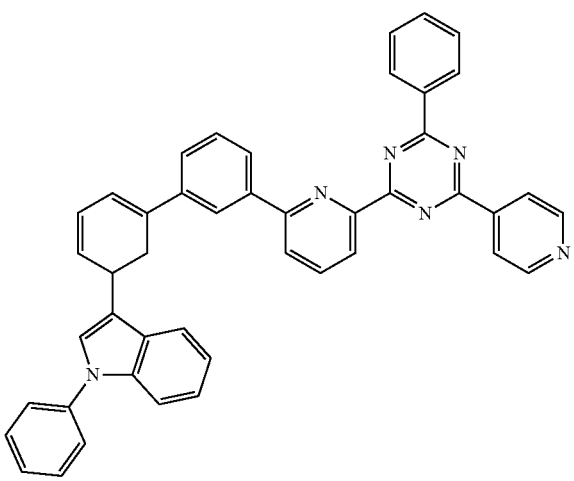
R157

R159 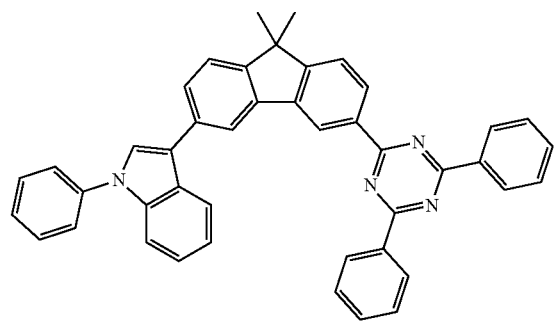
R179 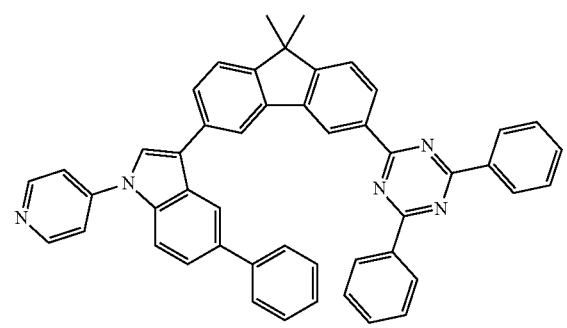
R166 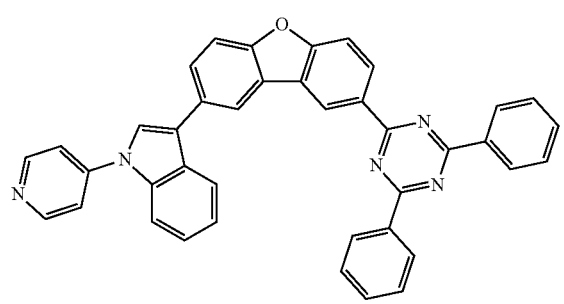
R186 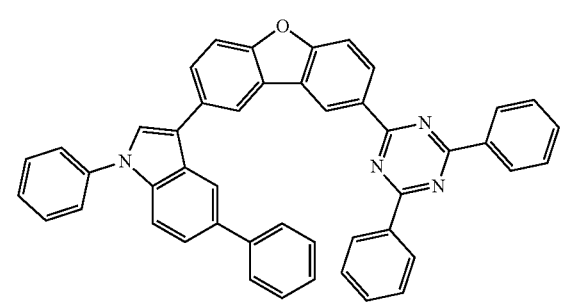
R174 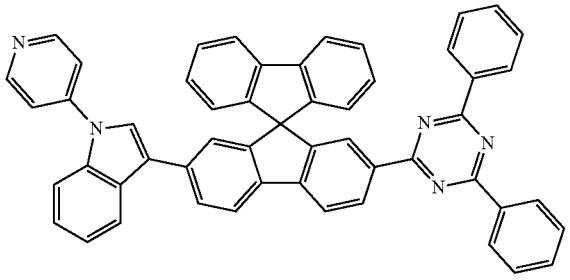
R194 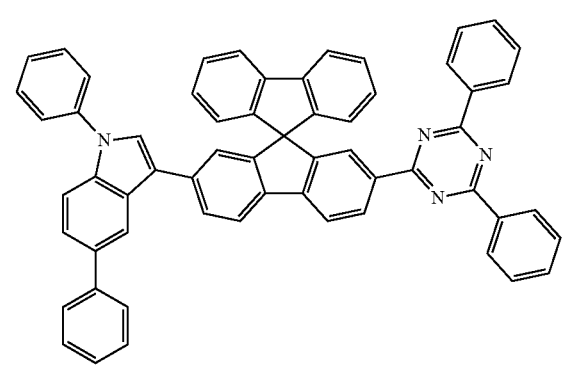
R177 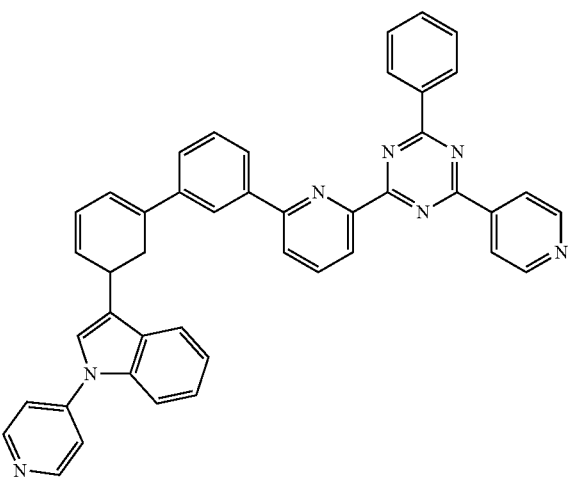
R197 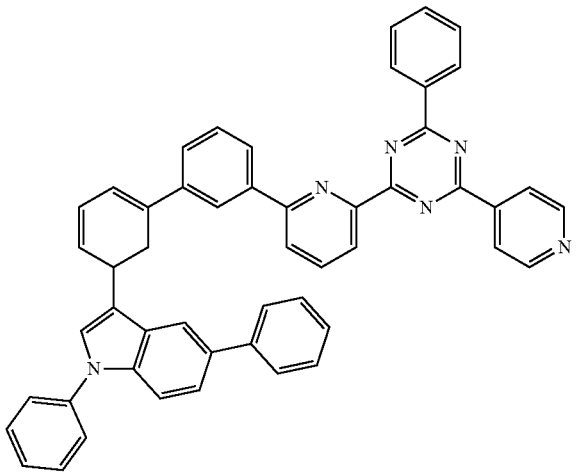
and -continued

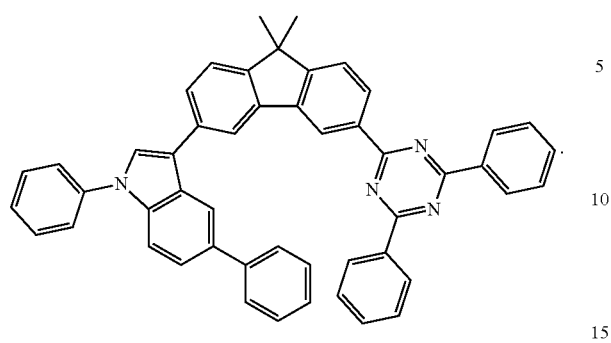

R199

2. An organic electroluminescent device comprising:
an anode;
a cathode; and
one or more organic material layers provided between the anode and the cathode,
wherein at least one of the one or more organic material layers includes a compound of claim 1.

3. The organic electroluminescent device of claim 2, wherein the organic material layer includes one or more layers selected from the group consisting of a hole injection layer, a hole transport layer, a hole transport auxiliary layer, an electron transport layer, an electron transport auxiliary layer and a light emitting layer.

* * * * *